US010464947B2

(12) United States Patent
Combs et al.

(10) Patent No.: US 10,464,947 B2
(45) Date of Patent: *Nov. 5, 2019

(54) TRICYCLIC HETEROCYCLES AS BET PROTEIN INHIBITORS

(71) Applicants: Incyte Corporation, Wilmington, DE (US); Incyte Holdings Corporation, Wilmington, DE (US)

(72) Inventors: Andrew P. Combs, Kennett Square, PA (US); Richard B. Sparks, Wilmington, DE (US); Thomas P. Maduskuie, Jr., Wilmington, DE (US); James D. Rodgers, Jupiter, FL (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/906,163

(22) Filed: Feb. 27, 2018

(65) Prior Publication Data

US 2018/0346481 A1    Dec. 6, 2018

Related U.S. Application Data

(63) Continuation of application No. 15/398,907, filed on Jan. 5, 2017, now Pat. No. 9,938,294, which is a continuation of application No. 14/923,105, filed on Oct. 26, 2015, now Pat. No. 9,624,241, which is a continuation of application No. 14/212,721, filed on Mar. 14, 2014, now Pat. No. 9,227,985.

(60) Provisional application No. 61/794,812, filed on Mar. 15, 2013.

(51) Int. Cl.
C07D 498/06 (2006.01)
C07D 498/16 (2006.01)
C07D 471/06 (2006.01)
C07D 519/00 (2006.01)

(52) U.S. Cl.
CPC ......... C07D 498/06 (2013.01); C07D 471/06 (2013.01); C07D 498/16 (2013.01); C07D 519/00 (2013.01)

(58) Field of Classification Search
CPC ..................... C07D 498/04; C07D 498/06
USPC ........................ 544/101; 514/230.2
See application file for complete search history.

(56) References Cited

U.S. PATENT DOCUMENTS

| 5,589,476 | A | 12/1996 | Jegham et al. |
| 8,633,186 | B2 | 1/2014 | Tachdjian et al. |
| 8,669,249 | B2 | 3/2014 | Brown et al. |
| 9,012,642 | B2 | 4/2015 | Haydar et al. |
| 9,227,985 | B2 * | 1/2016 | Combs .................. C07D 498/06 |
| 9,290,514 | B2 | 3/2016 | Combs et al. |
| 9,309,246 | B2 | 4/2016 | Rodgers et al. |
| 9,315,501 | B2 | 4/2016 | Yue et al. |
| 9,399,640 | B2 | 7/2016 | Yue et al. |
| 9,527,864 | B2 | 12/2016 | Combs et al. |
| 9,533,997 | B2 | 1/2017 | Combs et al. |
| 9,540,368 | B2 | 1/2017 | Combs et al. |
| 9,624,241 | B2 * | 4/2017 | Combs .................. C07D 498/06 |
| 9,737,516 | B2 | 8/2017 | Yue et al. |
| 9,777,003 | B2 | 10/2017 | Shepard et al. |
| 9,834,565 | B2 | 12/2017 | Combs et al. |
| 9,850,257 | B2 | 12/2017 | Combs et al. |
| 9,918,990 | B2 | 3/2018 | Yue et al. |
| 9,938,294 | B2 * | 4/2018 | Combs .................. C07D 498/06 |
| 9,957,268 | B2 | 5/2018 | Combs et al. |
| 9,957,628 | B2 | 5/2018 | Combs et al. |
| 10,189,832 | B2 | 1/2019 | Chen et al. |
| 10,227,359 | B2 | 3/2019 | Combs et al. |
| 2002/0004510 | A1 | 1/2002 | McCall et al. |
| 2007/0191447 | A1 | 8/2007 | Kodo et al. |
| 2007/0244096 | A1 | 10/2007 | Fox et al. |
| 2008/0306093 | A1 | 12/2008 | Servant et al. |
| 2009/0306122 | A1 | 12/2009 | Staehle et al. |
| 2013/0045229 | A1 | 2/2013 | Iadonato et al. |
| 2013/0261109 | A1 | 10/2013 | Miyoshi et al. |

(Continued)

FOREIGN PATENT DOCUMENTS

CA      2171579      9/1996
EP      0646583      4/1995

(Continued)

OTHER PUBLICATIONS

Australian Office Action in Australian Application No. 2015249810, dated Aug. 21, 2018, 4 pages.
Chilean Office Action in Chilean Application No. 2016-002681, dated Jul. 19, 2018, 9 pages.
Chung et al., "Fragment-based discovery of bromodomain inhibitors part 1: inhibitor binding modes and implications for lead discovery," J Med Chem,. 2011, 6 pages.
Doroshow et al., "BET inhibitors: a novel epigenetic approach," Ann Oncol., Aug. 1, 2017, 28(8):1776-1787.

(Continued)

Primary Examiner — Kahsay Habte
(74) Attorney, Agent, or Firm — Fish & Richardson P.C.

(57) ABSTRACT

The present invention relates to tricyclic heterocycles of Formula (I):

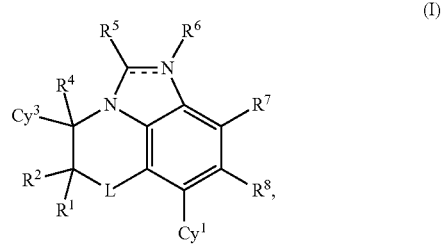

which are inhibitors of BET proteins such as BRD2, BRD3, BRD4, and BRD-t and are useful in the treatment of diseases such as cancer.

56 Claims, No Drawings

(56) References Cited

U.S. PATENT DOCUMENTS

| | | |
|---|---|---|
| 2013/0281396 A1 | 10/2013 | McLure et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2014/0135316 A1 | 5/2014 | Albrecht et al. |
| 2014/0275030 A1 | 9/2014 | Combs et al. |
| 2015/0011540 A1 | 1/2015 | Combs et al. |
| 2015/0148342 A1 | 5/2015 | Yue et al. |
| 2015/0148372 A1 | 5/2015 | Yue et al. |
| 2015/0148375 A1 | 5/2015 | Yue et al. |
| 2015/0175604 A1 | 6/2015 | Rodgers et al. |
| 2015/0307493 A1 | 10/2015 | Combs et al. |
| 2016/0046650 A1 | 2/2016 | Combs et al. |
| 2016/0075721 A1 | 3/2016 | Combs et al. |
| 2016/0159817 A1 | 6/2016 | Combs et al. |
| 2016/0168148 A1 | 6/2016 | Shepard |
| 2016/0213654 A1 | 7/2016 | Yue et al. |
| 2017/0014418 A1 | 1/2017 | Yue et al. |
| 2017/0121347 A1 | 5/2017 | Chen et al. |
| 2017/0158689 A1 | 6/2017 | Combs et al. |
| 2017/0158710 A1 | 6/2017 | Combs et al. |
| 2017/0210754 A1 | 7/2017 | Combs et al. |
| 2017/0127985 A1 | 8/2017 | Combs et al. |
| 2017/0362229 A1 | 12/2017 | Chen et al. |
| 2018/0222920 A1 | 8/2018 | Combs et al. |
| 2018/0273546 A1 | 9/2018 | Chen et al. |
| 2018/0312506 A1 | 11/2018 | Combs et al. |
| 2018/0346481 A1 | 12/2018 | Combs et al. |

FOREIGN PATENT DOCUMENTS

| | | |
|---|---|---|
| EP | 0 732 334 | 9/1996 |
| EP | 1462103 | 9/2004 |
| EP | 2 239 264 | 10/2010 |
| EP | 2415767 | 2/2012 |
| EP | 2568287 | 3/2013 |
| EP | 2573559 | 3/2013 |
| FR | 2747678 | 10/1997 |
| JP | H 03014566 | 1/1991 |
| JP | H 05-097849 | 4/1993 |
| JP | 08-269058 | 10/1996 |
| JP | 2004-502650 | 1/2004 |
| JP | 2006-509764 | 3/2006 |
| JP | 2008-532954 | 8/2008 |
| JP | 2009-503069 | 1/2009 |
| JP | 2012-529536 | 11/2012 |
| JP | 2012-530053 | 11/2012 |
| JP | 2013/010719 | 1/2013 |
| KR | 20150037711 | 4/2015 |
| WO | WO 2002/000196 | 1/2002 |
| WO | WO 2004/024736 | 3/2004 |
| WO | WO 2005/080334 | 1/2005 |
| WO | WO 2007/018998 | 2/2007 |
| WO | WO 2008/154221 | 12/2008 |
| WO | WO 2009/020559 | 2/2009 |
| WO | WO 2009/020677 | 2/2009 |
| WO | WO 2009/084693 | 7/2009 |
| WO | WO 2010/046190 | 4/2010 |
| WO | WO 2010/144679 | 12/2010 |
| WO | WO 2010/144680 | 12/2010 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/054851 | 5/2011 |
| WO | WO 2011/133722 | 10/2011 |
| WO | WO 2011/143651 | 11/2011 |
| WO | WO 2011/143657 | 11/2011 |
| WO | WO 2011/143660 | 11/2011 |
| WO | WO 2011/143669 | 11/2011 |
| WO | WO 2011/161031 | 12/2011 |
| WO | WO 2012/075383 | 6/2012 |
| WO | WO 2012/075456 | 6/2012 |
| WO | WO 2012/107465 | 8/2012 |
| WO | WO 2012/116170 | 8/2012 |
| WO | WO 2012/143413 | 10/2012 |
| WO | WO 2012/143415 | 10/2012 |
| WO | WO 2012/143416 | 10/2012 |
| WO | WO 2012/150234 | 11/2012 |
| WO | WO 2012/151512 | 11/2012 |
| WO | WO 2012/174487 | 12/2012 |
| WO | WO 2012/178208 | 12/2012 |
| WO | WO 2013/019710 | 2/2013 |
| WO | WO 2013/024104 | 2/2013 |
| WO | WO 2013/027168 | 2/2013 |
| WO | WO 2013/029548 | 3/2013 |
| WO | WO 2013/030150 | 3/2013 |
| WO | WO 2013/033268 | 3/2013 |
| WO | WO 2013/033269 | 3/2013 |
| WO | WO 2013/033270 | 3/2013 |
| WO | WO 2013/043553 | 3/2013 |
| WO | WO 2013/044511 | 4/2013 |
| WO | WO 2013/064900 | 5/2013 |
| WO | WO 2013/097052 | 7/2013 |
| WO | WO 2013/097601 | 7/2013 |
| WO | WO 2013/148197 | 10/2013 |
| WO | WO 2013/155695 | 10/2013 |
| WO | WO 2013/156869 | 10/2013 |
| WO | WO 2013/158952 | 10/2013 |
| WO | WO 2013/175281 | 11/2013 |
| WO | WO 2013/184876 | 12/2013 |
| WO | WO 2013/184878 | 12/2013 |
| WO | WO 2013/185284 | 12/2013 |
| WO | WO 2013/186612 | 12/2013 |
| WO | WO 2013/188381 | 12/2013 |
| WO | WO 2014/001356 | 1/2014 |
| WO | WO 2014/015175 | 1/2014 |
| WO | WO 2014/026997 | 2/2014 |
| WO | WO 2014/028547 | 2/2014 |
| WO | WO 2014/048945 | 4/2014 |
| WO | WO 2014/068402 | 5/2014 |
| WO | WO 2014/076146 | 5/2014 |
| WO | WO 2014/078257 | 5/2014 |
| WO | WO 2014/080290 | 5/2014 |
| WO | WO 2014/080291 | 5/2014 |
| WO | WO 2014/095774 | 6/2014 |
| WO | WO 2014/095775 | 6/2014 |
| WO | WO 2014/096965 | 6/2014 |
| WO | WO 2014/128655 | 8/2014 |
| WO | WO 2014/134232 | 9/2014 |
| WO | WO 2014/134267 | 9/2014 |
| WO | WO 2014/139324 | 9/2014 |
| WO | WO 2014/140076 | 9/2014 |
| WO | WO 2014/140077 | 9/2014 |
| WO | WO 2014/143768 | 9/2014 |
| WO | WO 2014/145051 | 9/2014 |
| WO | WO 2014/152029 | 9/2014 |
| WO | WO 2014/154760 | 10/2014 |
| WO | WO 2014/154762 | 10/2014 |
| WO | WO 2014/159392 | 10/2014 |
| WO | WO 2014/159837 | 10/2014 |
| WO | WO 2014/160873 | 10/2014 |
| WO | WO 2014/164596 | 10/2014 |
| WO | WO 2014/164771 | 10/2014 |
| WO | WO 2014/164780 | 10/2014 |
| WO | WO 2014/165127 | 10/2014 |
| WO | WO 2014/165143 | 10/2014 |
| WO | WO 2014/170350 | 10/2014 |
| WO | WO 2014/173241 | 10/2014 |
| WO | WO 2014/182929 | 11/2014 |
| WO | WO 2014/191894 | 12/2014 |
| WO | WO 2014/191896 | 12/2014 |
| WO | WO 2014/191906 | 12/2014 |
| WO | WO 2014/191911 | 12/2014 |
| WO | WO 2014/202578 | 12/2014 |
| WO | WO 2014/206150 | 12/2014 |
| WO | WO 2014/206345 | 12/2014 |
| WO | WO 2014/210425 | 12/2014 |
| WO | WO 2015/002754 | 1/2015 |
| WO | WO 2015/004533 | 1/2015 |
| WO | WO 2015/004534 | 1/2015 |

(56) References Cited

FOREIGN PATENT DOCUMENTS

| WO | WO 2015/006193 | 1/2015 |
|---|---|---|
| WO | WO 2015/007711 | 1/2015 |
| WO | WO 2015/013635 | 1/2015 |
| WO | WO 2015/081203 | 6/2015 |
| WO | WO 2015/095445 | 6/2015 |
| WO | WO 2015/162169 | 10/2015 |
| WO | WO 2015/163485 | 10/2015 |
| WO | WO 2015/164480 | 10/2015 |
| WO | WO 2015/168555 | 11/2015 |
| WO | WO 2015/168621 | 11/2015 |
| WO | WO 2015/169951 | 11/2015 |
| WO | WO 2015/169953 | 11/2015 |
| WO | WO 2015/184257 | 12/2015 |
| WO | WO 2016/044130 | 3/2016 |
| WO | WO 2017/127930 | 3/2016 |
| WO | WO 2016/077378 | 5/2016 |
| WO | WO 2016/194806 | 12/2016 |
| WO | WO 2017/133681 | 8/2017 |

OTHER PUBLICATIONS

International Preliminary Report on Patentability in International Application No. PCT/US2015/027047, dated Oct. 25, 2016, 10 pages.
International Preliminary Report on Patentability in International Application No. PCT/US2017/038121, dated Dec. 25, 2018, 10 pages.
Israeli Office Action in Israeli Application No. 248,415, dated Jan. 31, 2019, 7 pages.
Japanese Office Action in Japanese Application No. 2016-563976, dated Nov. 20, 2018, 9 pages.
Mexican Office Action in Mexican Application No. MX/a/2015/013149, dated Sep. 10, 2018, 5 pages.
Philippian Office Action in Philippian application No. 1/2016/502115, dated Sep. 6, 2018, 4 pages.
Taiwan Office Action in Taiwan application No. 103109291, dated Oct. 9 2018, 6 pages.
Ai et al., "Signal-induced Brd4 release from chromatin is essential for its role transition from chromatin targeting to transcriptional regulation," Nucleic Acids Res., 2011, 1-13.
Australian Office Action in Australian Application No. 2014228175, dated May 10, 2018, 4 pages.
Bamborough et al., "Fragment-Based Discovery of Bromodomain Inhibitors Part 2: Optimization of Phenylisoxazole Sulfonamides," J Med Chem., 2012, 55:587-596.
Bartholomeeusen et al., "BET bromodomain inhibition activates transcription via a transient release of P-TEFb from 7SK snRNP," JBC, 2012, 16 pages.
Bauer, "Pharmaceutical Solids—The Amorphous Phase," Journal of Validation Technology, Jan. 2009, 15(3): 63-68.
Belkina and Denis, "BET domain co-regulators in obesity inflammation and cancer," Nat Rev Cancer, Jul. 2012, 12:465-477.
Belkina et al., "BET Protein Function is Required for Inflammation. Brd2 Genetic Disruption and BET Inhibitor JQ1 Impair Mouse Macrophage Inflammatory Responses," J Immunol., 2013, 190:3670-3678.
Berge et al., "Pharmaceutical Salts," J Pharm. Sci., 1977, 66(1):1-19.
Blom et al., "Optimizing Preparative LC-MS Configurations and Methods for Parallel Synthesis Purification," J Comb Chem., 2003, 5(5):670-683.
Blom et al., "Preparative LCMS Purification: Improved Compound Specific Method Optimization," J Comb Chem., 2004, 6(6):874-883.
Blom, "Two-pump at-column-dilution configuration for preparative liquid chromatography-mass spectrometry," J Comb Chem., 2002, 4(4):295-301.
Byrn et al., "Pharmaceutical Solids: A Strategic Approach to Regulatory Considerations," Pharmaceutical Research, Jul. 1995, 12(7): 945-954.

Caira, "Crystalline Polymorphism of Organic Compounds," Topics in Current Chemistry, 1998, 198: 163-208.
Cheng et al., "Inhibition of BET Bromodomain Targets Genetically Diverse Glioblastoma," Clin Cancer Res 19:1748-1759, Feb. 2013.
Chiang, "Brd4 engagement from chromatin targeting to transcriptional regulation: selective contact with acetylated histone H3 and H4," Biology Reports, Dec. 2009, 1:98, 7 pages.
Chilean Office Action in Chilean Application No. 201502734, dated Jan. 18, 2017, 8 pages (English Translation).
Chinese Office Action in Chinese Application No. 201480025137, dated May 17, 2016, 14 pages (English Translation).
Chinese Office Action in Chinese Application No. 201480025137, dated Feb. 16, 2017, 21 pages (w/ English Translation).
Chinese Office Action in Chinese Application No. 201480025137, dated Oct. 13, 2017, 7 pages (English Translation).
Chung et al., "Discovery and Characterization of Small Molecule Inhibitors of the BET Family Bromodomains," J Med Chem., 2011, 54:3827-3838.
Chung et al., "Fragment-Based Discovery of Bromodomain Inhibitors Part 1: Inhibitor Binding Modes and Implications for Lead Discovery," J Med Chem., 2011, 11 pages.
Chung et al., "Fragment-based discovery of bromodomain inhibitors part 1: inhibitor binding modes and implications for lead discovery," Supporting Information, 2011, 6 pages.
Colombian Office Action in Colombian Application No. NC2016/0003978, dated Jul. 16, 2018, 7 pages.
Colombian Office Action in Colombian Application No. 15-227.987, dated May 23, 2017, 5 pages.
Dawson et al., "Inhibition of BET recruitment to chromatin as an effective treatment for MLL-fusion leukaemia," Nature, 2011, 5 pages.
Dawson, "Supplementary Information: Inhibition of BET recruitment to chromatin as an effective treatment for MLL-fusion leukaemia," Nature, 2011, 50 pages.
Delmore et al., "BET bromodomain inhibition as a therapeutic strategy to target c-Myc," Cell, 2011, 146(6):904-917, Supplemental Information: S1-S11.
Delmore et al., "BET bromodomain inhibition as a therapeutic strategy to target c-Myc," Cell, Sep. 2011, 146(6):904-917.
Devaiah et al., "BRD4 is an atypical kinase that phosphorylates serine2 of the RNA polymerase II carboxy-terminal domain," Proc. Nat. Acad. Sci. USA., 2012, 109(18):6927-6932.
Draker et al., "A Combination of H2A.Z and H4 Acetylation Recruits Brd2 to Chromatin during Transcriptional Activation," PLoS Genet., Nov. 2012, 8(11):e1003047, 17 pages.
Dorwald, F. Zaragoza. Side Reactions in Organic Synthesis: A Guide to Successful Synthesis Design, Weinheim: WILEY-VCH Verlag GmbH & Co. KGaA, 2005, Preface.
Eurasian Office Action in Eurasian Application No. 201692134, dated Jun. 6, 2017, 4 pages (English Translation).
Filippakopoulos and Knapp, "Targeting bromodomains: epigenetic readers of lysine acetylation," Nature Rev Drug Disc., May 2014, 13:337-356.
Filippakopoulos et al., "Benzodiazepines and benzotriazepines as protein interaction inhibitors targeting bromodomains of the BET family," Bioorg Med Chem., 2011, 9 pages.
Filippakopoulos et al., "Histone Recognition and Large-Scale Structural Analysis of the Human Bromodomain Family," Cell, Mar. 2012, 149:214-231.
Filippakopoulos et al., "Selective inhibition of BET bromodomains," Nature, 2010, 468:1067-1073.
Filippakopoulos et al., "Supplemental Information: Selective inhibition of BET bromodomains," Nature, 2010, 468:1067-1073.
Floyd et al., "Supplemental Information: The bromodomain protein Brd4 insulates chromatin from DNA damage signalling," Nature, 2013, 14 pages.
Floyd et al., "The bromodomain protein Brd4 insulates chromatin from DNA damage signalling," Nature, 2013, 498:246-250.
French et al., "BRD4-NUT fusion oncogene: a novel mechanism in aggressive carcinoma," Cancer Res., 2003, 63(2):304-307.
French et al., "BRD-NUT oncoproteins: a family of closely related nuclear proteins that block epithelial differentiation and maintain the growth of carcinoma cells," Oncogene, 2008, 27:2237-2242.

(56) References Cited

OTHER PUBLICATIONS

French et al., "Midline carcinoma of children and young adults with NUT rearrangement," J Clin. Oneal., 2004, 22(20):4135-4139.
French, "Demystified molecular pathology of NUT midline carcinomas," J Clin Pathol., 2010, 63:492-496.
French, "NUT midline carcinoma," Cancer Genet Cytogenetics, 2010, 203:16-20.
Frizzo et al., "Structural and thermodynamic properties of new pyrazolo [3,4-d] pyridazinones," Thermochimica Acta., Oct. 2013, 574:63-72.
Gallenkamp et al., "Bromodomains and their Pharmacological Inhibitors," Chem Med Chem., Mar. 2014, 9(3):438-464.
Garnier et al., "BET bromodoma in inhibitors: a patent review," Exp Opin Therapeutic Patents, Feb. 2014, 24(2):185-199.
Greenwald et al., "Eμ-BRD2 transgenic mice develop B-cell lymphoma and leukemia," Blood 103(4):1475-1484, Feb. 2004.
Hackam et al., JAMA, 296(14), 2006, 1731-1732.
Hewings et al., "3,5-Dimethylisoxazoles Act as Acetyl-lysine-mimetic Bromodomain Ligands," J Med Chem., 2011, 54:6761-6770.
Hewings et al., "Progress in the Development and Applciation of Small Molecule Inhibitors of Bromodomain-Acetyl-lysine Interactions," J Med Chem., Nov. 2012, 104 pages (Author Manuscript).
Hewings et al., "Progress in the Development and Applciation of Small Molecule Inhibitors of Bromodomain-Acetyl-lysine Interactions," J Med Chem., Nov. 2012, 55(22):9393-9413.
Houzelstein et al., "Growth and Early Postimplantation Defects in Mice Deficient for the Bromodomain-Containing Protein Brd4," Mole Cell Biol., Jun. 2002, 22(11):3794-3802.
Huang et al., "Brd4 coactivates transcriptional activation of NF-κB via specific binding to acetylated RelA," Mol. Cell Biol., 2009, 29(5):1375-1387.
Indonesian Office Action P-00201506648, dated May 7, 2018, 5 pages (english translation).
International Preliminary Report on Patentability in International Application No. PCT/US2014/045543, dated Jan. 21, 2016, 7 pages.
International Search Report and Written Opinion in International Application No. PCT/US2014/027872, dated Jun. 30, 2014, 12 pages.
International Search Report and Written Opinion in International Application No. PCT/US2014/045543, dated Sep. 10, 2014, 11 pages.
International Search Report and Written Opinion in International Application No. PCT/US2014/067598, dated Feb. 13, 2015, 9 pages.
International Search Report and Written Opinion in International Application No. PCT/US2014/067629, dated Feb. 16, 2015, 11 pages.
International Search Report and Written Opinion in International Application No. PCT/US2014/067691, dated Feb. 2, 2015, 10 pages.
International Search Report and Written Opinion in International Application No. PCT/US2014/071102, dated Feb. 13, 2015, 9 pages.
International Preliminary Report on Patentability in International Application No. PCT/US2014/027872, dated Sep. 24, 2015, 8 pages.
International Search Report and Written Opinion in International Application No. PCT/US2015/027047, dated Jul. 10, 2015, 14 pages.
International Search Report and Written Opinion in International Application No. PCT/US2015/049909, dated Dec. 7, 2015, 13 pages.
International Preliminary Report on Patentability in International Application No. PCT/US2014/067691, dated May 31, 2016, 7 pages.
International Preliminary Report on Patentability in International Application No. PCT/US2014/067629, dated May 31, 2016, 7 pages.
International Preliminary Report on Patentability in International Application No. PCT/US2014/067598, dated May 31, 2016, 7 pages.
International Preliminary Report on Patentability in International Application No. PCT/US2014/071102, dated Jun. 21, 2016, 7 pages.
International Search Report and Written Opinion in International Application No. PCT/US2016/059360, dated Feb. 13, 2017, 20 pages.
International Search Report and Written Opinion in International Application No. PCT/US2017/038121, dated Oct. 20, 2017, 20 pages.
Jang et al., "The bromodomain protein Brd4 is a positive regulatory component of P-TEFb and stimulates RNA polymerase II-dependent transcription," Mol. Cell, Aug. 2005, 19(4):523-534.
Japanese Office Action in Japanese Application No. 2017-134538, dated Jun. 12, 2018, 7 pages (English Translation)
Japanese Office Action in Japanese Application No. 2016-502650, dated Jan. 10, 2017, 3 pages (English translation only).
Jin et al., "c-Myb binds MLL through menin in human leukemia cells and is an important driver of MLL-associated leukemogenesis," J Clinc Invest., 2010, 120(2):593-606.
Jordan, V.C. Nature Reviews: Drug Discovery, 2, 2003, 205.
Jung et al., "Affinity Map of BRD4 Interactions with the Histone H4 Tail and the Small Molecule Inhibitor JQ1," J Biol Chem., 2014, 28 pages.
Lamonica et al., "Bromodomain protein Brd3 associates with acetylated GATA1 to promote its chromatin occupancy at erythroid target genes," Proc. Nat. Acad. Sci., USA, 2011, 108(22):E159-168.
Leroy et al., "The double bromodomain proteins Brd2 and Brd3 couple histone acetylation to transcription," Mol. Cell, Apr. 2008, 30(1):51-60.
Lockwood et al., "Sensitivity of human lung adenocarcinoma cell lines to targeted inhibition of BET epigenetic signaling proteins," PNAS Early Edition, 2012, 14 pages.
Martin et al., "Cyclin-Dependent Kinase Inhibitor Dinaciclib Interacts with the Acetyl-Lysine Recognition Site of Bromodomains," ACS Chem Biol., 2013, 8:2360-2365.
Maruyama et al., "A Mammalian Bromodomain Protein, Brd4, Interacts with Replication Factor C and Inhibits Progression to S Phase," Mol Cell Biol., 2002, 22(18):6509-6520.
Matzuk et al., "Small-Molecule Inhibition of BRDT for Male Contraception," Cell, Aug. 2012, 150:673-684.
McLure et al., "RVX-208, an Inducer of ApoA-I in Humans, Is a BET Bromodomain Antagonist," PLOS ONE, Dec. 2013, 8(12):e83190, 12 pages.
Mertz et al., "Targeting MYC dependence in cancer by inhibiting BET bromodomains," PNAS, 2011, 108(40):16669-16674.
Mirguet et al., "From ApoA1 upregulation to BET family bromodomain inhibition: Discovery of I-BET151," Bioorg Med Chem Lett., 2012, 22:2963-2967.
Mochizuki et al., "The bromodomain protein Brd4 stimulates G1 gene transcription and promotes progression to S phase," J Biol. Chem. 2008, 283(14):9040-9048.
Moriniere et al., "Cooperative binding of two acetylation marks on a histone tail by a single bromodomain," Nature, 2009, 461:664-669.
Muller et al., "Bromodomains as therapeutic targets," Expert Reviews, 2011, 13:e29, 21 pages.
Nicodeme et al., "Supplementary Information: Suppression of inflammation by a synthetic histone mimic," Nature, 2010, 40 pages.
Nicodeme et al., "Suppression of inflammation by a synthetic histone mimic," Nature, 2010, 468:1119-1123.
Nishiyama et al., "Brd4 Is Required for Recovery from Antimicrotubule Drug-induced Mitotic Arrest: Preservation of Acetylated Chromatin," Mol Biol Cell, Feb. 2006, 17:814-823.
Ott et al., "BET bromodomain inhibition targets both c-MYC and IL7R in high-risk acute lymphoblastic leukemia," Blood, published online 2012, 29 pages.
Peturssion et al., "Protecting Groups in Carbohydrate Chemistry," J Chem. Educ., 1997, 74(11):1297-1303.

(56) References Cited

OTHER PUBLICATIONS

Picaud et al., "RVX-208, an inhibitor of BET transcriptional regulators with selectivity for the second bromodomain," PNAS Early Edition, 2013, 6 pages.
Picaud et al., "Supplemental Information: RVX-208, an inhibitor of BET transcriptional regulators with selectivity for the second bromodomain," PNAS Early Edition, 2013, 9 pages.
Prinjhas et al., "Place your BETs: the therapeutic potential of bromodomains," Trends Pharmacol Sci., 2012, 33(3):146-153.
Puissant et al., "Targeting MYCN in Neuroblastoma by BET Bromodomain Inhibition," Cancer Discovery, 16 pages, Mar. 2013.
Rahman et al., "The Brd4 Extraterminal Domain Confers Transcription Activation Independent of pTEFb by Recruiting Multiple Proteins, Including NSD3," Mol Cell Biol., Jul. 2011, 31(13):2641-2652.
Ravin, "Preformulation," Remington's Pharmaceutical Sciences, 17th Ed., (Mack Publishing Company, Easton, 1985), pp. 1409-1423.
Sanchez and Zhou, "The role of human bromodomains in chromatin biology and gene transcription," Curr Opin Drug Discov Devel., Sep. 2009, 12(5):659-665 (Author Manuscript).
Shimamura et al., "Efficacy of BET Bromodomain Inhibition in Kras-Mutant Non-Small Cell Lung Cancer," Clin Cancer Res, 10 pages, 2013.
Schroder et al., "Two-pronged Binding with Bromodomain-containing Protein 4 Liberates Positive Transcription Elongation Factor b from Inactive Ribonucleoprotein Complexes," J Biol Chem., Jan. 6, 2012, 287(2):1000-1009.
Schwartz et al., "Differentiation of NUT Midline Carcinoma by Epigenomic Reprogramming," Cancer Res., 2011, 71:2686-2696.
Seal et al., "Identification of a novel series of BET family bromodomain inhibitors: Binding mode and profile of I-BET151 (GSK1210151A)," Bioorg Med Chem., 2012, 22:2968-2972.
Segura et al., "BRD4 Sustains Melanoma Proliferation and Represents a New Target for Epigenetic Therapy," Cancer Res 73:6264-6276, Aug. 2013.
Smith et al., "Genome-wide siRNA screen identifies SMCX, EP400, and Brd4 as E2-dependent regulators of human papillomavirus oncogene expression," PNAS, Feb. 23, 2010, 107(8):3752-3757.
Stenman et al., "New tricks from an old oncogene: Gene fusion and copy number alterations of MYB in human cancer," Cell Cyle, Aug. 2010, 9(15):2986-2955.
Ukrainian Office Action in Ukrainian Application No. A201510087, dated Aug. 9, 2018, 69 pages.
Vidler et al., "Druggability Analysis and Structural Classification of Bromodomain Acetyl-lysine Binding Sites," J Med Chem., 2012, 14 pages.
Wang et al., "Brd2 disruption in mice causes severe obesity without Type 2 diabetes," Biochem. J., 2010, 425(1):71-83.
Wang et al., "The Bromodomain Protein Brd4 Associated with Acetylated Chromatin is Important for Maintenance of Higher-Order Chromatin Structure," JBC, 2012, 22 pages.

Weidner-Glunde et al., "What do viruses BET on?" Frontiers Biosci., Jan. 2010, 15:537-549.
Wu and Chiang et al., "The Double Bromodomaincontaining Chromatin Adaptor Brd4 and Transcriptional Regulation," J Biol Chem., May 2007, 282(18):13141-13145.
Wu et al., "Brd4 links chromatin targeting to HPV transcriptional silencing," Genes Dev., 2006, 20:2383-2396.
Wyce et al., "Inhibition of BET bromodomain proteins as a therapeutic appraoch in prostate cancer," Oncotarget, 13 pages, Nov. 2013.
Yan et al., "Perturbation of BRD4 Protein Function by BRD4-NUT Protein Abrogates Cellular Differentiation in NUT Midline Carcinoma," J Biol Chem., Aug. 2011, 286(31):27663-27675.
Yan et al., "Supplemental Data: Perturbation of BRD4 Protein Function by BRD4-NUT Protein Abrogates Cellular Differentiation in NUT Midline Carcinoma," J Biol Chem., Aug. 2011, 12 pages.
Yang et al., "Brd4 Recruits P-TEFb to Chromosomes at Late Mitosis to Promote G1 Gene Expression and Cell Cycle Progression," Mol Cell Biol., Feb. 2008, 28(3):967-976.
You et al., "Interaction of the bovine papillomavirus E2 protein with Brd4 tethers the viral DNA to host mitotic chromosomes," Cell, 2004, 117(3):349-60.
You et al., "Regulation of Aurora B Expression by the Bromodomain Protein Brd4," Mol Cell Biol., Sep. 2009, 29(18):5094-5103.
Zhang et al., "Bromodomain-Containing-Protein 4 (BRD4) Regulates RNA Polymerase II Serine 2 Phosphorylation in Human CD4+ T Cells," JBC, 2012, 30 pages.
Zhu et al., "Reactivation of latent HIV-1 by inhibition of BRD4," Cell Reports, 2012, 2(4):807-816.
Zuber et al., "An integrated approach to dissecting oncogene addiction implicates a Myb-coordinated self-renewal program as essential for leukemia maintenance," Genes Dev., 2011, 25:1628-1640.
Zuber et al., "RNAi screen identifies Brd4 as a therapeutic target in acute myeloid leukaemia," Nature, 2011, 478(7370):524-528.
Zuber et al., "Supplemental Information: RNAi screen identifies Brd4 as a therapeutic target in acute myeloid leukaemia," Nature, 2011, 33 pages.
Japanese Office Action in Japanese Application No. 2016-525398, dated May 15, 2018, 5 pages (English Translation).
Chilean Office Action in Chilean Application No. 2734-2015, dated Apr. 1, 2019, 4 pages.
Eurasian Office Action in Eurasian Application No. 201692134, dated Feb. 21, 2019, 4 pages.
Eurasian Office Action in Eurasian Application No. 201591785, dated Apr. 4, 2019, 4 pages.
Mexican Office Action in Mexican Application No. MX/a/2015/013149, dated Mar. 15, 2019, 2 pages.
Taiwan Office Action in Taiwan application No. 104112916, dated Feb. 23, 2019, 7 pages.
Vietnamese Office Action in Vietnamese Office Application No. 1-2015-03963, dated Apr. 22, 2019, 4 pages.

\* cited by examiner

TRICYCLIC HETEROCYCLES AS BET PROTEIN INHIBITORS

TECHNICAL FIELD

The present disclosure relates to tricyclic heterocycles which are inhibitors of BET proteins such as BRD2, BRD3, BRD4, and BRD-t and are useful in the treatment of diseases such as cancer.

BACKGROUND

The genomes of eukaryotic organisms are highly organized within the nucleus of the cell. DNA is packaged into chromatin by wrapping around a core of histone proteins to form a nucleosome. These nucleosomes are further compacted by aggregation and folding to form a highly condensed chromatin structure. A range of different states of condensation are possible, and the tightness of this structure varies during the cell cycle, being most compact during the process of cell division. Chromatin structure plays a critical role in regulating gene transcription by regulating protein access to the DNA. The chromatin structure is controlled by a series of post translational modifications to histone proteins, mainly within the tails of histones H3 and H4 that extend beyond the core nucleosome structure. These reversible modifications include acetylation, methylation, phosphorylation, ubiquitination and SUMOylation. These epigenetic marks are written and erased by specific enzymes that modify specific residues within the histone tail, thereby forming an epigenetic code. Other nuclear proteins bind to these marks and effect outputs specified by this information through the regulation of chromatin structure and gene transcription. Increasing evidence links genetic changes to genes encoding epigenetic modifiers and regulators leading to aberrant histone marks in diseases such as neurodegenerative disorders, metabolic diseases, inflammation and cancer.

Histone acetylation is typically associated with the activation of gene transcription, as the modification weakens the interaction between the DNA and the histone proteins, permitting greater access to DNA by the transcriptional machinery. Specific proteins bind to acetylated lysine residues within histones to "read" the epigenetic code. A highly conserved protein module called the bromodomain binds to acetylated lysine residues on histone and other proteins. There are more than 60 bromodomain-containing proteins in the human genome.

The BET (Bromodomain and Extra-Terminal) family of bromodomain containing proteins comprises 4 proteins (BRD2, BRD3, BRD4 and BRD-t) that share a conserved structural organization containing tandem N-terminal bromodomains capable of binding to acetylated lysine residues of histones and other proteins. BRD2, BRD3 and BRD4 are ubiquitously expressed while BRD-t is restricted to germ cells. BRD proteins play essential, but non-overlapping roles in regulating gene transcription and controlling cell growth. BET proteins are associated with large protein complexes including Mediator, PAFc and super elongation complex that regulate many aspects of gene transcription. BRD2 and BRD4 proteins have been shown to remain in complex with chromosomes during mitosis and are required to promote transcription of critical genes including cyclin D and c-Myc that initiate the cell cycle. Mochizuki et al., *J. Biol. Chem.* 2008, 283, 9040-9048. BRD4 is essential for recruiting the protein translational elongation factor B complex to the promoters of inducible genes resulting in the phosphorylation of RNA polymerase II and stimulating productive gene transcription and elongation. Jang et al., *Mol. Cell,* 2005, 19, 523-534. In some instances, a kinase activity of BRD4 may directly phosphorylate and activate RNA polymerase II. Devaiah et al., *Proc. Nat. Acad. Sci., USA.* 2012, 109, 6927-6932. Cells lacking BRD4 show impaired progression through cell cycle. BRD2 and BRD3 are reported to associate with histones along actively transcribed genes and may be involved in facilitating transcriptional elongation. Leroy et al., *Mol. Cell,* 2008, 30, 51-60. In addition to acetylated histones, BET proteins have been shown to bind selectively to acetylated transcription factors including the RelA subunit of NF-kB and GATA1 thereby directly regulating the transcriptional activity of these proteins to control expression of genes involved in inflammation and hematopoietic differentiation. Huang et al., *Mol. Cell Biol.,* 2009, 29, 1375-1387; Lamonica et al., *Proc. Nat. Acad. Sci., USA,* 2011, 108, E159-168.

A recurrent translocation involving NUT (nuclear protein in testes) with BRD3 or BRD4 to form a novel fusion oncogene, BRD-NUT, is found in a highly malignant form of epithelial neoplasia. French et al., *Cancer Res.,* 2003, 63, 304-307; French et al., *J. Clin. Oncol.,* 2004, 22, 4135-4139. Selective ablation of this oncogene restores normal cellular differentiation and reverses the tumorigenic phenotype. Filippakopoulos et al., *Nature,* 2010, 468, 1068-1073. Genetic knockdown of BRD2, BRD3 and BRD4 has been shown to impair the growth and viability of a wide range of hematological and solid tumor cells. Zuber et al., *Nature,* 2011, 478, 524-528; Delmore et al., *Cell,* 2011, 146, 904-917. Aside from a role in cancer, BET proteins regulate inflammatory responses to bacterial challenge, and a BRD2 hypomorph mouse model showed dramatically lower levels of inflammatory cytokines and protection from obesity induced diabetes. Wang et al., *Biochem. J.,* 2009, 425, 71-83; Belkina et al., *J. Immunol.* 102838, online publication before print, Feb. 18, 2013. In addition, some viruses make use of these BET proteins to tether their genomes to the host cell chromatin, as part of the process of viral replication or use BET proteins to facilitate viral gene transcription and repression. You et al., *Cell,* 2004, 117, 349-60; Zhu et al., *Cell Reports,* 2012, 2, 807-816.

Accordingly, there is a need for compounds that modulate the activity of the BET family of proteins, including BRD2, BRD3, and BRD4, that can be used to treat BET protein-associated diseases such as cancer. The compounds of the invention help meet this need.

SUMMARY

The present disclosure provides, inter alia, a compound of Formula (I):

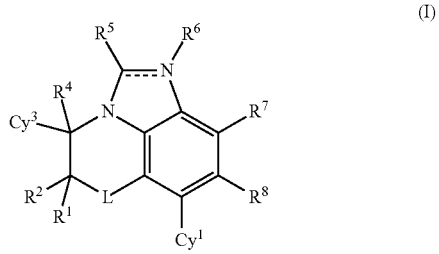

or a pharmaceutically acceptable salt thereof; wherein the variables are as defined below.

The present disclosure also provides a composition comprising a compound of Formula (I), or a pharmaceutically acceptable salt thereof, and at least one pharmaceutically acceptable carrier.

The present disclosure also provides methods of treating cancer and other diseases comprising administering to a patient a therapeutically effective amount of a compound of Formula (I), or a pharmaceutically acceptable salt thereof.

The details of one or more embodiments are set forth in the description below. Other features, objects, and advantages will be apparent from the description and from the claims.

DETAILED DESCRIPTION

For the terms "e.g." and "such as," and grammatical equivalents thereof, the phrase "and without limitation" is understood to follow unless explicitly stated otherwise.

The singular forms "a," "an," and "the" include plural referents unless the context clearly dictates otherwise.

The term "about" means "approximately" (e.g., plus or minus approximately 10% of the indicated value).

I. Compounds

The present disclosure relates, inter alia, to a compound of a BET protein-inhibiting compound of Formula (I):

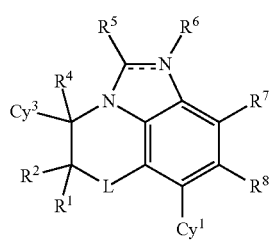

(I)

or a pharmaceutically acceptable salt thereof, wherein:
═══ represents a single bond or a double bond;
L is $CR^9R^{9a}$, O, S, SO, or $SO_2$;
$Cy^1$ is selected from phenyl or a 5-6 membered heteroaryl group comprising carbon and 1, 2, 3 or 4 heteroatoms selected from N, O and S, wherein said phenyl or 5-6 membered heteroaryl of $Cy^1$ is optionally substituted with 1, 2, 3, or 4 groups independently selected from $R^{11}$;
$R^1$ and $R^2$ are independently selected from H, halo, CN, OH, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$, wherein said $C_{1-6}$ alkyl, $C_{2-6}$ alkenyl, and $C_{2-6}$ alkynyl of $R^1$ and $R^2$ are optionally substituted with 1, 2, or 3 groups independently selected from halo, CN, OH, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$ $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

provided neither $R^1$ nor $R^2$ are Cl, Br, I, CN, or OH when L is O or S;
alternatively, $R^1$ and $R^2$ together with the carbon atom to which they are attached are combined to form a $C_{3-7}$ cycloalkyl group, wherein said cycloalkyl group is optionally substituted with 1, 2, 3, or 4 groups independently selected from $R^{20}$;

$Cy^3$ is selected from phenyl, $C_{3-7}$ cycloalkyl, a 5-10 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said phenyl, $C_{3-7}$ cycloalkyl, 5-10 membered heteroaryl, and 4-10 membered heterocycloalkyl of $Cy^3$ is optionally substituted with 1, 2, 3, or 4 groups independently selected from $R^{13}$, wherein a ring-forming nitrogen atom of said 5-10 membered heteroaryl group or a ring-forming nitrogen atom of said 4-10 membered heterocycloalkyl group is optionally oxidized;

$R^4$ is H, $C(=O)NR^{14a}R^{14b}$, $C(=O)R^{14a}$, $C(=O)OR^{14a}$, or $C_{1-6}$ alkyl optionally substituted by 1, 2, or 3 substituents independently selected from halo, $NR^{14a}R^{14b}$, $OR^{14a}$, $SR^{14a}$, CN, $C(=O)R^{14a}$, $C(=O)NR^{14a}R^{14b}$, $C(=O)OR^{14a}$, $OC(=O)R^{14b}$, $OC(=O)NR^{14a}R^{14b}$, $NR^{14a}C(=O)R^{14b}$, $NR^{14a}C(=O)NR^{14a}R^{14b}$, $NR^{14a}C(=O)OR^{14b}$, $S(=O)R^{14a}$, $S(=O)NR^{14a}R^{14b}$, $S(=O)_2R^{14a}$, $NR^{14a}S(=O)_2R^{14b}$, and $S(=O)_2NR^{14a}R^{14b}$;

$R^5$ is selected from ═O and ═S when C═N is a single bond,
alternatively, when C═N is a double bond then $R^5$ is selected from H, $C_{1-6}$ alkyl, $C_{2-6}$ alkenyl, $C_{2-6}$ alkynyl, $C_{1-6}$ haloalkyl, $NR^{15a}R^{15b}$, $—C(=O)NR^{15a}R^{15b}$, $—C(=O)OR^{15a}$, phenyl, $C_{3-7}$ cycloalkyl, 5-6 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said alkyl, phenyl, $C_{3-7}$ cycloalkyl, 5-6 membered heteroaryl, and 4-10 membered heterocycloalkyl of $R^5$ is optionally substituted by 1, 2, 3, or 4 groups independently selected from $R^{15}$;

$R^6$ is selected from H, $C_{1-6}$ alkyl, $C_{2-6}$ alkenyl, $C_{2-6}$ alkynyl, $C_{1-6}$ alkoxy, and $C_{1-6}$ haloalkyl, wherein said alkyl, alkenyl, and alkynyl of $R^6$ are each optionally substituted by 1, 2, 3, or 4 groups independently selected $R^{16}$;

alternatively, $R^6$ is selected from $C_{6-10}$ aryl, $C_{3-7}$ cycloalkyl, 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^6$ are each optionally substituted by 1, 2, 3, or 4 groups independently selected $R^{20}$;

$R^7$ is selected from H, halo, CN, $OR^a$, $NR^cR^d$, $SR^b$, $C(=O)NR^cR^d$, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, alkenyl, alkynyl, phenyl, cycloalkyl, 5-6 membered heteroaryl group, and a 4-7 membered heterocycloalkyl group of $R^7$ are optionally substituted with 1, 2, or 3 groups independently selected from $R^{17}$;

$R^8$ is selected from H, $C_{1-3}$ alkyl, $C_{2-3}$ alkenyl, $C_{2-3}$ alkynyl, $C_{1-3}$ haloalkyl, halo, CN, $OR^a$, $NR^cR^d$, $SR^b$, and $C(=O)NR^cR^d$, wherein said $C_{1-3}$ alkyl of $R^8$ is optionally substituted with 1, 2, or 3 groups independently selected from $R^{18}$;

$R^9$ and $R^{9a}$ are independently selected from H, $C_{1-3}$ alkyl, $C_{1-3}$ haloalkyl, halo, CN, $OR^a$, $NR^cR^d$, $SR^b$, and $C(=O)NR^cR^d$;

$R^{11}$ is independently at each occurrence selected from H, $C_{1-3}$ alkyl, $C_{1-3}$ haloalkyl, halo, CN, $OR^a$, $NR^cR^d$, $SR^b$, and $C(=O)NR^cR^d$, wherein said $C_{1-3}$ alkyl is optionally substituted by OH;

$R^{13}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$, wherein said $C_{1-6}$ alkyl, $C_{2-6}$ alkenyl, and $C_{2-6}$ alkynyl of $R^{13}$ is optionally substituted with 1, 2, or 3 groups independently selected from halo, CN, OH, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$;

$R^{15}$ is independently at each occurrence selected from H, $C_{1-6}$ alkyl, $C_{3-7}$ cycloalkyl, 4-7 membered heterocycloalkyl, phenyl, 5-6 membered heteroaryl, halo, CN, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$ $NR^{c5}C(=O)NR^{c5}R^{d5}$, $NR^{c5}C(=O)OR^{a5}$, $S(=O)R^{b5}$, $S(=O)NR^{c5}R^{d5}$, $S(=O)_2R^{b5}$, $NR^{c5}S(=O)_2R^{b5}$, and $S(=O)_2NR^{c5}R^{d5}$, wherein said $C_{1-6}$ alkyl, $C_{3-7}$ cycloalkyl, 4-7 membered heterocycloalkyl, phenyl, and 5-6 membered heteroaryl are each optionally substituted by 1, 2, or 3 substituents independently selected from halo, CN, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $S(=O)R^{b5}$, $S(=O)NR^{c5}R^{d5}$, $S(=O)_2R^{b5}$, $NR^{c5}S(=O)_2R^{b5}$, $S(=O)_2NR^{c5}R^{d5}$, 5-6 membered heteroaryl, 4-7 membered heterocycloalkyl, phenyl, and $C_{3-7}$ cycloalkyl;

$R^{14a}$ and $R^{14b}$ are independently at each occurrence selected from H and $C_{1-6}$ alkyl, wherein said $C_{1-6}$ alkyl of $R^{14a}$ and $R^{14b}$ is optionally substituted with 1, 2, or 3 substituents selected from $R^{20}$;

or $R^{14a}$ and $R^{14b}$ together with the N atom to which they are attached form a 4-7 membered heterocycloalkyl ring optionally substituted with 1, 2, or 3 substituents selected from $R^{20}$;

$R^{15a}$ and $R^{15b}$ are independently at each occurrence selected from H and $C_{1-6}$ alkyl, wherein said $C_{1-6}$ alkyl of $R^{15a}$ and $R^{15b}$ is optionally substituted with 1, 2, or 3 substituents selected from $R^{20}$;

or $R^{15a}$ and $R^{15b}$ together with the N atom to which they are attached form a 4-7 membered heterocycloalkyl ring optionally substituted with 1, 2, or 3 substituents selected from $R^{20}$;

$R^{16}$ is independently at each occurrence selected from halo, CN, OH, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)NR^{c6}R^{d6}$, $NR^{c6}C(=O)OR^{a6}$, $S(=O)R^{b6}$, $S(=O)NR^{c6}R^{d6}$, $S(=O)_2R^{b6}$, $NR^{c6}S(=O)_2R^{b6}$ and $S(=O)_2NR^{c6}R^{d6}$, $C_{6-10}$ aryl, $C_{3-7}$ cycloalkyl, 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^{16}$ are each optionally substituted by 1, 2, 3, or 4 groups independently selected $R^{20}$;

$R^{17}$ and $R^{18}$ are independently at each occurrence selected from halo, $C_{1-4}$ alkyl, CN, $OR^a$, $NR^cR^d$, $SR^b$, $C(=O)NR^cR^d$, $C(=O)OR^a$, and $NR^cC(=O)R^a$;

$R^a$, $R^c$, and $R^d$ are independently at each occurrence selected from H, $C_{1-6}$ alkyl, $C(O)R^e$, $S(=O)_2R^f$, $C(=O)NR^gR^h$, and phenyl optionally substituted by $C_{1-4}$ alkoxy;

$R^b$ is at each occurrence $C_{1-6}$ alkyl;

$R^e$ is at each occurrence $C_{1-4}$ alkyl optionally substituted by a group selected from phenyl, $C_{1-4}$ alkoxy, amino, $C_{1-4}$ alkylamino, and $C_{2-8}$ dialkylamino;

$R^f$ is $C_{1-4}$ alkyl;

$R^g$ and $R^h$ are independently at each occurrence selected from H and $C_{1-4}$ alkyl;

$R^{a1}$, $R^{b1}$, $R^{c1}$ and $R^{d1}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a1}$, $R^{b1}$, $R^{c1}$ and $R^{d1}$ are each optionally substituted with 1, 2, or 3 substituents independently selected from $R^{20}$;

$R^{a3}$, $R^{b3}$, $R^{c3}$ and $R^{d3}$ are independently at each occurrence selected from H, $C_{1-6}$ alkyl, $C_{2-6}$ alkenyl, $C_{2-6}$ alkynyl, $C_{3-6}$ cycloalkyl, and $C_{1-6}$ haloalkyl, wherein said $C_{1-6}$ alkyl, $C_{2-6}$ alkenyl, and $C_{2-6}$ alkynyl forming $R^{a3}$, $R^{b3}$, $R^{c3}$ and $R^{d3}$ are each optionally substituted with 1, 2, or 3 substituents independently selected from halo, CN, OH, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$ $NR^{c4}C(=O)R^{b4}$, $NR^{c4}C(=O)NR^{c4}R^{d4}$ $NR^{c4}C(=O)OR^{a4}$, $S(=O)R^{b4}$, $S(=O)NR^{c4}R^{d4}$, $S(=O)_2R^{b4}$, $NR^{c4}S(=O)_2R^{b4}$ and $S(=O)_2NR^{c4}R^{d4}$;

$R^{a4}$, $R^{b4}$, $R^{c4}$ and $R^{d4}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a4}$, $R^{b4}$, $R^{c4}$ and $R^{d4}$ are each optionally substituted with 1, 2, or 3 substituents independently selected from $R^{20}$;

$R^{a5}$, $R^{b5}$, $R^{c5}$ and $R^{d5}$ are independently at each occurrence selected from H, $C_{1-6}$ alkyl, $C_{2-6}$ alkenyl, $C_{2-6}$ alkynyl, $C_{3-6}$ cycloalkyl, 5-6 membered heterocycloalkyl, and $C_{1-6}$ haloalkyl wherein said $C_{1-6}$ alkyl, $C_{2-6}$ alkenyl, and $C_{2-6}$ alkynyl forming $R^{a5}$, $R^{b5}$, $R^{c5}$ and $R^{d5}$ are each optionally substituted with 1, 2, or 3 substituents independently selected from $R^{20}$;

or $R^{c5}$ and $R^{d5}$ together with the N atom to which they are attached form a 4-7 membered heterocycloalkyl ring optionally substituted with 1, 2, or 3 substituents independently selected from $R^{20}$;

$R^{a6}$, $R^{c6}$ and $R^{d6}$ are independently at each occurrence selected from H, $C_{1-6}$ alkyl, $C_{2-6}$ alkenyl, $C_{2-6}$ alkynyl, and $C_{1-6}$ haloalkyl wherein said $C_{1-6}$ alkyl, $C_{2-6}$ alkenyl, and $C_{2-6}$ alkynyl forming $R^{a6}$, $R^{c6}$ and $R^{d6}$ are each optionally substituted with 1, 2, or 3 substituents independently selected from $R^{20}$;

alternatively, $R^{c6}$ and $R^{d6}$ together with the nitrogen atom to which they are attached form a 4-7 membered heterocycloalkyl group comprising carbon, nitrogen, and 0, 1, or 2 additional heteroatoms selected from N, O and S, wherein said 4-7 membered heterocycloalkyl group is optionally substituted with 1, 2, or 3 substituents independently selected from $R^{20}$;

$R^{b6}$ is independently at each occurrence selected from $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, alkenyl, alkynyl, phenyl, cycloalkyl, 5-6 membered heteroaryl group, and 4-7 membered heterocycloalkyl group are each optionally substituted with 1, 2, or 3 substituents independently selected from $R^{20}$; and $R^{20}$ is at each occurrence independently selected from H, halo, OH, CN, amino, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, $C_{1-4}$ haloalkoxy, $C_{1-4}$ alkyl-C(=O)—, $C_{1-4}$ alkyl-C(=O)O—, $C_{1-4}$ alkyl-OC(=O)—, HOC(=O)—, $H_2NC(=O)$—, $C_{1-4}$ alkyl-NHC(=O)—, di($C_{1-4}$ alkyl)NC(=O)—, $C_{1-4}$ alkyl-C(=O)NH—, $C_{1-4}$ alkyl-O—C(=O)NH—, $C_{1-4}$ alkyl-S(=O)—, $H_2NS(=O)$—, $C_{1-4}$ alkyl-NHS(=O)—, di($C_{1-4}$ alkyl)NS(=O)—, $C_{1-4}$ alkyl-S(=O)$_2$—, $C_{1-4}$ alkyl-S(=O)$_2$NH—, $H_2NS(=O)_2$—, $C_{1-4}$ alkyl-NHS(=O)$_2$—, and di($C_{1-4}$ alkyl)NS(=O)$_2$—.

The present disclosure relates, inter alia, to a compound of a BET protein-inhibiting compound of Formula (I):

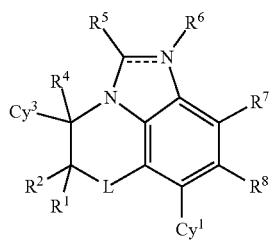

or a pharmaceutically acceptable salt thereof, wherein:

=== represents a single bond or a double bond;

L is $CR^9R^{9a}$, O, S, SO, or $SO_2$;

$Cy^1$ is selected from phenyl or a 5-6 membered heteroaryl group comprising carbon and 1, 2, 3 or 4 heteroatoms selected from N, O and S, wherein said phenyl or 5-6 membered heteroaryl of $Cy^1$ is optionally substituted with 1, 2, 3, or 4 groups independently selected from $R^{11}$;

$R^1$ and $R^2$ are independently selected from H, halo, CN, OH, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$, wherein said $C_{1-6}$ alkyl, $C_{2-6}$ alkenyl, and $C_{2-6}$ alkynyl of $R^1$ and $R^2$ are optionally substituted with 1, 2, or 3 groups independently selected from halo, CN, OH, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

provided neither $R^1$ nor $R^2$ are Cl, Br, I, CN, or OH when L is O or S;

alternatively, $R^1$ and $R^2$ together with the carbon atom to which they are attached may be combined to form a $C_{3-7}$ cycloalkyl group, wherein said cycloalkyl group is optionally substituted with 1, 2, 3, or 4 groups independently selected from $R^{20}$;

$Cy^3$ is selected from phenyl, $C_{3-7}$ cycloalkyl, a 5-10 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said phenyl, $C_{3-7}$ cycloalkyl, 5-10 membered heteroaryl, and 4-10 membered heterocycloalkyl of $Cy^3$ is optionally substituted with 1, 2, 3, or 4 groups independently selected from $R^{13}$, wherein a ring-forming nitrogen atom of said 5-10 membered heteroaryl group or a ring-forming nitrogen atom of said 4-10 membered heterocycloalkyl group is optionally oxidized;

$R^4$ is H or $C_{1-6}$ alkyl;

$R^5$ is selected from =O and =S when C═N is a single bond, alternatively, when C═N is a double bond then $R^5$ is selected from H, $C_{1-6}$ alkyl, $C_{2-6}$ alkenyl, $C_{2-6}$ alkynyl, $C_{1-6}$ haloalkyl, $NR^{15a}R^{15b}$, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, phenyl, $C_{3-7}$ cycloalkyl, 5-6 membered heteroaryl, and 4-7 membered heterocycloalkyl of $R^5$ is optionally substituted by 1, 2, 3, or 4 groups independently selected from $R^{15}$;

$R^6$ is selected from H, $C_{1-6}$ alkyl, $C_{2-6}$ alkenyl, $C_{2-6}$ alkynyl, and $C_{1-6}$ haloalkyl, wherein said alkyl, alkenyl, and alkynyl of $R^6$ are each optionally substituted by 1, 2, 3, or 4 groups independently selected $R^{16}$;

alternatively, $R^6$ is selected from $C_{6-10}$ aryl, $C_{3-7}$ cycloalkyl, 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^6$ are each optionally substituted by 1, 2, 3, or 4 groups independently selected $R^{20}$;

$R^7$ is selected from H, halo, CN, $OR^a$, $NR^cR^d$, $SR^b$, $C(=O)NR^cR^d$, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, alkenyl, alkynyl, phenyl, cycloalkyl, 5-6 membered heteroaryl group, and a 4-7 membered heterocycloalkyl group of $R^7$ are optionally substituted with 1, 2, or 3 groups independently selected from $R^{17}$;

$R^8$ is selected from H, $C_{1-3}$ alkyl, $C_{2-3}$ alkenyl, $C_{2-3}$ alkynyl, $C_{1-3}$ haloalkyl, halo, CN, $OR^a$, $NR^cR^d$, $SR^b$, and $C(=O)NR^cR^d$, wherein said $C_{1-3}$ alkyl of $R^8$ is optionally substituted with 1, 2, or 3 groups independently selected from $R^{18}$;

$R^9$ and $R^{9a}$ are independently selected from H, $C_{1-3}$ alkyl, $C_{1-3}$ haloalkyl, halo, CN, $OR^a$, $NR^cR^d$, $SR^b$, and $C(=O)NR^cR^d$;

$R^{11}$ is independently at each occurrence selected from H, $C_{1-3}$ alkyl, $C_{1-3}$ haloalkyl, halo, CN, $OR^a$, $NR^cR^d$, $SR^b$, and $C(=O)NR^cR^d$;

$R^{13}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$, wherein said $C_{1-6}$ alkyl, $C_{2-6}$ alkenyl, and $C_{2-6}$ alkynyl of $R^{13}$ is optionally substituted with 1, 2, or 3 groups independently selected from halo, CN, OH, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$;

$R^{15}$ is independently at each occurrence selected from H, halo, CN, OH, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $S(=O)R^{b5}$, $S(=O)NR^{c5}R^{d5}$, $S(=O)_2R^{b5}$, $NR^{c5}S(=O)_2R^{b5}$ and $S(=O)_2NR^{c5}R^{d5}$;

$R^{15a}$ and $R^{15b}$ are independently selected from H and $C_{1-6}$ alkyl, wherein said alkyl of $R^{15a}$ and $R^{15b}$ is optionally substituted with 0, 1, 2, or 3 substituents selected from $R^{20}$;

$R^{16}$ is independently at each occurrence selected from halo, CN, OH, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}NR^{c6}C(=O)NR^{c6}R^{d6}$, $NR^{c6}C(=O)OR^{a6}$, $S(=O)R^{b6}$, $S(=O)NR^{c6}R^{d6}$, $S(=O)_2R^{b6}$, $NR^{c6}S(=O)_2R^{b6}$ and $S(=O)_2NR^{c6}R^{d6}$, $C_{6-10}$ aryl, $C_{3-7}$ cycloalkyl, 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^{16}$ are each optionally substituted by 1, 2, 3, or 4 groups independently selected $R^{20}$;

$R^{17}$ and $R^{18}$ are independently at each occurrence selected from halo, CN, $OR^a$, $NR^cR^d$ $SR^b$, and $C(=O)NR^cR^d$;

$R^a$, $R^c$, and $R^d$ are independently at each occurrence selected from H and $C_{1-6}$ alkyl;

$R^b$ is at each occurrence selected $C_{1-6}$ alkyl;

$R^{a1}$, $R^{b1}$, $R^{c1}$ and $R^{d1}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a1}$, $R^{b1}$, $R^{c1}$ and $R^{d1}$ are each optionally substituted with 1, 2, or 3 substituents independently selected from $R^{20}$;

$R^{a3}$, $R^{b3}$, $R^{c3}$ and $R^{d3}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a3}$, $R^{b3}$, $R^{c3}$ and $R^{d3}$ are each optionally substituted with 1, 2, or 3 substituents independently selected from halo, CN, OH, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$ $NR^{c4}C(=O)R^{b4}$, $NR^{c4}C(=O)NR^{c4}R^{d4}$ $NR^{c4}C(=O)OR^{a4}$, $S(=O)R^{b4}$, $S(=O)NR^{c4}R^{d4}$, $S(=O)_2R^{b4}$, $NR^{c4}S(=O)_2R^{b4}$ and $S(=O)_2NR^{c4}R^{d4}$;

$R^{a4}$, $R^{b4}$, $R^{c4}$ and $R^{d4}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a4}$, $R^{b4}$, $R^{c4}$ and $R^{d4}$ are each optionally substituted with 1, 2, or 3 substituents independently selected from $R^{20}$;

$R^{a5}$, $R^{b5}$, $R^{c5}$ and $R^{d5}$ are independently at each occurrence selected from H, $C_{1-6}$ alkyl, $C_{2-6}$ alkenyl, $C_{2-6}$ alkynyl, and $C_{1-6}$ haloalkyl wherein said $C_{1-6}$ alkyl, $C_{2-6}$ alkenyl, and $C_{2-6}$ alkynyl forming $R^{a5}$, $R^{b5}$, $R^{c5}$ and $R^{d5}$ are each optionally substituted with 1, 2, or 3 substituents independently selected from $R^{20}$;

$R^{a6}$, $R^{c6}$ and $R^{d6}$ are independently at each occurrence selected from H, $C_{1-6}$ alkyl, $C_{2-6}$ alkenyl, $C_{2-6}$ alkynyl, and $C_{1-6}$ haloalkyl wherein said $C_{1-6}$ alkyl, $C_{2-6}$ alkenyl, and $C_{2-6}$ alkynyl forming $R^{a6}$, $R^{c6}$ and $R^{d6}$ are each optionally substituted with 1, 2, or 3 substituents independently selected from $R^{20}$;

alternatively, $R^{c6}$ and $R^{d6}$ together with the nitrogen atom to which they are attached may be combined to form a 4-7 membered heterocycloalkyl group comprising carbon, nitrogen, and 0, 1, or 2 additional heteroatoms selected from N, O and S, wherein said 4-7 membered heterocycloalkyl group is optionally substituted with 1, 2, or 3 substituents independently selected from $R^{20}$;

$R^{b6}$ is independently at each occurrence selected from $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, alkenyl, alkynyl, phenyl, cycloalkyl, 5-6 membered heteroaryl group, and 4-7 membered heterocycloalkyl group are each optionally substituted with 1, 2, or 3 substituents independently selected from $R^{20}$; and $R^{20}$ is at each occurrence independently selected from H, halo, OH, CN, amino, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, $C_{1-4}$ haloalkoxy, $C_{1-4}$ alkyl-C(=O)—, $C_{1-4}$ alkyl-C(=O)O—, $C_{1-4}$ alkyl-OC(=O)—, HOC(=O)—, $H_2NC(=O)$—, $C_{1-4}$ alkyl-NHC(=O)—, di($C_{1-4}$ alkyl)NC(=O)—, $C_{1-4}$ alkyl-C(=O)NH—, $C_{1-4}$ alkyl-S(=O)—, $H_2NS(=O)$—, $C_{1-4}$ alkyl-NHS(=O)—, di($C_{1-4}$ alkyl)NS(=O)—, $C_{1-4}$ alkyl-S(=O)$_2$—, $C_{1-4}$ alkyl-S(=O)$_2$NH—, $H_2NS(=O)_2$—, $C_{1-4}$ alkyl-NHS(=O)$_2$—, and di($C_{1-4}$ alkyl)NS(=O)$_2$—.

In some embodiments of the compounds of Formula (I):

═ represents a single bond or a double bond;

L is $CR^9R^{9a}$, O, S, SO, or $SO_2$;

$Cy^1$ is selected from phenyl or a 5-6 membered heteroaryl group comprising carbon and 1, 2, 3 or 4 heteroatoms selected from N, O and S, wherein said phenyl or 5-6 membered heteroaryl of $Cy^1$ is optionally substituted with 1, 2, 3, or 4 groups independently selected from $R^{11}$;

$R^1$ is selected from H, halo, CN, OH, $C_{1-6}$ alkyl, $C_{2-6}$ alkenyl, $C_{2-6}$ alkynyl, $C_{1-6}$ haloalkyl, $OR^{a1}$, $SR^{a1}$, C(=O)$R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$, wherein said $C_{1-6}$ alkyl, $C_{2-6}$ alkenyl, and $C_{2-6}$ alkynyl of $R^1$ and $R^2$ are optionally substituted with 1, 2, or 3 groups independently selected from halo, CN, OH, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

$R^2$ is selected from H, halo, CN, OH, $C_{1-6}$ alkyl, $C_{1-6}$ haloalkyl, $C_{1-6}$ alkyl-O—, and $C_{1-6}$ haloalkyl-O—;

provided neither $R^1$ nor $R^2$ are Cl, Br, I, CN, or OH when L is O or S;

$Cy^3$ is selected from phenyl, $C_{3-7}$ cycloalkyl, a 5-10 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said phenyl, $C_{3-7}$ cycloalkyl, 5-10 membered heteroaryl, and 4-10 membered heterocycloalkyl of $Cy^3$ is optionally substituted with 1, 2, 3, or 4 groups independently selected from $R^{13}$; additionally, wherein a ring-forming nitrogen atom of said 5-10 membered heteroaryl group or a ring-forming nitrogen atom of said 4-10 membered heterocycloalkyl group is optionally oxidized;

$R^4$ is H or $C_{1-6}$ alkyl;

$R^5$ is selected from =O and =S when C═N is a single bond, alternatively, when C═N is a double bond then $R^5$ is selected from H, $C_{1-6}$ alkyl, $C_{2-6}$ alkenyl, $C_{2-6}$ alkynyl, $C_{1-6}$ haloalkyl, $NR^{15a}R^{15b}$, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, phenyl, $C_{3-7}$ cycloalkyl, 5-6 membered heteroaryl, and 4-7 membered heterocycloalkyl of $R^5$ is optionally substituted by 1, 2, 3, or 4 groups independently selected from $R^{15}$;

$R^6$ is selected from H, $C_{1-6}$ alkyl, $C_{2-6}$ alkenyl, $C_{2-6}$ alkynyl, and $C_{1-6}$ haloalkyl, wherein said alkyl, alkenyl, and alkynyl of $R^6$ are each optionally substituted by 1, 2, 3, or 4 groups independently selected $R^{16}$;

alternatively, $R^6$ is selected from $C_{6-10}$ aryl, $C_{3-7}$ cycloalkyl, 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^6$ are each optionally substituted by 1, 2, 3, or 4 groups independently selected $R^{20}$;

$R^7$ is selected from H, halo, CN, $OR^a$, $NR^cR^d$, $SR^b$, $C(=O)NR^cR^d$, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, alkenyl, alkynyl, phenyl, cycloalkyl, 5-6 membered heteroaryl group, and a 4-7 membered heterocycloalkyl group of $R^7$ are optionally substituted with 1, 2, or 3 groups independently selected from $R^{17}$;

$R^8$ is selected from H, halo, CN, OH, $C_{1-6}$ alkyl, $C_{1-6}$ haloalkyl, $C_{1-6}$ alkyl-O—, and $C_{1-6}$ haloalkyl-O—;

$R^9$ and $R^{9a}$ are independently selected from H and $C_{1-3}$ alkyl;

$R^{11}$ is independently at each occurrence selected from H, $C_{1-3}$ alkyl, $C_{1-3}$ haloalkyl, halo, CN, $OR^a$, $NR^cR^d$, $SR^b$, and $C(=O)NR^cR^d$;

$R^{13}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a3}$, $SR^{a3}$, $C(=O)R^{b3}$, $C(=O)NR^{c3}R^{d3}$, $C(=O)OR^{a3}$ $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$, wherein said $C_{1-6}$ alkyl, $C_{2-6}$ alkenyl, and $C_{2-6}$ alkynyl of $R^{13}$ is optionally substituted with 1, 2, or 3 groups independently selected from halo, CN, OH, $OR^{a3}$, $SR^{a3}$, $C(=O)R^{b3}$, $C(=O)NR^{c3}R^{d3}$, $C(=O)OR^{a3}OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$;

$R^{15}$ is independently at each occurrence selected from H, halo, CN, OH, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $S(=O)R^{b5}$, $S(=O)NR^{c5}R^{d5}$, $S(=O)_2R^{b5}$, $NR^{c5}S(=O)_2R^{b5}$ and $S(=O)_2NR^{c5}R^{d5}$;

$R^{15a}$ and $R^{15b}$ are independently selected from H and $C_{1-6}$ alkyl, wherein said alkyl of $R^{15a}$ and $R^{15b}$ is optionally substituted with 0, 1, 2, or 3 substituents selected from $R^{20}$;

$R^{16}$ is independently at each occurrence selected from halo, CN, OH, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}NR^{c6}C(=O)NR^{c6}R^{d6}$, $NR^{c6}C(=O)OR^{a6}$, $S(=O)R^{b6}$, $S(=O)NR^{c6}R^{d6}$, $S(=O)_2R^{b6}$, $NR^{c6}S(=O)_2R^{b6}$ and $S(=O)_2NR^{c6}R^{d6}$, $C_{6-10}$ aryl, $C_{3-7}$ cycloalkyl, 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^{16}$ are each optionally substituted by 1, 2, 3, or 4 groups independently selected $R^{20}$;

$R^{17}$ is independently at each occurrence selected from halo, CN, $OR^a$, $NR^cR^d$, $SR^b$, and $C(=O)NR^cR^d$;

$R^a$, $R^c$, and $R^d$ are independently at each occurrence selected from H and $C_{1-6}$ alkyl;

$R^b$ is at each occurrence $C_{1-6}$ alkyl;

$R^{a1}$, $R^{b1}$, $R^{c1}$ and $R^{d1}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a1}$, $R^{b1}$, $R^{c1}$ and $R^{d1}$ are each optionally substituted with 1, 2, or 3 substituents independently selected from $R^{20}$;

$R^{a3}$, $R^{b3}$, $R^{c3}$ and $R^{d3}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a3}$, $R^{b3}$, $R^{c3}$ and $R^{d3}$ are each optionally substituted with 1, 2, or 3 substituents independently selected from halo, CN, OH, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$ $NR^{c4}C(=O)R^{b4}$, $NR^{c4}C(=O)NR^{c4}R^{d4}$ $NR^{c4}C(=O)OR^{a4}$, $S(=O)R^{b4}$, $S(=O)NR^{c4}R^{d4}$, $S(=O)_2R^{b4}$, $NR^{c4}S(=O)_2R^{b4}$ and $S(=O)_2NR^{c4}R^{d4}$;

$R^{a4}$, $R^{b4}$, $R^{c4}$ and $R^{d4}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a4}$, $R^{b4}$, $R^{c4}$ and $R^{d4}$ are each optionally substituted with 1, 2, or 3 substituents independently selected from $R^{20}$;

$R^{a5}$, $R^{b5}$, $R^{c5}$ and $R^{d5}$ are independently at each occurrence selected from H, $C_{1-6}$ alkyl, $C_{2-6}$ alkenyl, $C_{2-6}$ alkynyl, and $C_{1-6}$ haloalkyl wherein said $C_{1-6}$ alkyl, $C_{2-6}$ alkenyl, and $C_{2-6}$ alkynyl forming $R^aS$, $R^{b5}$, $R^{c5}$ and $R^{d5}$ are each optionally substituted with 1, 2, or 3 substituents independently selected from $R^{20}$;

$R^{a6}$, $R^{c6}$ and $R^{d6}$ are independently at each occurrence selected from H, $C_{1-6}$ alkyl, $C_{2-6}$ alkenyl, $C_{2-6}$ alkynyl, and $C_{1-6}$ haloalkyl wherein said $C_{1-6}$ alkyl, $C_{2-6}$ alkenyl, and $C_{2-6}$ alkynyl forming $R^{a6}$, $R^{c6}$ and $R^{d6}$ are each optionally substituted with 1, 2, or 3 substituents independently selected from $R^{20}$;

alternatively, $R^{c6}$ and $R^{d6}$ together with the nitrogen atom to which they are attached may be combined to form a 4-7 membered heterocycloalkyl group comprising carbon, nitrogen, and 0, 1, or 2 additional heteroatoms selected from N, O and S, wherein said 4-7 membered heterocycloalkyl group is optionally substituted with 1, 2, or 3 substituents independently selected from $R^{20}$;

$R^{b6}$ is independently at each occurrence selected from $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, alkenyl, alkynyl, phenyl, cycloalkyl, 5-6 membered heteroaryl group, and 4-7 membered heterocycloalkyl group are each optionally substituted with 1, 2, or 3 substituents independently selected from $R^{20}$; and $R^{20}$ is at each occurrence independently selected from H, halo, OH, CN, amino, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, $C_{1-4}$ haloalkoxy, $C_{1-4}$ alkyl-C(=O)—, $C_{1-4}$ alkyl-C(=O)O—, $C_{1-4}$ alkyl-OC(=O)—, HOC(=O)—, $H_2NC(=O)$—, $C_{1-4}$ alkyl-NHC(=O)—, di($C_{1-4}$ alkyl)NC(=O)—, $C_{1-4}$ alkyl-C(=O)NH—, $C_{1-4}$ alkyl-S(=O)—, $H_2NS(=O)$—, $C_{1-4}$ alkyl-NHS(=O)—, di($C_{1-4}$ alkyl)NS(=O)—, $C_{1-4}$ alkyl-S ($=$O)$_2$—, C$_{1-4}$ alkyl-S($=$O)$_2$NH—, H$_2$NS($=$O)$_2$—, C$_{1-4}$ alkyl-NHS($=$O)$_2$—, and di(C$_{1-4}$ alkyl)NS($=$O)$_2$—.

In some embodiments of the compounds of Formula (I): $=\!\!=$ represents a single bond or a double bond;

L is O;

Cy$^1$ is a five membered heteroaryl group comprising carbon and 1, 2, 3 or 4 heteroatoms selected from N, O and S, wherein said five membered heteroaryl of Cy$^1$ is optionally substituted with 1, 2, or 3 groups independently selected from R$^{11}$;

R$^1$ is selected from H, F, C$_{1-6}$ alkyl, C$_{2-6}$ alkenyl, C$_{2-6}$ alkynyl, C$_{1-6}$ haloalkyl, OR$^{a1}$, SR$^{a1}$, C($=$O)R$^{b1}$, C($=$O)NR$^{c1}$R$^{d1}$, C($=$O)OR$^{a1}$, OC($=$O)R$^{b1}$, OC($=$O)NR$^{c1}$R$^{d1}$, NR$^{c1}$R$^{d1}$, NR$^{c1}$C($=$O)R$^{b1}$, NR$^{c1}$C($=$O)NR$^{c1}$R$^{d1}$, NR$^{c1}$C($=$O)OR$^{a1}$, S($=$O)R$^{b1}$, S($=$O)NR$^{c1}$R$^{d1}$, S($=$O)$_2$R$^{b1}$, NR$^{c1}$S($=$O)$_2$R$^{b1}$ and S($=$O)$_2$NR$^{c1}$R$^{d1}$, wherein said C$_{1-6}$ alkyl, C$_{2-6}$ alkenyl, and C$_{2-6}$ alkynyl of R$^1$ and R$^2$ are optionally substituted with 1, 2, or 3 groups independently selected from halo, CN, OH, OR$^{a1}$, SR$^{a1}$, C($=$O)R$^{b1}$, C($=$O)NR$^{c1}$R$^{d1}$, C($=$O)OR$^{a1}$, OC($=$O)R$^{b1}$, OC($=$O)NR$^{c1}$R$^{d1}$, NR$^{c1}$R$^{d1}$ NR$^{c1}$C(O)R$^{b1}$ NR$^{c1}$C($=$O)NR$^{c1}$R$^{d1}$, NR$^{c1}$C($=$O)OR$^{a1}$, S($=$O)R$^{b1}$, S($=$O)NR$^{c1}$R$^{d1}$, S($=$O)$_2$R$^{b1}$, NR$^{c1}$S($=$O)$_2$R$^{b1}$ and S($=$O)$_2$NR$^{c1}$R$^{d1}$;

R$^2$ is selected from H, F, and C$_{1-6}$ alkyl;

Cy$^3$ is selected from phenyl, C$_{3-7}$ cycloalkyl, a 5-10 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said phenyl, C$_{3-7}$ cycloalkyl, 5-10 membered heteroaryl, and 4-10 membered heterocycloalkyl of Cy$^3$ is optionally substituted with 1, 2, 3, or 4 groups independently selected from R$^{13}$; additionally, wherein a ring-forming nitrogen atom of said 5-10 membered heteroaryl group or a ring-forming nitrogen atom of said 4-10 membered heterocycloalkyl group is optionally oxidized;

R$^4$ is H or C$_{1-6}$ alkyl;

R$^5$ is selected from $=$O and $=$S when C$=\!\!=$N is a single bond, alternatively, when C$=\!\!=$N is a double bond then R$^5$ is selected from H, C$_{1-6}$ alkyl, C$_{2-6}$ alkenyl, C$_{2-6}$ alkynyl, C$_{1-6}$ haloalkyl, NR$^{15a}$R$^{15b}$, phenyl, C$_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, phenyl, C$_{3-7}$ cycloalkyl, 5-6 membered heteroaryl, and 4-7 membered heterocycloalkyl of R$^5$ is optionally substituted by 1, 2, 3, or 4 groups independently selected from R$^{15}$;

R$^6$ is selected from H, C$_{1-6}$ alkyl, C$_{2-6}$ alkenyl, C$_{2-6}$ alkynyl, and C$_{1-6}$ haloalkyl, wherein said alkyl, alkenyl, and alkynyl of R$^6$ are each optionally substituted by 1, 2, 3, or 4 groups independently selected R$^{16}$;

R$^7$ is selected from H, halo, CN, OR$^a$, NR$^c$R$^d$, SR$^b$, C($=$O)NR$^c$R$^d$, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, alkenyl, alkynyl, phenyl, cycloalkyl, 5-6 membered heteroaryl group, and a 4-7 membered heterocycloalkyl group of R$^7$ are optionally substituted with 1, 2, or 3 groups independently selected from R$^{17}$;

R$^8$ is selected from H, halo, CN, OH, C$_{1-6}$ alkyl, C$_{1-6}$ haloalkyl, C$_{1-6}$ alkyl-O—, and C$_{1-6}$ haloalkyl-O—;

R$^{11}$ is independently at each occurrence selected from H, C$_{1-3}$ alkyl, C$_{1-3}$ haloalkyl, halo, CN, OR$^a$, NR$^c$R$^d$, SR$^b$, and C($=$O)NR$^c$R$^d$;

R$^{13}$ is independently at each occurrence selected from H, halo, CN, OH, C$_{1-6}$ alkyl, C$_{2-6}$ alkenyl, C$_{2-6}$ alkynyl, C$_{1-6}$ haloalkyl, OR$^{a3}$, SR$^{a3}$, C($=$O)R$^{b3}$, C($=$O)NR$^{c3}$R$^{d3}$, C($=$O)OR$^{a3}$, OC($=$O)R$^{b3}$, OC($=$O)NR$^{c3}$R$^{d3}$, NR$^{c3}$R$^{d3}$, NR$^{c3}$C($=$O)R$^{b3}$, NR$^{c3}$C($=$O)NR$^{c3}$R$^{d3}$, NR$^{c3}$C($=$O)OR$^{a3}$, S($=$O)R$^{b3}$, S($=$O)NR$^{c3}$R$^{d3}$, S($=$O)$_2$R$^{b3}$, NR$^{c3}$S($=$O)$_2$R$^{b3}$ and S($=$O)$_2$NR$^{c3}$R$^{d3}$, wherein said C$_{1-6}$ alkyl, C$_{2-6}$ alkenyl, and C$_{2-6}$ alkynyl of R$^{13}$ is optionally substituted with 1, 2, or 3 groups independently selected from halo, CN, OH, OR$^{a3}$, SR$^{a3}$, C($=$O)R$^{b3}$, C($=$O)NR$^{c3}$R$^{d3}$, C($=$O)OR$^{a3}$, OC($=$O)R$^{b3}$, OC($=$O)NR$^{c3}$R$^{d3}$, NR$^{c3}$R$^{d3}$, NR$^{c3}$C($=$O)R$^{b3}$, NR$^{c3}$C($=$O)NR$^{c3}$R$^{d3}$, NR$^{c3}$C($=$O)OR$^{a3}$, S($=$O)R$^{b3}$, S($=$O)NR$^{c3}$R$^{d3}$, S($=$O)$_2$R$^{b3}$, NR$^{c3}$S($=$O)$_2$R$^{b3}$ and S($=$O)$_2$NR$^{c3}$R$^{d3}$;

R$^{15}$ is independently at each occurrence selected from H, halo, CN, OH, OR$^{a5}$, SR$^{a5}$, C($=$O)R$^{b5}$, C($=$O)NR$^{c5}$R$^{d5}$, C($=$O)OR$^{a5}$, OC($=$O)R$^{b5}$, OC($=$O)NR$^{c5}$R$^{d5}$, NR$^{c5}$R$^{d5}$, NR$^{c5}$C($=$O)R$^{b5}$, NR$^{c5}$C($=$O)NR$^{c5}$R$^{d5}$, NR$^{c5}$C($=$O)OR$^{a5}$, S($=$O)R$^{b5}$, S($=$O)NR$^{c5}$R$^{d5}$, S($=$O)$_2$R$^{b5}$, NR$^{c5}$S($=$O)$_2$R$^{b5}$ and S($=$O)$_2$NR$^{c5}$R$^{d5}$;

R$^{15a}$ and R$^{15b}$ are independently selected from H and C$_{1-6}$ alkyl, wherein said alkyl of R$^{15a}$ and R$^{15b}$ is optionally substituted with 0, 1, 2, or 3 substituents selected from R$^{20}$;

R$^{16}$ is independently at each occurrence selected from halo, CN, OH, OR$^{a6}$, SR$^{a6}$, C($=$O)R$^{b6}$, C($=$O)NR$^{c6}$R$^{d6}$, C($=$O)OR$^{a6}$, OC($=$O)R$^{b6}$, OC($=$O)NR$^{c6}$R$^{d6}$, NR$^{c6}$R$^{d6}$, NR$^{c6}$C($=$O)R$^{b6}$, NR$^{c6}$C($=$O)NR$^{c6}$R$^{d6}$, NR$^{c6}$C($=$O)OR$^{a6}$, S($=$O)R$^{b6}$, S($=$O)NR$^{c6}$R$^{d6}$, S($=$O)$_2$R$^{b6}$, NR$^{c6}$S($=$O)$_2$R$^{b6}$ and S($=$O)$_2$NR$^{c6}$R$^{d6}$, C$_{6-10}$ aryl, C$_{3-7}$ cycloalkyl, 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said C$_{6-10}$ aryl, C$_{3-7}$ cycloalkyl, 5-10 membered heteroaryl, and 4-7 membered heterocycloalkyl of R$^{16}$ are each optionally substituted by 1, 2, 3, or 4 groups independently selected R$^{20}$;

R$^{17}$ is independently at each occurrence selected from halo, CN, OR$^a$, NR$^c$R$^d$, SR$^b$, and C($=$O)NR$^c$R$^d$;

R$^a$, R$^c$, and R$^d$ are independently at each occurrence selected from H and C$_{1-6}$ alkyl; R$^b$ is at each occurrence C$_{1-6}$ alkyl;

R$^{a1}$, R$^{b1}$, R$^{c1}$ and R$^{d1}$ are independently at each occurrence selected from H, C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl forming R$^{a1}$, R$^{b1}$, R$^{c1}$ and R$^{d1}$ are each optionally substituted with 1, 2, or 3 substituents independently selected from R$^{20}$;

R$^{a3}$, R$^{b3}$, R$^{c3}$ and R$^{d3}$ are independently at each occurrence selected from H, C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl forming R$^{a3}$, R$^{b3}$, R$^{c3}$ and R$^{d3}$ are each optionally substituted with 1, 2, or 3 substituents independently selected from halo, CN, OH, OR$^{a4}$, SR$^{a4}$, C($=$O)R$^{b4}$, C($=$O)NR$^{c4}$R$^{d4}$, C($=$O)OR$^{a4}$, OC($=$O)R$^{b4}$, OC($=$O)NR$^{c4}$R$^{d4}$, NR$^{c4}$R$^{d4}$ NR$^{c4}$C($=$O)R$^{b4}$, NR$^{c4}$C($=$O)NR$^{c4}$R$^{d4}$ NR$^{c4}$C($=$O)OR$^{a4}$, S($=$O)R$^{b4}$, S($=$O)NR$^{c4}$R$^{d4}$, S($=$O)$_2$R$^{b4}$, NR$^{c4}$S($=$O)$_2$R$^{b4}$ and S($=$O)$_2$NR$^{c4}$R$^{d4}$;

R$^{a4}$, R$^{b4}$, R$^{c4}$ and R$^{d4}$ are independently at each occurrence selected from H, C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl forming R$^{a4}$, R$^{b4}$, R$^{c4}$ and R$^{d4}$ are each optionally substituted with 1, 2, or 3 substituents independently selected from R$^{20}$;

$R^{a5}$, $R^{b5}$, $R^{c5}$ and $R^{d5}$ are independently at each occurrence selected from H, $C_{1-6}$ alkyl, $C_{2-6}$ alkenyl, $C_{2-6}$ alkynyl, and $C_{1-6}$ haloalkyl wherein said $C_{1-6}$ alkyl, $C_{2-6}$ alkenyl, and $C_{2-6}$ alkynyl forming $R^{a5}$, $R^{b5}$, $R^{c5}$ and $R^{d5}$ are each optionally substituted with 1, 2, or 3 substituents independently selected from $R^{20}$;

$R^{a6}$, $R^{c6}$ and $R^{d6}$ are independently at each occurrence selected from H, $C_{1-6}$ alkyl, $C_{2-6}$ alkenyl, $C_{2-6}$ alkynyl, and $C_{1-6}$ haloalkyl wherein said $C_{1-6}$ alkyl, $C_{2-6}$ alkenyl, and $C_{2-6}$ alkynyl forming $R^{a6}$, $R^{c6}$ and $R^{d6}$ are each optionally substituted with 1, 2, or 3 substituents independently selected from $R^{20}$;

alternatively, $R^{c6}$ and $R^{d6}$ together with the nitrogen atom to which they are attached may be combined to form a 4-7 membered heterocycloalkyl group comprising carbon and 1, 2, or 3 heteroatoms selected from N, O and S, wherein said 4-7 membered heterocycloalkyl group is optionally substituted with 1, 2, or 3 substituents independently selected from $R^{20}$;

$R^{b6}$ is independently at each occurrence selected from $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, alkenyl, alkynyl, phenyl, cycloalkyl, 5-6 membered heteroaryl group, and 4-7 membered heterocycloalkyl group are each optionally substituted with 1, 2, or 3 substituents independently selected from $R^{20}$; and $R^{20}$ is at each occurrence independently selected from H, halo, OH, CN, amino, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, $C_{1-4}$ haloalkoxy, $C_{1-4}$ alkyl-C(=O)—, $C_{1-4}$ alkyl-C(=O)O—, $C_{1-4}$ alkyl-OC(=O)—, HOC(=O)—, $H_2NC(=O)$—, $C_{1-4}$ alkyl-NHC(=O)—, di($C_{1-4}$ alkyl)NC(=O)—, $C_{1-4}$ alkyl-C(=O)NH—, $C_{1-4}$ alkyl-S(=O)—, $H_2NS(=O)$—, $C_{1-4}$ alkyl-NHS(=O)—, di($C_{1-4}$ alkyl)NS(=O)—, $C_{1-4}$ alkyl-S(=O)$_2$—, $C_{1-4}$ alkyl-S(=O)$_2$NH—, $H_2NS(=O)_2$—, $C_{1-4}$ alkyl-NHS(=O)$_2$—, and di($C_{1-4}$ alkyl)NS(=O)$_2$—.

In some embodiments:

= represents a single bond or a double bond;

L is O;

$Cy^1$ is a five membered heteroaryl group comprising carbon and 1, 2, 3 or 4 heteroatoms selected from N, O and S, wherein said five membered heteroaryl of $Cy^1$ is optionally substituted with 1, 2, or 3 groups independently selected from $R^{11}$;

$R^1$ is selected from H, F, $C_{1-6}$ alkyl, $C_{2-6}$ alkenyl, $C_{2-6}$ alkynyl, $C_{1-6}$ haloalkyl, $OR^{a1}$, $C(=O)R^{b1}$, $C(=O)NR^{c1}R^{d1}$, and $C(=O)OR^{a1}$;

$R^2$ is selected from H, F, and $C_{1-6}$ alkyl;

$Cy^3$ is selected from phenyl, $C_{3-7}$ cycloalkyl, a 5-10 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said phenyl, $C_{3-7}$ cycloalkyl, 5-10 membered heteroaryl, and 4-10 membered heterocycloalkyl of $Cy^3$ is optionally substituted with 1, 2, 3, or 4 groups independently selected from $R^{13}$; additionally, wherein a ring-forming nitrogen atom of said 5-10 membered heteroaryl group or a ring-forming nitrogen atom of said 4-10 membered heterocycloalkyl group is optionally oxidized;

$R^4$ is H or $C_{1-6}$ alkyl;

$R^5$ is selected from =O and =S when C=N is a single bond, alternatively, when C=N is a double bond then $R^5$ is selected from H, $C_{1-6}$ alkyl, $C_{2-6}$ alkenyl, $C_{2-6}$ alkynyl, $C_{1-6}$ haloalkyl, $NR^{15a}R^{15b}$, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said alkyl, phenyl, $C_{3-7}$ cycloalkyl, 5-6 membered heteroaryl, and 4-7 membered heterocycloalkyl of $R^5$ is optionally substituted by 1, 2, 3, or 4 groups independently selected from $R^{15}$;

$R^6$ is selected from H and $C_{1-6}$ alkyl, wherein said alkyl of $R^6$ is optionally substituted by 1, 2, or 3 groups independently selected $R^{16}$;

$R^7$ is selected from H, halo, CN, $C_{1-6}$ alkyl, $C_{1-6}$ alkoxy, phenyl, and 5-6 membered heteroaryl group comprising carbon and 1, 2, 3 or 4 heteroatoms selected from N, O and S, wherein said alkyl, phenyl, or 5-6 membered heteroaryl group, of $R^7$ are optionally substituted with 1, 2, or 3 groups independently selected from $R^{17}$;

$R^8$ is selected from H, halo, CN, OH, and $C_{1-6}$ alkyl;

$R^{11}$ is independently at each occurrence selected from H, $C_{1-3}$ alkyl, $C_{1-3}$ haloalkyl, halo, CN, $OR^a$, $NR^cR^d$, $SR^b$, and $C(=O)NR^cR^d$;

$R^{13}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$, wherein said $C_{1-6}$ alkyl, $C_{2-6}$ alkenyl, and $C_{2-6}$ alkynyl of $R^{13}$ is optionally substituted with 1, 2, or 3 groups independently selected from halo, CN, OH, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$;

$R^{15}$ is independently at each occurrence selected from H, halo, CN, OH, $OR^{a5}$, $C(=O)R^{b5}$, $C(=O)NR^{c5}R^{d5}$, $C(=O)OR^{a5}$, $NR^{c5}R^{d5}$, and $NR^{c5}C(=O)R^{b5}$;

$R^{15a}$ and $R^{15b}$ are independently selected from H and $C_{1-6}$ alkyl, wherein said alkyl of $R^{15a}$ and $R^{15b}$ is optionally substituted with 0, 1, 2, or 3 substituents selected from $R^{20}$;

$R^{16}$ is independently at each occurrence selected from halo, CN, OH, $OR^{a6}$, $C(=O)R^{b6}$, $C(=O)NR^{c6}R^{d6}$, $C(=O)OR^{a6}$, $OC(=O)R^{b6}$, $NR^{c6}R^{d6}$, $NR^{c6}C(=O)R^{b6}$, and a 4-7 membered heterocycloalkyl group comprising carbon and 1, 2, or 3 heteroatoms selected from N, O and S, wherein said 4-7 membered heterocycloalkyl of $R^{16}$ is optionally substituted by 1, 2, 3, or 4 groups independently selected $R^{20}$;

$R^{17}$ is independently at each occurrence selected from halo, CN, $OR^a$, $NR^cR^d$, $SR^b$, and $C(=O)NR^cR^d$;

$R^a$, $R^c$, and $R^d$ are independently at each occurrence selected from H and $C_{1-6}$ alkyl;

$R^b$ is at each occurrence $C_{1-6}$ alkyl;

$R^{a1}$, $R^{b1}$, $R^{c1}$ and $R^{d1}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a1}$, $R^{b1}$, $R^{c1}$ and $R^{d1}$ are each optionally substituted with 1, 2, or 3 substituents independently selected from $R^{20}$;

$R^{a3}$, $R^{b3}$, $R^{c3}$ and $R^{d3}$ are independently at each occurrence selected from H and $C_{1-6}$ alkyl, wherein said $C_{1-6}$ alkyl forming $R^{a3}$, $R^{b3}$, $R^{c3}$ and $R^{d3}$ is optionally substituted with 1, 2, or 3 substituents independently selected from halo, CN, OH, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C$ (=O)R$^{b4}$, NR$^{c4}$C(=O)NR$^{c4}$R$^{d4}$, NR$^{c4}$C(=O)OR$^{a4}$, S(=O)R$^{b4}$, S(=O)NR$^{c4}$R$^{d4}$, S(=O)$_2$R$^{b4}$, NR$^{c4}$S(=O)$_2$R$^{b4}$ and S(=O)$_2$NR$^{c4}$R$^{d4}$;

R$^{a4}$, R$^{b4}$, R$^{c4}$ and R$^{d4}$ are independently at each occurrence selected from H and C$_{1-6}$ alkyl, wherein said C$_{1-6}$ alkyl forming R$^{a4}$, R$^{b4}$, R$^{c4}$ and R$^{d4}$ is optionally substituted with 1, 2, or 3 substituents independently selected from R$^{20}$;

R$^{a5}$, R$^{b5}$, R$^{c5}$ and R$^{d5}$ are independently at each occurrence selected from H and C$_{1-6}$ alkyl, wherein said C$_{1-6}$ alkyl forming R$^{a5}$, R$^{b5}$, R$^{c5}$ and R$^{d5}$ is optionally substituted with 1, 2, or 3 substituents independently selected from R$^{20}$;

R$^{a6}$, R$^{c6}$ and R$^{d6}$ are independently at each occurrence selected from H and C$_{1-6}$ alkyl;

alternatively, R$^{c6}$ and R$^{d6}$ together with the nitrogen atom to which they are attached may be combined to form a 4-7 membered heterocycloalkyl group comprising carbon, nitrogen, and 0, 1, or 2 additional heteroatoms selected from N, O and S, wherein said 4-7 membered heterocycloalkyl group is optionally substituted with 1, 2, or 3 substituents independently selected from R$^{20}$;

R$^{b6}$ is independently at each occurrence selected from C$_{1-6}$ alkyl; and

R$^{20}$ is at each occurrence independently selected from H, halo, OH, CN, amino, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, C$_{1-4}$ haloalkoxy, C$_{1-4}$ alkyl-C(=O)—, C$_{1-4}$ alkyl-C(=O)O—, C$_{1-4}$ alkyl-OC(=O)—, HOC(=O)—, H$_2$NC(=O)—, C$_{1-4}$ alkyl-NHC(=O)—, di(C$_{1-4}$ alkyl)NC(=O)—, C$_{1-4}$ alkyl-C(=O)NH—, C$_{1-4}$ alkyl-S(=O)—, H$_2$NS(=O)—, C$_{1-4}$ alkyl-NHS(=O)—, di(C$_{1-4}$ alkyl)NS(=O)—, C$_{1-4}$ alkyl-S(=O)$_2$—, C$_{1-4}$ alkyl-S(=O)$_2$NH—, H$_2$NS(=O)$_2$—, C$_{1-4}$ alkyl-NHS(=O)$_2$—, and di(C$_{1-4}$ alkyl)NS(=O)$_2$—.

In some embodiments of the compounds of Formula (I), the compound is a compound of Formula (Ia):

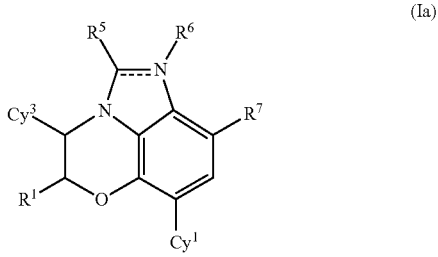

(Ia)

or a pharmaceutically acceptable salt thereof, wherein:
═ represents a single bond or a double bond;
Cy$^1$ is selected from isoxazolyl and pyrazolyl, wherein said isoxazolyl and pyrazolyl of Cy$^1$ is optionally substituted with 1 or 2 groups independently selected from R$^{11}$;
R$^1$ is selected from H, methyl, —C(=O)OCH$_2$CH$_3$, —C(=O)N(H)CH$_2$CH$_3$, —C(=O)N(H)CH$_2$CH$_2$OH, and —C(=O)N(CH$_3$)$_2$;
Cy$^3$ is selected from phenyl, pyridinyl, oxidopyridinyl, thiazolyl, cyclohexyl, dihydrobenzofuranyl and tetrahydrofuranyl, wherein said phenyl, pyridinyl, oxidopyridinyl, thiazolyl, cyclohexyl, dihydrobenzofuranyl and tetrahydrofuranyl of Cy$^3$ is optionally substituted with 1, 2, 3, or 4 groups independently selected from R$^{13}$;
R$^5$ is =O when C═N is a single bond,
alternatively, when C═N is a double bond then R$^5$ is H, methyl, —CH=CH$_2$, —N(H)CH$_3$, —N(H)CH$_2$CH$_3$, —N(H)CH(CH$_3$)$_2$, —N(CH$_3$)$_2$, —N(H)CH$_2$CH$_2$OH, —N(H)CH(CH$_3$)CH$_2$OH, —N(H)CH$_2$CH(OH)CH$_3$, —N(H)C(CH$_3$)$_2$CH$_2$OH, —N(CH$_3$)CH$_2$CH$_2$OH, morpholinyl, pyrrolidinyl, hydroxypyrrolidinyl, piperidinyl, hydroxypiperidinyl, azetidinyl, hydroxyazetidinyl, piperazinyl, butoxycarbonylpiperazinyl, and phenyl;
R$^6$ is selected from H, methyl, ethyl, and propyl wherein said methyl, ethyl, and propyl of R$^6$ are each optionally substituted by 1, 2, or 3 groups independently selected R$^{16}$;
R$^7$ is selected from H, F, Cl, Br, methyl, methoxy, ethoxy, CN, phenyl, and pyridinyl;
R$^{11}$ is independently at each occurrence selected from H, methyl, ethyl, chloro, and methoxy;
R$^{13}$ is independently at each occurrence selected from H, F, CN, methoxy, —CF$_3$, —OCH$_2$C(=O)OH, —OCH$_2$C(=O)N(H)CH$_2$CH$_3$, —OCH$_2$C(=O)N(H)CH$_2$CH$_2$OH, and —OCH$_2$C(=O)N(CH$_3$)$_2$; and
R$^{16}$ is independently at each occurrence selected from H, morpholinyl, and piperidinyl.

In some embodiments of the compounds described above, L is O.

In some embodiments, L is S.
In some embodiments, L is CR$^9$R$^{9a}$.
In some embodiments, L is CH$_2$.
In some embodiments, Cy$^1$ is isoxazolyl substituted with 1 or 2 groups independently selected from R$^{11}$.
In some embodiments, Cy$^1$ is pyrazolyl substituted with 1 or 2 groups independently selected from R$^{11}$.
In some embodiments, R$^1$ is selected from H, methyl, —CH$_2$OH, —C(=O)OCH$_2$CH$_3$, —C(=O)N(H)CH$_2$CH$_3$, —C(=O)N(H)CH$_3$, —C(=O)NH$_2$, —C(=O)N(H)CH$_2$CH$_2$OH, and —C(=O)N(CH$_3$)$_2$.
In some embodiments, R$^1$ is selected from H, methyl, —C(=O)OCH$_2$CH$_3$, —C(=O)N(H)CH$_2$CH$_3$, —C(=O)N(H)CH$_2$CH$_2$OH, and —C(=O)N(CH$_3$)$_2$.
In some embodiments, R$^1$ is H.
In some embodiments, R$^1$ is methyl.
In some embodiments, R$^1$ is —C(=O)OCH$_2$CH$_3$.
In some embodiments, R$^1$ is C(=O)N(H)CH$_2$CH$_3$.
In some embodiments, R$^1$ is C(=O)N(H)CH$_2$CH$_2$OH.
In some embodiments, R$^1$ is —C(=O)N(CH$_3$)$_2$.
In some embodiments, R$^1$ is —C(=O)N(H)CH$_3$.
In some embodiments, R$^1$ is —C(=O)NH$_2$.
In some embodiments, R$^1$ is —CH$_2$OH.
In some embodiments, R$^2$ is H.
In some embodiments, R$^2$ is methyl.
In some embodiments, Cy$^3$ is selected from phenyl, pyridinyl, oxidopyridinyl, thiazolyl, cyclohexyl, dihydrobenzofuranyl, tetrahydrofuranyl, and piperinyl, wherein said phenyl, pyridinyl, oxidopyridinyl, thiazolyl, cyclohexyl, dihydrobenzofuranyl, tetrahydrofuranyl, and piperidinyl of Cy$^3$ is optionally substituted with 1, 2, 3, or 4 groups independently selected from R$^{13}$.
In some embodiments, Cy$^3$ is selected from phenyl, pyridinyl, oxidopyridinyl, thiazolyl, cyclohexyl, dihydrobenzofuranyl and tetrahydrofuranyl, wherein said phenyl, pyridinyl, oxidopyridinyl, thiazolyl, cyclohexyl, dihydrobenzofuranyl and tetrahydrofuranyl of Cy$^3$ is optionally substituted with 1, 2, 3, or 4 groups independently selected from R$^{13}$.
In some embodiments, Cy$^3$ is phenyl optionally substituted with 1, 2, 3, or 4 groups independently selected from R$^{13}$.
In some embodiments, Cy$^3$ is pyridinyl optionally substituted with 1, 2, 3, or 4 groups independently selected from R$^{13}$.
In some embodiments, Cy$^3$ is oxidopyridinyl optionally substituted with 1, 2, 3, or 4 groups independently selected from R$^{13}$.

In some embodiments, $Cy^3$ is thiazolyl optionally substituted with 1, 2, 3, or 4 groups independently selected from $R^{13}$.

In some embodiments, $Cy^3$ is cyclohexyl optionally substituted with 1, 2, 3, or 4 groups independently selected from $R^{13}$.

In some embodiments, $Cy^3$ is dihydrobenzofuranyl optionally substituted with 1, 2, 3, or 4 groups independently selected from $R^{13}$.

In some embodiments, $Cy^3$ is tetrahydrofuranyl optionally substituted with 1, 2, 3, or 4 groups independently selected from $R^{13}$.

In some embodiments, $Cy^3$ is piperidinyl optionally substituted with 1, 2, 3, or 4 groups independently selected from $R^{13}$.

In some embodiments, $R^4$ is H, —C(=O)NH$_2$, —CH$_2$NH$_2$, —CH$_2$N(H)C(=O)CH$_3$, —C(=O)N(H)CH$_3$, —CH$_2$CH$_3$, or —CH$_3$.

In some embodiments, $R^4$ is H.

In some embodiments, $R^5$ is =O when C═N is a single bond.

In some embodiments, $R^5$ is =S when C═N is a single bond.

In some embodiments, when C═N is a double bond then $R^5$ is selected from H, $C_{1-4}$ alkyl, —CH═CH$_2$, NR$^{15a}$R$^{15b}$, —C(=O)NR$^{15a}$R$^{15b}$, phenyl, and a 4-10 membered heterocycloalkyl group comprising carbon and 1, 2, or 3 heteroatoms selected from N, O and S, wherein said alkyl, and 4-10 membered heterocycloalkyl of $R^5$ is optionally substituted by 1 or 2 groups independently selected from $R^{15}$.

In some embodiments, when C═N is a double bond then $R^5$ is selected from H, $C_{1-4}$ alkyl, —CH═CH$_2$, NR$^{15a}$R$^{15b}$, —C(=O)R$^{15a}$R$^{15b}$, phenyl, azetidinyl, pyrrolidinyl, piperidinyl, piperazinyl, 1,2,3,6-tetrahydropyridinyl, 2,5-dihydro-1H-pyrrolyl, 1,4-diazepanyl, morpholinyl, and octahydropyrrolo[1,2-a]pyrazinyl, wherein said $C_{1-4}$ alkyl, phenyl, azetidinyl, pyrolidinyl, piperidinyl, piperazinyl, 1,2,3,6-tetrahydropyridinyl, 2,5-dihydro-1H-pyrrolyl, 1,4-diazepanyl, morpholinyl, and octahydropyrrolo[1,2-a]pyrazinyl of $R^5$ is optionally substituted by 1 or 2 groups independently selected from $R^{15}$.

In some embodiments, when C═N is a double bond then $R^5$ is H, methyl —CH═CH$_2$, —N(H)CH$_3$, —N(H)CH$_2$CH$_3$, —N(H)CH(CH$_3$)$_2$, —N(CH$_3$)$_2$, —N(H)CH$_2$CH$_2$OH, —N(H)CH(CH$_3$)CH$_2$OH, —N(H)CH$_2$CH(OH)CH$_3$, —N(H)C(CH$_3$)$_2$CH$_2$OH, —N(CH$_3$)CH$_2$CH$_2$OH, morpholinyl, pyrrolidinyl, hydroxypyrrolidinyl, piperidinyl, hydroxypiperidinyl, azetidinyl, hydroxyazetidinyl, piperazinyl, butoxycarbonylpiperazinyl, or phenyl.

In some embodiments, when C═N is a double bond then $R^5$ is selected from a 4-6 membered heterocycloalkyl group comprising carbon and 1, 2, or 3 heteroatoms selected from N, O and S, wherein said 4-6 membered heterocycloalkyl of $R^5$ is optionally substituted by 1 or 2 groups independently selected from $R^{15}$.

In some embodiments, when C═N is a double bond then $R^5$ is pyrrolidinyl, piperidinyl, azetidinyl, or piperazinyl, wherein said pyrrolidinyl, piperidinyl, azetidinyl, or piperazinyl of $R^5$ is optionally substituted by 1 or 2 groups independently selected from $R^{15}$.

In some embodiments, when C═N is a double bond than $R^5$ is pyrrolidinyl, wherein said pyrrolidinyl of $R^5$ is optionally substituted by 1 or 2 groups independently selected from $R^{15}$.

In some embodiments, when C═N is a double bond then $R^5$ is piperidinyl, wherein said piperidinyl of $R^5$ is optionally substituted by 1 or 2 groups independently selected from $R^{15}$.

In some embodiments, when C═N is a double bond then $R^5$ is azetidinyl, wherein said azetidinyl of $R^5$ is optionally substituted by 1 or 2 groups independently selected from $R^{15}$.

In some embodiments, when C═N is a double bond then $R^5$ is piperazinyl, wherein said piperazinyl of $R^5$ is optionally substituted by 1 or 2 groups independently selected from $R^{15}$.

In some embodiments, $R^{15}$ is independently at each occurrence selected from $C_{1-6}$ alkyl, CN, OR$^{a5}$, C(=O)R$^{b5}$, C(=O)NR$^{c5}$R$^{d5}$, C(=O)OR$^{a5}$, NR$^{c5}$R$^{d5}$, NR$^{c5}$C(=O)R$^{b5}$, NR$^{c5}$C(=O)NR$^{c5}$R$^{d5}$, NR$^{c5}$C(=O)OR$^{a5}$, S(=O)$_2$R$^{b5}$, NR$^{c5}$S(=O)$_2$R$^{b5}$, and S(=O)$_2$NR$^{c5}$R$^{d5}$, wherein said $C_{1-6}$ alkyl, is optionally substituted by 1, 2, or 3 substituents independently selected from halo, CN, OR$^{a5}$, SR$^{a5}$, C(=O)R$^{b5}$, C(=O)NR$^{c5}$R$^{d5}$, C(=O)OR$^{a5}$, OC(=O)R$^{b5}$, OC(=O)NR$^{c5}$R$^{d5}$, NR$^{c5}$R$^{d5}$, NR$^{c5}$C(=O)R$^{b5}$, NR$^{c5}$C(=O)NR$^{c5}$R$^{d5}$, NR$^{c5}$C(=O)OR$^{a5}$, S(=O)R$^{b5}$, S(=O)NR$^{c5}$R$^{d5}$, S(=O)$_2$R$^{b5}$, NR$^{c5}$S(=O)$_2$R$^{b5}$, S(=O)$_2$NR$^{c5}$R$^{d5}$, 5-6 membered heteroaryl, 4-7 membered heterocycloalkyl, phenyl, and $C_{3-7}$ cycloalkyl.

In some embodiments, $R^6$ is H, $C_{1-4}$ alkyl, or $C_{1-4}$ alkoxy.

In some embodiments, $R^6$ is H, methyl, or methoxy.

In some embodiments, $R^6$ is H.

In some embodiments, $R^7$ is selected from H, halo, CN, NR$^c$R$^d$, $C_{1-6}$ alkyl, $C_{2-6}$ alkenyl, 5-6 membered heteroaryl group comprising carbon and 1, 2, 3 or 4 heteroatoms selected from N, O and S, and a 5-6 membered heterocycloalkyl group comprising carbon and 1, 2, or 3 heteroatoms selected from N, O and S, wherein said alkyl, alkenyl, 5-6 membered heteroaryl group, and 5-6 membered heterocycloalkyl group of $R^7$ are optionally substituted with 1, 2, or 3 groups independently selected from $R^{17}$.

In some embodiments, $R^7$ is selected from H, F, Cl, Br, CN, NR$^c$R$^d$, $C_{1-4}$ alkyl, $C_{2-4}$ alkenyl, pyrazolyl, pyridinyl, pyrimidinyl, and 1,2,3,6-tetrahydropyridinyl, wherein said $C_{1-6}$ alkyl, $C_{2-6}$ alkenyl, pyrazolyl, pyridinyl, pyrimidinyl, and 1,2,3,6-tetrahydropyridinyl of $R^7$ are optionally substituted with 1, 2, or 3 groups independently selected from $R^{17}$.

In some embodiments, $R^7$ is selected from H, halo, $C_{1-4}$ alkyl, and CN.

In some embodiments, $R^7$ is selected from H, Br, methyl, and CN.

In some embodiments, $R^7$ is H.
In some embodiments, $R^7$ is Br.
In some embodiments, $R^7$ is methyl.
In some embodiments, $R^7$ is CN.

In some embodiments, $R^8$ is selected from H, halo, $C_{1-4}$ alkyl, and CN.

In some embodiments, $R^8$ is H.

It is understood that when C═N is a double bond then $R^6$ is absent.

In some embodiments of the compounds of Formula (I), the compound is selected from the following compounds:
7-(3,5-dimethylisoxazol-4-yl)-4-phenyl-4,5-dihydroimidazo[1,5,4-de][1,4]benzoxazin-2(1H)-one;
(4R)-7-(3,5-dimethylisoxazol-4-yl)-4-phenyl-4,5-dihydroimidazo[1,5,4-de][1,4]benzoxazin-2(1H)-one;
(4S)-7-(3,5-dimethylisoxazol-4-yl)-4-phenyl-4,5-dihydroimidazo[1,5,4-de][1,4]benzoxazin-2(1H)-one;
7-(3,5-dimethylisoxazol-4-yl)-1-methyl-4-phenyl-4,5-dihydroimidazo[1,5,4-de][1,4]benzoxazin-2(1H)-one;

7-(3,5-dimethylisoxazol-4-yl)-5-methyl-4-phenyl-4,5-dihydroimidazo[1,5,4-de][1,4]benzoxazin-2(1H)-one;
4-[7-(3,5-dimethylisoxazol-4-yl)-2-oxo-1,2,4,5-tetrahydroimidazo[1,5,4-de][1,4]benzoxazin-4-yl]benzonitrile;
7-(3,5-dimethylisoxazol-4-yl)-4-pyridin-3-yl-4,5-dihydroimidazo[1,5,4-de][1,4]benzoxazin-2(1H)-one;
7-(3,5-dimethylisoxazol-4-yl)-4-(3-methoxyphenyl)-4,5-dihydroimidazo[1,5,4-de][1,4]benzoxazin-2(1H)-one;
7-(3,5-dimethylisoxazol-4-yl)-4-(2-methoxyphenyl)-4,5-dihydroimidazo[1,5,4-de][1,4]benzoxazin-2(1H)-one;
7-(3,5-dimethylisoxazol-4-yl)-4-(2,4-difluorophenyl)-4,5-dihydroimidazo[1,5,4-de][1,4]benzoxazin-2(1H)-one;
7-(3,5-dimethylisoxazol-4-yl)-2-methyl-4-phenyl-4,5-dihydroimidazo[1,5,4-de][1,4]benzoxazine;
7-(3,5-dimethylisoxazol-4-yl)-1-(2-morpholin-4-ylethyl)-4-phenyl-4,5-dihydroimidazo[1,5,4-de][1,4]benzoxazin-2(1H)-one;
7-(3,5-dimethyl-1H-pyrazol-4-yl)-4-phenyl-4,5-dihydroimidazo[1,5,4-de][1,4]benzoxazin-2(1H)-one;
7-(3-methyl-1H-pyrazol-4-yl)-4-phenyl-4,5-dihydroimidazo[1,5,4-de][1,4]benzoxazin-2(1H)-one;
7-(3,5-dimethylisoxazol-4-yl)-4-pyridin-2-yl-4,5-dihydroimidazo[1,5,4-de][1,4]benzoxazin-2(1H)-one;
(4R)-7-(3,5-dimethylisoxazol-4-yl)-4-pyridin-2-yl-4,5-dihydroimidazo[1,5,4-de][1,4]benzoxazin-2(1H)-one;
(4S)-7-(3,5-dimethylisoxazol-4-yl)-4-pyridin-2-yl-4,5-dihydroimidazo[1,5,4-de][1,4]benzoxazin-2(1H)-one;
7-(3,5-dimethylisoxazol-4-yl)-4-(1-oxidopyridin-2-yl)-4,5-dihydroimidazo[1,5,4-de][1,4]benzoxazin-2(1H)-one;
4-cyclohexyl-7-(3,5-dimethylisoxazol-4-yl)-4,5-dihydroimidazo[1,5,4-de][1,4]benzoxazin-2(1H)-one;
7-(3,5-dimethylisoxazol-4-yl)-4-(tetrahydrofuran-2-yl)-4,5-dihydroimidazo[1,5,4-de][1,4]benzoxazin-2(1H)-one;
7-(3,5-dimethylisoxazol-4-yl)-4-(5-fluoropyridin-2-yl)-4,5-dihydroimidazo[1,5,4-de][1,4]benzoxazin-2(1H)-one;
ethyl 7-(3,5-dimethylisoxazol-4-yl)-2-oxo-4-pyridin-2-yl-1,2,4,5-tetrahydroimidazo[1,5,4-de][1,4]benzoxazine-5-carboxylate;
7-(3,5-dimethylisoxazol-4-yl)-4-(1,3-thiazol-2-yl)-4,5-dihydroimidazo[1,5,4-de][1,4]benzoxazin-2(1H)-one;
2-{2-[7-(3,5-dimethylisoxazol-4-yl)-2-oxo-1,2,4,5-tetrahydroimidazo[1,5,4-de][1,4]benzoxazin-4-yl]phenoxy}-N-ethylacetamide;
ethyl 7-(3,5-dimethylisoxazol-4-yl)-2-oxo-4-phenyl-1,2,4,5-tetrahydroimidazo[1,5,4-de][1,4]benzoxazine-5-carboxylate;
7-(3,5-dimethylisoxazol-4-yl)-N-ethyl-2-oxo-4-phenyl-1,2,4,5-tetrahydroimidazo[1,5,4-de][1,4]benzoxazine-5-carboxamide;
7-(3,5-dimethylisoxazol-4-yl)-N-isopropyl-4-phenyl-4,5-dihydroimidazo[1,5,4-de][1,4]benzoxazin-2-amine;
7-(3,5-dimethylisoxazol-4-yl)-N-methyl-4-phenyl-4,5-dihydroimidazo[1,5,4-de][1,4]benzoxazin-2-amine;
7-(3,5-dimethylisoxazol-4-yl)-N-ethyl-4-phenyl-4,5-dihydroimidazo[1,5,4-de][1,4]benzoxazin-2-amine;
7-(3,5-dimethylisoxazol-4-yl)-N,N-dimethyl-4-phenyl-4,5-dihydroimidazo[1,5,4-de][1,4]benzoxazin-2-amine;
2-{[7-(3,5-dimethylisoxazol-4-yl)-4-phenyl-4,5-dihydroimidazo[1,5,4-de][1,4]benzoxazin-2-yl]amino}ethanol;
2-{[7-(3,5-dimethylisoxazol-4-yl)-4-phenyl-4,5-dihydroimidazo[1,5,4-de][1,4]benzoxazin-2-yl]amino}propan-1-ol;
1-{[7-(3,5-dimethylisoxazol-4-yl)-4-phenyl-4,5-dihydroimidazo[1,5,4-de][1,4]benzoxazin-2-yl]amino}propan-2-ol;
2-{[7-(3,5-dimethylisoxazol-4-yl)-4-phenyl-4,5-dihydroimidazo[1,5,4-de][1,4]benzoxazin-2-yl]amino}-2-methylpropan-1-ol;
2-[[7-(3,5-dimethylisoxazol-4-yl)-4-phenyl-4,5-dihydroimidazo[1,5,4-de][1,4]benzoxazin-2-yl](methyl)amino]ethanol;
7-(1-methyl-1H-pyrazol-5-yl)-4-phenyl-4,5-dihydroimidazo[1,5,4-de][1,4]benzoxazin-2(1H)-one;
9-bromo-7-(1-methyl-1H-pyrazol-5-yl)-4-phenyl-4,5-dihydroimidazo[1,5,4-de][1,4]benzoxazin-2(1H)-one;
9-methyl-7-(1-methyl-1H-pyrazol-5-yl)-4-phenyl-4,5-dihydroimidazo[1,5,4-de][1,4]benzoxazin-2(1H)-one;
7-(4-chloro-1-methyl-1H-pyrazol-5-yl)-4-phenyl-4,5-dihydroimidazo[1,5,4-de][1,4]benzoxazin-2(1H)-one;
7-(3,5-dimethylisoxazol-4-yl)-4-phenyl-4,5-dihydroimidazo[1,5,4-de][1,4]benzoxazine;
7-(3,5-dimethylisoxazol-4-yl)-4-phenyl-2-piperazin-1-yl-4,5-dihydroimidazo[1,5,4-de][1,4]benzoxazine;
7-(3,5-dimethylisoxazol-4-yl)-2,4-diphenyl-4,5-dihydroimidazo[1,5,4-de][1,4]benzoxazine;
7-(3,5-dimethylisoxazol-4-yl)-2-oxo-4-phenyl-1,2,4,5-tetrahydroimidazo[1,5,4-de][1,4]benzoxazine-9-carbonitrile;
7-(3,5-dimethylisoxazol-4-yl)-4,9-diphenyl-4,5-dihydroimidazo[1,5,4-de][1,4]benzoxazin-2(1H)-one;
7-(1,4-dimethyl-1H-pyrazol-5-yl)-4-pyridin-2-yl-4,5-dihydroimidazo[1,5,4-de][1,4]benzoxazin-2(1H)-one;
9-bromo-7-(3,5-dimethylisoxazol-4-yl)-4-phenyl-4,5-dihydroimidazo[1,5,4-de][1,4]benzoxazin-2(1H)-one;
7-(3,5-dimethylisoxazol-4-yl)-9-methyl-4-phenyl-4,5-dihydroimidazo[1,5,4-de][1,4]benzoxazin-2(1H)-one;
7-(3,5-dimethylisoxazol-4-yl)-N,N-dimethyl-2-oxo-4-phenyl-1,2,4,5-tetrahydroimidazo[1,5,4-de][1,4]benzoxazine-5-carboxamide;
7-(3,5-dimethylisoxazol-4-yl)-N-(2-hydroxyethyl)-2-oxo-4-phenyl-1,2,4,5-tetrahydroimidazo[1,5,4-de][1,4]benzoxazine-5-carboxamide;
7-(3,5-dimethylisoxazol-4-yl)-4-(4-fluorophenyl)-4,5-dihydroimidazo[1,5,4-de][1,4]benzoxazin-2(1H)-one;
2-{2-[7-(3,5-dimethylisoxazol-4-yl)-2-oxo-1,2,4,5-tetrahydroimidazo[1,5,4-de][1,4]benzoxazin-4-yl]phenoxy}-N-(2-hydroxyethyl)acetamide;
2-{2-[7-(3,5-dimethylisoxazol-4-yl)-2-oxo-1,2,4,5-tetrahydroimidazo[1,5,4-de][1,4]benzoxazin-4-yl]phenoxy}-N,N-dimethylacetamide;
7-(3,5-dimethylisoxazol-4-yl)-4-phenyl-9-pyridin-3-yl-4,5-dihydroimidazo[1,5,4-de][1,4]benzoxazin-2(1H)-one;
7-(3,5-dimethylisoxazol-4-yl)-2-morpholin-4-yl-4-phenyl-4,5-dihydroimidazo[1,5,4-de][1,4]benzoxazine;
7-(3,5-dimethylisoxazol-4-yl)-4-phenyl-2-pyrrolidin-1-yl-4,5-dihydroimidazo[1,5,4-de][1,4]benzoxazine;
1-[7-(3,5-dimethylisoxazol-4-yl)-4-phenyl-4,5-dihydroimidazo[1,5,4-de][1,4]benzoxazin-2-yl]pyrrolidin-3-ol;
7-(3,5-dimethylisoxazol-4-yl)-4-phenyl-2-piperidin-1-yl-4,5-dihydroimidazo[1,5,4-de][1,4]benzoxazine;
1-[7-(3,5-dimethylisoxazol-4-yl)-4-phenyl-4,5-dihydroimidazo[1,5,4-de][1,4]benzoxazin-2-yl]piperidin-4-ol;
1-[7-(3,5-dimethylisoxazol-4-yl)-4-phenyl-4,5-dihydroimidazo[1,5,4-de][1,4]benzoxazin-2-yl]piperidin-3-ol;
1-[7-(3,5-dimethylisoxazol-4-yl)-4-phenyl-4,5-dihydroimidazo[1,5,4-de][1,4]benzoxazin-2-yl]azetidin-3-ol; and
4-[7-(3,5-dimethylisoxazol-4-yl)-4-phenyl-4,5-dihydroimidazo[1,5,4-de][1,4]benzoxazin-2-yl]piperazine-1-carboxylate;
or a pharmaceutically acceptable salt thereof.

In some embodiments of the compounds of Formula (I), the compound is selected from the following compounds:

7-(3,5-Dimethylisoxazol-4-yl)-5,5-dimethyl-4-pyridin-2-yl-4,5-dihydroimidazo[1,5,4-de][1,4]benzoxazin-2(1H)-one;

7-(3,5-Dimethylisoxazol-4-yl)-5-(hydroxymethyl)-4-pyridin-2-yl-4,5-dihydroimidazo[1,5,4-de][1,4]benzoxazin-2(1H)-one;

7-(3,5-Dimethylisoxazol-4-yl)-4-piperidin-2-yl-4,5-dihydroimidazo[1,5,4-de][1,4]benzoxazin-2(1H)-one;

4-(1-Acetylpiperidin-2-yl)-7-(3,5-dimethylisoxazol-4-yl)-4,5-dihydroimidazo[1,5,4-de][1,4]benzoxazin-2(1H)-one;

[7-(3,5-Dimethylisoxazol-4-yl)-2-oxo-1,2,4,5-tetrahydroimidazo[1,5,4-de][1,4]benzoxazin-4-yl]methyl acetate;

7-(3,5-Dimethylisoxazol-4-yl)-4-(hydroxymethyl)-4,5-dihydroimidazo[1,5,4-de][1,4]benzoxazin-2(1H)-one;

7-(3,5-Dimethylisoxazol-4-yl)-4-methyl-4-pyridin-2-yl-4,5-dihydroimidazo[1,5,4-de][1,4]benzoxazin-2(1H)-one;

7-(3,5-Dimethylisoxazol-4-yl)-4-ethyl-4-pyridin-2-yl-4,5-dihydroimidazo[1,5,4-de][1,4]benzoxazin-2(1H)-one;

7-(3,5-Dimethylisoxazol-4-yl)-N-methyl-2-oxo-4-pyridin-2-yl-1,2,4,5-tetrahydroimidazo[1,5,4-de][1,4]benzoxazine-4-carboxamide;

N-{[7-(3,5-Dimethylisoxazol-4-yl)-2-oxo-4-pyridin-2-yl-1,2,4,5-tetrahydroimidazo[1,5,4-de][1,4]benzoxazin-4-yl]methyl}acetamide;

4-(Aminomethyl)-7-(3,5-dimethylisoxazol-4-yl)-4-pyridin-2-yl-4,5-dihydroimidazo[1,5,4-de][1,4]benzoxazin-2(1H)-one;

7-(3,5-Dimethylisoxazol-4-yl)-2-oxo-4-pyridin-2-yl-1,2,4,5-tetrahydroimidazo[1,5,4-de][1,4]benzoxazine-4-carboxamide;

7-(3,5-dimethylisoxazol-4-yl)-5-methyl-4-pyridin-2-yl-4,5-dihydroimidazo[1,5,4-de][1,4]benzoxazin-2(1H)-one;

7-(3,5-Dimethylisoxazol-4-yl)-N-methyl-2-oxo-4-pyridin-2-yl-1,2,4,5-tetrahydroimidazo[1,5,4-de][1,4]benzoxazine-5-carboxamide;

7-(3,5-dimethylisoxazol-4-yl)-2-oxo-4-pyridin-2-yl-1,2,4,5-tetrahydroimidazo[1,5,4-de][1,4]benzoxazine-5-carboxamide;

7-(3,5-dimethylisoxazol-4-yl)-4-(5-fluoropyridin-3-yl)-4,5-dihydroimidazo[1,5,4-de][1,4]benzoxazin-2(1H)-one;

7-(3,5-dimethylisoxazol-4-yl)-4-[1-(methylsulfonyl)piperidin-2-yl]-4,5-dihydroimidazo[1,5,4-de][1,4]benzoxazin-2(1H)-one;

2-[7-(3,5-dimethylisoxazol-4-yl)-2-oxo-1,2,4,5-tetrahydroimidazo[1,5,4-de][1,4]benzoxazin-4-yl]-N-isopropylpiperidine-1-carboxamide;

(4S)-7-(3,5-dimethylisoxazol-4-yl)-9-(1-methyl-1H-pyrazol-4-yl)-4-pyridin-2-yl-4,5-dihydroimidazo[1,5,4-de][1,4]benzoxazin-2(1H)-one;

5-[(4S)-7-(3,5-dimethylisoxazol-4-yl)-2-oxo-4-pyridin-2-yl-1,2,4,5-tetrahydroimidazo[1,5,4-de][1,4]benzoxazin-9-yl]-N,N-dimethylpyridine-2-carboxamide;

tert-butyl 4-[(4S)-7-(3,5-dimethylisoxazol-4-yl)-2-oxo-4-pyridin-2-yl-1,2,4,5-tetrahydroimidazo[1,5,4-de][1,4]benzoxazin-9-yl]-3,6-dihydropyridine-1(2H)-carboxylate;

(4S)-7-(3,5-dimethylisoxazol-4-yl)-4-pyridin-2-yl-9-pyrimidin-5-yl-4,5-dihydroimidazo[1,5,4-de][1,4]benzoxazin-2(1H)-one;

(4S)-7-(3,5-dimethylisoxazol-4-yl)-9-(1-methyl-1H-pyrazol-5-yl)-4-pyridin-2-yl-4,5-dihydroimidazo[1,5,4-de][1,4]benzoxazin-2(1H)-one;

ethyl (2E)-3-[(4S)-7-(3,5-dimethylisoxazol-4-yl)-2-oxo-4-pyridin-2-yl-1,2,4,5-tetrahydroimidazo[1,5,4-de][1,4]benzoxazin-9-yl]acrylate;

(4S)-7-(3,5-dimethylisoxazol-4-yl)-4-pyridin-2-yl-9-(1,2,3,6-tetrahydropyridin-4-yl)-4,5-dihydroimidazo[1,5,4-de][1,4]benzoxazin-2(1H)-one;

(4S)-7-(3,5-Dimethylisoxazol-4-yl)-4-pyridin-2-yl-2-vinyl-4,5-dihydroimidazo[1,5,4-de][1,4]benzoxazine;

(1R)-1-[(4S)-7-(3,5-Dimethylisoxazol-4-yl)-4-pyridin-2-yl-4,5-dihydroimidazo[1,5,4-de][1,4]benzoxazin-2-yl]ethane-1,2-diol;

1-[(4S)-7-(3,5-Dimethylisoxazol-4-yl)-4-pyridin-2-yl-4,5-dihydroimidazo[1,5,4-de][1,4]benzoxazin-2-yl]ethanol;

(4S)-7-(3,5-Dimethylisoxazol-4-yl)-N,N-dimethyl-4-pyridin-2-yl-4,5-dihydroimidazo[1,5,4-de][1,4]benzoxazine-2-carboxamide;

(4S)-7-(3,5-Dimethylisoxazol-4-yl)-4-pyridin-2-yl-4,5-dihydroimidazo[1,5,4-de][1,4]benzoxazine;

tert-Butyl (4S)-7-(3,5-dimethylisoxazol-4-yl)-4-pyridin-2-yl-4,5-dihydroimidazo[1,5,4-de][1,4]benzoxazine-2-carboxylate;

(4S)-7-(3,5-Dimethylisoxazol-4-yl)-2-(morpholin-4-ylcarbonyl)-4-pyridin-2-yl-4,5-dihydroimidazo[1,5,4-de][1,4]benzoxazine;

(4S)-7-(3,5-Dimethylisoxazol-4-yl)-N-methyl-4-pyridin-2-yl-4,5-dihydroimidazo[1,5,4-de][1,4]benzoxazine-2-carboxamide;

(4S)-7-(3,5-Dimethylisoxazol-4-yl)-4-pyridin-2-yl-4,5-dihydroimidazo[1,5,4-de][1,4]benzoxazine-2-carboxamide;

tert-Butyl 4-[(4S)-7-(3,5-dimethylisoxazol-4-yl)-4-pyridin-2-yl-4,5-dihydroimidazo[1,5,4-de][1,4]benzoxazin-2-yl]-3,6-dihydropyridine-1(2H)-carboxylate;

tert-Butyl 3-[(4S)-7-(3,5-dimethylisoxazol-4-yl)-4-pyridin-2-yl-4,5-dihydroimidazo[1,5,4-de][1,4]benzoxazin-2-yl]-2,5-dihydro-1H-pyrrole-1-carboxylate;

tert-Butyl 5-[(4S)-7-(3,5-dimethylisoxazol-4-yl)-4-pyridin-2-yl-4,5-dihydroimidazo[1,5,4-de][1,4]benzoxazin-2-yl]-3,6-dihydropyridine-1(2H)-carboxylate;

tert-Butyl 4-[(4S)-7-(3,5-dimethylisoxazol-4-yl)-4-pyridin-2-yl-4,5-dihydroimidazo[1,5,4-de][1,4]benzoxazin-2-yl]piperidine-1-carboxylate;

tert-Butyl 3-[(4S)-7-(3,5-dimethylisoxazol-4-yl)-4-pyridin-2-yl-4,5-dihydroimidazo[1,5,4-de][1,4]benzoxazin-2-yl]pyrrolidine-1-carboxylate;

tert-Butyl 3-[(4S)-7-(3,5-dimethylisoxazol-4-yl)-4-pyridin-2-yl-4,5-dihydroimidazo[1,5,4-de][1,4]benzoxazin-2-yl]piperidine-1-carboxylate;

(4S)-2-(1-Acetylpiperidin-4-yl)-7-(3,5-dimethylisoxazol-4-yl)-4-pyridin-2-yl-4,5-dihydroimidazo[1,5,4-de][1,4]benzoxazine;

(4S)-7-(3,5-dimethylisoxazol-4-yl)-4-pyridin-2-yl-2-(1,2,3,6-tetrahydropyridin-4-yl)-4,5-dihydroimidazo[1,5,4-de][1,4]benzoxazine;

(4S)-2-(2,5-dihydro-1H-pyrrol-3-yl)-7-(3,5-dimethylisoxazol-4-yl)-4-pyridin-2-yl-4,5-dihydroimidazo[1,5,4-de][1,4]benzoxazine;

(4S)-7-(3,5-dimethylisoxazol-4-yl)-4-pyridin-2-yl-2-pyrrolidin-3-yl-4,5-dihydroimidazo[1,5,4-de][1,4]benzoxazine;

(4S)-7-(3,5-dimethylisoxazol-4-yl)-4-pyridin-2-yl-2-(1,2,5,6-tetrahydropyridin-3-yl)-4,5-dihydroimidazo[1,5,4-de][1,4]benzoxazine;

(4S)-7-(3,5-dimethylisoxazol-4-yl)-2-piperidin-3-yl-4-pyridin-2-yl-4,5-dihydroimidazo[1,5,4-de][1,4]benzoxazine;

(4S)-2-(1-Acetylpiperidin-4-yl)-7-(3,5-dimethylisoxazol-4-yl)-4-pyridin-2-yl-4,5-dihydroimidazo[1,5,4-de][1,4]benzoxazine;

(4S)-2-(1-acetyl-1,2,3,6-tetrahydropyridin-4-yl)-7-(3,5-dimethylisoxazol-4-yl)-4-pyridin-2-yl-4,5-dihydroimidazo[1,5,4-de][1,4]benzoxazine;

(4S)-2-[1-(cyclopropylcarbonyl)piperidin-4-yl]-7-(3,5-dimethylisoxazol-4-yl)-4-pyridin-2-yl-4,5-dihydroimidazo[1,5,4-de][1,4]benzoxazine;

(4S)-7-(3,5-dimethylisoxazol-4-yl)-2-[1-(methylsulfonyl)piperidin-4-yl]-4-pyridin-2-yl-4,5-dihydroimidazo[1,5,4-de][1,4]benzoxazine;

(4S)-2-(1-acetylpyrrolidin-3-yl)-7-(3,5-dimethylisoxazol-4-yl)-4-pyridin-2-yl-4,5-dihydroimidazo[1,5,4-de][1,4]benzoxazine;

(4S)-2-[1-(cyclopropylcarbonyl)pyrrolidin-3-yl]-7-(3,5-dimethylisoxazol-4-yl)-4-pyridin-2-yl-4,5-dihydroimidazo[1,5,4-de][1,4]benzoxazine;

(4S)-7-(3,5-dimethylisoxazol-4-yl)-2-[1-(methylsulfonyl)pyrrolidin-3-yl]-4-pyridin-2-yl-4,5-dihydroimidazo[1,5,4-de][1,4]benzoxazine;

(4S)-2-(1-acetyl-1,2,5,6-tetrahydropyridin-3-yl)-7-(3,5-dimethylisoxazol-4-yl)-4-pyridin-2-yl-4,5-dihydroimidazo[1,5,4-de][1,4]benzoxazine;

(4S)-2-(1-acetylpiperidin-3-yl)-7-(3,5-dimethylisoxazol-4-yl)-4-pyridin-2-yl-4,5-dihydroimidazo[1,5,4-de][1,4]benzoxazine;

(4S)-2-[1-(cyclopropylcarbonyl)piperidin-3-yl]-7-(3,5-dimethylisoxazol-4-yl)-4-pyridin-2-yl-4,5-dihydroimidazo[1,5,4-de][1,4]benzoxazine;

(4S)-7-(3,5-dimethylisoxazol-4-yl)-2-[1-(methylsulfonyl)piperidin-3-yl]-4-pyridin-2-yl-4,5-dihydroimidazo[1,5,4-de][1,4]benzoxazine;

7-(3,5-Dimethylisoxazol-4-yl)-4-phenyl-5,6-dihydro-4H-imidazo[4,5,1-ij]quinolin-2(1H)-one;

7-(3,5-Dimethylisoxazol-4-yl)-1-methyl-4-phenyl-5,6-dihydro-4H-imidazo[4,5,1-ij]quinolin-2(1H)-one;

7-(3,5-Dimethylisoxazol-4-yl)-1-methoxy-4-pyridin-2-yl-5,6-dihydro-4H-imidazo[4,5,1-ij]quinolin-2(1H)-one;

7-(3,5-Dimethylisoxazol-4-yl)-4-pyridin-2-yl-5,6-dihydro-4H-imidazo[4,5,1-ij]quinolin-2(1H)-one;

7-[5-(Hydroxymethyl)-3-methylisoxazol-4-yl]-4-pyridin-2-yl-4,5-dihydroimidazo[1,5,4-de][1,4]benzoxazin-2(1H)-one;

7-[5-(Fluoromethyl)-3-methylisoxazol-4-yl]-4-pyridin-2-yl-4,5-dihydroimidazo[1,5,4-de][1,4]benzoxazin-2(1H)-one;

3-[7-(3,5-Dimethylisoxazol-4-yl)-2-oxo-1,2,4,5-tetrahydroimidazo[1,5,4-de][1,4]benzoxazin-4-yl]pyridine-2-carbonitrile;

3-[7-(3,5-Dimethylisoxazol-4-yl)-2-oxo-1,2,4,5-tetrahydroimidazo[1,5,4-de][1,4]benzoxazin-4-yl]pyridine-2-carboxamide;

3-[7-(3,5-Dimethylisoxazol-4-yl)-2-oxo-1,2,4,5-tetrahydroimidazo[1,5,4-de][1,4]benzoxazin-4-yl]-N-methylpyridine-2-carboxamide;

3-[7-(3,5-Dimethylisoxazol-4-yl)-2-oxo-1,2,4,5-tetrahydroimidazo[1,5,4-de][1,4]benzoxazin-4-yl]-N,N-dimethylpyridine-2-carboxamide;

4-[2-(Aminomethyl)pyridin-3-yl]-7-(3,5-dimethylisoxazol-4-yl)-4,5-dihydroimidazo[1,5,4-de][1,4]benzoxazin-2(1H)-one;

N-({3-[7-(3,5-Dimethylisoxazol-4-yl)-2-oxo-1,2,4,5-tetrahydroimidazo[1,5,4-de][1,4]benzoxazin-4-yl]pyridin-2-yl}methyl)acetamide;

Methyl 3-[7-(3,5-dimethylisoxazol-4-yl)-2-oxo-1,2,4,5-tetrahydroimidazo[1,5,4-de][1,4]benzoxazin-4-yl]pyridine-2-carboxylate;

3-[7-(3,5-dimethylisoxazol-4-yl)-2-oxo-1,2,4,5-tetrahydroimidazo[1,5,4-de][1,4]benzoxazin-4-yl]-N-ethylpyridine-2-carboxamide;

N-Cyclopropyl-3-[7-(3,5-dimethylisoxazol-4-yl)-2-oxo-1,2,4,5-tetrahydroimidazo[1,5,4-de][1,4]benzoxazin-4-yl]pyridine-2-carboxamide;

3-[7-(3,5-Dimethylisoxazol-4-yl)-2-oxo-1,2,4,5-tetrahydroimidazo[1,5,4-de][1,4]benzoxazin-4-yl]-N-(2-hydroxyethyl)pyridine-2-carboxamide;

3-[7-(3,5-dimethylisoxazol-4-yl)-2-oxo-1,2,4,5-tetrahydroimidazo[1,5,4-de][1,4]benzoxazin-4-yl]-N-(2,2,2-trifluoroethyl)pyridine-2-carboxamide;

(4S)-9-(Aminomethyl)-7-(3,5-dimethylisoxazol-4-yl)-4-pyridin-2-yl-4,5-dihydroimidazo[1,5,4-de][1,4]benzoxazin-2(1H)-one;

N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}acetamide;

N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}-2-phenylacetamide;

N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}-2-methoxyacetamide;

N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}methanesulfonamide;

N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}-N'-isopropylurea;

2-(Dimethylamino)-N-{[(4S)-7-(3,5-dimethylisoxazol-4-yl)-2-oxo-4-pyridin-2-yl-1,2,4,5-tetrahydroimidazo[1,5,4-de][1,4]benzoxazin-9-yl]methyl}acetamide;

(4S)-7-(3,5-dimethylisoxazol-4-yl)-9-(1-hydroxyethyl)-4-pyridin-2-yl-4,5-dihydroimidazo[1,5,4-de][1,4]benzoxazin-2(1H)-one;

(3R)-1-[(4S)-7-(3,5-Dimethylisoxazol-4-yl)-4-pyridin-2-yl-4,5-dihydroimidazo[1,5,4-de][1,4]benzoxazin-2-yl]-N-isopropylpyrrolidine-3-carboxamide;

1-[(4S)-7-(3,5-Dimethylisoxazol-4-yl)-4-pyridin-2-yl-4,5-dihydroimidazo[1,5,4-de][1,4]benzoxazin-2-yl]-3-methylpyrrolidin-3-ol;

4-[(4S)-7-(3,5-Dimethylisoxazol-4-yl)-4-pyridin-2-yl-4,5-dihydroimidazo[1,5,4-de][1,4]benzoxazin-2-yl]-1,4-diazepane-1-sulfonamide;

(4S)-2-(4-Acetyl-1,4-diazepan-1-yl)-7-(3,5-dimethylisoxazol-4-yl)-4-pyridin-2-yl-4,5-dihydroimidazo[1,5,4-de][1,4]benzoxazine;

(4S)-7-(3,5-Dimethylisoxazol-4-yl)-2-[4-(methylsulfonyl)-1,4-diazepan-1-yl]-4-pyridin-2-yl-4,5-dihydroimidazo[1,5,4-de][1,4]benzoxazine;

(4S)-7-(3,5-Dimethylisoxazol-4-yl)-2-piperazin-1-yl-4-pyridin-2-yl-4,5-dihydroimidazo[1,5,4-de][1,4]benzoxazine;

2-{4-[(4S)-7-(3,5-Dimethylisoxazol-4-yl)-4-pyridin-2-yl-4,5-dihydroimidazo[1,5,4-de][1,4]benzoxazin-2-yl]piperazin-1-yl}-N,N-dimethylacetamide;

2-Cyano-N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N-methylacetamide;

N-{(3R)-1-[(4S)-7-(3,5-Dimethylisoxazol-4-yl)-4-pyridin-2-yl-4,5-dihydroimidazo[1,5,4-de][1,4]benzoxazin-2-yl]pyrrolidin-3-yl}morpholine-4-carboxamide;

7-(3,5-Dimethylisoxazol-4-yl)-2-methyl-4-pyridin-2-yl-4,5-dihydroimidazo[1,5,4-de][1,4]benzoxazine;

Methyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate;

7-(3,5-Dimethylisoxazol-4-yl)-9-fluoro-N,N-dimethyl-4-pyridin-3-yl-4,5-dihydroimidazo[1,5,4-de][1,4]benzoxazin-2-amine;

1-[7-(3,5-Dimethylisoxazol-4-yl)-9-fluoro-4-pyridin-3-yl-4,5-dihydroimidazo[1,5,4-de][1,4]benzoxazin-2-yl]pyrrolidin-3-ol;

7-(3,5-Dimethylisoxazol-4-yl)-N-ethyl-9-fluoro-4-pyridin-3-yl-4,5-dihydroimidazo[1,5,4-de][1,4]benzoxazin-2-amine;

(3R)-1-[7-(3,5-Dimethylisoxazol-4-yl)-4-pyridin-3-yl-4,5-dihydroimidazo[1,5,4-de][1,4]benzoxazin-2-yl]pyrrolidin-3-ol;

1-[7-(3,5-Dimethylisoxazol-4-yl)-4-pyridin-3-yl-4,5-dihydroimidazo[1,5,4-de][1,4]benzoxazin-2-yl]azetidin-3-ol;

(4S)-7-(3,5-dimethylisoxazol-4-yl)-2-morpholin-4-yl-4-pyridin-2-yl-4,5-dihydroimidazo[1,5,4-de][1,4]benzoxazine;

(4S)-7-(3,5-dimethylisoxazol-4-yl)-4-pyridin-2-yl-2-pyrrolidin-1-yl-4,5-dihydroimidazo[1,5,4-de][1,4]benzoxazine;

(4S)-7-(3,5-dimethylisoxazol-4-yl)-2-(4-methylpiperazin-1-yl)-4-pyridin-2-yl-4,5-dihydroimidazo[1,5,4-de][1,4]benzoxazine;

(4S)-2-azetidin-1-yl-7-(3,5-dimethylisoxazol-4-yl)-4-pyridin-2-yl-4,5-dihydroimidazo[1,5,4-de][1,4]benzoxazine;

1-[(4S)-7-(3,5-dimethylisoxazol-4-yl)-4-pyridin-2-yl-4,5-dihydroimidazo[1,5,4-de][1,4]benzoxazin-2-yl]azetidin-3-ol;

4-[(4S)-7-(3,5-dimethylisoxazol-4-yl)-4-pyridin-2-yl-4,5-dihydroimidazo[1,5,4-de][1,4]benzoxazin-2-yl]-1-methylpiperazin-2-one;

ethyl 4-[(4S)-7-(3,5-dimethylisoxazol-4-yl)-4-pyridin-2-yl-4,5-dihydroimidazo[1,5,4-de][1,4]benzoxazin-2-yl]piperazine-1-carboxylate;

(3R)-1-[(4S)-7-(3,5-Dimethylisoxazol-4-yl)-4-pyridin-3-yl-4,5-dihydroimidazo[1,5,4-de][1,4]benzoxazin-2-yl]pyrrolidin-3-ol;

(3S)-1-[(4S)-7-(3,5-Dimethylisoxazol-4-yl)-4-pyridin-3-yl-4,5-dihydroimidazo[1,5,4-de][1,4]benzoxazin-2-yl]pyrrolidin-3-ol;

1-[(4S)-7-(3,5-dimethylisoxazol-4-yl)-4-pyridin-2-yl-4,5-dihydroimidazo[1,5,4-de][1,4]benzoxazin-2-yl]piperidin-4-ol;

(3R)-1-[(4S)-7-(3,5-dimethylisoxazol-4-yl)-4-pyridin-2-yl-4,5-dihydroimidazo[1,5,4-de][1,4]benzoxazin-2-yl]piperidin-3-ol;

(3S)-1-[(4S)-7-(3,5-dimethylisoxazol-4-yl)-4-pyridin-2-yl-4,5-dihydroimidazo[1,5,4-de][1,4]benzoxazin-2-yl]piperidin-3-ol;

1-[(4S)-7-(3,5-dimethylisoxazol-4-yl)-4-pyridin-2-yl-4,5-dihydroimidazo[1,5,4-de][1,4]benzoxazin-2-yl]-N,N-dimethylpiperidin-4-amine;

4-[(4S)-7-(3,5-dimethylisoxazol-4-yl)-4-pyridin-2-yl-4,5-dihydroimidazo[1,5,4-de][1,4]benzoxazin-2-yl]piperazin-2-one;

(4S)-7-(3,5-dimethylisoxazol-4-yl)-2-[4-(methylsulfonyl)piperazin-1-yl]-4-pyridin-2-yl-4,5-dihydroimidazo[1,5,4-de][1,4]benzoxazine;

(4S)-7-(3,5-dimethylisoxazol-4-yl)-2-(4-isopropylpiperazin-1-yl)-4-pyridin-2-yl-4,5-dihydroimidazo[1,5,4-de][1,4]benzoxazine;

1-[(4S)-7-(3,5-dimethylisoxazol-4-yl)-4-pyridin-2-yl-4,5-dihydroimidazo[1,5,4-de][1,4]benzoxazin-2-yl]piperidine-4-carbonitrile;

{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}methanol;

2-{4-[(4S)-7-(3,5-dimethylisoxazol-4-yl)-4-pyridin-2-yl-4,5-dihydroimidazo[1,5,4-de][1,4]benzoxazin-2-yl]piperazin-1-yl}ethanol;

(4S)-7-(3,5-dimethylisoxazol-4-yl)-2-(4-phenylpiperazin-1-yl)-4-pyridin-2-yl-4,5-dihydroimidazo[1,5,4-de][1,4]benzoxazine;

(4S)-2-(4-benzylpiperazin-1-yl)-7-(3,5-dimethylisoxazol-4-yl)-4-pyridin-2-yl-4,5-dihydroimidazo[1,5,4-de][1,4]benzoxazine;

(3R)-1-[(4S)-7-(3,5-dimethylisoxazol-4-yl)-4-pyridin-2-yl-4,5-dihydroimidazo[1,5,4-de][1,4]benzoxazin-2-yl]-N,N-dimethylpyrrolidin-3-amine;

(3S)-1-[(4S)-7-(3,5-dimethylisoxazol-4-yl)-4-pyridin-2-yl-4,5-dihydroimidazo[1,5,4-de][1,4]benzoxazin-2-yl]-N,N-dimethylpyrrolidin-3-amine;

(3R)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidin-3-amine;

(3S)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidin-3-amine;

tert-butyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate;

tert-butyl {(3S)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate;

(4S)-2-[4-(cyclopropylmethyl)piperazin-1-yl]-7-(3,5-dimethylisoxazol-4-yl)-4-pyridin-2-yl-4,5-dihydroimidazo[1,5,4-de][1,4]benzoxazine;

(4S)-7-(3,5-dimethylisoxazol-4-yl)-2-[4-(2-methoxyethyl)piperazin-1-yl]-4-pyridin-2-yl-4,5-dihydroimidazo[1,5,4-de][1,4]benzoxazine;

2-[[7-(3,5-dimethylisoxazol-4-yl)-4-pyridin-2-yl-4,5-dihydroimidazo[1,5,4-de][1,4]benzoxazin-2-yl](methyl)amino]ethanol;

7-(3,5-dimethylisoxazol-4-yl)-N-methyl-4-pyridin-2-yl-4,5-dihydroimidazo[1,5,4-de][1,4]benzoxazin-2-amine;

7-(3,5-dimethylisoxazol-4-yl)-N,N-dimethyl-4-pyridin-2-yl-4,5-dihydroimidazo[1,5,4-de][1,4]benzoxazin-2-amine;

1-[(4S)-7-(3,5-dimethylisoxazol-4-yl)-4-pyridin-2-yl-4,5-dihydroimidazo[1,5,4-de][1,4]benzoxazin-2-yl]piperidine-4-carboxamide;

1-[(4S)-7-(3,5-dimethylisoxazol-4-yl)-4-pyridin-2-yl-4,5-dihydroimidazo[1,5,4-de][1,4]benzoxazin-2-yl]-N-methylpiperidine-4-carboxamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}acetamide;

2-{4-[(4S)-7-(3,5-dimethylisoxazol-4-yl)-4-pyridin-2-yl-4,5-dihydroimidazo[1,5,4-de][1,4]benzoxazin-2-yl]piperazin-1-yl}acetamide;

(4S)-7-(3,5-dimethylisoxazol-4-yl)-2-(4-ethylpiperazin-1-yl)-4-pyridin-2-yl-4,5-dihydroimidazo[1,5,4-de][1,4]benzoxazine;

(4S)-7-(3,5-dimethylisoxazol-4-yl)-2-[(8aS)-hexahydropyrrolo[1,2-a]pyrazin-2(1H)-yl]-4-pyridin-2-yl-4,5-dihydroimidazo[1,5,4-de][1,4]benzoxazine;

(4S)-7-(3,5-dimethylisoxazol-4-yl)-2-[(8aR)-hexahydropyrrolo[1,2-a]pyrazin-2(1H)-yl]-4-pyridin-2-yl-4,5-dihydroimidazo[1,5,4-de][1,4]benzoxazine;

1-[(4S)-7-(3,5-dimethylisoxazol-4-yl)-4-pyridin-2-yl-4,5-dihydroimidazo[1,5,4-de][1,4]benzoxazin-2-yl]-4-methylpiperidin-4-ol;

4-[(4S)-7-(3,5-dimethylisoxazol-4-yl)-4-pyridin-2-yl-4,5-dihydroimidazo[1,5,4-de][1,4]benzoxazin-2-yl]-3-methylpiperazin-2-one;

tert-butyl {1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}carbamate;

tert-butyl 4-[(4S)-7-(3,5-dimethylisoxazol-4-yl)-4-pyridin-2-yl-4,5-dihydroimidazo[1,5,4-de][1,4]benzoxazin-2-yl]-1,4-diazepane-1-carboxylate;

2-{[(4S)-7-(3,5-dimethylisoxazol-4-yl)-4-pyridin-2-yl-4,5-dihydroimidazo[1,5,4-de][1,4]benzoxazin-2-yl]amino}ethanol;

tert-butyl (2-{[(4S)-7-(3,5-dimethylisoxazol-4-yl)-4-pyridin-2-yl-4,5-dihydroimidazo[1,5,4-de][1,4]benzoxazin-2-yl]amino}ethyl)carbamate;

N-[(4S)-7-(3,5-dimethylisoxazol-4-yl)-4-pyridin-2-yl-4,5-dihydroimidazo[1,5,4-de][1,4]benzoxazin-2-yl]ethane-1,2-diamine;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}acetamide;

N-{(3S)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}acetamide;

(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-amine;

(3S)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-amine;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2,2,2-trifluoroacetamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2-methoxyacetamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}cyclopropanecarboxamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl)}methanesulfonamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}propanamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2-methylpropanamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}cyclobutanecarboxamide;

2-cyano-N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}acetamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}tetrahydro-2H-pyran-4-carboxamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}ethanesulfonamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}propane-1-sulfonamide;

N'-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N,N-dimethylurea;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}propane-2-sulfonamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}cyclopropanesulfonamide;

methyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}methylcarbamate;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N-methylmethanesulfonamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2-methoxy-N-methylacetamide;

N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N-methylacetamide;

(4S)-2-(4-acetylpiperazin-1-yl)-7-(3,5-dimethylisoxazol-4-yl)-4-pyridin-2-yl-4,5-dihydroimidazo[1,5,4-de][1,4]benzoxazine;

(4S)-7-(3,5-dimethylisoxazol-4-yl)-2-(4-propionylpiperazin-1-yl)-4-pyridin-2-yl-4,5-dihydroimidazo[1,5,4-de][1,4]benzoxazine;

(4S)-7-(3,5-dimethylisoxazol-4-yl)-2-[4-(ethylsulfonyl)piperazin-1-yl]-4-pyridin-2-yl-4,5-dihydroimidazo[1,5,4-de][1,4]benzoxazine;

(4S)-7-(3,5-dimethylisoxazol-4-yl)-2-[4-(2-oxo-2-pyrrolidin-1-ylethyl)piperazin-1-yl]-4-pyridin-2-yl-4,5-dihydroimidazo[1,5,4-de][1,4]benzoxazine;

4-[(4S)-7-(3,5-dimethylisoxazol-4-yl)-4-pyridin-2-yl-4,5-dihydroimidazo[1,5,4-de][1,4]benzoxazin-2-yl]piperazine-1-sulfonamide;

1-[(4S)-7-(3,5-dimethylisoxazol-4-yl)-4-pyridin-2-yl-4,5-dihydroimidazo[1,5,4-de][1,4]benzoxazin-2-yl]azetidin-3-amine;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}acetamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}propanamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}-2-methylpropanamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}-2-methoxyacetamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}cyclopropanecarboxamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}cyclobutanecarboxamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}methanesulfonamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}ethanesulfonamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}propane-2-sulfonamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}methanesulfonamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-2-methoxyacetamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-2,2,2-trifluoroacetamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}propanamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}propanamide;

(4S)-7-(3,5-dimethylisoxazol-4-yl)-2-(4-propionyl-1,4-diazepan-1-yl)-4-pyridin-2-yl-4,5-dihydroimidazo[1,5,4-de][1,4]benzoxazine;

(4S)-7-(3,5-dimethylisoxazol-4-yl)-2-[4-(ethylsulfonyl)-1,4-diazepan-1-yl]-4-pyridin-2-yl-4,5-dihydroimidazo[1,5,4-de][1,4]benzoxazine;

(3R)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidine-3-carboxamide;

(3R)-1-[(4S)-7-(3,5-dimethylisoxazol-4-yl)-4-pyridin-2-yl-4,5-dihydroimidazo[1,5,4-de][1,4]benzoxazin-2-yl]-N-ethylpyrrolidine-3-carboxamide;

(3R)—N-cyclopropyl-1-[(4S)-7-(3,5-dimethylisoxazol-4-yl)-4-pyridin-2-yl-4,5-dihydroimidazo[1,5,4-de][1,4]benzoxazin-2-yl]pyrrolidine-3-carboxamide;

(4S)-8,9-dichloro-7-(3,5-dimethylisoxazol-4-yl)-4-pyridin-2-yl-4,5-dihydroimidazo[1,5,4-de][1,4]benzoxazin-2(1H)-one;

7-(3,5-Dimethylisoxazol-4-yl)-9-[(isopropylamino)methyl]-4-pyridin-2-yl-4,5-dihydroimidazo[1,5,4-de][1,4]benzoxazin-2(1H)-one;

7-(3,5-Dimethylisoxazol-4-yl)-9-(hydroxymethyl)-4-pyridin-2-yl-4,5-dihydroimidazo[1,5,4-de][1,4]benzoxazin-2(1H)-one;

7-(3,5-Dimethylisoxazol-4-yl)-4-pyridin-2-yl-4,5-dihydroimidazo[1,5,4-de][1,4]benzoxazine-2(1H)-thione;

7-(3,5-dimethylisoxazol-4-yl)-9-(1H-pyrazol-4-yl)-4-pyridin-2-yl-4,5-dihydroimidazo[1,5,4-de][1,4]benzoxazin-2(1H)-one;

7-(3,5-dimethylisoxazol-4-yl)-9-(3-methyl-1H-pyrazol-4-yl)-4-pyridin-2-yl-4,5-dihydroimidazo[1,5,4-de][1,4]benzoxazin-2(1H)-one;

7-(3,5-dimethylisoxazol-4-yl)-9-(3,5-dimethyl-1H-pyrazol-4-yl)-4-pyridin-2-yl-4,5-dihydroimidazo[1,5,4-de][1,4]benzoxazin-2(1H)-one;

(4S)-7-(3,5-dimethylisoxazol-4-yl)-9-(6-hydroxypyridin-3-yl)-4-pyridin-2-yl-4,5-dihydroimidazo[1,5,4-de][1,4]benzoxazin-2(1H)-one;

(4S)-7-(3,5-dimethylisoxazol-4-yl)-9-(2-hydroxypyridin-4-yl)-4-pyridin-2-yl-4,5-dihydroimidazo[1,5,4-de][1,4]benzoxazin-2(1H)-one;

(4S)-7-(3,5-dimethylisoxazol-4-yl)-9-(2-hydroxypyridin-3-yl)-4-pyridin-2-yl-4,5-dihydroimidazo[1,5,4-de][1,4]benzoxazin-2(1H)-one;

9-(anilinomethyl)-7-(3,5-dimethylisoxazol-4-yl)-4-pyridin-2-yl-4,5-dihydroimidazo[1,5,4-de][1,4]benzoxazin-2(1H)-one;

7-(3,5-dimethylisoxazol-4-yl)-9-{[(4-methoxybenzyl)amino]methyl}-4-pyridin-2-yl-4,5-dihydroimidazo[1,5,4-de][1,4]benzoxazin-2(1H)-one;

7-(3,5-dimethylisoxazol-4-yl)-9-(1-hydroxy-2-methylpropyl)-4-pyridin-2-yl-4,5-dihydroimidazo[1,5,4-de][1,4]benzoxazin-2(1H)-one;

7-(3,5-dimethylisoxazol-4-yl)-9-fluoro-4-pyridin-2-yl-4,5-dihydroimidazo[1,5,4-de][1,4]benzoxazin-2(1H)-one;

9-chloro-7-(3,5-dimethylisoxazol-4-yl)-4-pyridin-2-yl-4,5-dihydroimidazo[1,5,4-de][1,4]benzoxazin-2(1H)-one;

9-bromo-7-(3,5-dimethylisoxazol-4-yl)-4-pyridin-2-yl-4,5-dihydroimidazo[1,5,4-de][1,4]benzoxazin-2(1H)-one;

7-(3,5-dimethylisoxazol-4-yl)-9-methyl-4-pyridin-2-yl-4,5-dihydroimidazo[1,5,4-de][1,4]benzoxazin-2(1H)-one; and 7-(3,5-dimethylisoxazol-4-yl)-2-oxo-4-pyridin-2-yl-1,2,4,5-tetrahydroimidazo[1,5,4-de][1,4]benzoxazine-9-carbonitrile;

or a pharmaceutically acceptable salt thereof.

When the compounds listed above contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "substituted" means that an atom or group of atoms formally replaces hydrogen as a "substituent" attached to another group. The hydrogen atom is formally removed and replaced by a substituent. A single divalent substituent, e.g., oxo, can replace two hydrogen atoms. The term "optionally substituted" means unsubstituted or substituted. The substituents are independently selected, and substitution may be at any chemically accessible position. It is to be understood that substitution at a given atom is limited by valency. Throughout the definitions, the term "$C_{n-m}$" indicates a range which includes the endpoints, wherein n and m are integers and indicate the number of carbons. Examples include $C_{1-4}$, $C_{1-6}$, and the like.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the term "$C_{n-m}$ alkyl," employed alone or in combination with other terms, refers to a saturated hydrocarbon group that may be straight-chain or branched, having n to m carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{n-m}$ alkoxy," employed alone or in combination with other terms, refers to a group of formula —O-alkyl, wherein the alkyl group has n to m carbons. Example alkoxy groups include methoxy, ethoxy, and propoxy (e.g., n-propoxy and isopropoxy). In some embodiments, the alkyl group has 1 to 3 carbon atoms.

As used herein, the term "alkylene," employed alone or in combination with other terms, refers to a divalent alkyl linking group. Examples of alkylene groups include, but are not limited to, ethan-1, 2-diyl, propan-1, 3-diyl, propan-1, 2-diyl, butan-1,4-diyl, butan-1, 3-diyl, butan-1, 2-diyl, 2-methyl-propan-1, 3-diyl, and the like.

As used herein, "$C_{n-m}$ alkenyl," employed alone or in combination with other terms, refers to an alkyl group having one or more double carbon-carbon bonds and having n to m carbons. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl," employed alone or in combination with other terms, refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkylamino," employed alone or in combination with other terms, refers to a group of formula —NH(alkyl), wherein the alkyl group has n to m carbon atoms. In some embodiments, the alkyl group has 1 to 6 or 1 to 4 carbon atoms.

As used herein, the term "di-$C_{n-m}$-alkylamino," employed alone or in combination with other terms, refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "thio," employed alone or in combination with other terms, refers to a group of formula —SH.

As used herein, the term "$C_{n-m}$ alkylthio," employed alone or in combination with other terms, refers to a group of formula —S-alkyl, wherein the alkyl group has n to m carbon atoms. In some embodiments, the alkyl group has 1 to 6 or 1 to 4 carbon atoms.

As used herein, the term "$C_{n-m}$ alkylsulfinyl," employed alone or in combination with other terms, refers to a group of formula —S(=O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonyl," employed alone or in combination with other terms, refers to a group of formula —S(=O)$_2$-alkyl, wherein the alkyl group has n to m carbon atoms. In some embodiments, the alkyl group has 1 to 6 or 1 to 4 carbon atoms.

As used herein, the term "amino," employed alone or in combination with other terms, refers to a group of formula —NH$_2$.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "arylalkyl," employed alone or in combination with other terms, refers to a group of formula -alkylene-aryl. In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is benzyl.

As used herein, the term "carbonyl," employed alone or in combination with other terms, refers to a —C(=O)— group.

As used herein, the term "carboxy," employed alone or in combination with other terms, refers to a group of formula —C(=O)OH.

As used herein, the term "cycloalkyl," employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-7}$ cycloalkyl, which is monocyclic or bicyclic. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, the cycloalkyl group is cyclopropyl, cyclobutyl, cyclopentyl, or cyclohexyl.

As used herein, the term "cycloalkylalkyl," employed alone or in combination with other terms, refers to a group of formula -alkylene-cycloalkyl. In some embodiments, cycloalkylalkyl is $C_{3-7}$ cycloalkyl-$C_{1-3}$ alkyl, wherein the cycloalkyl portion is monocyclic or bicyclic. In some embodiments, cycloalkylalkyl is $C_{3-7}$ cycloalkyl-$C_{1-4}$ alkyl, wherein the cycloalkyl portion is monocyclic or bicyclic.

As used herein, "$C_{n-m}$ haloalkoxy," employed alone or in combination with other terms, refers to a group of formula —O-haloalkyl having n to m carbon atoms. An example haloalkoxy group is OCF$_3$. An additional example haloalkoxy group is OCHF$_2$. In some embodiments, the haloalkoxy group is fluorinated only. In some embodiments, the alkyl group has 1 to 6 or 1 to 4 carbon atoms.

As used herein, the term "halo," employed alone or in combination with other terms, refers to a halogen atom selected from F, Cl, I or Br. In some embodiments, "halo" refers to a halogen atom selected from F, Cl, or Br. In some embodiments, exemplary halo groups are F.

As used herein, the term "$C_{n-m}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is 5- to 10-membered $C_{1-9}$ heteroaryl, which is monocyclic or bicyclic and which has 1, 2, 3, or 4 heteroatom ring members independently selected from nitrogen, sulfur and oxygen. When the heteroaryl group contains more than one heteroaryl ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, or the like.

A five-membered ring heteroaryl is a heteroaryl group having five ring atoms comprising carbon and one or more (e.g., 1, 2, or 3) ring atoms independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "heteroarylalkyl," employed alone or in combination with other terms, refers to a group of formula -alkylene-heteroaryl. In some embodiments, heteroarylalkyl is $C_{1-9}$ heteroaryl-$C_{1-3}$ alkyl, wherein the heteroaryl portion is monocyclic or bicyclic and has 1, 2, 3, or 4 heteroatom ring members independently selected from nitrogen, sulfur and oxygen. In some embodiments, heteroarylalkyl is $C_{1-9}$ heteroaryl-$C_{1-4}$ alkyl, wherein the heteroaryl portion is monocyclic or bicyclic and has 1, 2, 3, or 4 heteroatom ring members independently selected from nitrogen, sulfur and oxygen.

As used herein, the term "heterocycloalkyl," employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1,2,3,4-tetrahydro-quinoline, dihydrobenzofuran and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is 5- to 10-membered $C_{2-9}$ heterocycloalkyl, which is monocyclic or bicyclic and which has 1, 2, 3, or 4 heteroatom ring members independently selected from nitrogen, sulfur and oxygen. Examples of heterocycloalkyl groups include 1, 2, 3, 4-tetrahydro-quinoline, dihydrobenzofuran, azetidine, azepane, pyrrolidine, piperidine, piperazine, morpholine, thiomorpholine, and pyran.

As used herein, the term "heterocycloalkylalkyl," employed alone or in combination with other terms, refers to a group of formula -alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen. In some embodiments, heterocycloalkylalkyl is $C_{2-9}$ heterocycloalkyl-$C_{1-4}$ alkyl, wherein the heterocycloalkyl portion is monocyclic or bicyclic and has 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1, 2, 4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); µg (microgram(s)); µL (microliter(s)); µM (micromolar); wt % (weight percent).

II. Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative*

*LCMS Purification: Improved Compound Specific Method Optimization*" Karl F. Blom, Brian Glass, Richard Sparks, Andrew P. Combs *J. Combi. Chem.* 2004, 6(6), 874-883) and normal phase silica chromatography.

Compounds of Formula (I) can be formed as shown in Scheme I. The thiols (L=S) or phenols (L=O) (i) can be alkylated using standard alkylating conditions ($Cy^3COC(R^1R^2)$—X (ii), X=leaving group, such as halo (Br, Cl, I or mesylate) or Mitsunobu conditions (e.g., $Cy^3COC(R^1R^2)$—X, where X=OH (ii), DEAD, $Ph_3P$) to afford thioether or ether derivatives (iii), respectively. Cyclization in situ or upon heating can afford imine (iv) which upon treatment with a Grignard reagent of formula $R^4$—$MgX^1$ ($X^1$=halo) and reduction of the nitro group (e.g., $H_2$ Pd/C or Fe) to give an amine (v). Compounds (v) can either be reacted with carbonyldiamidazole or phosgene to form an urea and then halogenated with N-chlorosuccinimide, N-bromosuccinimide or N-iodosuccinimide to give tricyclic halide (vi) where X=Cl, Br or I or halogenated first and then reacted with carbonyldiamidazole or phosgene to form an urea and give tricyclic halide (vi). Compound (vi) can be alkylated (e.g., $R^6$—X, where X=halo (X=Br, Cl, or I) and a base, such as triethylamine, NaH or $Na_2CO_3$; or under Mitsunobu conditions) to afford the tetrasubstituted urea (vii). Finally, the halo group of (vii) can be coupled to M-$Cy^1$, where M is a boronic acid, boronic ester or an appropriately substituted metal (e.g., $Cy^1$-M is $Cy^1$-$B(OH)_2$, $Cy^1$-$Sn(Bu)_4$, or Zn-$Cy^1$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (viii) wherein $R^5$ is =O. Alternatively, M-$Cy^1$ can be an amine containing heterocycle (where M is H and is attached to the amine nitrogen of the heterocycle $Cy^1$) with coupling to compound (vii) being performed by heating with a base or under Buchwald conditions (e.g., in the presence of a palladium(0) catalyst, such as tetrakis(triphenylphosphine)palladium(0) and a base (e.g., an alkoxide base)) to give a derivative of Formula (I) (viii). Alternatively, urea (vi) can be coupled to M-$Cy^1$, where M is a boronic acid, boronic ester or an appropriately substituted metal (e.g., $Cy^1$-M is $Cy^1$-$B(OH)_2$, $Cy^1$-$Sn(Bu)_4$, or Zn-$Cy^1$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (ix) which can be alkylated (e.g., $R^6$—X, where X=halo (X=Br, Cl, or I) and a base, such as triethylamine, NaH or $Na_2CO_3$; or under Mitsunobu conditions) to afford the tetrasubstituted urea of Formula (I) (viii). Alternatively, urea (vi) can be converted to the 2-halo-imidazole, such as Cl upon treatment with $POCl_3$, and then treated with an amine (HNRR) to give benzoimidazole (x) where $R^5$=NRR. Benzoimidazole (x) can then be coupled to M-$Cy^1$, where M is a boronic acid, boronic ester or an appropriately substituted metal (e.g., $Cy^1$-M is $Cy^1$-$B(OH)_2$, $Cy^1$-$Sn(Bu)_4$, or Zn-$Cy^1$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (xi). M-$Cy^1$ can be an amine containing heterocycle (where M is H and is attached to the amine nitrogen of the heterocycle $Cy^1$) with coupling to compound (x) being performed by heating with a base or under Buchwald conditions (e.g., in the presence of a palladium(0) catalyst, such as tetrakis(triphenylphosphine) palladium(0) and a base (e.g., an alkoxide base)) to give a derivative of Formula (I) (xi). Alternatively, urea (ix) can be converted to the 2-halo-imidazole, such as Cl upon treatment with $POCl_3$, and then treated with an amine (HNRR) to give benzimidazole (xi) where $R^5$=NRR or the chloride derivative can be coupled to M-$R^5$, where M is a boronic acid, boronic ester or an appropriately substituted metal (e.g., $R^5$-M is $R^5$—$B(OH)_2$, $R^5$—$Sn(Bu)_4$, or Zn—$R^5$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (xi). M-$Cy^1$ can be an amine containing heterocycle (where M is H and is attached to the amine nitrogen of the heterocycle $Cy^1$) with coupling to the halide of (ix) being performed by heating with a base or under Buchwald conditions (e.g., in the presence of a palladium(0) catalyst, such as tetrakis(triphenylphosphine) palladium(0) and a base (e.g., an alkoxide base)) to give a derivative of Formula (I) (xi). Amino compound (v) can either be treated with an ortho-ester, such as $R^5C(OEt)_3$, or an aldehyde $R^5CHO$ and $NaHSO_3$ to give a benzimidazole which can be halogenated with N-chlorosuccinimide, N-bromosuccinimide or N-iodosuccinimide to give halo-benzimidazole (x), where X=Cl, Br, or I, or these two steps can be run in the opposite order to give the same benzimidazole (x) which can be further converted to compounds of Formula (I) (xi) as previously described above.

Scheme I

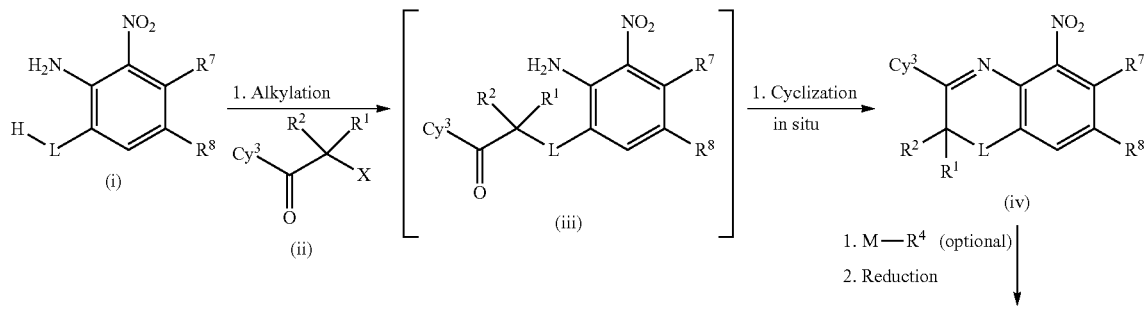

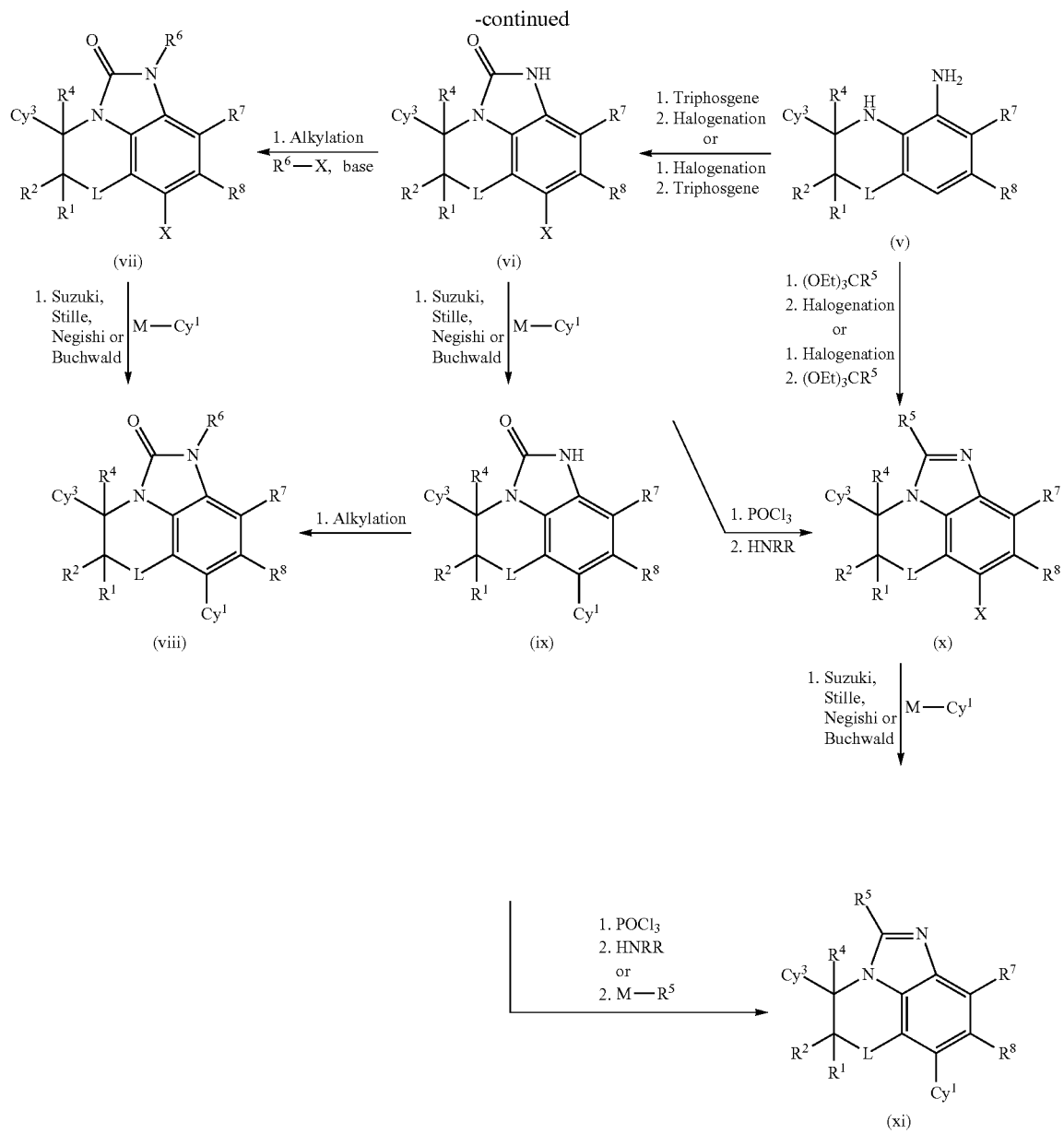

Compounds of Formula (I) can be formed as shown in Scheme II. The nitro-halide (i) can be reacted with an amine, such as $HNR^6$, to give an amino derivative which can be alkylated with $(Cy^3COC(R^1R^2))$—X (ii) using standard alkylating conditions, X=leaving group, such as halo (Br, Cl, I) or mesylate) or Mitsunobu conditions (e.g., $Cy^3COC(R^1R^2)$—X, where X=OH (ii), DEAD, $Ph_3P$) to afford thioether or ether derivatives (iii), respectively. Reduction of the nitro group of (iii) under standard conditions (e.g., Fe or Zn) can give the amino compound which can cyclize in situ or upon heating to afford an imine which upon treatment with a Grignard reagent of formula $R^4$—$MgX^1$ ($X^1$=halo) to give an amine (iv) or (iii) can be reduced with $H_2$ over Pd/C to give amine (iv) where $R^4$=H. Compounds (iv) can either be reacted with carbonyldiimidazole or phosgene to form an urea and then halogenated with N-chlorosuccinimide, N-bromosuccinimide or N-iodosuccinimide to give tricyclic halide (v) where X=Cl, Br or I or halogenated first and then reacted with carbonyldiimidazole or phosgene to form an urea and give tricyclic halide (v). Finally, the halo group of (v) can be coupled to M-$Cy^1$, where M is a boronic acid, boronic ester or an appropriately substituted metal (e.g., $Cy^1$-M is $Cy^1$-$B(OH)_2$, $Cy^1$-$Sn(Bu)_4$, or Zn-$Cy^1$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (vi). M-$Cy^1$ can be an amine containing heterocycle (where M is H and is attached to the amine nitrogen of the heterocycle $Cy^1$) with coupling to compound (v) being performed by heating with a base or under Buchwald conditions (e.g., in the presence of a palladium(0) catalyst, such as tetrakis(triphenylphosphine) palladium(0) and a base (e.g., an alkoxide base)) to give a derivative of Formula (I) (vi).

Scheme II

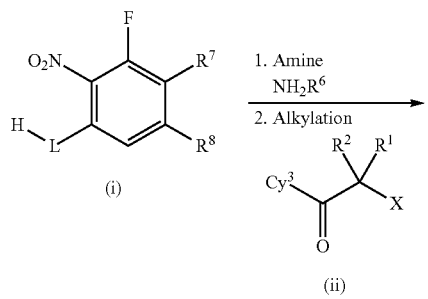

Compounds of Formula (I) can be formed as shown in Scheme III. The nitro-halide (i) can be reacted with an amine of formula HO$_2$CC(R$^1$R$^2$)C(Cy$^3$R$^4$)—NH$_2$, to give a carboxylic acid derivative (iii). Conversion of the carboxylic acid (iii) to an acyl-halide, such as acyl-chloride by treating with oxalyl-chloride, can affect a Friedel-Crafts intramolecular cyclization to give ketone (iv). Reduction of the ketone group and nitro group of (iv) under standard conditions (e.g., H$_2$ over Pd/C or a Wolff-Kishner reaction (NH$_2$NH$_2$, KOH) followed by reduction of the nitro group with Fe) can give the diamine derivative (v). Diamine (v) can then be converted to compounds of Formula (I) (where L=CH$_2$) by similar methods for diamine (v) shown in Scheme I.

Scheme III

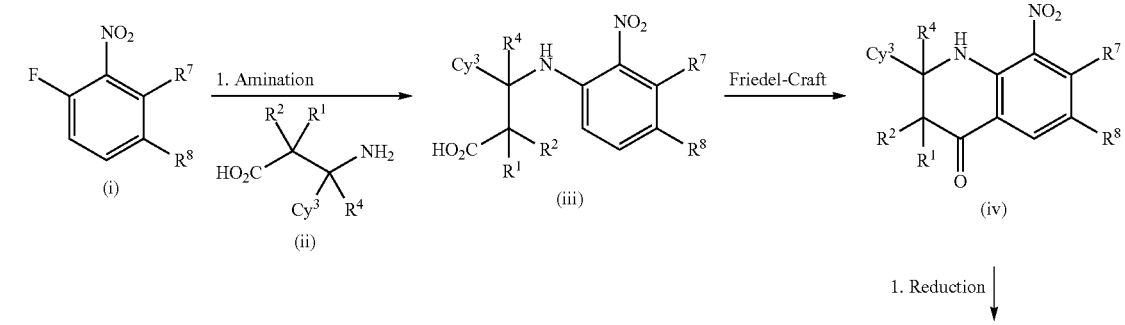

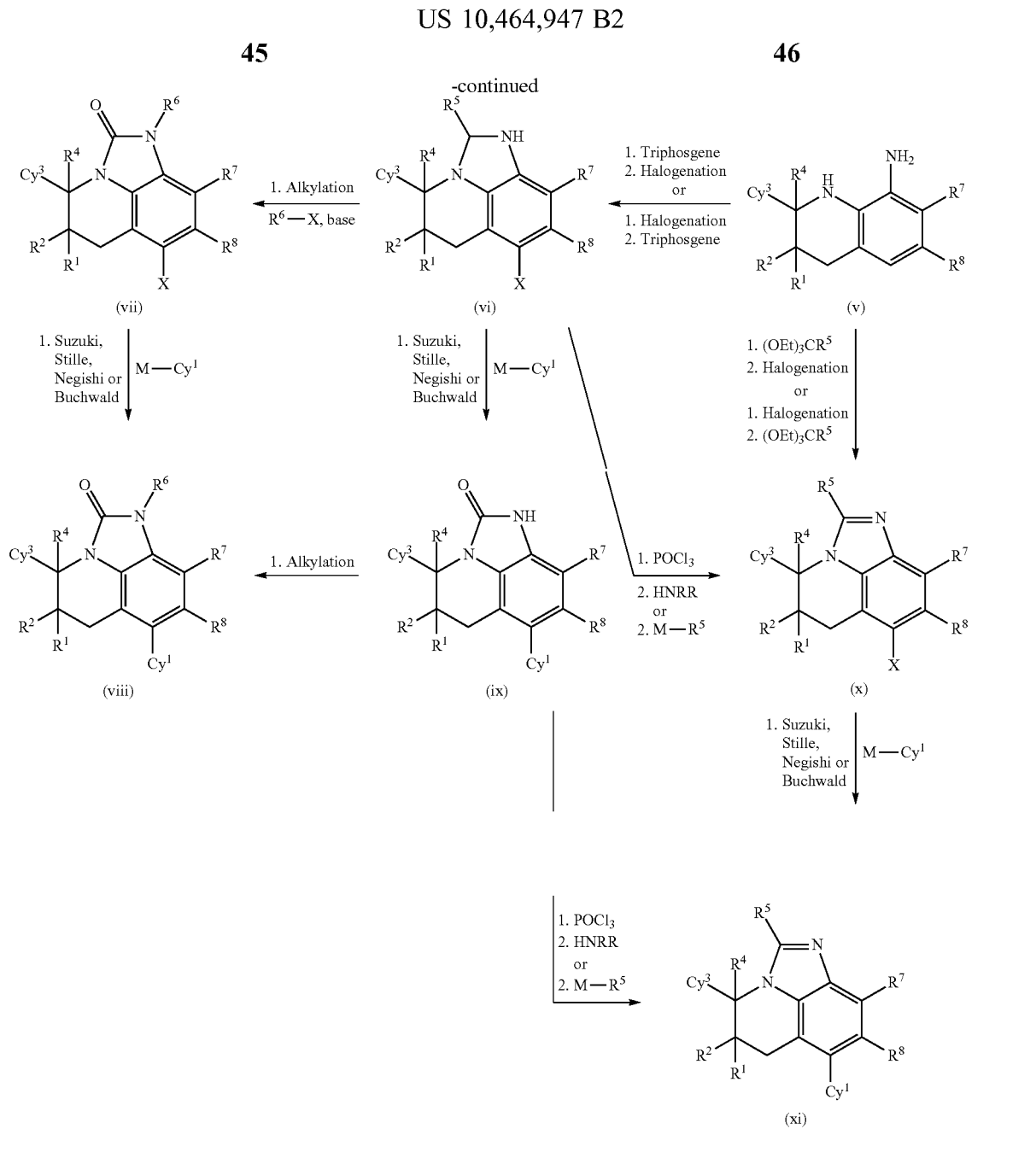

Compounds of Formula (I) can be formed as shown in Scheme IV. Compounds (i) can be halogenated with N-chlorosuccinimide, N-bromosuccinimide or N-iodosuccinimide to give tricyclic halide (v) where X=Cl, Br or I and the halo group of (ii) can be coupled to M-R⁷, where M is a boronic acid, boronic ester or an appropriately substituted metal (e.g., R⁷-M is R⁷—B(OH)₂, R⁷—Sn(Bu)₄, or Zn—R⁷), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (vi). M-R⁷ can be an amine containing heterocycle (where M is H and is attached to the amine nitrogen of the heterocycle R⁷) with coupling to compound (ii) being performed by heating with a base or under Buchwald conditions (e.g., in the presence of a palladium(0) catalyst, such as tetrakis(triphenylphosphine) palladium(0) and a base (e.g., an alkoxide base)) to give a derivative of Formula (I) (iii).

Scheme IV

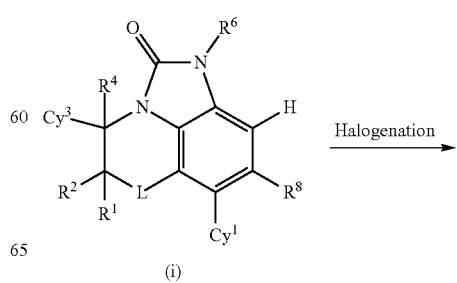

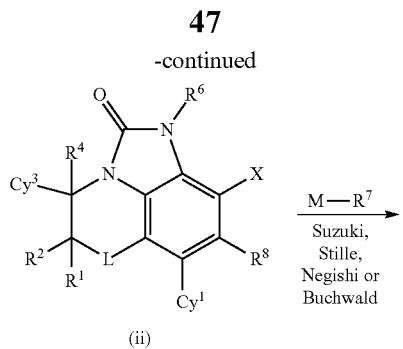

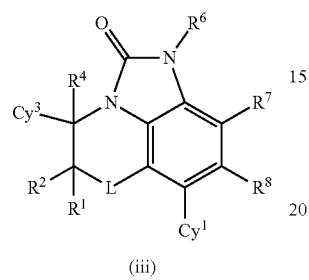

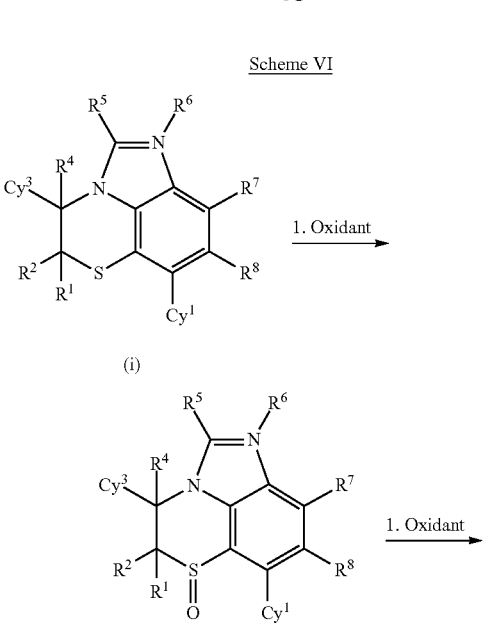

Compounds of Formula (I) can be formed as shown in Scheme V. The nitro-aniline (i) can be reacted with an aldehyde of formula OHCC(R¹)=CHCy³ (ii), to give quinolone derivatives (iii). Reduction of the quinoline group and nitro group of (iii) under standard conditions (e.g., H₂ over Pd/C can give the diamine derivative (iv). Diamine (iv) can then be converted to compounds of Formula (I) (where L=CH₂) by similar methods for diamine (v) shown in Scheme I.

Scheme V

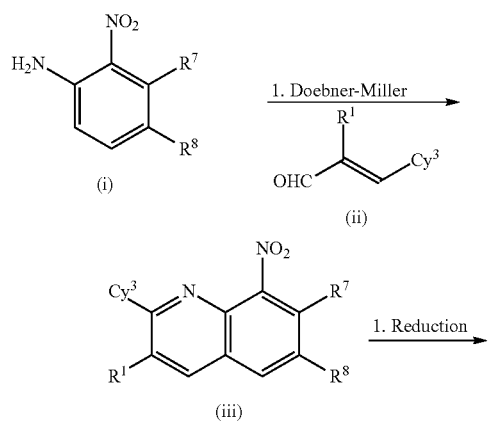

Compounds of Formula (I) can be formed as shown in Scheme VI. The sulfide (i) can be reacted with an oxidant, such as mCPBA or H₂O₂ or dioxirane, to give the sulfoxide (ii) which can be further oxidized with an oxidant, such as mCPBA or H₂O₂ or dioxirane, to give the sulfone (iii).

Halo-ketones intermediate (ii) of Scheme I and Scheme II can be synthesized as shown in Scheme VII. The carboxylic acid (i) can be activated with a coupling agent (e.g., HBTU, HATU or EDC) and then reacted with N, O-dimethylhydroxylamine to give an N-methoxy-N-methylcarboxamide derivative (ii). Amide (ii) may then be reacted with a Grignard reagent of formula R¹R²—CH—MgX¹ (X¹=halo) to give a ketone (iii) which can be halogenated with Br₂ or NXS (X=Br, Cl or I) to give halo-ketone (iv). The halo-ketone (iv) can be transformed using similar methods as shown in Scheme I and Scheme II to afford compounds of Formula (I).

Scheme VII

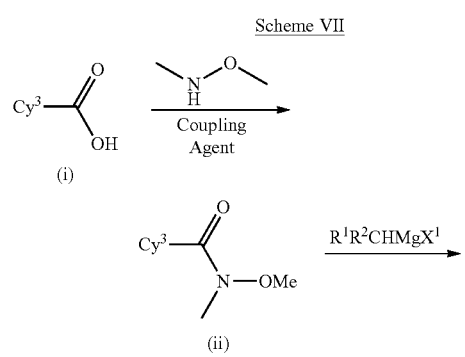

49

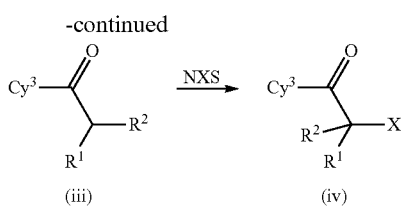

Compounds of Formula (I) can be formed as shown in Scheme VIII. 2-Bromoquinoline (i) can be coupled to M-Cy³, where M is a boronic acid, boronic ester or an appropriately substituted metal (e.g., Cy¹-M is Cy¹-B(OH)₂, Cy¹-Sn(Bu)₄, or Zn-Cy¹), under standard Suzuki conditions or standard Stille conditions (e.g., in the presence of a palladium(0) catalyst, such as tetrakis(triphenylphosphine) palladium(0) and a base (e.g., a bicarbonate or carbonate base) or standard Negishi conditions (e.g., in the presence of a palladium(0) catalyst, such as tetrakis(triphenylphosphine)palladium(0), to give compound (ii). Compound (ii) can be reduced (eg. borane/pyridine or 1,4-dihydro-3,5-dicarbethoxy-2,6-dimethylpyridine/diphenyl hydrogen phosphate) to give compound (iii). Compound (iii) can be converted to (iv) using triphosgene/methoxylamine or 4-nitrophenyl methoxycarbamate. Cyclization of (iv) can be accomplished with [I,I-bis(trifluoroacetoxy)iodo]benzene to give (v). The methoxy group of (v) can be removed by hydrogenation (Pd/C) to give (vi). Compound (vi) can be halogenated with N-chlorosuccinimide, N-bromosuccinimide or N-iodosuccinimide to give tricyclic halide (vii) where X=Cl, Br or I. Finally, the halo group of (vii) can be coupled to M-Cy¹, where M is a boronic acid, boronic ester or an appropriately substituted metal (e.g., Cy¹-M is Cy¹-B(OH)₂, Cy¹-Sn(Bu)₄, or Zn-Cy¹), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (viii).

Scheme VIII

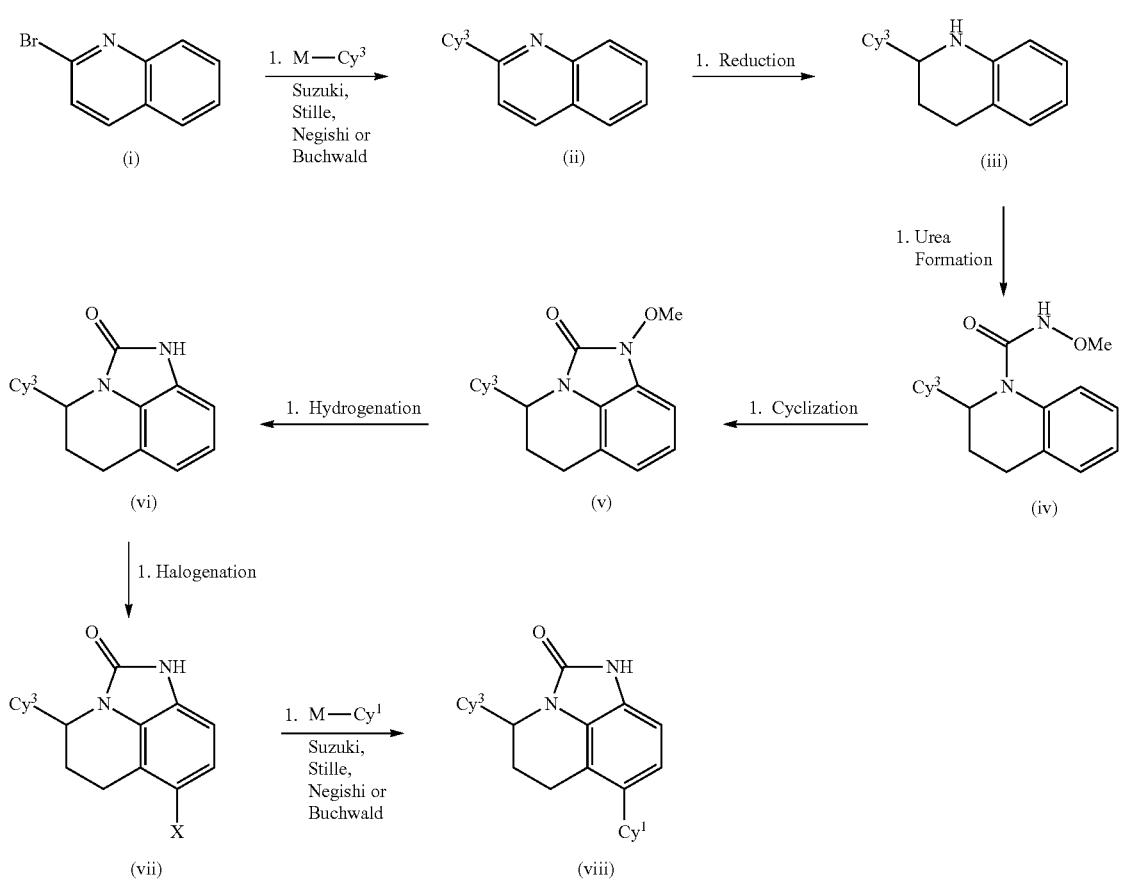

For the synthesis of particular compounds, the general schemes described above can be modified. For example, the products or intermediates can be modified to introduce particular functional groups. Alternatively, the substituents can be modified at any step of the overall synthesis by methods know to one skilled in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis, Vols.* 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

III. Uses of the Compounds

Compounds of the invention are BET protein inhibitors and, thus, are useful in treating diseases and disorders associated with activity of BET proteins. For the uses described herein, any of the compounds of the invention, including any of the embodiments thereof, may be used.

The compounds of Formula (I) can inhibit one or more of BET proteins BRD2, BRD3, BRD4, and BRD-t. In some embodiments, the compounds of the invention selectively inhibit one or more BET proteins over another. "Selective" means that the compound binds to or inhibits a BET protein with greater affinity or potency, respectively, compared to a reference, such as another BET protein. For example, the compounds can be selective for BRD2 over BRD3, BRD4 and BRD-t, selective for BRD3 over BRD2, BRD4 and BRD-t, selective for BRD4 over BRD2, BRD3 and BRD-t, or selective for BRD-t over BRD2, BRD3 and BRD4. In some embodiments, the compounds inhibit two or more of the BET proteins, or all of the BET proteins. In general, selectivity can be at least about 5-fold, at least about 10-fold, at least about 20-fold, at least about 50-fold, at least about 100-fold, at least about 200-fold, at least about 500-fold or at least about 1000-fold.

The compounds of Formula (I) are therefore useful for treating BET protein mediated disorders. The term "BET-mediated" refers to any disease or condition in which one or more of the BET proteins, such as BRD2, BRD3, BRD4 and/or BRD-t, or a mutant thereof, plays a role, or where the disease or condition is associated with expression or activity of one or more of the BET proteins. The compounds of the invention can therefore be used to treat or lessen the severity of diseases and conditions where BET proteins, such as BRD2, BRD3, BRD4, and/or BRD-t, or a mutant thereof, are known to play a role.

Diseases and conditions treatable using the compounds of Formula (I) include cancer and other proliferative disorders, autoimmune disease, chronic inflammatory diseases, acute inflammatory diseases, sepsis, and viral infection. The diseases can be treated by administering to an individual (e.g., a patient) in need of the treatment a therapeutically effective amount or dose of a compound of Formula (I), or any of the embodiments thereof, or a pharmaceutical composition thereof. The present disclosure also provides a compound of Formula (I), or any of the embodiments thereof, or a pharmaceutical composition thereof, for use in treating a BET-mediated disease or disorder. Also provided is the use of a compound of Formula (I), or any of the embodiments thereof, or a pharmaceutical composition thereof, in the manufacture of a medicament for treating a BET-mediated disease or disorder.

Diseases that can be treated with the compounds of Formula (I) include cancers. The cancers can include adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

The diseases treatable using the compounds of Formula (I) also include MYC dependent cancers wherein the cancer is associated with at least one of myc RNA expression or MYC protein expression. A patient can be identified for such treatment by determining myc RNA expression or MYC protein expression in the cancerous tissue or cells.

Diseases that can be treated with compounds of Formula (I) also include non-cancerous proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The diseases and conditions that can be treated with the compounds of Formula (I) also include chronic autoimmune and inflammatory conditions. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthriti, satopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis nodosa, psoriasis, retinitis, scleritis, scleracierma, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

The diseases and conditions that can be treated with the compounds of Formula (I) also include diseases and conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

The diseases for which the compounds of Formula (I) are indicated also include diseases associated with a systemic inflammatory response syndrome, such as sepsis, burns, pancreatitis, major trauma, hemorrhage and ischemia. The compound of Formula (I) can be administered to reduce the incidence of: SIRS, the onset of shock, multi-organ dysfunction syndrome, which includes the onset of acute lung injury, ARDS, acute renal, hepatic, cardiac and gastrointestinal injury and mortality. For example, the compounds of the invention can be administered prior to surgical or other procedures associated with a high risk of sepsis, hemorrhage, extensive tissue damage, SIRS or MODS.

Other diseases that can be treated with the compounds of Formula (I) include viral infections. Examples of viral infections that can be treated include Epstein-Barr virus, hepatitis B virus, hepatitis C virus, herpes virus, human immunodeficiency virus, human papilloma virus, adenovirus, poxvirus and other episome-based DNA viruses. The compounds can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment the compounds of Formula (I) are indicated for the treatment of human papilloma virus infections of skin or cervical epithelia.

The diseases and conditions that can be treated with the compounds of Formula (I) also include conditions that are associated with ischemia-reperfusion injury. Examples of such conditions include, but are not limited to conditions such as myocardial infarction, cerebrovascular ischemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

The compounds of Formula (I) are also useful in the treatment of disorders of lipid metabolism via the regulation of APO-A1 such as hypercholesterolemia, atherosclerosis and Alzheimer's disease.

The compounds of Formula (I) can also be used for the treatment of fibrotic conditions such as idiopathic pulmonary fibrosis, renal fibrosis, post-operative stricture, keloid formation, scleroderma and cardiac fibrosis.

The compounds of Formula (I) can also be used to treat ophthalmological indications such as dry eye.

As used herein, the term "contacting" refers to the bringing together of indicated moieties in an in vitro system or an in vivo system. For example, "contacting" a BET protein with a compound of the invention includes the administration of a compound of the present invention to an individual or patient, such as a human, having a BET protein, as well as, for example, introducing a compound of the invention into a sample containing a cellular or purified preparation containing the BET protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

The compounds of Formula (I) can be used in combination treatments where the compound of the invention is administered in conjunction with other treatment such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, and JAK kinase inhibitors for treatment of BET protein-associated diseases, disorders or conditions. The one or more additional pharmaceutical agents can be administered to a patient simultaneously or sequentially.

In some embodiments, the compounds of Formula (I) can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. histone deacetylase inhibitors include, e.g., vorinostat.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of formula (I) can be used in combination with ruxolitinib.

For treating autoimmune or inflammatory conditions, the compound of Formula (I) can be administered in combination with a corticosteroid such as triamcinolone, dexamethasone, fluocinolone, cortisone, prednisolone, or flumetholone.

For treating autoimmune or inflammatory conditions, the compound of Formula (I) can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of Formula (I) can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of Formula (I) can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a compound of Formula (I) may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

In some embodiments, the compounds of the invention can be used in combination with one or more therapeutic agents selected from: Janus kinase inhibitors (e.g., ruxolitinib, tofacitinib, baricitinib, CYT387, GLPG0634, lestaurtinib, pacritinib, TG101348), Pim kinase inhibitors, PI3 kinase inhibitors (including PI3K-delta selective and broad spectrum PI3K inhibitors), MEK inhibitors, cyclin dependent kinase inhibitors, b-RAF inhibitors, mTOR inhibitors, proteasome inhibitors (e.g., bortezomib, carfilzomib), HDAC-inhibitors (e.g., panobinostat, vorinostat), DNA methyl transferase inhibitors, dexamethasone, melphalan, and immunomodulators such as lenolidomide and pomalidomide. In some embodiments, the Janus kinase inhibitor is selective for JAK1. In some embodiments, the Janus kinase inhibitor is selective for JAK1 and JAK2.

IV. Formulation, Dosage Forms and Administration

When employed as pharmaceuticals, the compounds of Formula (I) can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intra-arterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

V. Labeled Compounds and Assay Methods

In another aspect, the present disclosure provides labeled compounds of Formula (I) (radio-labeled, fluorescent-labeled, etc.) that can be useful not only in imaging techniques but also in assays, both in vitro and in vivo, for localizing and quantitating BET proteins in tissue samples, including human, and for identifying BET protein ligands by inhibition binding of a labeled compound. Accordingly, the disclosure provides BET protein assays that contain such labeled compounds.

An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro BET protein labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2, or 3 deuterium atoms. Synthetic methods for incorporating radio-isotopes into organic compounds are known in the art.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a BET protein by monitoring its concentration variation when contacting with the BET protein, through tracking of the labeling. For example, a test compound (labeled) can be evaluated for its ability to reduce binding of another compound which is known to bind to a BET protein (i.e., standard compound). Accordingly, the ability of a test compound to compete with the standard compound for binding to the BET protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present invention also includes pharmaceutical kits useful, for example, in the treatment or prevention of BET protein-associated diseases or disorders, such as cancer, which include one or more containers containing a pharmaceutical composition comprising a therapeutically effective amount of a compound of Formula (I), or any of the embodiments thereof. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more BET proteins as described below.

EXAMPLES

Example 1

7-(3,5-Dimethylisoxazol-4-yl)-4-phenyl-4,5-dihydroimidazo[1,5,4-de][1,4]benzoxazin-2(1H)-one

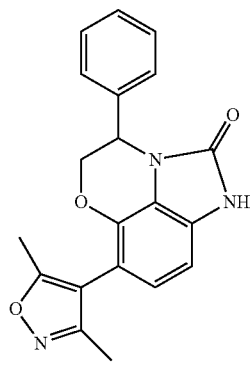 [SMILES: Cc1noc(C)c1-c1ccc2[nH]c(=O)n3c2c1OCC3c1ccccc1]

Step 1. 5-Nitro-3-phenyl-2H-1,4-benzoxazine

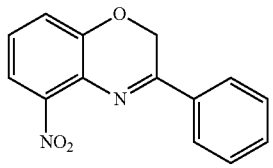 [SMILES: O=[N+]([O-])c1cccc2c1N=C(c1ccccc1)CO2]

The 2-bromoacetophenone (3.9 g, 19 mmol) [Aldrich, cat. #115835] was added portion wise to a stirred suspension of 2-amino-3-nitrophenol (2.5 g, 16 mmol) [Aldrich, cat. #297003] and K$_2$CO$_3$ (3.4 g, 24 mmol) in MeCN (100 mL) at room temperature. The reaction was monitored by LC/MS. After stirring for 3 h the reaction was complete and then EtOAc added and solution filtered to remove the solids and the organic layer was washed with water, 1 N HCl, brine, dried over MgSO$_4$, filtered and concentrated to give 5-nitro-3-phenyl-2H-1,4-benzoxazine as a dark oil (4.1 g, 100%). LCMS calc. for C$_{14}$H$_{11}$N$_2$O$_3$ (M+H)$^+$: m/z=255.3; found: 255.1.

Step 2. 3-Phenyl-3,4-dihydro-2H-1,4-benzoxazin-5-amine

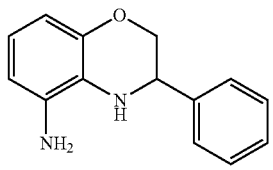 [SMILES: Nc1cccc2c1NC(c1ccccc1)CO2]

The 5-nitro-3-phenyl-2H-1,4-benzoxazine oil was taken up in MeOH (50 mL) in a Parr shaker bottle, deoxygenated with nitrogen, the catalyst 10% Pd on carbon (0.25 g) was added, the reaction vessel was charged to 55 psi with hydrogen and shaken. After 2 h the reaction was complete by LC/MS. The reaction was filtered to remove the catalyst and concentrated under reduced pressure to give 3-phenyl-3,4-dihydro-2H-1,4-benzoxazin-5-amine as a dark oil. (3.5 g, 97%). LCMS calc. for C$_{14}$H$_{15}$N$_2$O (M+H)$^+$: m/z=227.1; found: 227.1. $^1$H NMR (500 MHz, DMSO-d$_6$) δ 7.44 (d, J=7.4 Hz, 2H), 7.37 (dd, J=7.5 Hz, 2H), 7.31 (t, J=7.2 Hz, 1H), 6.35 (dd, J=7.9 Hz, 1H), 6.21 (dd, J=7.8, 1.0 Hz, 1H), 6.07 (d, J=7.9 Hz, 1H), 5.00 (s, 1H), 4.62 (s, 2H), 4.44 (dd, J=4.9, 2.6 Hz, 1H), 4.21-4.13 (m, 1H), 3.87 (dd, J=10.4, 7.7 Hz, 1H).

Step 3. 4-Phenyl-4,5-dihydroimidazo[1,5,4-de][1,4]benzoxazin-2(1H)-one

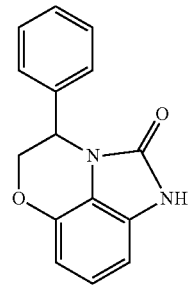 [SMILES: O=c1[nH]c2cccc3c2n1C(c1ccccc1)CO3]

The 3-phenyl-3,4-dihydro-2H-1,4-benzoxazin-5-amine (0.95 g, 4.2 mmol) was dissolved in THF (30 mL) and DIPEA (1.5 mL, 8.4 mmol) at room temperature (room temperature). The N,N-carbonyldiimidazole (0.82 g, 5.0 mmol) was added portion wise over 10 min. The reaction was heated to 70° C. for 1 h and allowed to cool to room temperature and stirred overnight. To the reaction mixture was added EtOAc, and then the mixture was washed with water, sodium bicarbonate water and brine, then dried over magnesium sulfate and concentrated to give crude product as a dark oil. The oil was triturated with ethyl ether to give a precipitate. The solids were triturated twice with ethyl ether and then the solids were collected and air dried to give 4-phenyl-4,5-dihydroimidazo[1,5,4-de][1,4]benzoxazin-2(1H)-one as a brown solid (0.51 g, 48%). LCMS calc. for C$_{15}$H$_{13}$N$_2$O$_2$ (M+H)$^+$: m/z=253.1; found: 253.1. $^1$H NMR (300 MHz, DMSO-d$_6$) δ 10.88 (s, 1H), 7.39-7.22 (m, 3H), 7.15-7.04 (m, 2H), 6.88 (t, J=8.0 Hz, 1H), 6.67 (d, J=7.8 Hz, 1H), 6.57 (d, J=8.2 Hz, 1H), 5.45 (s, 1H), 4.54 (dd, J=11.6, 2.2 Hz, 1H), 4.37 (dd, J=11.6, 3.0 Hz, 1H).

Step 4. 7-Bromo-4-phenyl-4,5-dihydroimidazo[1,5,4-de][1,4]benzoxazin-2(1H)-one

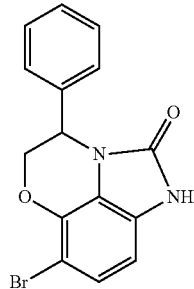

A mixture of 4-phenyl-4,5-dihydroimidazo[1,5,4-de][1,4]benzoxazin-2(1H)-one (400 mg, 2 mmol) and N-bromosuccinimide (310 mg, 1.7 mmol) in AcOH (10 mL) was stirred at room temperature for 2 h. The reaction mixture was allowed to cool and was concentrated to remove AcOH. The residue was taken up in EtOAc and was washed with water saturated NaHCO$_3$, brine, dried over magnesium sulfate, filtered and concentrated to give crude product. The product was purified by flash column chromatography on a Biotage system eluting with a hexane:EtOAc gradient (0-40%) to give 7-bromo-4-phenyl-4,5-dihydroimidazo[1,5,4-de][1,4]benzoxazin-2(1H)-one as an amber oil (0.30 g, 60%). LCMS calc. for $C_{15}H_{12}BrN_2O_2$ (M+H)$^+$: m/z=331.1, 333.1; found: 331.0, 333.0. $^1$H NMR (300 MHz, CD$_3$OD) δ 7.42-7.23 (m, 3H), 7.23-7.09 (m, 3H), 6.70 (d, J=8.4 Hz, 1H), 5.46 (dd, J=2.6 Hz, 1H), 4.66 (dd, J=11.6, 2.4 Hz, 1H), 4.47 (dd, J=11.6, 3.1 Hz, 1H).

Step 5. 7-(3,5-Dimethylisoxazol-4-yl)-4-phenyl-4,5-dihydroimidazo[1,5,4-de][1,4]benzoxazin-2(1H)-one 7-Bromo-4-phenyl-4,5-dihydroimidazo[1,5,4-de][1,4]benzoxazin-2(1H)-one (200 mg, 0.6 mmol) and 3,5-dimethyl-4-(4,4,5,5-tetramethyl-1,3,2-dioxaborolan-2-yl)isoxazole (160 mg, 0.72 mmol) [Aldrich, cat. #643882] were dissolved in 1,4-dioxane (20 mL) and potassium carbonate (200 mg, 1 mmol) in water (8 mL). The reaction was deoxygenated with nitrogen and the catalyst [1,1'-bis(diphenylphosphino)ferrocene]dichloropalladium(II) complexed with DCM (1:1) (20 mg, 0.03 mmol) was added. The reaction mixture was deoxygenated with nitrogen and was heated at 100° C. After heating for 2 h the reaction was complete by LCMS. The reaction mixture was allowed to cool to room temperature, EtOAc was added and the mixture was washed with water, brine, then dried over magnesium sulfate and concentrated to give the crude product. The product was purified on preparative HPLC on a C-18 column eluting with a water:MeCN gradient buffered pH 2 with TFA to give 7-(3,5-dimethylisoxazol-4-yl)-4-phenyl-4,5-dihydroimidazo[1,5,4-de][1,4]benzoxazin-2(1H)-one as white solid (0.10 g, 50%). LCMS calc. for $C_{20}H_{18}N_3O_3$ (M+H)$^+$: m/z=348.1; found: 348.1. $^1$H NMR (500 MHz, DMSO-d$_6$) δ 10.96 (s, 1H), 7.38-7.24 (m, 3H), 7.16 (d, J=7.2 Hz, 2H), 6.84 (d, J=8.0 Hz, 1H), 6.76 (d, J=8.0 Hz, 1H), 5.47 (s, 1H), 4.57 (dd, J=11.6, 2.2 Hz, 1H), 4.40 (dd, J=11.6, 3.1 Hz, 1H), 2.25 (s, 3H), 2.08 (s, 3H).

Example 1A 7-(3,5-Dimethylisoxazol-4-yl)-4-phenyl-4,5-dihydroimidazo[1,5,4-de][1,4]benzoxazin-2(1H)-one (Enantiomer 1)

Example 1B 7-(3,5-Dimethylisoxazol-4-yl)-4-phenyl-4,5-dihydroimidazo[1,5,4-de][1,4]benzoxazin-2(1H)-one (Enantiomer 2)

The enantiomers were separated from racemic 7-(3,5-dimethylisoxazol-4-yl)-4-phenyl-4,5-dihydroimidazo[1,5,4-de][1,4]benzoxazin-2(1H)-one from Example 1, Step 5 by chiral column HPLC using a Phenomenex Lux Cellulose-4 column, 5 micron, 21.2×250 mm, eluting 30% ethanol in hexanes with a flow rate of 18 mL/min., loading approx. 36 mg per injection with UV, 220 nm detection to give peak 1 at: 14.32 min. and peak 2 at: 18.89 min.

Enantiomer 1: Peak 1: Example 1A (more active enantiomer), LCMS calc. for $C_{20}H_{18}N_3O_3$ (M+H)$^+$: m/z=348.1; found: 348.1. $^1$H NMR (500 MHz, DMSO-d$_6$) δ 10.96 (s, 1H), 7.38-7.24 (m, 3H), 7.16 (d, J=7.2 Hz, 2H), 6.84 (d, J=8.0 Hz, 1H), 6.76 (d, J=8.0 Hz, 1H), 5.47 (s, 1H), 4.57 (dd, J=11.6, 2.2 Hz, 1H), 4.40 (dd, J=11.6, 3.1 Hz, 1H), 2.25 (s, 3H), 2.08 (s, 3H).

Enantiomer 1: Peak 2: Example 1B (less active enantiomer), LCMS calc. for $C_{20}H_{18}N_3O_3$ (M+H)$^+$: m/z=348.1; found: 348.1. $^1$H NMR (500 MHz, DMSO-d$_6$) δ 10.96 (s, 1H), 7.38-7.24 (m, 3H), 7.16 (d, J=7.2 Hz, 2H), 6.84 (d, J=8.0 Hz, 1H), 6.76 (d, J=8.0 Hz, 1H), 5.47 (s, 1H), 4.57 (dd, J=11.6, 2.2 Hz, 1H), 4.40 (dd, J=11.6, 3.1 Hz, 1H), 2.25 (s, 3H), 2.08 (s, 3H).

Example 2

7-(3,5-Dimethylisoxazol-4-yl)-1-methyl-4-phenyl-4,5-dihydroimidazo[1,5,4-de][1,4]benzoxazin-2(1H)-one

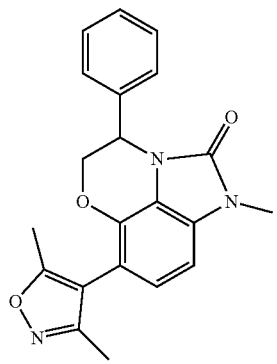 [SMILES: Cc1noc(C)c1-c1ccc2c3c1OCC(c1ccccc1)n3c(=O)n2C]

Sodium hydride in mineral oil 60% (3.2 mg, 0.13 mmol) was added to a solution of 7-(3,5-dimethylisoxazol-4-yl)-4-phenyl-4,5-dihydroimidazo[1,5,4-de][1,4]benzoxazin-2(1H)-one (0.040 g, 0.10 mmol) from Example 1, Step 5 in DMF (3 mL) cooled in an ice bath. The reaction mixture was stirred for 15 min. and methyl iodide (8 μL, 0.1 mmol) was added. The reaction mixture was stirred for 30 min. and was complete by LCMS. The reaction mixture was partitioned between water and EtOAc. The organic layer was concentrated and purified on preparative HPLC on a C-18 column eluting with a water:MeCN gradient buffered pH 2 with TFA to give the title compound as a solid product solid (0.015 g, 37%). LCMS calc. for $C_{21}H_{20}N_3O_3$ (M+H)$^+$: m/z=362.1; found: 362.1. $^1$H NMR (300 MHz, DMSO-d$_6$) δ 7.39-7.24 (m, 5H), 7.19-7.12 (m, 2H), 5.52 (s, 1H), 4.59 (dd, J=9.2 Hz, 1H), 4.41 (dd, J=8.4 Hz, 1H), 3.38 (s, 3H), 2.26 (s, 3H), 2.09 (s, 3H).

Example 3

7-(3,5-Dimethylisoxazol-4-yl)-5-methyl-4-phenyl-4,5-dihydroimidazo[1,5,4-de][1,4]benzoxazin-2(1H)-one

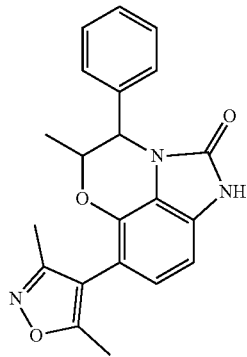 [SMILES: Cc1noc(C)c1-c1ccc2[nH]c(=O)n3c2c1OC(C)C3c1ccccc1]

The title compound was prepared by methods analogous to Example 1 but using 2-bromo-1-phenylpropan-1-one [Alfa Aesar, cat. # A10661] in Step 1. The product was purified by preparative HPLC on a C-18 column eluting with a water:MeCN gradient buffered pH 2 with TFA to give the title compound as a white amorphous solid (0.015 g, 37%). LCMS calc. for $C_{21}H_{20}N_3O_3$ (M+H)$^+$: m/z=362.1; found: 362.1. $^1$H NMR (500 MHz, DMSO-d$_6$) δ 10.89 (s, 1H), 7.36-7.26 (m, 3H), 7.06-7.01 (m, 2H), 6.87 (d, J=8.0 Hz, 1H), 6.76 (d, J=8.0 Hz, 1H), 5.30 (d, J=2.8 Hz, 1H), 4.62-4.54 (m, 1H), 2.30 (s, 3H), 2.14 (s, 3H), 1.12 (d, J=6.4 Hz, 3H).

Example 4

4-[7-(3,5-Dimethylisoxazol-4-yl)-2-oxo-1,2,4,5-tetrahydroimidazo[1,5,4-de][1,4]benzoxazin-4-yl]benzonitrile

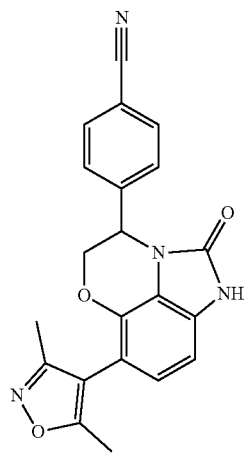 [SMILES: Cc1noc(C)c1-c1ccc2[nH]c(=O)n3c2c1OCC3c1ccc(C#N)cc1]

The title compound was prepared by methods analogous to Example 1 but using 4-(2-bromoacetyl)benzonitrile [Aldrich, cat. #539392] in Step 1. The product was purified by preparative HPLC on a C-18 column eluting with water:MeCN gradient buffered pH 2 with TFA to give the title compound as a white amorphous solid (0.021 g, 52%). LCMS calc. for $C_{21}H_{17}N_4O_3$ (M+H)$^+$: m/z=373.1; found: 373.2. $^1$H NMR (500 MHz, DMSO-d$_6$) δ 11.03 (s, 1H), 7.83 (d, J=8.3 Hz, 2H), 7.37 (d, J=8.3 Hz, 2H), 6.86 (d, J=8.0 Hz, 1H), 6.78 (d, J=8.0 Hz, 1H), 5.60 (s, 1H), 4.60 (dd, J=11.7, 2.4 Hz, 1H), 4.43 (dd, J=11.7, 3.1 Hz, 1H), 2.25 (s, 3H), 2.08 (s, 3H).

Example 5

7-(3,5-Dimethylisoxazol-4-yl)-4-pyridin-3-yl-4,5-dihydroimidazo[1,5,4-de][1,4]benzoxazin-2(1H)-one

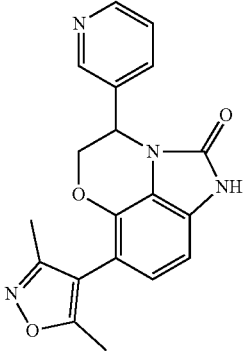 [SMILES: Cc1noc(C)c1-c1ccc2[nH]c(=O)n3c2c1OCC3c1cccnc1]

The title compound was prepared by methods analogous to Example 1 but using 2-bromo-1-(pyridin-3-yl)ethanone [Oakwood, cat. #005885] in Step 1. The product was purified by preparative HPLC on a C-18 column eluting with water:MeCN gradient buffered pH 2 with TFA to give the TFA salt of the title compound as a white amorphous solid (0.010 g, 25%). LCMS calc. for $C_{19}H_{17}N_4O_3$ (M+H)$^+$: m/z=349.1; found: 349.1. $^1$H NMR (500 MHz, DMSO-d$_6$+TFA) δ 11.09 (s, 1H), 8.94 (bs, 2H), 8.37 (d, J=8.1 Hz, 1H), 8.04 (s, 1H), 6.89 (d, J=8.0 Hz, 1H), 6.81 (d, J=8.0 Hz, 1H), 5.76 (s, 1H), 4.65 (dd, J=11.7, 3.5 Hz, 1H), 4.53 (dd, J=11.7, 3.1 Hz, 1H), 2.28 (s, 3H), 2.11 (s, 3H).

Example 6

7-(3,5-Dimethylisoxazol-4-yl)-4-(3-methoxyphenyl)-4,5-dihydroimidazo[1,5,4-de][1,4]benzoxazin-2(1H)-one

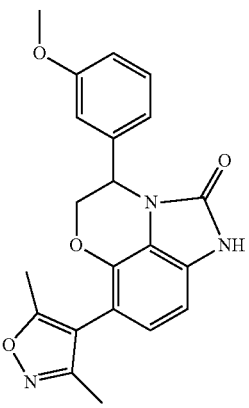 [SMILES: COc1cccc(C2COc3c(-c4c(C)noc4C)ccc4[nH]c(=O)n2c34)c1]

The title compound was prepared by methods analogous to Example 1 but using 2-bromo-1-(3-methoxyphenyl)ethanone [Aldrich, cat. #115673] in Step 1 and using dicyclohexyl(2',4',6'-triisopropylbiphenyl-2-yl)phosphine-(2'-aminobiphenyl-2-yl)(chloro)palladium as catalyst in Step 5. The product was purified by preparative HPLC on a C-18 column eluting with a water:MeCN gradient buffered pH 2 with TFA to give the title compound as a white amorphous solid (0.015 g, 37%). LCMS calc. for $C_{21}H_{20}N_3O_4$ (M+H)$^+$: m/z=378.1; found: 378.1. $^1$H NMR (300 MHz, DMSO-d$_6$) δ 10.97 (s, 1H), 7.21 (t, J=7.9 Hz, 1H), 6.88-6.79 (m, 2H), 6.77-6.71 (m, 2H), 6.63 (d, J=7.8 Hz, 1H), 5.42 (s, 1H), 4.57 (dd, J=11.5 Hz, 1H), 4.36 (dd, J=11.6, 2.9 Hz, 1H), 3.67 (s, 3H), 2.23 (s, 3H), 2.06 (s, 3H).

Example 7

7-(3,5-Dimethylisoxazol-4-yl)-4-(2-methoxyphenyl)-4,5-dihydroimidazo[1,5,4-de][1,4]benzoxazin-2(1H)-one

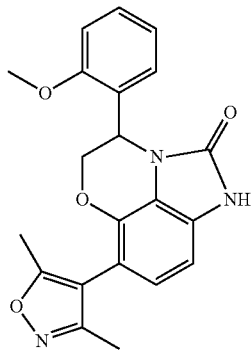 [SMILES: COc1ccccc1C1COc2c(-c3c(C)noc3C)ccc3[nH]c(=O)n1c23]

The title compound was prepared by methods analogous to Example 1 but using 2-bromo-1-(2-methoxyphenyl)ethanone [Aldrich, cat. #100854] in Step 1 and using dicyclohexyl(2',4',6'-triisopropylbiphenyl-2-yl)phosphine-(2'-aminobiphenyl-2-yl)(chloro)palladium as catalyst in Step 5. The product was purified by preparative HPLC on a C-18 column eluting with water:MeCN gradient buffered pH 2 with TFA to give the title compound as a white amorphous solid (0.010 g, 25%). LCMS calc. for $C_{21}H_{20}N_3O_4$ (M+H)$^+$: m/z=378.1; found: 378.1. $^1$H NMR (300 MHz, DMSO-d$_6$) δ 11.03 (s, 1H), 7.37-7.21 (m, 1H), 7.09 (d, J=7.6 Hz, 1H), 6.91-6.74 (m, 3H), 6.38 (d, J=7.5 Hz, 1H), 5.61 (s, 1H), 4.49 (dd, J=11.5 Hz, 1H), 4.37 (dd, J=11.3, 3.0 Hz, 1H), 3.88 (s, 3H), 2.22 (s, 3H), 2.05 (s, 3H).

Example 8

7-(3,5-Dimethylisoxazol-4-yl)-4-(2,4-difluorophenyl)-4,5-dihydroimidazo[1,5,4-de][1,4]benzoxazin-2(1H)-one

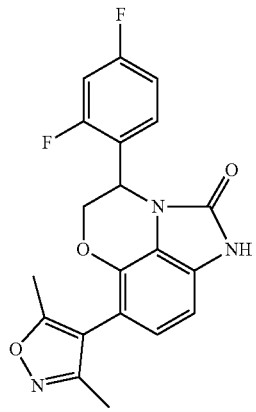 [SMILES: Cc1noc(C)c1-c1ccc2[nH]c(=O)n3c2c1OCC3c1ccc(F)cc1F]

The title compound was prepared by methods analogous to Example 1 but using 2-bromo-1-(2,4-difluorophenyl)ethanone [Aldrich, cat. #595152] in Step 1 and using dicyclohexyl(2',4',6'-triisopropylbiphenyl-2-yl)phosphine-(2'-aminobiphenyl-2-yl)(chloro)palladium as catalyst in Step 5. The product was purified by preparative HPLC on a C-18 column eluting with water:MeCN gradient buffered pH 2 with TFA to give the title compound as a white amorphous solid (0.018 g, 45%). LCMS calc. for $C_{20}H_{16}F_2N_3O_3$(M+H)$^+$: m/z=384.1; found: 384.1. $^1$H NMR (300 MHz, DMSO-d$_6$) δ 11.05 (s, 1H), 7.44-7.27 (m, 1H), 7.09-6.97 (m, 1H), 6.95-6.82 (m, 2H), 6.78 (d, J=8.0 Hz, 1H), 5.62 (s, 1H), 4.54-4.36 (m, 2H), 2.26 (s, 3H), 2.09 (s, 3H).

Example 9

7-(3,5-Dimethylisoxazol-4-yl)-2-methyl-4-phenyl-4,5-dihydroimidazo[1,5,4-de][1,4]benzoxazine

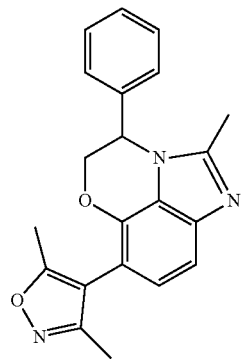 [SMILES: Cc1noc(C)c1-c1ccc2nc(C)n3c2c1OCC3c1ccccc1]

The title compound was prepared by methods analogous to Example 1 but using 1,1,1-trimethoxyethane [Aldrich, cat. #237876] in Step 3. The product was purified by preparative HPLC on a C-18 column eluting with water:MeCN gradient buffered pH 2 with TFA to give the TFA salt of the title compound as a white amorphous solid (0.003 g, 7%). LCMS calc. for $C_{21}H_{20}N_3O_2$ (M+H)$^+$: m/z=346.1; found: 346.2. $^1$H NMR (500 MHz, DMSO-d$_6$) δ 7.44-7.36 (m, 4H), 7.26 (d, J=8.4 Hz, 1H), 7.19 (d, J=5.8 Hz, 2H), 6.03 (s, 1H), 4.72 (dd, J=11.8, 3.9 Hz, 1H), 4.64 (dd, J=11.7, 3.3 Hz, 1H), 2.37 (s, 3H), 2.30 (s, 3H), 2.13 (s, 3H).

Example 10

7-(3,5-Dimethylisoxazol-4-yl)-1-(2-morpholin-4-ylethyl)-4-phenyl-4,5-dihydroimidazo[1,5,4-de][1,4]benzoxazin-2(1H)-one

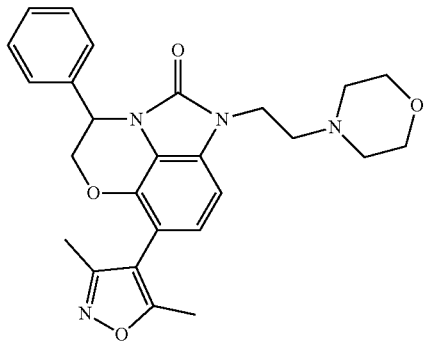 [SMILES: Cc1noc(C)c1-c1ccc2c3c1OCC(c1ccccc1)n3c(=O)n2CCN1CCOCC1]

Step 1. 7-Bromo-1-(2-morpholin-4-ylethyl)-4-phenyl-4,5-dihydroimidazo[1,5,4-de][1,4]benzoxazin-2(1H)-one

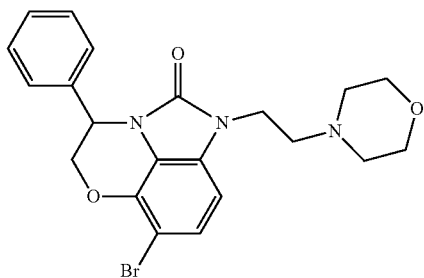 [SMILES: O=c1n(CCN2CCOCC2)c2ccc(Br)c3c2n1C(c1ccccc1)CO3]

To a 0° C. mixture of 7-bromo-4-phenyl-4,5-dihydroimidazo[1,5,4-de][1,4]benzoxazin-2(1H)-one (0.065 g, 0.20 mmol) from Example 1, step 4 and 4-(2-chloroethyl)morpholine hydrochloride (0.12 g, 0.63 mmol) in DMF (1 mL) was added NaH in mineral oil (0.048 g, 1.2 mmol). The reaction mixture was stirred over a weekend. EtOAc and water were added. The organic layer was washed with water and brine, dried over Na$_2$SO$_4$ and evaporated to dryness to give an orange oil. The crude was purified by LCMS (C18 column eluting with a gradient MeCN/H$_2$O containing 0.15% NH$_4$OH at 5 mL/min.) and gave a white solid (7.7 mg, 9% yield). $^1$H NMR (400 MHz, CD$_3$OD/CDCl$_3$): d 7.31 (3H, m); 7.18 (3H, m); 6.65 (1H, d); 5.19 (1H, m); 4.61 (1H, m); 4.43 (1H, m); 3.99 (2H, m); 3.6 (4H, m); 2.65 (2H, m); 2.51 (4H, m). LCMS calc. for $C_{26}H_{29}N_4O_4$ (M+H)$^+$: m/z=; found: 444.1, 446.1.

Step 2. 7-(3,5-Dimethylisoxazol-4-yl)-1-(2-morpholin-4-ylethyl)-4-phenyl-4,5-dihydroimidazo[1,5,4-de][1 4]benzoxazin-2(1H)-one A deoxygenated solution of 7-(3,5-dimethylisoxazol-4-yl)-1-(2-morpholin-4-ylethyl)-4-phenyl-4,5-dihydroimidazo[1,5,4-de][1,4]benzoxazin-2(1H)-one (7.0 mg, 0.015 mmol), 3,5-dimethyl-4-(4,4,5,5-tetramethyl-1,3,2-dioxaborolan-2-yl)isoxazole (4.6 mg, 0.021 mmol), dicyclohexyl(2',4',6'-triisopropylbiphenyl-2-yl)phosphine-(2'-aminobiphenyl-2-yl)(chloro)palladium (1:1) (0.0017 g, 0.0022 mmol) and potassium phosphate (0.013 g, 0.061 mmol) in 1,4-dioxane (0.2 mL) and water (0.08 mL) was refluxed for 2 h. The reaction mixture was cooled to room temperature and then additional reagents (3,5-dimethyl-4-(4,4,5,5-tetramethyl-1,3,2-dioxaborolan-2-yl)isoxazole (4.6 mg), potassium phosphate (12 mg) and catalyst (2.7 mg)) were added. The solution mixture was deoxygenated and then refluxed for 2.3 h. EtOAc and water were added. The organic layer was washed with brine and then concentrated to give a pale orange glass/oil (22 mg). The crude product was purified by LCMS (C18 column eluting with a gradient MeCN/H$_2$O containing 0.15% NH$_4$OH at 5 mL/min.) and gave the title compound as a white solid (7.6 mg, 95% yield). $^1$H NMR (500 MHz, DMSO-d$_6$): d 7.35 (3H, m); 7.18 (2H, m); 7.0 (1H, m); 6.95 (1H, m); 5.55 (1H, m); 4.61 (1H, m); 4.42 (1H, m); 3.99 (2H, m); 3.5 (4H, m); 2.63 (2H, m); 2.42 (4H, m); 2.23 (3H, s); 2.08 (3H, s). LCMS calc. for $C_{21}H_{23}BrN_3O_3$ (M+H)$^+$: m/z=460.2; found: 460.2.

Example 11

7-(3,5-Dimethyl-1H-pyrazol-4-yl)-4-phenyl-4,5-dihydroimidazo[1,5,4-de][1,4]benzoxazin-2(1H)-one

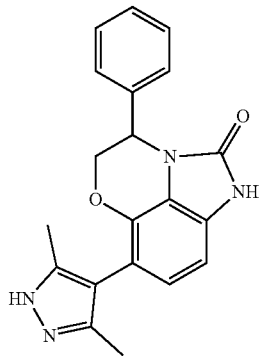 [SMILES: Cc1n[nH]c(C)c1-c1ccc2[nH]c(=O)n3c2c1OCC3c1ccccc1]

The title compound was prepared by methods analogous to Example 1 but using added 3,5-dimethyl-4-(4,4,5,5-tetramethyl-1,3,2-dioxaborolan-2-yl)-1H-pyrazole[Aldrich, cat. #636010] in Step 5. The product was purified by preparative HPLC on a C-18 column eluting with water:MeCN gradient buffered pH 2 with TFA to give the title compound as a white amorphous solid (0.018 g, 45%). LCMS calc. for $C_{20}H_{19}N_4O_2$ (M+H)$^+$: m/z=347.1; found: 347.2.

Example 12

7-(3-Methyl-1H-pyrazol-4-yl)-4-phenyl-4,5-dihydroimidazo[1,5,4-de][1,4]benzoxazin-2(1H)-one

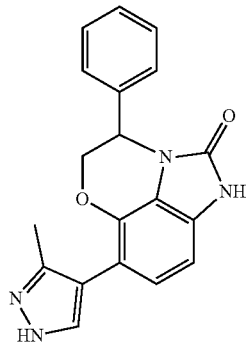

The title compound was prepared by methods analogous to Example 1 but using added 3-methyl-4-(4,4,5,5-tetramethyl-1,3,2-dioxaborolan-2-yl)-1H-pyrazole [Aldrich, cat. #706078] in Step 5. The product was purified by preparative HPLC on a C-18 column eluting with water:MeCN gradient buffered pH 2 with TFA to give the title compound as a white amorphous solid (0.018 g, 45%). LCMS calc. for $C_{19}H_{17}N_4O_2$ (M+H)$^+$: m/z=333.1; found: 333.2.

Example 13

7-(3,5-Dimethylisoxazol-4-yl)-4-pyridin-2-yl-4,5-dihydroimidazo[1,5,4-de][1,4]benzoxazin-2(1H)-one

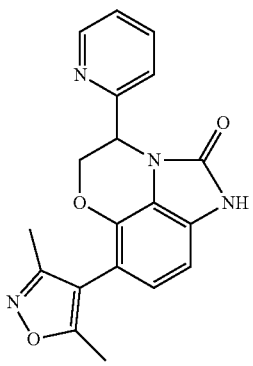 [SMILES: Cc1noc(C)c1-c1ccc2[nH]c(=O)n3c2c1OCC3c1ccccn1]

The title compound was prepared by methods analogous to Example 1 but using 2-bromo-1-(pyridin-2-yl)ethanone HBr [Maybridge CC04005DA] in Step 1. The product was purified by preparative HPLC on a C-18 column eluting with a water:MeCN gradient buffered pH 2 with TFA to give the TFA salt of the title compound as a white amorphous solid (0.015 g, 30%). LCMS calc. for $C_{19}H_{17}N_4O_3$ (M+H)$^+$: m/z=349.1; found: 349.1. $^1$H NMR (300 MHz, DMSO-d$_6$) δ 11.01 (s, 1H), 8.52 (d, J=4.8 Hz, 1H), 7.79 (td, 1H), 7.32 (dd, J=7.5, 4.9 Hz, 1H), 7.12 (d, J=7.8 Hz, 1H), 6.83 (d, J=8.0 Hz, 1H), 6.76 (d, J=8.0 Hz, 1H), 5.52 (s, 1H), 4.76 (dd, 1H), 4.44 (dd, J=11.4, 3.1 Hz, 1H), 2.22 (s, 3H), 2.05 (s, 3H).

Example 14

7-(3,5-Dimethylisoxazol-4-yl)-4-pyridin-2-yl-4,5-dihydroimidazo[1,5,4-de][1,4]benzoxazin-2(1H)-one (Enantiomer 1)

Example 15

7-(3,5-Dimethylisoxazol-4-yl)-4-pyridin-2-yl-4,5-dihydroimidazo[1,5,4-de][1,4]benzoxazin-2(1H)-one (Enantiomer 2)

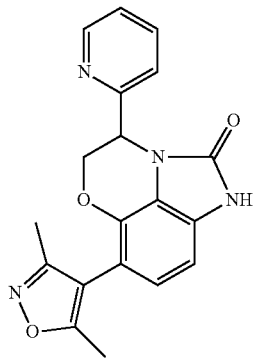 [SMILES: Cc1noc(C)c1-c1ccc2[nH]c(=O)n3c2c1OCC3c1ccccn1]

The enantiomers were prepared from racemic 7-(3,5-dimethylisoxazol-4-yl)-4-pyridin-2-yl-4,5-dihydroimidazo[1,5,4-de][1,4]benzoxazin-2(1H)-one from Example 13, by chiral column HPLC using a Phenomenex Lux Cellulose-C4 column, 5 micron, 21.2×250 mm, eluting with 60% ethanol in hexanes with a flow rate of 18 mL/min., loading approx. 36 mg per injection with UV (220 nm) detection to give peak 1 at: 7.51 min. and peak 2 at: 12.92 min.

Enantiomer 2. Peak 1: Example 15. LCMS calc. for $C_{19}H_{17}N_4O_3$ (M+H)$^+$: m/z=349.1; found: 349.1. $^1$H NMR (300 MHz, DMSO-d$_6$) δ 11.01 (s, 1H), 8.52 (d, J=4.8 Hz, 1H), 7.79 (td, 1H), 7.32 (dd, J=7.5, 4.9 Hz, 1H), 7.12 (d, J=7.8 Hz, 1H), 6.83 (d, J=8.0 Hz, 1H), 6.76 (d, J=8.0 Hz, 1H), 5.52 (s, 1H), 4.76 (dd, 1H), 4.44 (dd, J=11.4, 3.1 Hz, 1H), 2.22 (s, 3H), 2.05 (s, 3H). This enantiomer is believed to have the S configuration based on X-ray crystallography data.

Enantiomer 1. Peak 2: Example 14. LCMS calc. for $C_{19}H_{17}N_4O_3$ (M+H)$^+$: m/z=349.1; found: 349.1. $^1$H NMR (300 MHz, DMSO-d$_6$) δ 11.01 (s, 1H), 8.52 (d, J=4.8 Hz, 1H), 7.79 (td, 1H), 7.32 (dd, J=7.5, 4.9 Hz, 1H), 7.12 (d, J=7.8 Hz, 1H), 6.83 (d, J=8.0 Hz, 1H), 6.76 (d, J=8.0 Hz, 1H), 5.52 (s, 1H), 4.76 (dd, 1H), 4.44 (dd, J=11.4, 3.1 Hz, 1H), 2.22 (s, 3H), 2.05 (s, 3H).

Example 16

7-(3,5-Dimethylisoxazol-4-yl)-4-(1-oxidopyridin-2-yl)-4,5-dihydroimidazo[1,5,4-de][1,4]benzoxazin-2(1H)-one

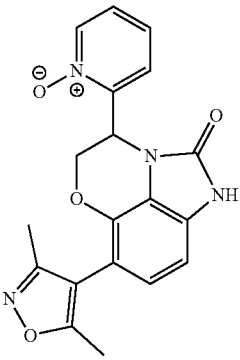 [SMILES: Cc1noc(C)c1-c1ccc2[nH]c(=O)n3c2c1OCC3c1cccc[n+]1[O-]]

Methyltrioxorhenium(VII) (2 mg, 0.008 mmol) was added to a solution of 7-(3,5-dimethylisoxazol-4-yl)-4-pyridin-2-yl-4,5-dihydroimidazo[1,5,4-de][1,4]benzoxazin-2(1H)-one (20 mg, 0.06 mmol) from Example 15, in tetrahydrofuran (2 mL) at room temperature and then 3.0 M hydrogen peroxide in water (0.04 mL) was added. The reaction mixture was heated to 80° C. for 20 min. allowed to cool and was diluted with water and EtOAc. The combined organic layers were washed with brine, dried over MgSO$_4$, filtered and concentrated to give the crude product. The product was purified by preparative HPLC on a C-18 column eluting with a water: MeCN gradient buffered pH 10 to give the title compound as a white amorphous solid (0.007 g, 30%). LCMS calc. for C$_{19}$H$_{17}$N$_4$O$_4$ (M+H)$^+$: m/z=365.1; found: 365.1. 1H NMR (400 MHz, DMSO-d6) δ 11.12 (s, 1H), 8.37 (d, J=5.8 Hz, 1H), 7.39 (td, J=7.2, 6.5, 2.0 Hz, 1H), 7.25 (td, J=7.7, 0.9 Hz, 1H), 6.84 (d, J=8.1 Hz, 1H), 6.77 (d, J=8.0 Hz, 1H), 6.63 (dd, J=7.9, 2.0 Hz, 1H), 5.84 (d, J=2.2 Hz, 1H), 4.78 (dd, J=11.6, 1.3 Hz, 1H), 4.36 (dd, J=11.6, 3.4 Hz, 1H), 2.17 (s, 3H), 2.00 (s, 3H).

Example 17

4-Cyclohexyl-7-(3,5-dimethylisoxazol-4-yl)-4,5-dihydroimidazo[1,5,4-de][1,4]benzoxazin-2(1H)-one

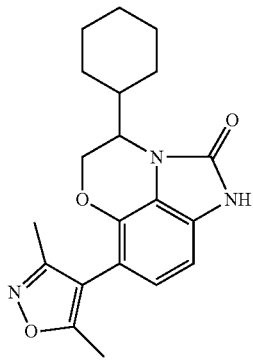 [SMILES: Cc1noc(C)c1-c1ccc2[nH]c(=O)n3c2c1OCC3C1CCCCC1]

Step 1. 2-Bromo-1-cyclohexylethanone

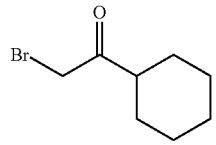

Cyclohexyl methyl ketone (0.30 mL, 2.4 mmol) [Alfa Aesar cat# L05501] was dissolved in methanol (3.0 mL, 74 mmol) cooled in an ice bath and bromine (0.38 g, 2.4 mmol) was added drop wise. The mixture was stirred for 2 h and then water (3.0 mL) was added and the reaction mixture was allowed to stir for 4 h. The reaction mixture was extracted with EtOAc:hexane (3:1). The combined organic layer was washed with water saturated potassium carbonate, brine, dried over magnesium sulfate and concentrated to give as 2-bromo-1-cyclohexylethanone as a clear oil (0.49 g, 100%). $^1$H NMR (300 MHz, CDCl$_3$) δ 3.96 (s, 2H), 2.86-2.55 (m, 1H), 2.24-1.08 (m, 10H).

Step 2

The title compound was prepared by methods analogous to Example 1 but using 2-bromo-1-cyclohexylethanone from Step 1 above. The product was purified by preparative HPLC on a C-18 column eluting with a water:MeCN gradient buffered pH 2 with TFA to give the title compound as a white amorphous solid (0.010 g, 30%). LCMS calc. for C$_{20}$H$_{24}$N$_3$O$_3$ (M+H)$^+$: m/z=354.1; found: 354.2. $^1$H NMR (400 MHz, DMSO-d$_6$) δ 10.86 (s, 1H), 6.78 (d, J=8.0 Hz, 1H), 6.68 (d, J=8.0 Hz, 1H), 4.65 (d, J=11.1 Hz, 1H), 4.04 (d, J=6.4 Hz, 1H), 3.97 (dd, J=11.8, 2.9 Hz, 1H), 2.28 (s, 3H), 2.12 (s, 3H), 1.82-1.51 (m, 6H), 1.13 (d, J=18.1 Hz, 5H).

Example 18A

7-(3,5-Dimethylisoxazol-4-yl)-4-(tetrahydrofuran-2-yl)-4,5-dihydroimidazo[1,5,4-de][1,4]benzoxazin-2(1H)-one (Diastereoisomer 1)

Example 18B

7-(3,5-Dimethylisoxazol-4-yl)-4-(tetrahydrofuran-2-yl)-4,5-dihydroimidazo[1,5,4-de][1,4]benzoxazin-2(1H)-one (Diastereoisomer 2)

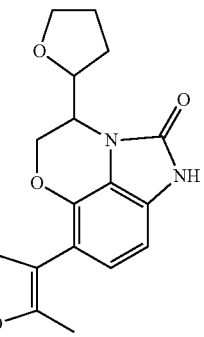

The title compound was prepared by methods analogous to Example 1, but using 2-bromo-1-(furan-2-yl)ethanone in Step 1 and the furan was reduced to the tetrahydrofuran in Step 2. The product was purified by preparative HPLC on a C-18 column eluting with a water: MeCN gradient buffered pH2 to give the title compound as two separated diastereoisomers Diastereoisomer 1. Peak 1. Example 18A. Solid residue. LCMS calc. for $C_{18}H_{20}N_3O_4$ (M+H)$^+$: m/z=342.1; found: 342.1.

Diastereoisomer 2. Peak 2. Example 18B. Solid residue. LCMS calc. for $C_{18}H_{20}N_3O_4$ (M+H)$^+$: m/z=342.1; found: 342.1.

Example 19

7-(3,5-Dimethylisoxazol-4-yl)-4-(5-fluoropyridin-2-yl)-4,5-dihydroimidazo[1,5,4-de][1,4]benzoxazin-2(1H)-one

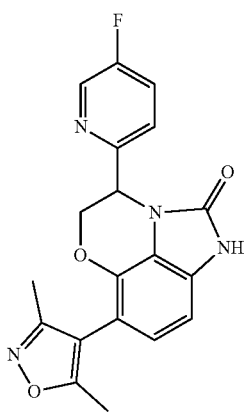 [SMILES: Cc1noc(C)c1-c1ccc2[nH]c(=O)n3c2c1OCC3c1ccc(F)cn1]

Step 1. 2-(1-Ethoxyvinyl)-5-fluoropyridine

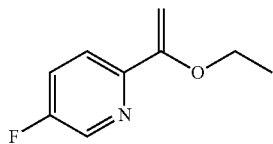

A mixture of 2-bromo-5-fluoropyridine (200 mg, 1 mmol), tributyl(1-ethoxyvinyl)tin (500 mg, 1 mmol), copper (I) iodide (20 mg, 0.1 mmol) and bis(triphenylphosphine)palladium(II) chloride (50 mg, 0.07 mmol) in MeCN (5 mL) was heated to 80° C. for 30 h. The reaction mixture was allowed to cool to room temperature and was diluted with EtOAc, washed with 5% NH$_4$OH, brine, dried over MgSO$_4$, filtered and concentrated to give a crude oil. The product was purified by flash column chromatography on silica gel eluting with a hexane; EtOAc gradient (0-30%) to give 2-(1-ethoxyvinyl)-5-fluoropyridine as a clear oil (0.2 g, 90%). LCMS calc. for $C_9H_{11}FNO$ (M+H)+: m/z=168.1; found: 168.2.

Step 2. 2-Bromo-1-(5-fluoropyridin-2-yl)ethanone

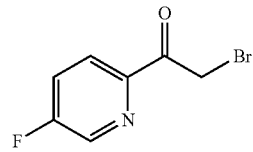

N-Bromosuccinimide (200 mg, 1 mmol) was added to a mixture of 2-(1-ethoxyvinyl)-5-fluoropyridine (200 mg, 1 mmol) in THF (6 mL) and water (2 mL). The reaction mixture was stirred at room temperature for 15 min., diluted with EtOAc and washed with brine. The combined organic layer was dried with MgSO$_4$, filtered and concentrated to give 2-bromo-1-(5-fluoropyridin-2-yl)ethanone as a clear oil, which was used in the next step.

Step 3. 7-(3,5-Dimethylisoxazol-4-yl)-4-(5-fluoropyridin-2-yl)-4,5-dihydroimidazo[1,5,4-de][1,4]benzoxazin-2(1H)-one The title compound was prepared by methods analogous to Example 1, but using 2-bromo-1-(5-fluoropyridin-2-yl)ethanone from above, in Step 1. The product was purified by preparative HPLC on a C-18 column eluting with a water: MeCN gradient buffered pH2 to give the title compound as a solid residue. LCMS calc. for $C_{19}H_{16}FN_4O_3$(M+H)+: m/z=367.1; found: 367.1.

Example 20

Ethyl 7-(3,5-dimethylisoxazol-4-yl)-2-oxo-4-pyridin-2-yl-1,2,4,5-tetrahydroimidazo[1,5,4-de][1,4]benzoxazine-5-carboxylate

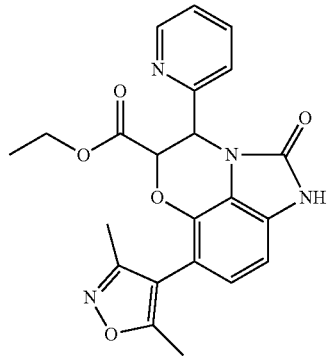 [SMILES: CCOC(=O)C1Oc2c(-c3c(C)noc3C)ccc3[nH]c(=O)n(c23)C1c1ccccn1]

Step 1. Ethyl 2-bromo-3-oxo-3-pyridin-2-ylpropanoate hydrobromide

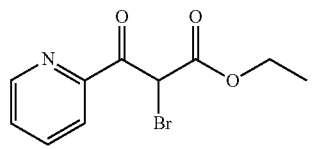

Bromine (0.83 g, 5.2 mmol) in chloroform (2 mL) was added slowly to a solution of ethyl 3-oxo-3-pyridin-2-ylpropanoate (1.0 g, 5.2 mmol) and chloroform (25.0 mL) at room temperature. The reaction mixture was stirred for 1 h and was concentrated under reduced pressure to give 1 ethyl 2-bromo-3-oxo-3-pyridin-2-ylpropanoate hydrobromide salt as an amber oil (1.8 g, 100%). LCMS calc. for $C_{10}H_{11}BrNO_3$ (M+H)+: m/z=272.0, 274.0; found: 272.0, 274.0.

Step 2. Ethyl 7-(3,5-dimethylisoxazol-4-yl)-2-oxo-4-pyridin-2-yl-1,2,4,5-tetrahydroimidazo[1,5,4-de][1,4]benzoxazine-5-carboxylate The title compound was prepared by methods analogous to Example 1, but using 2-bromo-3-oxo-3-pyridin-2-ylpropanoate from above, in Step 1. The product was purified by preparative HPLC on a C-18 column eluting with a water:MeCN gradient buffered pH 10 to give a mixture of the two diastereoisomers of the title compound as a solid residue. LCMS calc. for $C_{22}H_{21}N_4O_5$ (M+H)+: m/z=421.1; found: 421.1.

Example 21

7-(3,5-Dimethylisoxazol-4-yl)-4-(1,3-thiazol-2-yl)-4,5-dihydroimidazo[1,5,4-de][1,4]benzoxazin-2(1H)-one

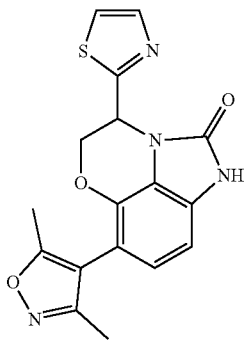 [SMILES: Cc1noc(C)c1-c1ccc2[nH]c(=O)n3c2c1OCC3c1nccs1]

Step 1. 2-Bromo-1-(1,3-thiazol-2-yl)ethanone

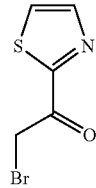

Bromine (70 μL, 1 mmol) was added to a mixture of 1-(1,3-thiazol-2-yl)ethanone (200 mg, 2 mmol) in AcOH (5 mL). The reaction mixture was stirred at 100° C. for 30 min. and was concentrated under reduced pressure to give 2-bromo-1-(1,3-thiazol-2-yl)ethanone as an oil (100%) used as crude.

Step 2. 7-(3,5-dimethylisoxazol-4-yl)-4-(1,3-thiazol-2-yl)-4,5-dihydroimidazo[1,5,4-de][1,4]benzoxazin-2 (1H)-one The title compound was prepared by a method analogous to Example 1, but using 2-bromo-1-(1,3-thiazol-2-yl)ethanone from above, in Step 1. The product was purified by preparative HPLC on a C-18 column eluting with a water:MeCN gradient buffered pH 2 to give the title compound as a solid residue. LCMS calc. for $C_{17}H_{15}N_4O_3S$ (M+H)+: m/z=355.1; found: 355.1. $^1$H NMR (500 MHz, DMSO-d6) δ 11.05 (s, 1H), 7.78 (d, J=3.2 Hz, 1H), 7.69 (d, J=3.2 Hz, 1H), 6.85 (d, J=8.0 Hz, 1H), 6.77 (d, J=8.0 Hz, 1H), 5.90 (s, 1H), 4.83 (d, J=10.4 Hz, 1H), 4.44 (dd, J=11.6, 2.9 Hz, 1H), 2.24 (s, 3H), 2.07 (s, 3H).

Example 22

2-{2-[7-(3,5-Dimethylisoxazol-4-yl)-2-oxo-1,2,4,5-tetrahydroimidazo[1,5,4-de][1,4]benzoxazin-4-yl]phenoxy}-N-ethylacetamide

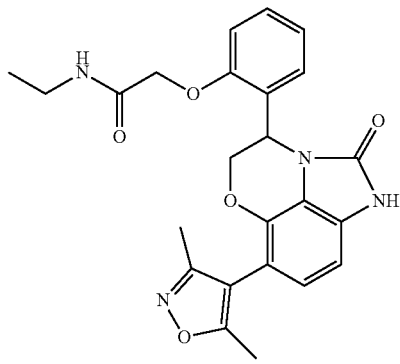 [SMILES: CCNC(=O)COc1ccccc1C1COc2c(-c3c(C)noc3C)ccc3[nH]c(=O)n1c23]

Step 1. Methyl (2-acetylphenoxy)acetate

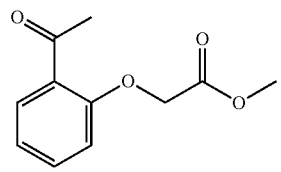

1-(2-Hydroxyphenyl)ethanone (1.0 g, 7.3 mmol) and methyl bromoacetate (0.70 mL, 7.3 mmol) were combined in acetone (20.0 mL) with potassium carbonate (2.0 g, 15 mmol) and was stirred at room temperature. The reaction mixture was stirred for 18 h, diluted with EtOAc and filtered to remove the solids. The organic layer was concentrated to give the sub-title compound as a clear oil (1.5 g, 100%). LCMS calc. for $C_{11}H_{13}O_4$(M+H)+: m/z=209.1; found: 209.1.

Step 2. Methyl [2-(bromoacetyl)phenoxy]acetate

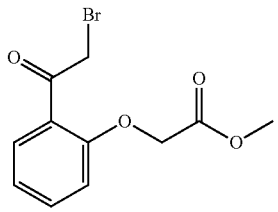 [SMILES: COC(=O)COc1ccccc1C(=O)CBr]

Bromine (1.2 g, 7.2 mmol) in chloroform (5 mL) was added drop wise to a solution of methyl (2-acetylphenoxy) acetate (1.5 g, 7.2 mmol) in chloroform (45 mL) at room temperature. The reaction mixture was stirred for 1 h at room temperature, diluted with EtOAc and washed with sodium bicarbonate water, brine, dried over magnesium sulfate and concentrated to give the sub-title compound as an oil which solidified (2.1 g, 100%). LCMS calc. for $C_{11}H_{12}BrO_4$ (M+H)+: m/z=287.0, 289.0; found: 287.0, 289.0.

Step 3. {2-[7-(3,5-dimethylisoxazol-4-yl)-2-oxo-1,2,4,5-tetrahydroimidazo[1,5,4-de][1,4]benzoxazin-4-yl]phenoxy}acetic acid

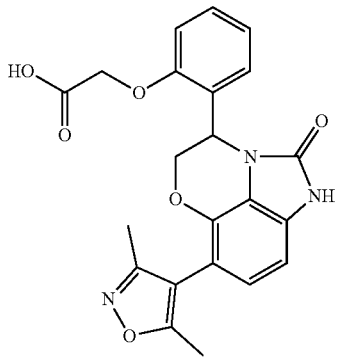 [SMILES: Cc1noc(C)c1-c1ccc2[nH]c(=O)n3c2c1OCC3c1ccccc1OCC(=O)O]

The intermediate compound was prepared by methods analogous to Example 1, but using methyl [2-(bromoacetyl) phenoxy]acetate from above, in Step 1 and the ester was found to saponify in Step 5 to give the sub-title compound as a solid residue. LCMS calc. for $C_{22}H_{20}N_3O_6$ (M+H)+: m/z=422.1; found: 422.1.

Step 4. 2-{2-[7-(3,5-Dimethylisoxazol-4-yl)-2-oxo-1,2,4,5-tetrahydroimidazo[1,5,4-de][1,4]benzoxazin-4-yl]phenoxy}-N-ethylacetamide A mixture of {2-[7-(3,5-dimethylisoxazol-4-yl)-2-oxo-1,2,4,5-tetrahydroimidazo[1,5,4-de][1,4]benzoxazin-4-yl] phenoxy}acetic acid (0.03 g, 0.07 mmol) in DMF (2.0 mL) with DIPEA (0.025 mL, 0.14 mmol) and HATU (0.027 g, 0.071 mmol) was stirred at room temperature for 10 min. and ethylamine (0.0064 g, 0.14 mmol) was added. The reaction mixture was stirred for 1 h and the product was purified without workup by preparative HPLC on a C-18 column eluting with a water:MeCN gradient buffered pH 2 buffered with TFA to give the title compound as an off-white amorphous solid. LCMS calc. for $C_{24}H_{25}N_4O_5$ (M+H)+: m/z=449.1; found: 449.2.

Example 23

Ethyl 7-(3,5-dimethylisoxazol-4-yl)-2-oxo-4-phenyl-1,2,4,5-tetrahydroimidazo[1,5,4-de][1,4]benzoxazine-5-carboxylate

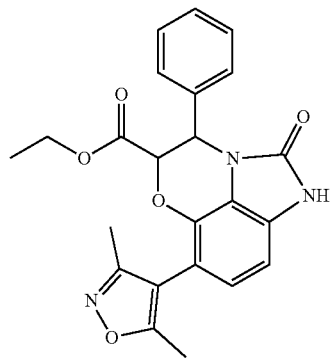 [SMILES: CCOC(=O)C1Oc2c(-c3c(C)noc3C)ccc3[nH]c(=O)n(c23)C1c1ccccc1]

Step 1. Ethyl 2-bromo-3-oxo-3-phenylpropanoate

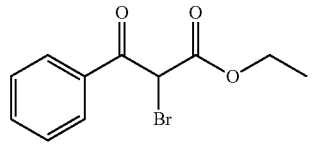

Ethyl benzoylacetate (0.27 mL, 1.6 mmol) [Fluka cat#12990] was dissolved in dimethyl sulfoxide (5.0 mL) at room temperature and the N-bromosuccinimide (0.30 g, 1.7 mmol) was added portion wise. The reaction mixture was stirred for 3 h and EtOAc was added and washed with water, water saturated sodium bicarbonate, brine, dried over magnesium sulfate and concentrated to give Ethyl 2-bromo-3-oxo-3-phenylpropanoate (0.40 g, 95%) as an oil %). LCMS calc. for $C_{11}H_{12}BrO_3$ (M+H)+: m/z=271.0, 273.0; found: 271.0, 273.0.

Step 2. Ethyl 7-(3,5-dimethylisoxazol-4-yl)-2-oxo-4-phenyl-1,2,4,5-tetrahydroimidazo[1,5,4-de][1,4] benzoxazine-5-carboxylate The title compound was prepared by a method analogous to Example 1, but using ethyl 2-bromo-3-oxo-3-phenylpropanoate Step 1 above. The product was purified by preparative HPLC on a C-18 column eluting with a water:MeCN gradient buffered pH 2 with TFA to give a mixture of diastereoisomers of the title compound as a white amorphous solid (0.012 g, 25%). LCMS calc. for $C_{23}H_{22}N_3O_5$ (M+H)+: m/z=320.1; found: 320.2. $^1$H NMR (300 MHz, DMSO-$d_6$) δ 11.01 (d, J=5.1 Hz, 1H), 7.38-7.19 (m, 3H), 7.14-6.94 (m, 2H), 6.94-6.65 (m, 2H), 5.70 (s, 0.4H), 5.54 (t, J=2.4 Hz, 1H), 5.36 (d, J=3.3 Hz, 0.6H), 3.99 (dq, J=14.2, 7.1 Hz, 2H), 2.29 (s, 1.8H), 2.19 (s, 1.2H), 2.14 (s, 1.8H), 2.02 (s, 1.2H), 0.99 (dt, J=9.8, 7.1 Hz, 3H).

Example 24A 7-(3,5-Dimethylisoxazol-4-yl)-N-ethyl-2-oxo-4-phenyl-1,2,4,5-tetrahydroimidazo[1,5,4-de][1,4]benzoxazine-5-carboxamide (Diastereoisomer 1)

Example 24B 7-(3,5-Dimethylisoxazol-4-yl)-N-ethyl-2-oxo-4-phenyl-1,2,4,5-tetrahydroimidazo[1,5,4-de][1,4]benzoxazine-5-carboxamide (Diastereoisomer 2)

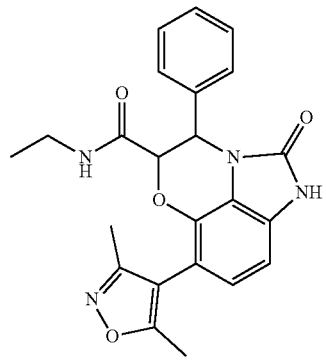 [SMILES: CCNC(=O)C1Oc2c(-c3c(C)noc3C)ccc3[nH]c(=O)n(c23)C1c1ccccc1]

Step 1. 7-(3,5-Dimethylisoxazol-4-yl)-2-oxo-4-phenyl-1,2,4,5-tetrahydroimidazo[1,5,4-de][1,4]benzoxazine-5-carboxylic acid

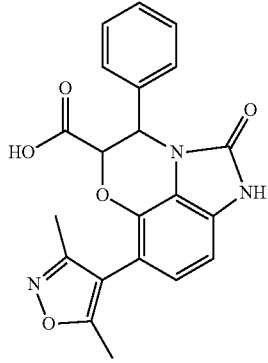 [SMILES: Cc1noc(C)c1-c1ccc2[nH]c(=O)n3c2c1OC(C(=O)O)C3c1ccccc1]

Ethyl 7-(3,5-dimethylisoxazol-4-yl)-2-oxo-4-phenyl-1,2,4,5-tetrahydroimidazo[1,5,4-de][1,4]benzoxazine-5-carboxylate (0.150 g, 0.358 mmol) from Example 23 was dissolved in MeOH (3.0 mL) and lithium hydroxide, monohydrate (0.030 g, 0.72 mmol) dissolved in water (1.0 mL) was added. The reaction mixture was stirred at room temperature for 2 h, diluted with EtOAc and washed with saturated water ammonium chloride, brine, dried over magnesium sulfate and concentrated to give a mixture of the diastereoisomers of the title compound as a solid residue (0.145 g, 100%). LCMS calc. for $C_{21}H_{18}N_3O_5$ (M+H)+: m/z=392.1; found: 392.1.

Step 2. 7-(3,5-Dimethylisoxazol-4-yl)-N-ethyl-2-oxo-4-phenyl-1,2,4,5-tetrahydroimidazo[1,5,4-de][1,4]benzoxazine-5-carboxamide 7-(3,5-Dimethylisoxazol-4-yl)-2-oxo-4-phenyl-1,2,4,5-tetrahydroimidazo[1,5,4-de][1,4]benzoxazine-5-carboxylic acid (0.04 g, 0.1 mmol) was dissolved in DMF (2.0 mL) with DIPEA (0.036 mL, 0.20 mmol) at room temperature. HATU (0.054 g, 0.14 mmol) was added and then the 2.0 M ethylamine in THF (0.20 mL, 0.41 mmol) was added. The reaction mixture was stirred at room temperature for an hour and was diluted with EtOAc. The organic layer was washed with 1 N HCl, brine, dried over magnesium sulfate and concentrated to give a solid. The product was purified by preparative HPLC on a C-18 column eluting with a water:MeCN gradient buffered pH 2 to give the title compound as two separated diastereoisomers.

Diastereoisomer 1. Peak 1. Example 24A. Solid residue (0.010 g, 25%). LCMS calc. for $C_{23}H_{23}N_4O_4$ (M+H)+: m/z=419.1; found: 419.1.

Diastereoisomer 2. Peak 2. Example 24B. Solid residue (0.008 g, 20%). LCMS calc. for $C_{23}H_{23}N_4O_4$ (M+H)+: m/z=419.1; found: 419.1.

Example 25

7-(3,5-Dimethylisoxazol-4-yl)-N-isopropyl-4-phenyl-4,5-dihydroimidazo[1,5,4-de][1,4]benzoxazin-2-amine

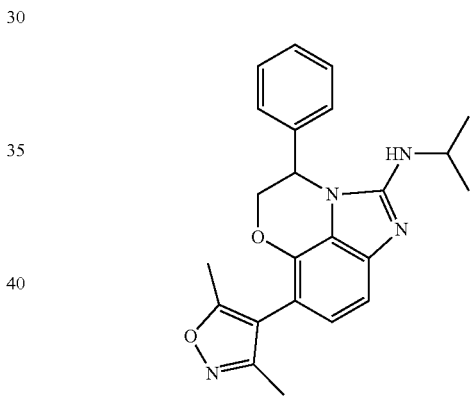

Step 1. 2-Chloro-7-(3,5-dimethylisoxazol-4-yl)-4-phenyl-4,5-dihydroimidazo[1,5,4-de][1,4]benzoxazine

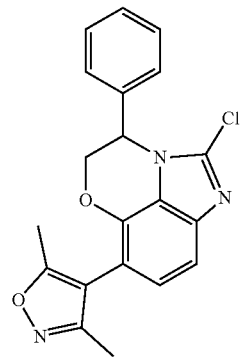 [SMILES: Cc1noc(C)c1-c1ccc2nc(Cl)n3c2c1OCC3c1ccccc1]

To 7-(3,5-dimethylisoxazol-4-yl)-4-phenyl-4,5-dihydroimidazo[1,5,4-de][1,4]benzoxazin-2(1H)-one (40.0 mg, 0.115 mmol) in a vial, phosphoryl chloride (1.5 mL, 16 mmol) was added and the mixture was heated at 95° C. overnight. The mixture was evaporated and extracted with EtOAc. The extracts were washed with saturated sodium bicarbonate, brine and dried over sodium sulfate. Filtration and evaporation gave the desired compound (42 mg, 100%). LCMS calc. for $C_{20}H_{17}ClN_3O_2(M+H)^+$: m/z=366.1; found: 366.1.

Step 2. 7-(3,5-Dimethylisoxazol-4-yl)-N-isopropyl-4-phenyl-4,5-dihydroimidazo[1,5,4-de][1,4]benzoxazin-2-amine To 2-chloro-7-(3,5-dimethylisoxazol-4-yl)-4-phenyl-4,5-dihydroimidazo[1,5,4-de][1,4]benzoxazine (9.1 mg, 0.025 mmol) in N-methylpyrrolidinone (0.40 mL), triethylamine (10 µL, 0.075 mmol) and 2-propanamine (21.2 µL, 0.25 mmol) were added and the mixture was heated at 120° C. overnight. The mixture was diluted with MeOH and purified by preparative LCMS (pH 10) to give the desired compound (2.8 mg, 29%). $^1$H NMR (500 MHz, DMSO-$d_6$): δ 7.29 (3H, m); 6.92 (3H, m); 6.78 (1H, m); 6.55 (1H, m); 5.80 (1H, s); 4.68 (1H, m); 4.45 (1H, m); 4.00 (1H, m); 2.20 (3H, s); 2.02 (3H, s); 1.20 (3H, m); 1.09 (3H, m). LCMS calc. for $C_{23}H_{25}N_4O_2$ $(M+H)^+$: m/z=389.2; found: 389.2.

Example 26

7-(3,5-Dimethylisoxazol-4-yl)-N-methyl-4-phenyl-4,5-dihydroimidazo[1,5,4-de][1,4]benzoxazin-2-amine

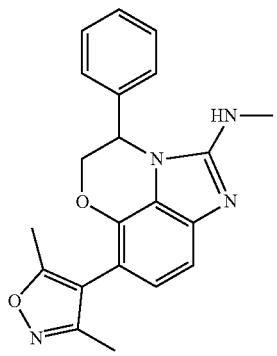 [SMILES: CNc1nc2ccc(-c3c(C)noc3C)c3c2n1C(c1ccccc1)CO3]

The title compound was prepared by a method analogous to Example 25, but using methylamine in Step 2. The product was purified by preparative HPLC on a C-18 column eluting with a water:MeCN gradient buffered pH 10 with ammonium hydroxide to give the title compound (2.1 mg, 13%). $^1$H NMR (500 MHz, DMSO-$d_6$): d 7.29 (3H, m); 6.93 (3H, m); 6.83 (1H, m); 6.79 (1H, m); 5.70 (1H, s); 4.61 (1H, m); 4.43 (1H, m); 2.87 (3H, m); 2.11 (3H, s); 2.03 (3H, s); 1.49 (1H, m). LCMS calc. for $C_{21}H_{21}N_4O_2$ $(M+H)^+$: m/z=361.2; found: 361.2.

Example 27

7-(3,5-Dimethylisoxazol-4-yl)-N-ethyl-4-phenyl-4,5-dihydroimidazo[1,5,4-de][1,4]benzoxazin-2-amine

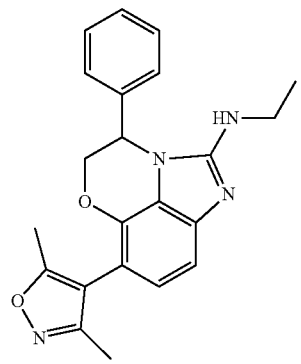 [SMILES: CCNc1nc2ccc(-c3c(C)noc3C)c3c2n1C(c1ccccc1)CO3]

The title compound was prepared by methods analogous to Example 25, but using ethyl amine in Step 2. The product was purified by preparative HPLC on a C-18 column eluting with a water:MeCN gradient buffered pH 10 with ammonium hydroxide to give the title compound (6.0 mg, 42%). $^1$H NMR (500 MHz, DMSO-$d_6$): δ 7.29 (3H, m); 6.93 (3H, m); 6.87 (1H, m); 6.78 (1H, m); 5.78 (1H, s); 4.63 (1H, m); 4.43 (1H, m); 3.32 (2H, m); 2.20 (3H, s); 2.02 (3H, s); 1.12 (3H, m). LCMS calc. for $C_{22}H_{23}N_4O_2$ $(M+H)^+$: m/z=375.2; found: 375.2.

Example 28

7-(3,5-Dimethylisoxazol-4-yl)-N,N-dimethyl-4-phenyl-4,5-dihydroimidazo[1,5,4-de][1,4]benzoxazin-2-amine

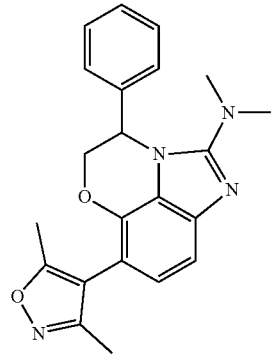 [SMILES: Cc1noc(C)c1-c1ccc2nc(N(C)C)n3c2c1OCC3c1ccccc1]

The title compound was prepared by methods analogous to Example 25, but using dimethylamine in Step 2. The product was purified by preparative HPLC on a C-18 column eluting with a water:MeCN gradient buffered pH 10 with ammonium hydroxide to give the title compound (6.7 mg, 72%). $^1$H NMR (500 MHz, DMSO-$d_6$): δ 7.29 (3H, m); 7.00 (1H, m); 6.85 (3H, m); 6.11 (1H, s); 4.52 (2H, m); 2.99 (6H, s); 2.20 (3H, s); 2.02 (3H, s). LCMS calc. for $C_{22}H_{23}N_4O_2$ $(M+H)^+$: m/z=375.2; found: 375.2.

Example 29

2-{[7-(3,5-Dimethylisoxazol-4-yl)-4-phenyl-4,5-dihydroimidazo[1,5,4-de][1,4]benzoxazin-2-yl]amino}ethanol

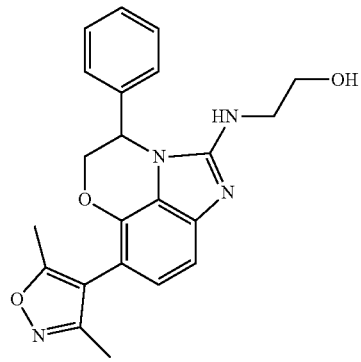 [SMILES: Cc1noc(C)c1-c1ccc2nc(NCCO)n3c2c1OCC3c1ccccc1]

The title compound was prepared by a method analogous to Example 25, but using ethanolamine [Aldrich #411000] in Step 2. The product was purified by preparative HPLC on a C-18 column eluting with a water:MeCN gradient buffered pH 10 with ammonium hydroxide to give the title compound (5.5 mg, 40%). LCMS calc. for $C_{22}H_{23}N_4O_3$ $(M+H)^+$: m/z=391.2; found: 391.2.

Example 30

2-{[7-(3,5-Dimethylisoxazol-4-yl)-4-phenyl-4,5-dihydroimidazo[1,5,4-de][1,4]benzoxazin-2-yl]amino}propan-1-ol (Diastereoisomer 1)

Example 31

2-{[7-(3,5-Dimethylisoxazol-4-yl)-4-phenyl-4,5-dihydroimidazo[1,5,4-de][1,4]benzoxazin-2-yl]amino}propan-1-ol (Diastereoisomer 2)

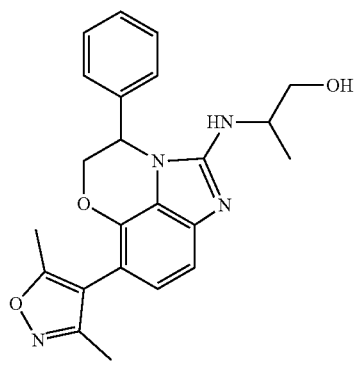 [SMILES: Cc1noc(C)c1-c1ccc2nc(NC(C)CO)n3c2c1OCC3c1ccccc1]

The title compound was prepared by a method analogous to Example 25, but using DL-alaninol [Aldrich #192171] in Step 2. The product was purified by preparative HPLC on a C-18 column eluting with a water:MeCN gradient buffered pH 10 with ammonium hydroxide to give the two racemic diastereoisomers of the title compound.

Diastereoisomer 1. Peak I. Example 30 (3.9 mg, 27%). $^1$H NMR (500 MHz, DMSO-$d_6$): δ 7.30 (4H, m); 6.92 (3H, m); 6.79 (1H, m); 6.53 (1H, m); 5.82 (1H, s); 4.76 (1H, m); 4.68 (1H, m); 4.43 (1H, m); 3.92 (1H, m); 3.45 (1H, m); 3.20 (1H, m); 2.20 (3H, s); 2.03 (3H, s); 1.19 (3H, m). LCMS calc. for $C_{23}H_{25}N_4O_3$ $(M+H)^+$: m/z=405.2; found: 405.2.

Diastereoisomer 2. Peak 2. Example 31. LCMS calc. for $C_{23}H_{25}N_4O_3$ $(M+H)^+$: m/z=405.2; found: 405.2.

Example 32

1-{[7-(3,5-Dimethylisoxazol-4-yl)-4-phenyl-4,5-dihydroimidazo[1,5,4-de][1,4]benzoxazin-2-yl]amino}propan-2-ol

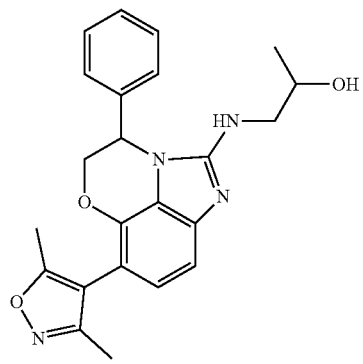 [SMILES: Cc1noc(C)c1-c1ccc2nc(NCC(C)O)n3c2c1OCC3c1ccccc1]

The title compound was prepared by a method analogous to Example 25, but using 1-amino-2-propanol [Aldrich #110248] in Step 2. The product was purified by preparative HPLC on a C-18 column eluting with a water:MeCN gradient buffered pH 10 with ammonium hydroxide to give the title compound (5.3 mg, 37%) as a mixture of diastereoisomers. LCMS calc. for $C_{23}H_{25}N_4O_3$ $(M+H)^+$: m/z=405.2; found: 405.2.

Example 33

2-{[7-(3,5-Dimethylisoxazol-4-yl)-4-phenyl-4,5-dihydroimidazo[1,5,4-de][1,4]benzoxazin-2-yl]amino}-2-methylpropan-1-ol

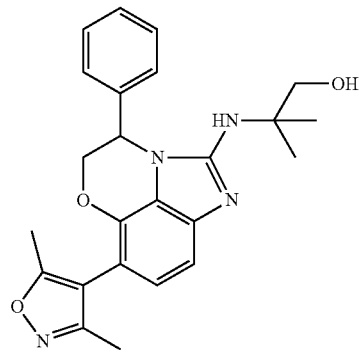 [SMILES: Cc1noc(C)c1-c1ccc2nc(NC(C)(C)CO)n3c2c1OCC3c1ccccc1]

The title compound was prepared by a method analogous to Example 25, but using 2-amino-2-methyl-1-propanol [Aldrich #A65182] in Step 2. The product was purified by preparative HPLC on a C-18 column eluting with a water:MeCN gradient buffered pH 10 with ammonium hydroxide to give the title compound (1.5 mg, 10%). LCMS calc. for $C_{24}H_{27}N_4O_3$ (M+H)$^+$: m/z=419.2; found: 419.2.

Example 34

2-[[7-(3,5-Dimethylisoxazol-4-yl)-4-phenyl-4,5-dihydroimidazo[1,5,4-de][1,4]benzoxazin-2-yl](methyl)amino]ethanol

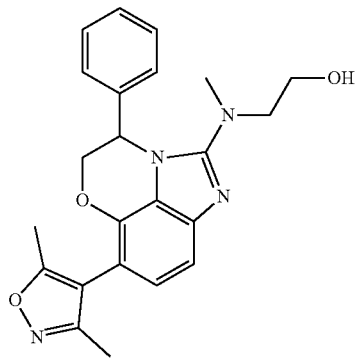 [SMILES: Cc1noc(C)c1-c1ccc2nc(N(C)CCO)n3c2c1OCC3c1ccccc1]

The title compound was prepared by a method analogous to Example 25, but using 2-(methylamino)ethanol [Aldrich #471445] in Step 2. The product was purified by preparative HPLC on a C-18 column eluting with a water:MeCN gradient buffered pH 10 with ammonium hydroxide to give the title compound (2.6 mg, 18%). LCMS calc. for $C_{23}H_{25}N_4O_3$ (M+H)$^+$: m/z=405.2; found: 405.2.

Example 35

7-(1-Methyl-1H-pyrazol-5-yl)-4-phenyl-4,5-dihydroimidazo[1,5,4-de][1,4]benzoxazin-2(1H)-one

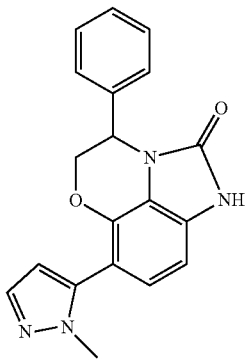 [SMILES: Cn1nccc1-c1ccc2[nH]c(=O)n3c2c1OCC3c1ccccc1]

7-Bromo-4-phenyl-4,5-dihydroimidazo[1,5,4-de][1,4]benzoxazin-2(1H)-one (100 mg, 0.3 mmol) was dissolved in 1,4-dioxane (2.4 mL). A solution of 1-methyl-5-(4,4,5,5-tetramethyl-1,3,2-dioxaborolan-2-yl)-1H-pyrazole (94 mg, 0.45 mmol) and potassium phosphate (100 mg, 0.6 mmol) in water (0.60 mL) was added. Reaction was deoxygenated with nitrogen. Dicyclohexyl(2',4',6'-triisopropylbiphenyl-2-yl)phosphine-(2'-aminobiphenyl-2-yl)(chloro)palladium (1:1) (7 mg, 0.009 mmol) was added and deoxygenated with nitrogen. The reaction mixture was stirred at 100° C. for 4 h. Water and EtOAc were added and the layers were separated. The organic layer was concentrated under reduced pressure. Purification on silica using EtOAc/hexanes gave the title compound (61 mg). LCMS calc. for $C_{19}H_{17}N_4O_2$ (M+H)$^+$: m/z=333.1; found: 333.2. $^1$H NMR (300 MHz, DMSO-d$_6$): d 7.40 (s, 1H); 7.31 (m, 3H); 7.13 (m, 2H); 6.92 (m, 1H); 6.79 (m, 1H); 6.22 (s, 1H); 5.49 (s, 1H); 4.59 (m, 1H); 4.41 (m, 1H); 3.60 (s, 3H).

Example 36

9-Bromo-7-(1-methyl-1H-pyrazol-5-yl)-4-phenyl-4,5-dihydroimidazo[1,5,4-de][1,4]benzoxazin-2(1H)-one

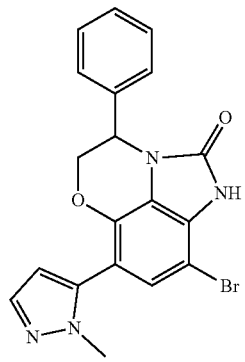 [SMILES: Cn1nccc1-c1cc(Br)c2[nH]c(=O)n3c2c1OCC3c1ccccc1]

To a solution of 7-(1-methyl-1H-pyrazol-5-yl)-4-phenyl-4,5-dihydroimidazo[1,5,4-de][1,4]benzoxazin-2(1H)-one (32 mg, 0.096 mmol) in THF (0.7 mL) was added N-bromosuccinimide (19 mg, 0.10 mmol). The solution was stirred at room temperature for 1 h and then concentrated under reduced pressure. Purification on silica gel using EtOAc/hexane gave the title compound, 24 mg. LCMS calc. for $C_{19}H_{16}BrN_4O_2$(M+H)$^+$: m/z=411.0, 413.0; found: 411.1, 413.1. $^1$H NMR (300 MHz, DMSO-d$_6$): d 7.40 (s, 1H); 7.31 (m, 3H); 7.13 (m, 2H); 7.08 (s, 1H); 6.30 (s, 1H); 5.50 (s, 1H); 4.59 (m, 1H); 4.41 (m, 1H); 3.60 (s, 3H).

Example 37

9-Methyl-7-(1-methyl-1H-pyrazol-5-yl)-4-phenyl-4,5-dihydroimidazo[1,5,4-de][1,4]benzoxazin-2(1H)-one

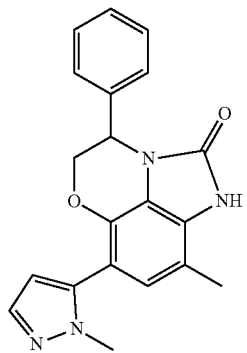 [SMILES: Cc1cc(-c2ccnn2C)c2c3c1[nH]c(=O)n3C(c1ccccc1)CO2]

A reaction mixture of 9-bromo-7-(1-methyl-1H-pyrazol-5-yl)-4-phenyl-4,5-dihydroimidazo[1,5,4-de][1,4]benzoxazin-2(1H)-one (17 mg, 0.04 mmol), a solution of 2.0 M methylzinc chloride in THF (0.10 mL) and tetrakis(triphenylphosphine)palladium(0) (2 mg, 0.002 mmol) in THF (0.5 mL) under nitrogen was heated in a microwave at 130° C. for 5 min. The title compound was purified by preparative LCMS using a pH10 buffer. LCMS calc. for $C_{20}H_{19}N_4O_2$ $(M+H)^+$: m/z=347.1; found: 347.2.

Example 38

7-(4-Chloro-1-methyl-1H-pyrazol-5-yl)-4-phenyl-4,5-dihydroimidazo[1,5,4-de][1,4]benzoxazin-2(1H)-one

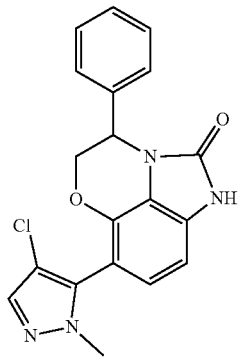 [SMILES: Cn1ncc(Cl)c1-c1ccc2[nH]c(=O)n3c2c1OCC3c1ccccc1]

Step 1. 4-Chloro-1-methyl-5-(4,4,5,5-tetramethyl-1,3,2-dioxaborolan-2-yl)-1H-pyrazole

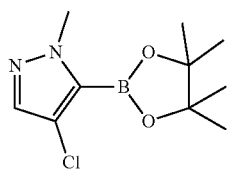 [SMILES: Cn1ncc(Cl)c1B1OC(C)(C)C(C)(C)O1]

A mixture of 1-methyl-5-(4,4,5,5-tetramethyl-1,3,2-dioxaborolan-2-yl)-1H-pyrazole (1.3 g, 6.3 mmol), N-chlorosuccinimide (0.93 g, 7.0 mmol) and THF (6.6 mL) was stirred at 70° C. for 3 h. The mixture was extracted with EtOAc, dried and concentrated under reduced pressure. The sub-title compound was purified by chromatography on silica gel using 40% EtOAc in hexanes gave the desired compound, 1.456 g, 95%.

Step 2. 7-(4-Chloro-1-methyl-1H-pyrazol-5-yl)-4-phenyl-4,5-dihydroimidazo[1,5,4-de][1,4]benzoxazin-2(1H)-one The title compound was prepared by a method analogous to Example 35, but using 4-chloro-1-methyl-5-(4,4,5,5-tetramethyl-1,3,2-dioxaborolan-2-yl)-1H-pyrazole. The product was purified by preparative HPLC on a C-18 column eluting with water:MeCN gradient buffered at pH2 to give the title compound. LCMS calc. for $C_{19}H_{16}ClN_4O_2(M+H)^+$: m/z=367.1; found: 367.1.

Example 39

7-(3,5-Dimethylisoxazol-4-yl)-4-phenyl-4,5-dihydroimidazo[1,5,4-de][1,4]benzoxazine

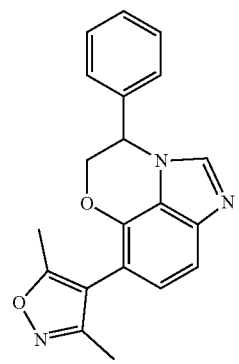 [SMILES: Cc1noc(C)c1-c1ccc2ncn3c2c1OCC3c1ccccc1]

A reaction mixture of 2-chloro-7-(3,5-dimethylisoxazol-4-yl)-4-phenyl-4,5-dihydroimidazo[1,5,4-de][1,4]benzoxazine (15 mg, 0.041 mmol), 0.5 M bromo(propyl)zinc in THF (0.5 mL) and tetrakis(triphenylphosphine)palladium(0) (2 mg, 0.002 mmol) in THF (0.4 mL) under nitrogen was heated in a microwave at 150° C. for 5 min. Purification of the product by preparative LCMS using pH 10 buffer gave the title compound. LCMS calc. for $C_{20}H_{17}N_3O_2$ $(M+H)^+$: m/z=332.1; found: 332.2.

Example 40

7-(3,5-Dimethylisoxazol-4-yl)-4-phenyl-2-piperazin-1-yl-4,5-dihydroimidazo[1,5,4-de][1,4]benzoxazine

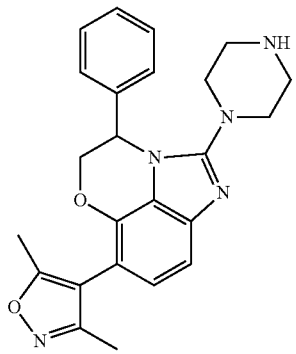 [SMILES: Cc1noc(C)c1-c1ccc2nc(N3CCNCC3)n3c2c1OCC3c1ccccc1]

4-[7-(3,5-Dimethylisoxazol-4-yl)-4-phenyl-4,5-dihydroimidazo[1,5,4-de][1,4]benzoxazin-2-yl]piperazine-1-carboxylate (Example 60) was stirred in 4 N HCl for 15 min. at room temperature and evaporated. Purification by preparative LCMS at pH 10 gave the desired compound which was isolated as the dihydrochloride salt. LCMS calc. for $C_{24}H_{26}N_5O_2$ $(M+H)^+$: m/z=416.2; found: 416.2.

Example 41

7-(3,5-Dimethylisoxazol-4-yl)-2,4-diphenyl-4,5-dihydroimidazo[1,5,4-de][1,4]benzoxazine

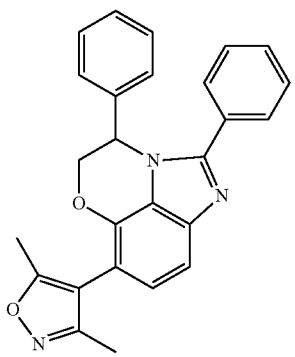 [SMILES: Cc1noc(C)c1-c1ccc2nc(-c3ccccc3)n3c2c1OCC3c1ccccc1]

A mixture of 2-chloro-7-(3,5-dimethylisoxazol-4-yl)-4-phenyl-4,5-dihydroimidazo[1,5,4-de][1,4]benzoxazine (14 mg, 0.039 mmol), phenylboronic acid (5.6 mg, 0.046 mmol), [1,1'-bis(diphenylphosphino)ferrocene]dichloropalladium(II), complex with DCM (1:1) (2 mg, 0.002 mmol) and potassium carbonate (16 mg, 0.12 mmol) in 1,4-dioxane (0.2 mL), and water (0.1 mL). The resulting mixture was heated at 80° C. for 3 h. The reaction mixture was diluted with MeOH and purified on Preparative LCMS using pH 10 buffer to give the desired compound.

LCMS calc. for $C_{26}H_{22}N_3O_2$ (M+H)$^+$: m/z=408.2; found: 408.2.

Example 42

7-(3,5-Dimethylisoxazol-4-yl)-2-oxo-4-phenyl-1,2,4,5-tetrahydroimidazo[1,5,4-de][1,4]benzoxazine-9-carbonitrile

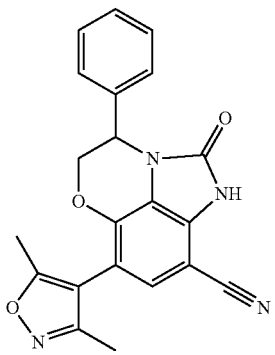 [SMILES: Cc1noc(C)c1-c1cc(C#N)c2[nH]c(=O)n3c2c1OCC3c1ccccc1]

9-Bromo-7-(3,5-dimethylisoxazol-4-yl)-4-phenyl-4,5-dihydroimidazo[1,5,4-de][1,4]benzoxazin-2(1H)-one (6.9 mg, 0.016 mmol), zinc cyanide (19 mg, 0.16 mmol) and tetrakis(triphenylphosphine)palladium(0) (2.8 mg, 0.0024 mmol) were dissolved in DMF (1.6 mL) and the solution was deoxygenated. The stirred reaction mixture was heated at 150° C. in a microwave for 5 min. The mixture was diluted with MeOH and purified by preparative LCMS using pH 10 buffer to give the title compound. LCMS calc. for $C_{21}H_{17}N_4O_3$ (M+H)$^+$: m/z=373.1; found: 373.2.

Example 43

7-(3,5-Dimethylisoxazol-4-yl)-4,9-diphenyl-4,5-dihydroimidazo[1,5,4-de][1,4]benzoxazin-2(1H)-one

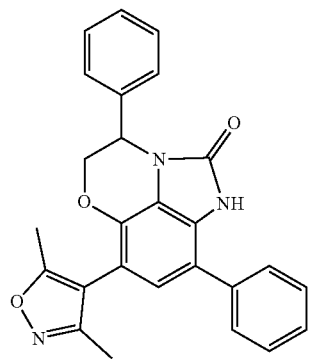 [SMILES: Cc1noc(C)c1-c1cc(-c2ccccc2)c2[nH]c(=O)n3c2c1OCC3c1ccccc1]

A mixture of 9-bromo-7-(3,5-dimethylisoxazol-4-yl)-4-phenyl-4,5-dihydroimidazo[1,5,4-de][1,4]benzoxazin-2(1H)-one (9.0 mg, 0.021 mmol), phenylboronic acid (3.1 mg, 0.025 mmol), [1,1'-bis(diphenylphosphino)ferrocene]dichloropalladium(II), complex with DCM (1:1) (0.9 mg, 0.001 mmol) and potassium carbonate (8.8 mg, 0.063 mmol) in 1,4-dioxane (0.1 mL), and water (0.07 mL) was heated at 80° C. for 3 h. The reaction mixture was diluted with MeOH and purified on by preparative LCMS using a pH 10 buffer to give the title compound. LCMS calc. for $C_{26}H_{22}N_3O_3$ (M+H)$^+$: m/z=424.2; found: 424.0.

Example 44

7-(1,4-Dimethyl-1H-pyrazol-5-yl)-4-pyridin-2-yl-4,5-dihydroimidazo[1,5,4-de][1,4]benzoxazin-2(1H)-one

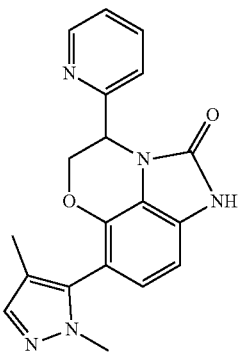 [SMILES: Cc1cnn(C)c1-c1ccc2[nH]c(=O)n3c2c1OCC3c1ccccn1]

Step 1. 1,4-Dimethyl-5-(4,4,5,5-tetramethyl-1,3,2-dioxaborolan-2-yl)-1H-pyrazole

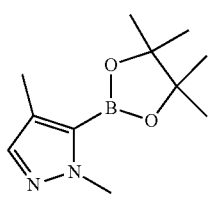 [SMILES: Cc1cnn(C)c1B1OC(C)(C)C(C)(C)O1]

1,4-Dimethyl-1H-pyrazole (50 mg, 0.5 mmol) was stirred in THF (2 mL) and cooled to 0° C. A solution of 1.6 M n-butyllithium in hexanes (390 mL) was added dropwise by syringe and the mixture was allowed to warm to room temperature for 2 h. The mixture was cooled to −78° C. and 2-isopropoxy-4,4,5,5-tetramethyl-1,3,2-dioxaborolane (110 mL, 0.52 mmol) was added dropwise by syringe. The mixture was stirred at −78° C. for 15 min. and at 0° C. for 3 h. The mixture was diluted with EtOAc and washed with brine, dried over sodium sulfate, filtered and concentrated under reduced pressure. Purification by chromatography on silica gel using EtOAc in hexanes gave the sub-title compound. LCMS calc. for $C_{11}H_{20}BN_2O_2(M+H)^+$: m/z=223.2; found: 223.0.

Step 2. 7-(1,4-dimethyl-1H-pyrazol-5-yl)-4-pyridin-2-yl-4,5-dihydroimidazo[1,5,4-de][1,4]benzoxazin-2(1H)-one 7-Bromo-4-pyridin-2-yl-4,5-dihydroimidazo[1,5,4-de][1,4]benzoxazin-2(1H)-one (28 mg, 0.084 mmol) was dissolved in 1,4-dioxane (0.67 mL). 1,4-Dimethyl-5-(4,4,5,5-tetramethyl-1,3,2-dioxaborolan-2-yl)-1H-pyrazole (28 mg, 0.13 mmol) and potassium phosphate (40 mg, 0.2 mmol) in water (0.17 mL) was added. The reaction mixture was deoxygenated with nitrogen. Dicyclohexyl(2',4',6'-triisopropylbiphenyl-2-yl)phosphine-(2'-aminobiphenyl-2-yl)(chloro)palladium (1:1) (2 mg, 0.002 mmol) was added and the mixture was again deoxygenated with nitrogen. The reaction mixture was then stirred at 90° C. under nitrogen for 2 h. Product was purified using preparative LCMS (pH 10) to give the title compound. LCMS calc. for $C_{19}H_{17}N_5O_2$ (M+H)$^+$: m/z=348.1; found: 348.0.

Example 45

9-Bromo-7-(3,5-Dimethylisoxazol-4-yl)-4-phenyl-4,5-dihydroimidazo[1,5,4-de][1,4]benzoxazin-2(1H)-one

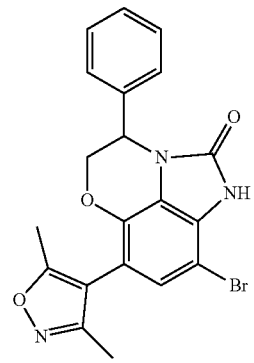 [SMILES: Cc1noc(C)c1-c1cc(Br)c2[nH]c(=O)n3c2c1OCC3c1ccccc1]

The title compound was prepared by methods analogous to Example 36, but using 7-(3,5-dimethylisoxazol-4-yl)-4-phenyl-4,5-dihydroimidazo[1,5,4-de][1,4]benzoxazin-2(1H)-one. LCMS calc. for $C_{20}H_{17}BrN_3O_3(M+H)^+$: m/z=426.0; found: 426.0.

Example 46

7-(3,5-Dimethylisoxazol-4-yl)-9-methyl-4-phenyl-4,5-dihydroimidazo[1,5,4-de][1,4]benzoxazin-2(1H)-one

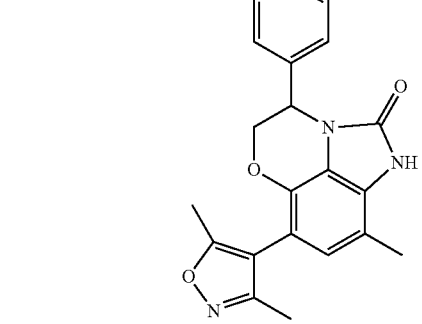

The title compound was prepared by methods analogous to Example 37, but using 9-bromo-7-(3,5-dimethylisoxazol-4-yl)-4-phenyl-4,5-dihydroimidazo[1,5,4-de][1,4]benzoxazin-2(1H)-one. LCMS calc. for $C_{21}H_{20}N_3O_3$ (M+H)$^+$: m/z=362.1; found: 362.2.

Examples 47A-52

The experimental procedures used to prepare the compounds of Examples 47A to 52 are summarized in Table 1 below. Examples 47A and 47B and Examples 48A and 48B are pairs of diastereoisomers which were chromatographically separated by methods analogous to the separations described above.

TABLE 1

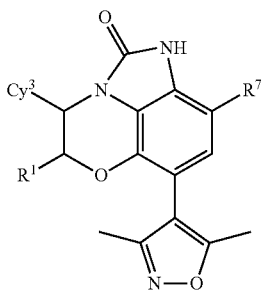

| Example No. | Name | R¹ | R⁷ | Cy³ | Proc.[1] |
|---|---|---|---|---|---|
| 47A | 7-(3,5-Dimethylisoxazol-4-yl)-N,N-dimethyl-2-oxo-4-phenyl-1,2,4,5-tetrahydroimidazo[1,5,4-de][1,4]benzoxazine-5-carboxamide (Diastereoisomer 1) | -C(O)N(CH₃)₂ | H | Ph | 23 |
| 47B | 7-(3,5-Dimethylisoxazol-4-yl)-N,N-dimethyl-2-oxo-4-phenyl-1,2,4,5-tetrahydroimidazo[1,5,4-de][1,4]benzoxazine-5-carboxamide (Diastereoisomer 2) | -C(O)N(CH₃)₂ | H | Ph | 23 |
| 48A | 7-(3,5-Dimethylisoxazol-4-yl)-N-(2-hydroxyethyl)-2-oxo-4-phenyl-1,2,4,5-tetrahydroimidazo[1,5,4-de][1,4]benzoxazine-5-carboxamide (Diastereoisomer 1) | -C(O)NHCH₂CH₂OH | H | Ph | 23 |
| 48B | 7-(3,5-Dimethylisoxazol-4-yl)-N-(2-hydroxyethyl)-2-oxo-4-phenyl-1,2,4,5-tetrahydroimidazo[1,5,4-de][1,4]benzoxazine-5-carboxamide (Diastereoisomer 2) | -C(O)NHCH₂CH₂OH | H | Ph | 23 |
| 49 | 7-(3,5-Dimethylisoxazol-4-yl)-4-(4-fluorophenyl)-4,5-dihydroimidazo[1,5,4-de][1,4]benzoxazin-2(1H)-one | H | H | 4-fluorophenyl | 1 |
| 50 | 2-{2-[7-(3,5-Dimethylisoxazol-4-yl)-2-oxo-1,2,4,5-tetrahydroimidazo[1,5,4-de][1,4]benzoxazin-4-yl]phenoxy}-N-(2-hydroxyethyl)acetamide | H | H | 2-(OCH₂C(O)NHCH₂CH₂OH)phenyl | 23 |
| 51 | 2-{2-[7-(3,5-Dimethylisoxazol-4-yl)-2-oxo-1,2,4,5-tetrahydroimidazo[1,5,4-de][1,4]benzoxazin-4-yl]phenoxy}-N,N-dimethylacetamide | H | H | 2-(OCH₂C(O)N(CH₃)₂)phenyl | 23 |

TABLE 1-continued

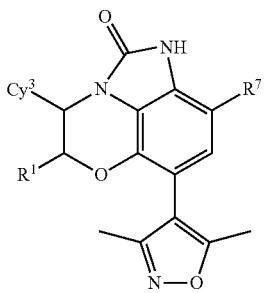

| Example No. | Name | R¹ | R⁷ | Cy³ | Proc.[1] |
|---|---|---|---|---|---|
| 52 | 7-(3,5-Dimethylisoxazol-4-yl)-4-phenyl-9-pyridin-3-yl-4,5-dihydroimidazo[1,5,4-de][1,4]benzoxazin-2(1H)-one | H | pyridin-3-yl | Ph | 43 |

[1]Synthesized according to an experimental procedure analogous to that used for the synthesis of the Example compound indicated.

Examples 53-60

The experimental procedures used to prepare the compounds of Examples 53 to 61 are summarized in Table 2 below.

TABLE 2

| Example No. | Name | R⁵ | Cy³ | Procedure[1] |
|---|---|---|---|---|
| 53 | 7-(3,5-Dimethylisoxazol-4-yl)-2-morpholin-4-yl-4-phenyl-4,5-dihydroimidazo[1,5,4-de][1,4]benzoxazine | morpholin-4-yl | Ph | 25 |
| 54 | 7-(3,5-Dimethylisoxazol-4-yl)-4-phenyl-2-pyrrolidin-1-yl-4,5-dihydroimidazo[1,5,4-de][1,4]benzoxazine | pyrrolidin-1-yl | Ph | 25 |
| 55 | 1-[7-(3,5-Dimethylisoxazol-4-yl)-4-phenyl-4,5-dihydroimidazo[1,5,4-de][1,4]benzoxazin-2-yl]pyrrolidin-3-ol | 3-hydroxypyrrolidin-1-yl | Ph | 25 |
| 56 | 7-(3,5-Dimethylisoxazol-4-yl)-4-phenyl-2-piperidin-1-yl-4,5-dihydroimidazo[1,5,4-de][1,4]benzoxazine | piperidin-1-yl | Ph | 25 |
| 57 | 1-[7-(3,5-Dimethylisoxazol-4-yl)-4-phenyl-4,5-dihydroimidazo[1,5,4-de][1,4]benzoxazin-2-yl]piperidin-4-ol | 4-hydroxypiperidin-1-yl | Ph | 25 |
| 58 | 1-[7-(3,5-Dimethylisoxazol-4-yl)-4-phenyl-4,5-dihydroimidazo[1,5,4-de][1,4]benzoxazin-2-yl]piperidin-3-ol | 3-hydroxypiperidin-1-yl | Ph | 25 |
| 59 | 1-[7-(3,5-(3,5-Dimethylisoxazol-4-yl)-4-phenyl-4,5-dihydroimidazo[1,5,4-de][1,4]benzoxazin-2-yl]azetidin-3-ol | 3-hydroxyazetidin-1-yl | Ph | 25 |

TABLE 2-continued

| Example No. | Name | R[5] | Cy[3] | Procedure[1] |
|---|---|---|---|---|
| 60 | 4-[7-(3,5-Dimethylisoxazol-4-yl)-4-phenyl-4,5-dihydroimidazo[1,5,4-de][1,4]benzoxazin-2-yl]piperazine-1-carboxylate | | | Ph 25 |

[1]Synthesized according to the experimental procedure of compound listed;

Example 61A 7-(3,5-Dimethylisoxazol-4-yl)-5,5-dimethyl-4-pyridin-2-yl-4,5-dihydroimidazo[1,5,4-de][1,4]benzoxazin-2(1H)-one (Diastereoisomer 1)

Example 61B 7-(3,5-Dimethylisoxazol-4-yl)-5,5-dimethyl-4-pyridin-2-yl-4,5-dihydroimidazo[1,5,4-de][1,4]benzoxazin-2(1H)-one (Diastereoisomer 2)

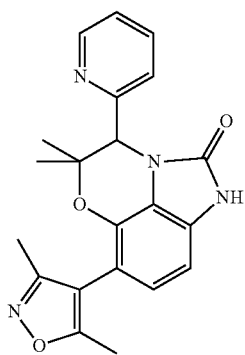 [SMILES: Cc1noc(C)c1-c1ccc2[nH]c(=O)n3c2c1OC(C)(C)C3c1ccccn1]

Step 1. 2-Bromo-2-methyl-1-(pyridin-2-yl)propan-1-one

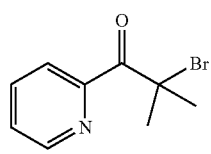

Bromine (2.1 g, 13.4 mmol) dissolved in acetic acid (1 mL) was added slowly to a mixture of 2-methyl-(1-pyridin-2-yl)propan-1-one (2.0 g, 13 mmol) in acetic acid (20 mL) at room temperature. The reaction was heated to 105° C. for 3 h, allowed to cool to room temperature, and concentrated in vacuo to give a dark semisolid. The crude product was partitioned between ethyl acetate and saturated aqueous sodium bicarbonate. The combined organic layer was washed with brine, dried over magnesium sulfate, and concentrated to give 2-bromo-2-methyl-1-(pyridin-2-yl)propan-1-one as a very dark oil (3.0 g, 98%). LCMS calculated for $C_9H_{11}BrNO$ (M+H)$^+$: m/z=227.9, 229.9; found: 228.1, 230.1.

Step 2. 7-(3,5-Dimethylisoxazol-4-yl)-5,5-dimethyl-4-pyridin-2-yl-4,5-dihydroimidazo[1,5,4-de][1,4]benzoxazin-2 (1H)-one The title compound was prepared by methods analogous to Example 13, but using 2-bromo-2-methyl-1-(pyridin-2-yl)propan-1-one in Step 1. The product was purified by prep HPLC on a C-18 column eluting a water:acetonitrile gradient buffered at pH 10 to give the title compound as a mixture of diastereomers. The isomers were separated by prep chiral column chromatography using the following conditions: Column: phenomenex Lux Cellulose C-2 5 µm, 21, 2×250 mm, Mobile phase: 45% EtOH/Hexanes, gradient condition: isocratic at 18 mL/min, Loading: 13.0 mg in 900 µL, run time: 18 min, peak time: 9.0, and 12.0 min.

Diastereoisomer 1, Peak 1 as a solid residue. LCMS calculated for $C_{21}H_{21}N_4O_3$ (M+H)$^+$: m/z=377.1; found: 377.1. 1H NMR (400 MHz, DMSO-d6) δ 10.87 (s, 1H), 8.41 (dt, J 4.0, 0.9 Hz, 1H), 7.74 (td, J 7.7, 1.8 Hz, 1H), 7.27 (ddd, J 7.6, 4.8, 1.1 Hz, 1H), 7.11 (d, J 7.9 Hz, 1H), 6.84 (d, J 8.0 Hz, 1H), 6.71 (d, J 8.0 Hz, 1H), 5.24 (s, 1H), 2.27 (s, 3H), 2.11 (s, 3H), 1.36 (s, 3H), 1.11 (s, 3H).

Diastereoisomer, Peak 2 as a solid residue. LCMS calculated for $C_{21}H_{21}N_4O_3$ (M+H)$^+$: m/z=377.1; found: 377.1. 1H NMR (400 MHz, DMSO-d6) δ 10.87 (s, 1H), 8.41 (dt, J 4.0, 0.9 Hz, 1H), 7.74 (td, J 7.7, 1.8 Hz, 1H), 7.27 (ddd, J 7.6, 4.8, 1.1 Hz, 1H), 7.11 (d, J 7.9 Hz, 1H), 6.84 (d, J 8.0 Hz, 1H), 6.71 (d, J 8.0 Hz, 1H), 5.24 (s, 1H), 2.27 (s, 3H), 2.11 (s, 3H), 1.36 (s, 3H), 1.11 (s, 3H).

Example 62A 7-(3,5-Dimethylisoxazol-4-yl)-5-(hydroxymethyl)-4-pyridin-2-yl-4,5-dihydroimidazo[1,5,4-de][1,4]benzoxazin-2(1H)-one (Diastereoisomer 1)

Example 62B 7-(3,5-Dimethylisoxazol-4-yl)-5-(hydroxymethyl)-4-pyridin-2-yl-4,5-dihydroimidazo[1,5,4-de][1,4]benzoxazin-2(1H)-one (Diastereoisomer 2)

Example 62C 7-(3,5-Dimethylisoxazol-4-yl)-5-(hydroxymethyl)-4-pyridin-2-yl-4,5-dihydroimidazo[1,5,4-de][1,4]benzoxazin-2(1H)-one (Diastereoisomer 3)

Example 62D 7-(3,5-Dimethylisoxazol-4-yl)-5-(hydroxymethyl)-4-pyridin-2-yl-4,5-dihydroimidazo[1,5,4-de][1,4]benzoxazin-2(1H)-one (Diastereoisomer 4)

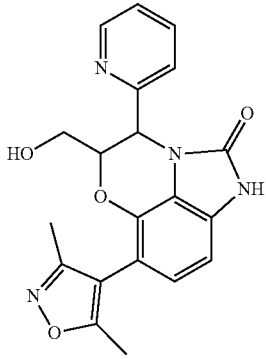 [SMILES: Cc1noc(C)c1-c1ccc2[nH]c(=O)n3c2c1OC(CO)C3c1ccccn1]

Lithium tetrahydroborate (1.6 mg, 0.071 mmol) was added to ethyl 7-(3,5-dimethylisoxazol-4-yl)-2-oxo-4-pyridin-2-yl-1,2,4,5-tetrahydroimidazo[1,5,4-de][1,4]benzoxazine-5-carboxylate (20 mg, 0.05 mmol), from Example 20, in tetrahydrofuran (3 mL). The reaction was stirred at 70° C. for 3 h, then partitioned between water and ethyl acetate. The organic layer was concentrated and the crude product was purified by FCC on silica gel eluting a hexane:ethyl acetate gradient to obtain the product as a mixture of diastereomers. The isomers were separated by prep chiral column chromatography using the following conditions: Column: phenomenex Lux Cellulose C-2 5 µm, 21, 2×250 mm, Mobile phase: 45% EtOH/Hexanes, Gradient condition: isocratic at 18 mL/min, Loading: 13.5 mg in 900 µL, run time: 18 min, peak time: 9.0, 12.1, 24.2 and 15.0 min.

Diastereoisomer 1, Peak 1 as a solid residue. LCMS calculated for $C_{20}H_{19}N_4O_4$ (M+H)$^+$: m/z=379.1; found: 379.1.

Diastereoisomer 2, Peak 2 as a solid residue. LCMS calculated for $C_{20}H_{19}N_4O_4$ (M+H)$^+$: m/z=379.1; found: 379.1. $^1$H NMR (400 MHz, DMSO-d6) δ 10.93 (s, 1H), 8.47 (d, J 4.1 Hz, 1H), 7.79-7.65 (m, 1H), 7.26 (dd, J 7.0, 5.2 Hz, 1H), 7.01 (d, J 7.9 Hz, 1H), 6.76 (d, J 8.0 Hz, 1H), 6.67 (d, J 8.0 Hz, 1H), 5.37 (d, J 3.2 Hz, 1H), 5.22 (t, J 5.4 Hz, 1H), 4.71-4.57 (m, 1H), 3.45 (q, J=5.5 Hz, 2H), 2.17 (s, 3H), 2.01 (s, 3H).

Diastereoisomer 3, Peak 3 as a solid residue. LCMS calculated for $C_{20}H_{19}N_4O_4$ (M+H)$^+$: m/z=379.1; found: 379.1.

Diastereoisomer 4, Peak 4 as a solid residue. LCMS calculated for $C_{20}H_{19}N_4O_4$ (M+H)$^+$: m/z=379.1; found: 379.1.

Example 63A 7-(3,5-Dimethylisoxazol-4-yl)-4-piperidin-2-yl-4,5-dihydroimidazo[1,5,4-de][1,4]benzoxazin-2(1H)-one 2,2,2-trifluoroacetate (Diastereoisomer 1)

Example 63B 7-(3,5-Dimethylisoxazol-4-yl)-4-piperidin-2-yl-4,5-dihydroimidazo[1,5,4-de][1,4]benzoxazin-2(1H)-one 2,2,2-trifluoroacetate (Diastereoisomer 2)

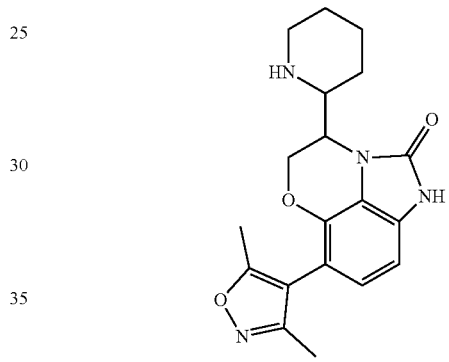

Step 1. 4-Piperidin-2-yl-4,5-dihydroimidazo[1,5,4-de][1,4]benzoxazin-2(1H)-one

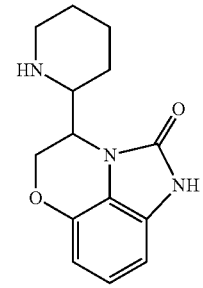 [SMILES: O=c1[nH]c2cccc3c2n1C(C1CCCCN1)CO3]

The tricycle intermediate, 4-pyridin-2-yl-4,5-dihydroimidazo[1,5,4-de][1,4]benzoxazin-2(1H)-one (0.25 g, 0.98 mmol) from Example 13, was partially dissolved in methanol (50.0 mL) and 12.0 M hydrogen chloride in water (1.0 mL, 12 mmol) in a Parr bottle. The reaction was degassed with nitrogen, followed by addition of palladium (10% on carbon), and the reaction was charged to 55 PSI hydrogen and shaken for 6 days. The reaction was filtered to remove the catalyst and concentrated in vacuo to give 4-piperidin-2-yl-4,5-dihydroimidazo[1,5,4-de][1,4]benzoxazin-2(1H)-one as a dark oil (0.21 g, 82%). LCMS calculated for $C_{14}H_{18}N_3O_2$ (M+H)$^+$: m/z=260.1; found: 260.1.

Step 2. 7-Bromo-4-piperidin-2-yl-4,5-dihydroimidazo[1,5,4-de][1,4]benzoxazin-2(1H)-one

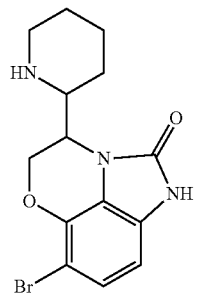 [SMILES: O=c1[nH]c2ccc(Br)c3c2n1C(C1CCCCN1)CO3]

The 4-piperidin-2-yl-4,5-dihydroimidazo[1,5,4-de][1,4]benzoxazin-2(1H)-one (0.20 g, 0.77 mmol) of Step 1 was dissolved in acetic acid (10.0 mL, 176 mmol) at room temperature and N-bromosuccinimide (0.14 g, 0.77 mmol) was slowly added. The reaction was stirred for 2 h and was concentrated in vacuo to give a residue. The residue was dissolved in ethyl acetate, washed with aqueous potassium carbonate, washed with brine, dried over magnesium sulfate, and concentrated to give 7-bromo-4-piperidin-2-yl-4,5-dihydroimidazo[1,5,4-de][1,4]benzoxazin-2(1H)-one as a dark oil (0.22 g, 85%). LCMS calculated for $C_{14}H_{17}BrN_3O_2$ $(M+H)^+$: m/z=338.0, 340.0; found: 338.0, 340.0.

Step 3. 7-(3,5-Dimethylisoxazol-4-yl)-4-piperidin-2-yl-4,5-dihydroimidazo[1,5,4-de][1,4]benzoxazin-2(1H)-one 2,2,2-trifluoroacetate The 7-bromo-4-piperidin-2-yl-4,5-dihydroimidazo[1,5,4-de][1,4]benzoxazin-2(1H)-one (0.025 g, 0.074 mmol) of Step 2 was combined with (3,5-dimethylisoxazol-4-yl)boronic acid (0.016 g, 0.11 mmol) in 1,4-dioxane (3.0 mL) with potassium carbonate (0.02 g, 0.15 mmol) in water (0.38 mL) and was degassed with nitrogen. The catalyst [1,1'-bis(diphenylphosphino)ferrocene]dichloropalladium(II) complex with dichloromethane (1:1) (0.006 g, 0.007 mmol) was added and the reaction was heated in a sealed tube to 100° C. After stirring for 2 h the reaction was allowed to cool to room temperature and was partitioned between ethyl acetate and water. The organic layer was washed with brine, dried over magnesium sulfate, and concentrated to give the crude product as a dark oil. The product was purified by prep HPLC on a C-18 column eluting a water:acetonitrile gradient buffered at pH 2 with TFA to give 7-(3,5-dimethylisoxazol-4-yl)-4-piperidin-2-yl-4,5-dihydroimidazo[1,5,4-de][1,4]benzoxazin-2(1H)-one as two fractions.

Diastereoisomer 1, Peak 1 as a solid residue (0.008 g, 30%). LCMS calculated for $C_{19}H_{23}N_4O_3$ $(M+H)^+$: m/z=355.1; found: 355.1. $^1$H NMR (400 MHz, DMSO-$d_6$) δ 11.13 (d, J 12.8 Hz, 1H), 8.78 (d, J 8.6 Hz, 1H), 6.86 (d, J 8.0 Hz, 1H), 6.78 (d, J 8.0 Hz, 1H), 4.79 (d, J 12.3 Hz, 1H), 4.42 (dd, J 8.7, 2.1 Hz, 1H), 4.02 (dd, J 12.3, 2.8 Hz, 1H), 3.37 (s, 2H), 3.26 (d, J 10.5 Hz, 2H), 2.84 (s, 1H), 2.28 (s, 3H), 2.12 (s, 3H), 2.01 (d, J 13.3 Hz, 1H), 1.75 (d, J=13.2 Hz, 1H), 1.64-1.52 (m, 1H), 1.47 (s, 1H).

Diastereoisomer 2, Peak 2 as a solid residue (0.007 g, 27%). LCMS calculated for $C_{19}H_{23}N_4O_3$ $(M+H)^+$: m/z=355.1; found: 355.1.

Example 69A 7-(3,5-Dimethylisoxazol-4-yl)-4-methyl-4-pyridin-2-yl-4,5-dihydroimidazo[1,5,4-de][1,4]benzoxazin-2(1H)-one (Diastereoisomer 1)

Example 69B 7-(3,5-Dimethylisoxazol-4-yl)-4-methyl-4-pyridin-2-yl-4,5-dihydroimidazo[1,5,4-de][1,4]benzoxazin-2(1H)-one (Diastereoisomer 2)

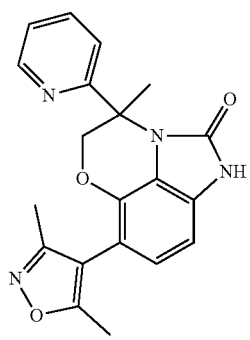 [SMILES: Cc1noc(C)c1-c1ccc2[nH]c(=O)n3c2c1OCC3(C)c1ccccn1]

Step 1. 2-(2-Amino-3-nitrophenoxy)-1-pyridin-3-ylethanone

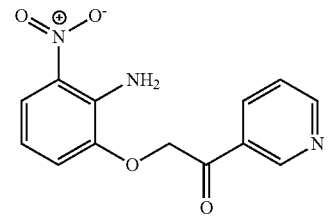 [SMILES: Nc1c(OCC(=O)c2cccnc2)cccc1[N+](=O)[O-]]

2-Bromo-1-(pyridin-3-yl)ethanone hydrobromide (600 mg, 2 mmol) (HBr salt) was added to a mixture of 2-amino-3-nitrophenol (300 mg, 2 mmol) and potassium carbonate (400 mg, 3 mmol) in acetone (30 mL, 400 mmol) at room temperature. The reaction was stirred at room temperature for 18 h, was diluted with water, and was then extracted with ethyl acetate. The combined organic layers were washed with brine, dried over magnesium sulfate, filtered, and concentrated to give crude 2-(2-amino-3-nitrophenoxy)-1-pyridin-3-ylethanone (0.35 g, 60%). LCMS calculated for $C_{13}H_{12}N_3O_4$ $(M+H)^+$: m/z=274.1; found: 274.1.

Step 2. 2-Nitro-6-[(2-pyridin-2-ylprop-2-en-1-yl)oxy]aniline

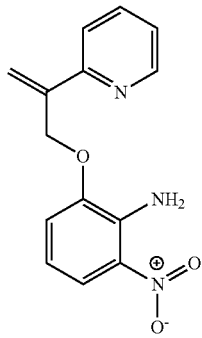 [SMILES: C=C(COc1cccc([N+](=O)[O-])c1N)c1ccccn1]

Potassium tert-butoxide (1.10 g, 9.9 mmol) was added to a suspension of methyl triphenylphosphonium bromide (3.0 g, 8 mmol) in tetrahydrofuran (30 mL) under nitrogen. The reaction was stirred at room temperature for 1 h, followed by addition of 2-(2-amino-3-nitrophenoxy)-1-pyridin-2-ylethanone (2 g, 8 mmol). The mixture was stirred for 3 h, and was then partitioned between water and ethyl ether. The organic layer was washed with brine, dried over magnesium sulfate, filtered, and concentrated to give the crude product. The product was purified by FCC on silica gel eluting with a hexane:ethyl acetate gradient to give 2-nitro-6-[(2-pyridin-2-ylprop-2-en-1-yl)oxy]aniline as light brown solid (0.5 g, 20%). LCMS calculated for $C_{14}H_{14}N_3O_3$ $(M+H)^+$: m/z=272.1; found: 272.1.

Step 3. 2-{1-[(2-Azido-3-nitrophenoxy)methyl]vinyl}pyridine

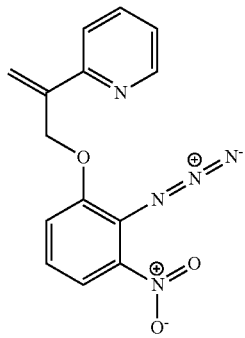 [SMILES: C=C(COc1cccc([N+](=O)[O-])c1N=[N+]=[N-])c1ccccn1]

Sodium nitrite (100 mg, 2 mmol) in water (4 mL, 60 mmol) was added to a solution of 2-nitro-6-[(2-pyridin-2-ylprop-2-en-1-yl)oxy]aniline (350 mg, 1.3 mmol) in 4.0 M hydrogen chloride in water (4 mL, 10 mmol) at 0° C. The reaction was stirred for 5 min and was then neutralized to pH 6-7 with solid sodium bicarbonate. Sodium azide (80 mg, 1 mmol) in water (2 mL) was added drop-wise to the mixture, followed by stirring for 30 min, over which time the reaction mixture became a thick slurry. The resulting mixture was filtered and dried to give 2-{1-[(2-azido-3-nitrophenoxy)methyl]vinyl}pyridine as a dark yellow solid (0.25 g, 83%). LCMS calculated for $C_{14}H_{12}N_5O_3$ $(M+H)^+$: m/z=298.1; found: 298.1.

Step 4. 7-Nitro-1a-pyridin-2-yl-1a,2-dihydro-1H-azireno[2,1-c][1,4]benzoxazine

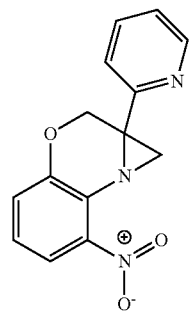 [SMILES: O=[N+]([O-])c1cccc2c1N1CC1(c1ccccn1)CO2]

A mixture of 2-{1-[(2-azido-3-nitrophenoxy)methyl]vinyl}pyridine (250 mg, 0.84 mmol) in benzene (15 mL) was refluxed at 80° C. for 15 h. The reaction was concentrated to give the crude product. The product was purified by FCC on silica gel eluting with a hexane:ethyl acetate gradient to give 7-nitro-1a-pyridin-2-yl-1a,2-dihydro-1H-azireno[2,1-c][1,4]benzoxazine as a solid (0.225 g, 90%). LCMS calculated for $C_{14}H_{12}N_3O_3$ $(M+H)^+$: m/z=270.1; found: 270.1.

Step 5. 3-Methyl-3-pyridin-2-yl-3,4-dihydro-2H-1,4-benzoxazin-5-amine

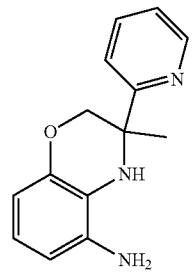 [SMILES: CC1(c2ccccn2)COc2cccc(N)c2N1]

A mixture of 7-nitro-1a-pyridin-2-yl-1a,2-dihydro-1H-azireno[2,1-c][1,4]benzoxazine (100 mg, 0.4 mmol) in methanol (6 mL) and tetrahydrofuran (2 mL) was degassed with nitrogen in a Parr bottle followed by addition of palladium (10% on carbon) (30 mg, 0.28 mmol). The reaction was charged with hydrogen to 40 psi and shaken for 6 hrs. The reaction was filtered and concentrated to give crude 3-methyl-3-pyridin-2-yl-3,4-dihydro-2H-1,4-benzoxazin-5-amine (0.030 g, 30%). LCMS calculated for $C_{14}H_{16}N_3O$ $(M+H)^+$: m/z=242.1; found: 242.1.

Step 6. 4-Methyl-4-pyridin-2-yl-4,5-dihydroimidazo[1,5,4-de][1,4]benzoxazin-2(1H)-one

Triphosgene (40 mg, 0.1 mmol) was added to the solution of 3-methyl-3-pyridin-2-yl-3,4-dihydro-2H-1,4-benzoxazin-5-amine (90 mg, 0.4 mmol) in tetrahydrofuran (10 mL) and N,N-diisopropylethylamine (100 µL) at room temperature. The reaction was stirred for 1 h and was then partitioned between ethyl acetate and water. The organic layer was washed with brine, dried over magnesium sulfate, filtered, and concentrated to give crude 4-methyl-4-pyridin-2-yl-4,5-dihydroimidazo[1,5,4-de][1,4]benzoxazin-2(1H)-one as a semisolid (0.10 g, 90%). LCMS calculated for $C_{15}H_{14}N_3O_2$ (M+H)$^+$: m/z=268.1; found: 268.0.

Step 7. 7-Bromo-4-methyl-4-pyridin-2-yl-4,5-dihydroimidazo[1,5,4-de][1,4]benzoxazin-2(1H)-one

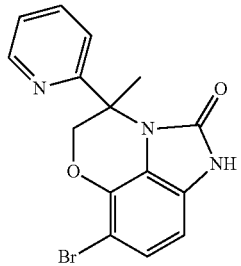 [SMILES: CC1(c2ccccn2)COc2c(Br)ccc3[nH]c(=O)n1c23]

N-Bromosuccinimide (60 mg, 0.3 mmol) was added to a solution of 4-methyl-4-pyridin-2-yl-4,5-dihydroimidazo[1,5,4-de][1,4]benzoxazin-2(1H)-one (90 mg, 0.3 mmol), acetic acid (6 mL) and acetonitrile (6 mL) at 0° C. The reaction mixture was stirred for 1 h at 0° C., quenched with water, and was concentrated to give the crude product. The crude product was dissolved in ethyl acetate and washed with saturated aqueous sodium bicarbonate. The combined organic layer was washed with brine, dried over magnesium sulfate, filtered, and concentrated to give a dark oil. The product was purified by FCC on silica gel eluting a hexane:ethyl acetate gradient containing 20% ethanol to give 7-bromo-4-methyl-4-pyridin-2-yl-4,5-dihydroimidazo[1,5,4-de][1,4]benzoxazin-2(1H)-one as an off white solid (0.090 g, 80%). LCMS calculated for $C_{15}H_{13}BrN_3O_2$(M+H)$^+$: m/z=346.1, 348.1; found: 345.9, 347.9.

Step 8. 7-(3,5-Dimethylisoxazol-4-yl)-4-methyl-4-pyridin-2-yl-4,5-dihydroimidazo[1,5,4-de][, 4]benzoxazin-2(1H)-one 7-Bromo-4-methyl-4-pyridin-2-yl-4,5-dihydroimidazo[1,5,4-de][1,4]benzoxazin-2(1H)-one (80 mg, 0.2 mmol) was combined in 1,4-dioxane (10 mL) with potassium (3,5-dimethylisoxazol-4-yl)(trifluoro)borate (0.070 g, 0.35 mmol) and potassium carbonate (60 mg, 0.5 mmol) in water (5 mL), and was degassed with nitrogen. The catalyst [1,1′-bis(diphenylphosphino)ferrocene]dichloropalladium (II) complex with dichloromethane (1:1) (30 mg, 0.04 mmol) was added and the reaction was stirred at 80° C. for 4 h, at which time reaction mixture was allowed to cool to room temperature and was partitioned between water and ethyl acetate. The combined organic layers were washed with brine, dried over magnesium sulfate and concentrated to give the crude product. The product was purified by FCC on silica gel eluting a hexane:ethyl acetate gradient containing 20% ethanol to give 7-(3,5-dimethylisoxazol-4-yl)-4-methyl-4-pyridin-2-yl-4,5-dihydroimidazo[1,5,4-de][1,4]benzoxazin-2(1H)-one as a clear oil. The enantiomers were separated on chiral column using the following conditions: Phenomenex Lux Cellulose C-4, 5 µm, 21×2×250 mm; mobile phase: 45% ethanol in Hexanes gradient: 18 mL/min isocratic; Run time: 11 min; Loading: 4 mg in 900 µL; Peak time: 7.1 & 8.8 min.

Diastereoisomer 1, Peak 1, as a white amorphous solid (0.010 g. 10%). LCMS calculated for $C_{20}H_{19}N_4O_3$ (M+H)$^+$: m/z=363.1; found: 363.1. $^1$H NMR (500 MHz, DMSO-d$_6$) δ 11.02 (s, 1H), 8.55 (d, J=4.5 Hz, 1H), 7.83-7.69 (m, 1H), 7.29 (dd, J=7.3, 4.9 Hz, 1H), 7.06 (d, J=8.0 Hz, 1H), 6.80 (d, J=8.0 Hz, 1H), 6.73 (d, J=8.0 Hz, 1H), 4.79 (d, J=11.1 Hz, 1H), 4.19 (d, J=11.1 Hz, 1H), 2.17 (s, 3H), 1.99 (s, 3H), 1.95 (s, 3H).

Diastereoisomer 2, Peak 2, as a white amorphous solid (0.010 g. 10%). LCMS calculated for $C_{20}H_{19}N_4O_3$ (M+H)$^+$: m/z=363.1; found: 363.1.

Example 70

7-(3,5-Dimethylisoxazol-4-yl)-4-ethyl-4-pyridin-2-yl-4,5-dihydroimidazo[1,5,4-de][1,4]benzoxazin-2(1H)-one 2,2,2-trifluoroacetate

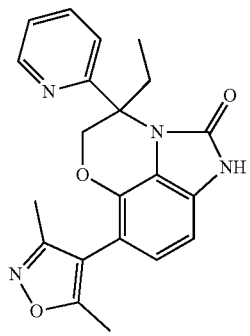 [SMILES: CCC1(c2ccccn2)COc2c(-c3c(C)noc3C)ccc3[nH]c(=O)n1c23]

Step 1. 5-Nitro-3-pyridin-2-yl-2H-1,4-benzoxazine

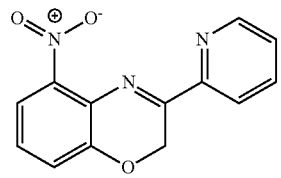 [SMILES: O=[N+]([O-])c1cccc2c1N=C(c1ccccn1)CO2]

The mixture of 5-nitro-3-pyridin-2-yl-2H-1,4-benzoxazine and 5-nitro-3-pyridin-2-yl-3,4-dihydro-2H-1,4-benzoxazin-3-ol (intermediate, Example 13) (200 mg, 0.7 mmol) was dissolved in acetonitrile (0.2 mL) and acetic acid (0.8 mL) at room temperature and stirred for 10 min. The reaction was diluted with acetonitrile (15 mL) and concentrated at room temperature to remove residual acetic acid to give 5-nitro-3-pyridin-2-yl-2H-1,4-benzoxazine as a light green solid (0.20 g. 100%). LCMS calculated for $C_{13}H_{10}N_3O_3$ (M+H)$^+$: m/z=256.1; found: 255.9.

Step 2. 3-Ethyl-5-nitro-3-pyridin-2-yl-3,4-dihydro-2H-1,4-benzoxazine

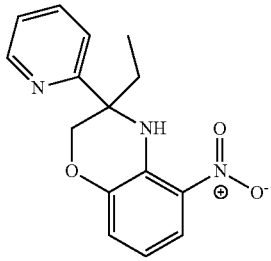 [SMILES: CCC1(c2ccccn2)COc2cccc([N+](=O)[O-])c2N1]

0.5 M Ethyl lithium in benzene-cyclohexane (1.8 mL, 0.88 mmol) was added drop-wise to a solution of 5-nitro-3-pyridin-2-yl-2H-1,4-benzoxazine (0.025 g, 0.88 mmol) in tetrahydrofuran (4 mL), cooled to −78° C. The reaction was stirred for 1 h at −78° C. and was then quenched with methanol. The reaction mixture was partitioned between ethyl acetate and water, and the organic layer was washed with brine, dried over magnesium sulfate, filtered, and concentrated to give crude product. The product was purified by FCC on silica gel eluting a hexane:ethyl acetate gradient to give 3-ethyl-5-nitro-3-pyridin-2-yl-3,4-dihydro-2H-1,4-benzoxazine as a solid (0.021 g. 84%). LCMS calculated for $C_{15}H_{16}N_3O_3$ (M+H)$^+$: m/z=286.1; found: 286.0.

Step 3. 3-Ethyl-3-pyridin-2-yl-3,4-dihydro-2H-1,4-benzoxazin-5-amine

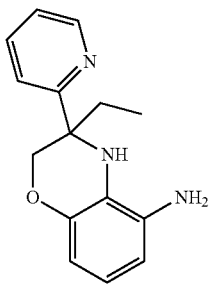 [SMILES: CCC1(c2ccccn2)COc2cccc(N)c2N1]

3-Ethyl-5-nitro-3-pyridin-2-yl-3,4-dihydro-2H-1,4-benzoxazine (10 mg, 0.3 mmol) was dissolved in methanol (10 mL) in a Parr bottle, degassed with nitrogen, and palladium (10% on carbon) (10 mg) was added. The reaction vessel was pressurized to 50 PSI with hydrogen and shaken for 2 h. The reaction mixture was filtered and concentrated to give crude 3-ethyl-3-pyridin-2-yl-3,4-dihydro-2H-1,4-benzoxazin-5-amine (0.005 g, 40%). LCMS calculated for $C_{15}H_{18}N_3O$ (M+H)$^+$: m/z=256.1; found: 256.0.

Step 4. 4-Ethyl-4-pyridin-2-yl-4,5-dihydroimidazo[1,5,4-de][1,4]benzoxazin-2(1H)-one

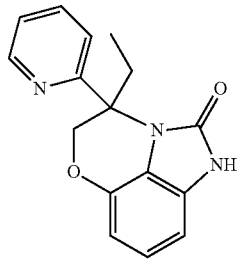 [SMILES: CCC1(c2ccccn2)COc2cccc3[nH]c(=O)n1c23]

Triphosgene (40 mg, 0.1 mmol) was added to a solution of 3-ethyl-3-pyridin-2-yl-3,4-dihydro-2H-1,4-benzoxazin-5-amine (80 mg, 0.3 mmol) in tetrahydrofuran (5 mL) and N,N-diisopropylethylamine (0.1 mL). The reaction was stirred at room temperature for 1 h and was then partitioned between water and ethyl acetate. The organic layer was washed with brine, dried over magnesium sulfate, filtered, and concentrated to give crude 4-ethyl-4-pyridin-2-yl-4,5-dihydroimidazo[1,5,4-de][1,4]benzoxazin-2(1H)-one (0.060 g. 60%). LCMS calculated for $C_{16}H_{16}N_3O_2$ (M+H)$^+$: m/z=282.1; found: 282.0.

Step 5. 7-Bromo-4-ethyl-4-pyridin-2-yl-4,5-dihydroimidazo[1,5,4-de][1,4]benzoxazin-2(1H)-one

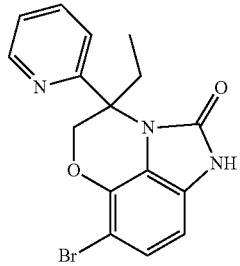 [SMILES: CCC1(c2ccccn2)COc2c(Br)ccc3[nH]c(=O)n1c23]

N-Bromosuccinimide (70 mg, 0.4 mmol) was added to a solution of 4-ethyl-4-pyridin-2-yl-4,5-dihydroimidazo[1,5,4-de][1,4]benzoxazin-2(1H)-one (80 mg, 0.4 mmol) in acetonitrile (5 mL) and acetic acid (10 mL) cooled to 0° C. The reaction was stirred for 30 min, was concentrated to remove residual acetic acid, and the resulting residue was dissolved in ethyl acetate. The organic layer was washed with saturated aqueous sodium bicarbonate, washed with brine, dried over magnesium sulfate, filtered, and concentrated to give crude 7-bromo-4-ethyl-4-pyridin-2-yl-4,5-dihydroimidazo[1,5,4-de][1,4]benzoxazin-2(1H)-one (0.07 g. 80%). LCMS calculated for $C_{16}H_{15}BrN_3O_2$(M+H)$^+$: m/z=360.1, 362.1; found: 359.8, 361.8.

Step 6. 7-(3,5-Dimethylisoxazol-4-yl)-4-ethyl-4-pyridin-2-yl-4,5-dihydroimidazo[1,5,4-de][1,4]benzoxazin-2(1H)-one 2,2,2-trifluoroacetate 7-Bromo-4-ethyl-4-pyridin-2-yl-4,5-dihydroimidazo[1,5,4-de][1,4]benzoxazin-2(1H)-one (50 mg, 0.1 mmol) was combined in 1,4-dioxane (6 mL) with potassium (3,5-dimethylisoxazol-4-yl)(trifluoro)borate (42 mg, 0.21 mmol) and potassium carbonate (40 mg, 0.3 mmol) in water (3 mL) and was degassed with nitrogen. The catalyst [1,1'-bis(diphenylphosphino)ferrocene]dichloropalladium(II) complex with dichloromethane (1:1) (20 mg, 0.02 mmol) was added and the mixture was stirred at 100° C. for 18 h. The reaction mixture was allowed to cool to room temperature and was then partitioned between ethyl acetate and water. The organic layer was washed with brine, dried over magnesium sulfate, and concentrated to give the crude product. The product was purified on prep HPLC using a C-18 column eluting a water:acetonitrile gradient buffered to pH 2 with TFA to give 7-(3,5-dimethylisoxazol-4-yl)-4-ethyl-4-pyridin-2-yl-4,5-dihydroimidazo[1,5,4-de][1,4]benzoxazin-2(1H)-one as a white solid (0.005 g, 10%). LCMS calculated for $C_{21}H_{21}N_4O_3$ $(M+H)^+$: m/z=377.1; found: 377.0. $^1$H NMR (400 MHz, DMSO-d6) δ 11.01 (s, 1H), 8.58-8.47 (m, 1H), 7.75 (td, J 7.7, 1.8 Hz, 1H), 7.28 (dd, J 6.6, 4.8 Hz, 1H), 7.13 (d, J 8.0 Hz, 1H), 6.79 (d, J 8.0 Hz, 1H), 6.71 (d, J 8.0 Hz, 1H), 4.84 (d, J 11.2 Hz, 1H), 4.29 (d, J 11.2 Hz, 1H), 2.71-2.51 (m, 1H), 2.37-2.21 (m, 1H), 2.16 (s, 3H), 1.98 (s, 3H), 0.98 (t, J 7.4 Hz, 3H).

Example 71

7-(3,5-Dimethylisoxazol-4-yl)-N-methyl-2-oxo-4-pyridin-2-yl-1,2,4,5-tetrahydroimidazo[1,5,4-de][1,4]benzoxazine-4-carboxamide 2,2,2-trifluoroacetate

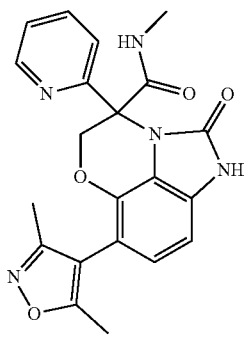 [SMILES: CNC(=O)C1(c2ccccn2)COc2c(-c3c(C)noc3C)ccc3[nH]c(=O)n1c23]

Step 1. 5-Nitro-3-pyridin-2-yl-3,4-dihydro-2H-1,4-benzoxazine-3-carbonitrile

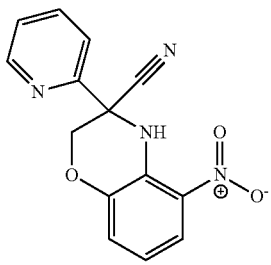 [SMILES: N#CC1(c2ccccn2)COc2cccc([N+](=O)[O-])c2N1]

Potassium cyanide (500 mg, 7 mmol) was added to a solution of 5-nitro-3-pyridin-2-yl-2H-1,4-benzoxazine (1 g, 4 mmol) (Example 70, Step 1), in acetonitrile (20 mL), and was stirred overnight at room temperature. The reaction was partitioned between ethyl acetate and water, and the organic layer was washed with brine, dried over magnesium sulfate, filtered, and concentrated to give the crude product. The product was crystallized from methylene chloride to give 5-nitro-3-pyridin-2-yl-3,4-dihydro-2H-1,4-benzoxazine-3-carbonitrile as a dark yellow powder (0.60 g, 60%). LCMS calculated for $C_{14}H_{11}N_4O_3$ $(M+H)^+$: m/z=283.1; found: 282.9.

Step 2. 5-Nitro-3-pyridin-2-yl-3,4-dihydro-2H-1,4-benzoxazine-3-carboxylic acid

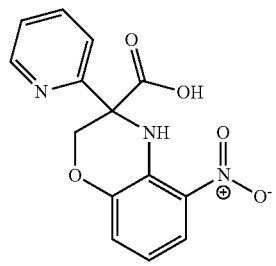 [SMILES: O=C(O)C1(c2ccccn2)COc2cccc([N+](=O)[O-])c2N1]

5-Nitro-3-pyridin-2-yl-3,4-dihydro-2H-1,4-benzoxazine-3-carbonitrile (80 mg, 0.3 mmol) was dissolved in concentrated hydrochloric acid (3 mL, 100 mmol) and heated to 100° C. for 2 h. The reaction was allowed to cool to room temperature, diluted with water, and the pH was adjusted to pH 7 with sodium bicarbonate. The neutralized solution was then extracted with ethyl acetate. The combined organic layers were washed with brine, dried over magnesium sulfate, and concentrated to give crude 5-nitro-3-pyridin-2-yl-3,4-dihydro-2H-1,4-benzoxazine-3-carboxylic acid as a solid (0.025 g, 30%). LCMS calculated for $C_{14}H_{12}N_3O_5$ $(M+H)^+$: m/z=302.1; found: 301.9.

Step 3. N-Methyl-5-nitro-3-pyridin-2-yl-3,4-dihydro-2H-1,4-benzoxazine-3-carboxamide

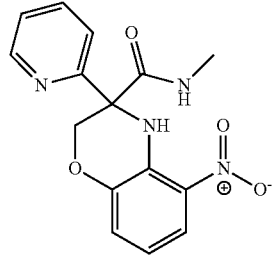 [SMILES: CNC(=O)C1(c2ccccn2)COc2cccc([N+](=O)[O-])c2N1]

5-Nitro-3-pyridin-2-yl-3,4-dihydro-2H-1,4-benzoxazine-3-carboxylic acid (0.044 g, 0.15 mmol) in N,N-dimethylformamide (3 mL) was combined with N,N,N',N'-tetramethyl-O-(7-azabenzotriazol-1-yl)uronium hexafluorophosphate [Oakwood #: 023926] (160 mg, 0.42 mmol) and N,N-diisopropylethylamine (100 μL, 0.6 mmol) at room temperature. 3.0 M methylamine in ethanol (0.2 mL, 0.6 mmol) was added, and the resulting mixture was stirred for 1 h, at which time the mixture was partitioned between water and ethyl acetate. The organic layer was washed with 1 N HCl, washed with brine, dried over magnesium sulfate, filtered, and concentrated to give crude N-methyl-5-nitro-3-pyridin-2-yl-3,4-dihydro-2H-1,4-benzoxazine-3-carboxamide solid (0.020 g, 30%). LCMS calculated for $C_{15}H_{15}N_4O_4$ $(M+H)^+$: m/z=315.1; found: 315.0.

Step 4. 5-Amino-N-methyl-3-pyridin-2-yl-3,4-dihydro-2H-1,4-benzoxazine-3-carboxamide

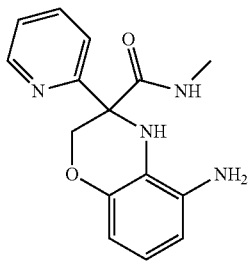 [SMILES: CNC(=O)C1(c2ccccn2)COc2cccc(N)c2N1]

N-Methyl-5-nitro-3-pyridin-2-yl-3,4-dihydro-2H-1,4-benzoxazine-3-carboxamide (25 mg, 0.080 mmol) was dissolved in methanol (5 mL) in a Parr bottle and degassed with nitrogen, followed by addition of palladium (10% on carbon) (5 mg, 0.05 mmol). The reaction vessel was charged to 50 PSI hydrogen and shaken for 2 h. The reaction mixture was filtered and concentrated in vacuo to give crude 5-amino-N-methyl-3-pyridin-2-yl-3,4-dihydro-2H-1,4-benzoxazine-3-carboxamide (0.005 g, 100%). LCMS calculated for $C_{15}H_{17}N_4O_2$ (M+H)$^+$: m/z=285.1; found: 285.0.

Step 5. N-Methyl-2-oxo-4-pyridin-2-yl-1,2,4,5-tetrahydroimidazo[1,5,4-de][1,4]benzoxazine-4-carboxamide

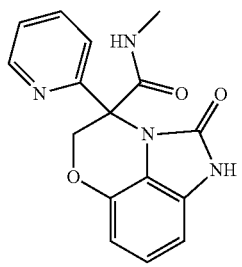 [SMILES: CNC(=O)C1(c2ccccn2)COc2cccc3[nH]c(=O)n1c23]

Triphosgene (10 mg, 0.04 mmol) was added to a solution of 5-amino-N-methyl-3-pyridin-2-yl-3,4-dihydro-2H-1,4-benzoxazine-3-carboxamide (30 mg, 0.1 mmol) in tetrahydrofuran (3 mL) and N,N-diisopropylethylamine (40 µL, 0.2 mmol) at room temperature and was stirred for 1 h. The reaction mixture was then partitioned between ethyl acetate and water, and the organic layer was washed with brine, dried over magnesium sulfate, and concentrated to give crude N-methyl-2-oxo-4-pyridin-2-yl-1,2,4,5-tetrahydroimidazo[1,5,4-de][1,4]benzoxazine-4-carboxamide as a semisolid (0.031 g, 100%). LCMS calculated for $C_{16}H_{15}N_4O_3$ (M+H)$^+$: m/z=311.1; found: 311.1.

Step 6. 7-Bromo-N-methyl-2-oxo-4-pyridin-2-yl-,2,4,5-tetrahydroimidazo[1,5,4-de][1,4]benzoxazine-4-carboxamide

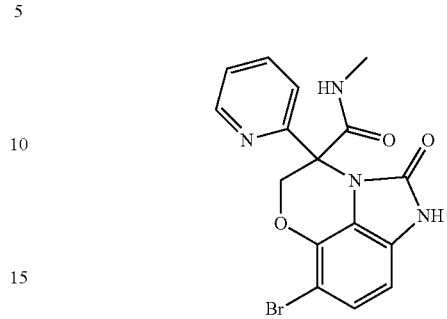

N-Methyl-2-oxo-4-pyridin-2-yl-1,2,4,5-tetrahydroimidazo[1,5,4-de][1,4]benzoxazine-4-carboxamide (20 mg, 0.1 mmol) was dissolved in acetonitrile (3 mL) and acetic acid (2 mL), and cooled to 0° C., followed by addition of N-bromosuccinimide (20 mg, 0.1 mmol). The reaction mixture was stirred for 1 h and was then concentrated to give a crude residue. The residue was dissolved in ethyl acetate, washed with saturated aqueous sodium bicarbonate, washed with brine, dried over magnesium sulfate, filtered, and concentrated to give crude 7-bromo-N-methyl-2-oxo-4-pyridin-2-yl-1,2,4,5-tetrahydroimidazo[1,5,4-de][1,4]benzoxazine-4-carboxamide (0.020 g, 50%). LCMS calculated for $C_{16}H_{14}BrN_4O_3$(M+H)$^+$: m/z=389.1, 391.1; found: 388.9, 390.9.

Step 7. 7-(3,5-Dimethylisoxazol-4-yl)-N-methyl-2-oxo-4-pyridin-2-yl-1,2,4,5-tetrahydroimidazo[1,5,4-de][1,4]benzoxazine-4-carboxamide 2,2,2-trifluoroacetate 7-Bromo-N-methyl-2-oxo-4-pyridin-2-yl-1,2,4,5-tetrahydroimidazo[1,5,4-de][1,4]benzoxazine-4-carboxamide (20 mg, 0.05 mmol) was combined with 1,4-dioxane (2 mL), potassium (3,5-dimethylisoxazol-4-yl)(trifluoro)borate (16 mg, 0.077 mmol) and potassium carbonate (10 mg, 0.1 mmol) in water (1 mL, 60 mmol) and was degassed with nitrogen. The catalyst [1,1′-Bis(diphenylphosphino)ferrocene]dichloropalladium(II) complex with dichloromethane (1:1) (7 mg, 0.008 mmol) was added, and the reaction mixture was stirred at 110° C. for 5 h. The reaction mixture was allowed to cool to room temperature and was then partitioned between ethyl acetate and water. The organic layer was washed with brine, dried over magnesium sulfate, and was concentrated to give crude product. The product was purified on prep HPLC on a C-18 column eluting a water:acetonitrile gradient buffered at pH 2 with TFA to give 7-(3,5-dimethylisoxazol-4-yl)-N-methyl-2-oxo-4-pyridin-2-yl-1,2,4,5-tetrahydroimidazo[1,5,4-de][1,4]benzoxazine-4-carboxamide as an off white solid (0.007 g, 30%). LCMS calculated for $C_{21}H_{20}N_5O_4$ (M+H)$^+$: m/z=406.1; found: 405.9. $^1$H NMR (400 MHz, DMSO-d$_6$) δ 11.03 (s, 1H), 8.57-8.45 (m, 1H), 8.19 (d, J=4.7 Hz, 1H), 7.82 (td, J=7.8, 1.8 Hz, 1H), 7.48 (d, J=8.0 Hz, 1H), 7.36 (ddd, J=7.6, 4.8, 1.0 Hz, 1H), 6.83 (d, J=8.0 Hz, 1H), 6.74 (d, J=8.0 Hz, 1H), 4.73 (s, 2H), 2.72-2.60 (m, 3H), 2.22 (s, 3H), 2.04 (s, 3H).

Example 72

N-{[7-(3,5-Dimethylisoxazol-4-yl)-2-oxo-4-pyridin-2-yl-1,2,4,5-tetrahydroimidazo[1,5,4-de][1,4]benzoxazin-4-yl]methyl}acetamide 2,2,2-trifluoroacetate

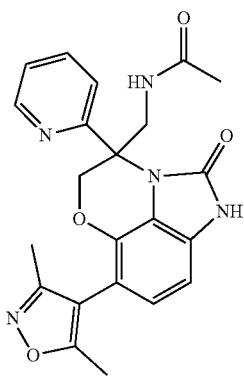 [SMILES: CC(=O)NCC1(c2ccccn2)COc2c(-c3c(C)noc3C)ccc3[nH]c(=O)n1c23]

Step 1. 1-(5-Nitro-3-pyridin-2-yl-3,4-dihydro-2H-1,4-benzoxazin-3-yl)methanamine

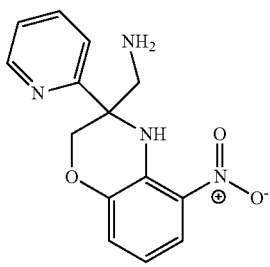 [SMILES: NCC1(c2ccccn2)COc2cccc([N+](=O)[O-])c2N1]

1.0 M Diisobutylaluminum hydride in toluene (200 μL, 0.2 mmol) was added drop-wise to a solution of 5-nitro-3-pyridin-2-yl-3,4-dihydro-2H-1,4-benzoxazine-3-carbonitrile (50 mg, 0.2 mmol) (Example 71, Step 1), in toluene (5 mL) at room temperature. The reaction mixture was stirred for 10 min, then quenched with methanol. The resulting mixture was partitioned between ethyl acetate and saturated aqueous sodium bicarbonate. The organic layer was washed with brine, dried over magnesium sulfate, filtered, and concentrated to give crude 1-(5-nitro-3-pyridin-2-yl-3,4-dihydro-2H-1,4-benzoxazin-3-yl)methanamine solid (0.05 g. 100%). LCMS calculated for $C_{14}H_{15}N_4O_3$ $(M+H)^+$: m/z=287.1; found: 287.1.

Step 2. N-[(5-Nitro-3-pyridin-2-yl-3,4-dihydro-2H-1,4-benzoxazin-3-yl)methyl]acetamide

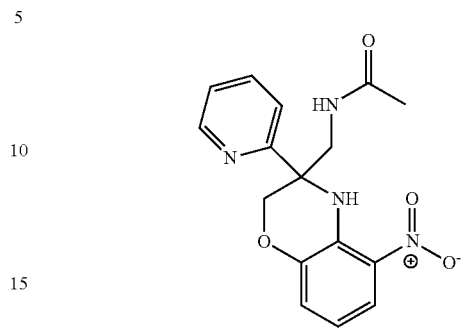

Acetyl chloride (15 μL, 0.21 mmol) was added to a mixture of 1-(5-nitro-3-pyridin-2-yl-3,4-dihydro-2H-1,4-benzoxazin-3-yl)methanamine (50 mg, 0.2 mmol) in methylene chloride (3 mL), N,N-diisopropylethylamine (60 μL) and was stirred at room temperature for 1 h. The reaction mixture was then partitioned between ethyl acetate and water. The organic layer was washed with brine, dried over magnesium sulfate, filtered, and concentrated to give crude N-[(5-nitro-3-pyridin-2-yl-3,4-dihydro-2H-1,4-benzoxazin-3-yl)methyl]acetamide (0.040 g. 70%). LCMS calculated for $C_{16}H_{17}N_4O_4$ $(M+H)^+$: m/z=329.1; found: 329.0.

Step 3. N-[(5-Amino-3-pyridin-2-yl-3,4-dihydro-2H-1,4-benzoxazin-3-yl)methyl]acetamide

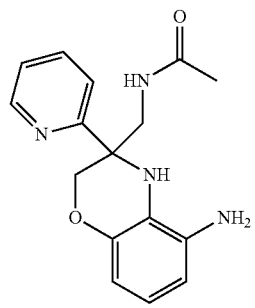 [SMILES: CC(=O)NCC1(c2ccccn2)COc2cccc(N)c2N1]

N-[(5-Nitro-3-pyridin-2-yl-3,4-dihydro-2H-1,4-benzoxazin-3-yl)methyl]acetamide (0.040 g. 0.122 mmol) was dissolved in ethanol (5 mL) in a Parr bottle and degassed with nitrogen, followed by addition of palladium (10% on carbon) (10 mg, 0.09 mmol) catalyst. The reaction vessel was charged to 50 PSI with hydrogen, and shaken for 2 h. The mixture was then filtered and concentrated to give crude N-[(5-amino-3-pyridin-2-yl-3,4-dihydro-2H-1,4-benzoxazin-3-yl)methyl]acetamide (0.040 g, 80%). LCMS calculated for $C_{16}H_{19}N_4O_2$ $(M+H)^+$: m/z=299.1; found: 299.0.

Step 4. N-[(2-Oxo-4-pyridin-2-yl-1,2,4,5-tetrahydroimidazo[1,5,4-de][1,4]benzoxazin-4-yl)methyl]acetamide

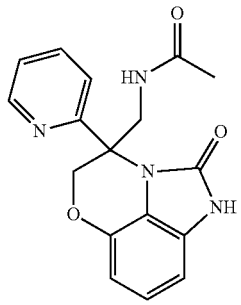 [SMILES: CC(=O)NCC1(c2ccccn2)COc2cccc3[nH]c(=O)n1c23]

Triphosgene (20 mg, 0.07 mmol) was added to a mixture of N-[(5-amino-3-pyridin-2-yl-3,4-dihydro-2H-1,4-benzoxazin-3-yl)methyl]acetamide (50 mg, 0.2 mmol), tetrahydrofuran (5 mL) and N,N-diisopropylethylamine (60 µL) at room temperature. The reaction was stirred for 1 h then partitioned between ethyl acetate and water. The organic layer was washed with brine, dried over magnesium sulfate, filtered, and concentrated to give crude N-[(2-oxo-4-pyridin-2-yl-1,2,4,5-tetrahydroimidazo[1,5,4-de][1,4]benzoxazin-4-yl)methyl]acetamide (0.040 g, 70%). LCMS calculated for $C_{17}H_{17}N_4O_3$ $(M+H)^+$: m/z=325.1; found: 325.1.

Step 5. N-[(7-Bromo-2-oxo-4-pyridin-2-yl-1,2,4,5-tetrahydroimidazo[1,5,4-de][1,4]benzoxazin-4-yl)methyl]acetamide

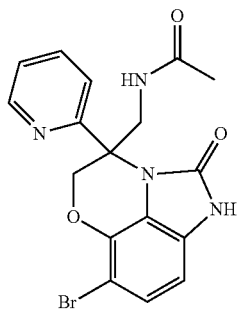 [SMILES: CC(=O)NCC1(c2ccccn2)COc2c(Br)ccc3[nH]c(=O)n1c23]

N-Bromosuccinimide (40 mg, 0.2 mmol) was added to a mixture of N-[(2-oxo-4-pyridin-2-yl-1,2,4,5-tetrahydroimidazo[1,5,4-de][1,4]benzoxazin-4-yl)methyl]acetamide in acetonitrile (5 mL) and acetic acid (3 mL), and cooled to 0° C. The reaction was stirred for 1 h, concentrated to remove residual acetic acid, and partitioned between ethyl acetate and saturated aqueous sodium bicarbonate. The organic layer was washed with brine, dried over magnesium sulfate, filtered, and concentrated to give crude N-[(7-bromo-2-oxo-4-pyridin-2-yl-1,2,4,5-tetrahydroimidazo[1,5,4-de][1,4]benzoxazin-4-yl)methyl]acetamide (0.040 g, 60%). LCMS calculated for $C_{17}H_{16}BrN_4O_3(M+H)^+$: m/z=403.1, 405.1; found: 402.9, 405.0.

Step 6. N-{[7-(3,5-Dimethylisoxazol-4-yl)-2-oxo-4-pyridin-2-yl-1,2,4,5-tetrahydroimidazo[1,5,4-de][1,4]benzoxazin-4-yl]methyl}acetamide 2,2,2-trifluoroacetate N-[(7-Bromo-2-oxo-4-pyridin-2-yl-1,2,4,5-tetrahydroimidazo[1,5,4-de][1,4]benzoxazin-4-yl)methyl]acetamide (20 mg, 0.05 mmol) was combined in 1,4-dioxane (2 mL) with potassium (3,5-dimethylisoxazol-4-yl)(trifluoro)borate (16 mg, 0.077 mmol) and potassium carbonate (10 mg, 0.1 mmol) in water (1 mL) and was degassed with nitrogen. The catalyst [1,1'-bis(diphenylphosphino)ferrocene]dichloropalladium(II) complex with dichloromethane (1:1) (7 mg, 0.008 mmol) was added and the reaction was stirred at 110° C. for 5 h. The reaction mixture was allowed to cool to room temperature, at which time it was partitioned between ethyl acetate and water. The organic layer was washed with brine, dried over magnesium sulfate, and was concentrated to give crude product. The product was purified by prep HPLC on a C-18 column eluting a water:acetonitrile gradient buffered at pH 2 with TFA to give N-{[7-(3,5-dimethylisoxazol-4-yl)-2-oxo-4-pyridin-2-yl-1,2,4,5-tetrahydroimidazo[1,5,4-de][1,4]benzoxazin-4-yl]methyl}acetamide as an off white solid (0.010 g, 50%). LCMS calculated for $C_{22}H_{22}N_5O_4$ $(M+H)^+$: m/z=420.1; found: 420.1.

Example 73

4-(Aminomethyl)-7-(3,5-dimethylisoxazol-4-yl)-4-pyridin-2-yl-4,5-dihydroimidazo[1,5,4-de][1,4]benzoxazin-2(1H)-one bis(2,2,2-trifluoroacetate)

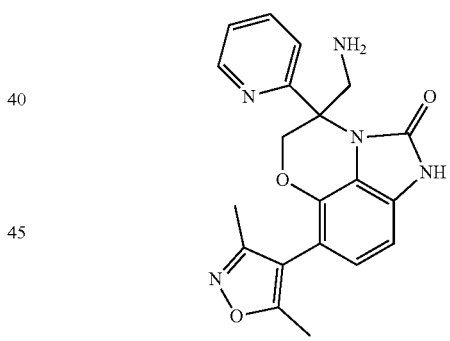

N-{[7-(3,5-Dimethylisoxazol-4-yl)-2-oxo-4-pyridin-2-yl-1,2,4,5-tetrahydroimidazo[1,5,4-de][1,4]benzoxazin-4-yl]methyl}acetamide (10 mg, 0.02 mmol) was dissolved in tetrahydrofuran (1 mL) and concentrated hydrochloric acid (200 µL, 6 mmol) in water (800 µL). The reaction was heated to 100° C. for 4 h and was then purified without workup by prep HPLC on a C-18 column eluting a water:acetonitrile gradient buffered at pH 2 with TFA to give 4-(aminomethyl)-7-(3,5-dimethylisoxazol-4-yl)-4-pyridin-2-yl-4,5-dihydroimidazo[1,5,4-de][1,4]benzoxazin-2(1H)-one as off white solid (0.0045 g, 40%). LCMS calculated for $C_{20}H_{20}N_5O_3$ $(M+H)^+$: m/z=378.1; found: 378.1. $^1$H NMR (400 MHz, DMSO-$d_6$) δ 11.40 (s, 1H), 8.68-8.58 (m, 1H), 8.20 (bs, 2H), 7.84 (td, J=7.8, 1.8 Hz, 1H), 7.48-7.37 (m, 1H), 7.16 (d, J=8.0 Hz, 1H), 6.91 (d, J=8.0 Hz, 1H), 6.84 (d, J=8.0 Hz, 1H), 4.73 (d, 1H), 4.41 (d, 1H), 4.12-3.97 (m, 1H), 3.75-3.58 (m, 1H), 2.18 (s, 3H), 2.00 (s, 3H).

Example 74

7-(3,5-Dimethylisoxazol-4-yl)-2-oxo-4-pyridin-2-yl-1,2,4,5-tetrahydroimidazo[1,5,4-de][1,4]benzoxazine-4-carboxamide 2,2,2-trifluoroacetate

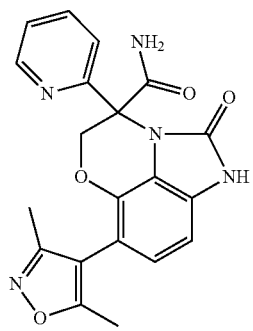 [SMILES: Cc1noc(C)c1-c1ccc2[nH]c(=O)n3c2c1OCC3(C(N)=O)c1ccccn1]

Step 1. 5-Nitro-3-pyridin-2-yl-3,4-dihydro-2H-1,4-benzoxazine-3-carboxamide

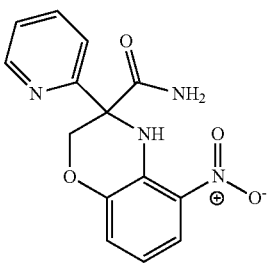 [SMILES: NC(=O)C1(c2ccccn2)COc2cccc([N+](=O)[O-])c2N1]

5-Nitro-3-pyridin-2-yl-3,4-dihydro-2H-1,4-benzoxazine-3-carbonitrile (100 mg, 0.4 mmol) was added to a vigorously stirring mixture of aluminum oxide (100 mg, 1 mmol) and methanesulfonic acid (2 mL, 30 mmol) at room temperature. The reaction mixture was then heated to 120° C. for 20 min, allowed to cool to room temperature, and partitioned between water and ethyl acetate. The organic layer was washed with brine, dried over magnesium sulfate, filtered, and concentrated to give crude product. The product was purified by FCC on silica gel eluting a hexane:ethyl acetate gradient to give 5-nitro-3-pyridin-2-yl-3,4-dihydro-2H-1,4-benzoxazine-3-carboxamide as clear oil (0.040 g. 40%). LCMS calculated for $C_{14}H_{13}N_4O_4$ (M+H)$^+$: m/z=301.1; found: 301.1.

Step 2. 5-Amino-3-pyridin-2-yl-3,4-dihydro-2H-1,4-benzoxazine-3-carboxamide

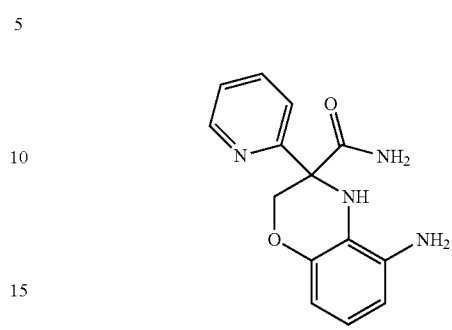

5-Nitro-3-pyridin-2-yl-3,4-dihydro-2H-1,4-benzoxazine-3-carboxamide (0.040 g, 0.13 mmol) was dissolved in methanol (5 mL) in a Parr bottle and degassed with nitrogen, followed by addition of palladium (10% on carbon) (20 mg, 0.2 mmol). The reaction vessel was charged to 50 PSI with hydrogen and shaken for 2 h. The reaction mixture was then filtered and concentrated to give crude 5-amino-3-pyridin-2-yl-3,4-dihydro-2H-1,4-benzoxazine-3-carboxamide as a glass (0.040 g. 100%). LCMS calculated for $C_{14}H_{15}N_4O_2$ (M+H)$^+$: m/z=271.1; found: 271.1.

Step 3. 2-Oxo-4-pyridin-2-yl-1,2,4,5-tetrahydroimidazo[1,5,4-de][1,4]benzoxazine-4-carboxamide

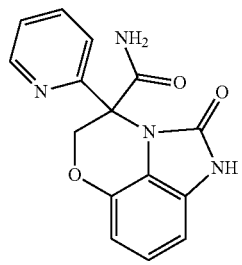 [SMILES: NC(=O)C1(c2ccccn2)COc2cccc3[nH]c(=O)n1c23]

Triphosgene (20 mg, 0.07 mmol) was added to a solution of 5-amino-3-pyridin-2-yl-3,4-dihydro-2H-1,4-benzoxazine-3-carboxamide (40 mg, 0.2 mmol) in tetrahydrofuran (5 mL) and N,N-diisopropylethylamine (60 μL, 0.3 mmol) at room temperature. The reaction was stirred for 1 h and then partitioned between ethyl acetate and water. The combined organic layer was washed with brine, dried over magnesium sulfate, filtered, and concentrated to give crude 2-oxo-4-pyridin-2-yl-1,2,4,5-tetrahydroimidazo[1,5,4-de][1,4]benzoxazine-4-carboxamide (0.040 g. 80%). LCMS calculated for $C_{15}H_{13}N_4O_3$ (M+H)$^+$: m/z=297.1; found: 297.1.

Step 4. 7-Bromo-2-oxo-4-pyridin-2-yl-1,2,4,5-tetra-hydroimidazo[1,5,4-de][1,4]benzoxazine-4-carboxamide

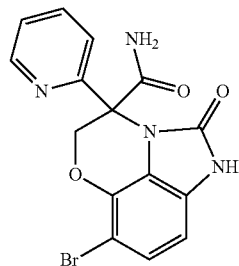 [SMILES: NC(=O)C1(c2ccccn2)COc2c(Br)ccc3[nH]c(=O)n1c23]

N-Bromosuccinimide (40 mg, 0.2 mmol) was added to a solution of 2-oxo-4-pyridin-2-yl-1,2,4,5-tetrahydroimidazo[1,5,4-de][1,4]benzoxazine-4-carboxamide, acetonitrile (5 mL) and acetic acid (3 mL) and cooled to 0° C. The reaction mixture was stirred for 1 h and then concentrated to remove residual acetic acid. The resulting residue was partitioned between ethyl acetate and saturated aqueous sodium bicarbonate. The organic layer was washed with brine, dried over magnesium sulfate, filtered, and concentrated to give crude 7-bromo-2-oxo-4-pyridin-2-yl-1,2,4,5-tetrahydroimidazo[1,5,4-de][1,4]benzoxazine-4-carboxamide (0.040 g. 60%). LCMS calculated for $C_{15}H_{12}BrN_4O_3(M+H)^+$: m/z=375.1, 377.1; found: 375.0, 376.9.

Step 5. 7-(3,5-Dimethylisoxazol-4-yl)-2-oxo-4-pyridin-2-yl-1,2,4,5-tetrahydroimidazo[1,5,4-de][1,4]benzoxazine-4-carboxamide 2,2,2-trifluoroacetate 7-Bromo-2-oxo-4-pyridin-2-yl-1,2,4,5-tetrahydroimidazo[1,5,4-de][1,4]benzoxazine-4-carboxamide (20 mg, 0.05 mmol) was combined in 1,4-dioxane (2 mL) with potassium (3,5-dimethylisoxazol-4-yl)(trifluoro)borate (16 mg, 0.077 mmol) and potassium carbonate (10 mg, 0.1 mmol) in water (1 mL) was degassed with nitrogen. The catalyst [1,1'-bis(diphenylphosphino)ferrocene]dichloropalladium(II), complex with dichloromethane (1:1) (7 mg, 0.008 mmol) was added and degassed with nitrogen. The reaction was stirred at 110° C. for 5 h, allowed to cool to room temperature, and partitioned between ethyl acetate and water. The organic layer was washed with brine, dried over magnesium sulfate, and concentrated to give crude product. The product was purified by prep HPLC on a C-18 column eluting a water:acetonitrile gradient buffered to pH 2 to give 7-(3,5-dimethylisoxazol-4-yl)-2-oxo-4-pyridin-2-yl-1,2,4,5-tetrahydroimidazo[1,5,4-de][1,4]benzoxazine-4-carboxamide as an off white solid (0.010 g. 50%). LCMS calculated for $C_{20}H_{18}N_5O_4$ (M+H)$^+$: m/z=392.1; found: 392.1. $^1$H NMR (400 MHz, DMSO-d$_6$) δ 11.04 (s, 1H), 8.56-8.48 (m, 1H), 7.83 (td, J=7.8, 1.8 Hz, 1H), 7.78-7.70 (m, 2H), 7.52 (d, J=8.1 Hz, 1H), 7.42-7.32 (m, 1H), 6.83 (d, J=8.0 Hz, 1H), 6.74 (d, J=8.0 Hz, 1H), 4.76 (d, J=11.2 Hz, 1H), 4.71 (d, 1H), 2.23 (s, 3H), 2.05 (s, 3H).

Example 79

7-(3,5-dimethylisoxazol-4-yl)-4-[1-(methylsulfonyl)piperidin-2-yl]-4,5-dihydroimidazo[1,5,4-de][1,4]benzoxazin-2(1H)-one

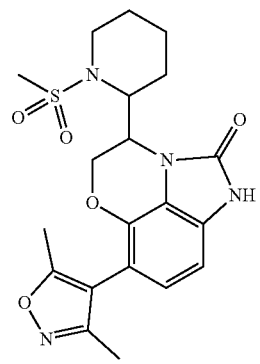 [SMILES: Cc1noc(C)c1-c1ccc2[nH]c(=O)n3c2c1OCC3C1CCCCN1S(C)(=O)=O]

The amine 7-(3,5-dimethylisoxazol-4-yl)-4-piperidin-2-yl-4,5-dihydroimidazo[1,5,4-de][1,4]benzoxazin-2(1H)-one (0.05 g, 0.14 mmol) (Example 63) was dissolved in methylene chloride (2.0 mL) and N,N-diisopropylethylamine (0.049 mL, 0.28 mmol) at rt under nitrogen. Methanesulfonyl chloride (0.010 mL, 0.14 mmol) was added and the reaction was stirred at rt. After stirring for 1 h, the reaction was dissolved in ethyl acetate and washed with water, brine, dried over magnesium sulfate and concentrated to give crude product as a dark oil. The product was purified by prep HPLC on a C-18 column eluting water:acetonitrile gradient buffered pH 2 with TFA to give 7-(3,5-dimethylisoxazol-4-yl)-4-[1-(methylsulfonyl)piperidin-2-yl]-4,5-dihydroimidazo[1,5,4-de][1,4]benzoxazin-2(1H)-one as two fractions:

Example 79, Peak 1 as a solid residue (0.015 g, 26%). LCMS calculated for $C_{20}H_{25}N_4O_5S$ (M+H)$^+$: m/z=433.1; found: 433.2. $^1$H NMR (400 MHz, DMSO-d$_6$) δ 10.69 (s, 1H), 6.78 (d, J=8.0 Hz, 1H), 6.65 (d, J=8.0 Hz, 1H), 4.89-4.65 (m, 3H), 4.4-3.9 (m, 2H), 3.62 (m, 1H), 2.28 (s, 3H), 2.11 (s, 3H), 1.96 (m, 1H), 1.82 (s, 3H), 1.73-1.51 (m, 3H), 1.41 (m, 1H), 1.1 (m, 1H).

Example 79, Peak 2 as a solid residue (0.010 g, 18%). LCMS calculated for $C_{20}H_{25}N_4O_4S$ (M+H)$^+$: m/z=433.1; found: 433.2.

Examples 75-87

The experimental procedures used to prepare the compounds of Examples 75 to 87 are summarized in Table 3 below.

TABLE 3

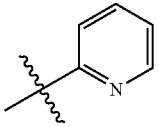 [SMILES: *c1ccccn1]

| Ex. No. | Name | R¹ | R⁷ | Cy³ | Salt | Proc.* |
|---|---|---|---|---|---|---|
| 75 | 7-(3,5-dimethylisoxazol-4-yl)-5-methyl-4-pyridin-2-yl-4,5-dihydroimidazo[1,5,4-de][1,4]benzoxazin-2(1H)-one | Me | H | 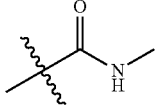 | | 13 |
| 76 | 7-(3,5-dimethylisoxazol-4-yl)-N-methyl-2-oxo-4-pyridin-2-yl-1,2,4,5-tetrahydroimidazo[1,5,4-de][1,4]benzoxazine-5-carboxamide 2,2,2-trifluoroacetate | 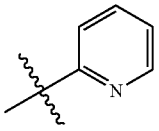 [SMILES: *c1ccccn1] | H | 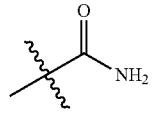 | TFA | 24 |
| 77 | 7-(3,5-dimethylisoxazol-4-yl)-2-oxo-4-pyridin-2-yl-1,2,4,5-tetrahydroimidazo[1,5,4-de][1,4]benzoxazine-5-carboxamide 2,2,2-trifluoroacetate | 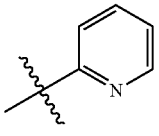 [SMILES: *c1ccccn1] | H | 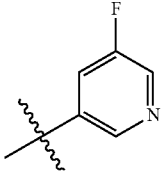 [SMILES: *c1cncc(F)c1] | TFA | 24 |
| 78 | 7-(3,5-dimethylisoxazol-4-yl)-4-(5-fluoropyridin-3-yl)-4,5-dihydroimidazo[1,5,4-de][1,4]benzoxazin-2(III)-one | H | H | 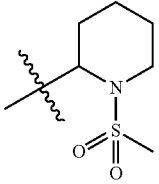 [SMILES: *C1CCCCN1S(C)(=O)=O] | | 5 |
| 79 | 7-(3,5-dimethylisoxazol-4-yl)-4-[1-2 (methylsulfonyl)piperidin-2-yl]-4,5-dihydroimidazo[1,5,4-de][1,4]benzoxazin-2(1H)-one | H | H | 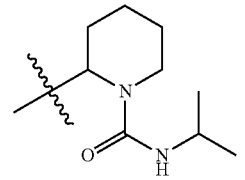 [SMILES: *C1CCCCN1C(=O)NC(C)C] | | 79 |
| 80 | 2-[7-(3,5-dimethylisoxazol-4-yl)-2-oxo-1,2,4,5-tetrahydroimidazo[1,5,4-de][1,4]benzoxazin-4-yl]-N-isopropylpiperidine-1-carboxamide | H | H | 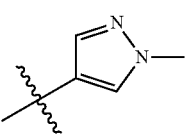 [SMILES: *c1cnn(C)c1] | | 79 |
| 81 | (4S)-7-(3,5-dimethylisoxazol-4-yl)-9-(1-methyl-1H-pyrazol-4-yl)-4-pyridin-2-yl-4,5-dihydroimidazo[1,5,4-de][1,4]benzoxazin-2(1H)-one 2,2,2-trifluoroacetate | H | 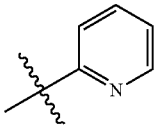 [SMILES: *c1ccccn1] | | TFA | 43 |

TABLE 3-continued

| Ex. No. | Name | R¹ | R⁷ | Cy³ | Salt | Proc.* |
|---|---|---|---|---|---|---|
| 82 | 5-[(4S)-7-(3,5-dimethylisoxazol-4-yl)-2-oxo-4-pyridin-2-yl-1,2,4,5-tetrahydroimidazo[1,5,4-de][1,4]benzoxazin-9-yl]-N,N-dimethylpyridine-2-carboxamide 2,2,2-bis(trifluoroacetate) | H | (5-pyridyl with 2-C(O)N(CH₃)₂) | 2-pyridyl | 2TFA | 43 |
| 83 | tert-butyl 4-[(4S)-7-(3,5-dimethylisoxazol-4-yl)-2-oxo-4-pyridin-2-yl-1,2,4,5-tetrahydroimidazo[1,5,4-de][1,4]benzoxazin-9-yl]-3,6-dihydropyridine-1(2H)-carboxylate 2,2,2-trifluoroacetate | H | (N-Boc-1,2,3,6-tetrahydropyridin-4-yl) | 2-pyridyl | TFA | 43 |
| 84 | (4S)-7-(3,5-dimethylisoxazol-4-yl)-4-pyridin-2-yl-9-pyrimidin-5-yl-4,5-dihydroimidazo[1,5,4-de][1,4]benzoxazin-2(1H)-one 2,2,2-trifluoroacetate | H | pyrimidin-5-yl | 2-pyridyl | TFA | 43 |
| 85 | (4S)-7-(3,5-dimethylisoxazol-4-yl)-9-(1-methyl-1H-pyrazol-5-yl)-4-pyridin-2-yl-4,5-dihydroimidazo[1,5,4-de][1,4]benzoxazin-2(1H)-one 2,2,2-trifluoroacetate | H | 1-methyl-1H-pyrazol-5-yl | 2-pyridyl | TFA | 43 |
| 86 | ethyl (2E)-3-[(4S)-7-(3,5-dimethylisoxazol-4-yl)-2-oxo-4-pyridin-2-yl-1,3,4,5-tetrahydroimidazo[1,5,4-de][1,4]benzoxazin-9-yl]acrylate 2,2,2-trifluoroacetate | H | (E)-CH=CH-C(O)OEt | 2-pyridyl | TFA | 43 |
| 87 | (4S)-7-(3,5-dimethylisoxazol-4-yl)-4-pyridin-2-yl-9-(1,2,3,6-tetrahydropyridin-4-yl)-4,5-dihydroimidazo[1,5,4-de][1,4]benzoxazin-2(1H)-one bis(2,2,2-trifluoroacetate) | H | 1,2,3,6-tetrahydropyridin-4-yl | 2-pyridyl | 2TFA | 43 |

*Synthesized according to the experimental procedure of Example number listed.

Example 88

(4S)-7-(3,5-Dimethylisoxazol-4-yl)-4-pyridin-2-yl-2-vinyl-4,5-dihydroimidazo[1,5,4-de][1,4]benzoxazine

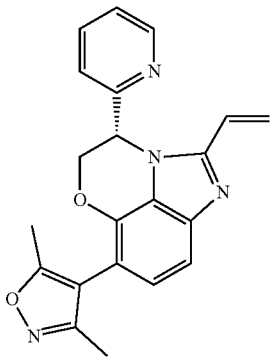 [SMILES: C=Cc1nc2ccc(-c3c(C)noc3C)c3c2n1[C@@H](c1ccccn1)CO3]

(4S)-2-Chloro-7-(3,5-dimethylisoxazol-4-yl)-4-pyridin-2-yl-4,5-dihydroimidazo[1,5,4-de][1,4]benzoxazine (277 mg, 0.755 mmol), 4,4,5,5-tetramethyl-2-vinyl-1,3,2-dioxaborolane (0.19 mL, 1.1 mmol) [Aldrich, cat. #633348], and potassium phosphate (0.3 g, 2 mmol) [Aldrich, cat. # P5629], were dissolved in water (2.4 mL) and 1,4-dioxane (10 mL). The reaction mixture was deoxygenated with nitrogen and dicyclohexyl(2',4',6'-triisopropylbiphenyl-2-yl)phosphine-(2'-aminobiphenyl-2-yl)(chloro)palladium (1:1) (0.03 g, 0.04 mmol) [Aldrich, cat. #741825] was added. The resulting mixture was deoxygenated with nitrogen and heated at 80° C. for 3 h. The reaction mixture was then allowed to cool to room temperature. Ethyl acetate was added, and the mixture was washed with water and brine, then dried over sodium sulfate and concentrated. The resulting residue was purified by flash chromatography eluting ethyl acetate in hexanes (75-100%, ethyl acetate containing 20% MeOH) to afford the desired product (0.21 g, 78%). LCMS for $C_{21}H_{19}O_2N_4$ (M+H)+: calculated m/z=359.2; found 359.3; $^1$H NMR (400 MHz, CD$_3$OD) δ 8.61-8.53 (m, 1H), 7.74 (m, 1H), 7.39 (d, J=8.4 Hz, 1H), 7.34 (dd, J=7.7, 4.8 Hz, 1H), 7.14 (d, J=8.4 Hz, 1H), 6.75 (d, J=4.1 Hz, 1H), 6.69 (d, J=11.4 Hz, 1H), 6.34 (dd, J=17.5, 1.0 Hz, 1H), 6.09 (dd, J=2.5 Hz, 2H), 5.68 (dd, J=11.4, 1.0 Hz, 1H), 4.96 (dd, J=11.6, 2.1 Hz, 1H), 4.64 (dd, J=11.6, 3.1 Hz, 1H), 2.29 (s, 3H), 2.15 (s, 3H).

Example 89

(1R)-1-[(4S)-7-(3,5-Dimethylisoxazol-4-yl)-4-pyridin-2-yl-4,5-dihydroimidazo[1,5,4-de][1,4]benzoxazin-2-yl]ethane-1,2-diol

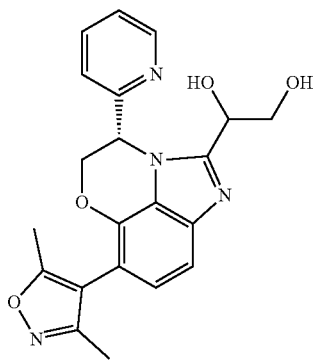 [SMILES: Cc1noc(C)c1-c1ccc2nc(C(O)CO)n3c2c1OC[C@@H]3c1ccccn1]

(4S)-7-(3,5-Dimethylisoxazol-4-yl)-4-pyridin-2-yl-2-vinyl-4,5-dihydroimidazo[1,5,4-de][1,4]benzoxazine (40 mg, 0.1 mmol) was dissolved in tert-butyl alcohol (4 mL) and water (4 mL). To the resulting solution, the mixture of A-D mix β (300 mg, 0.7 mmol) [Aldrich, cat. #392766] was added at room temperature. The resulting mixture was stirred overnight. Saturated aqueous sodium sulfite (2 mL) was added and the suspension was stirred for 15 min at room temperature. The mixture was then extracted with dichloromethane. The organic extracts were combined, washed with brine, dried over sodium sulfate, filtered, and concentrated. Purification by preparative LCMS (XBridge C18 column, eluting with a gradient of acetonitrile/water containing 0.1% ammonium hydroxide, at flow rate of 60 mL/min) afforded the desired product (0.021 g, 50%). LCMS for $C_{21}H_{21}O_4N_4$ (M+H)+: calculated m/z=393.2; found 393.2.

Example 90

1-[(4S)-7-(3,5-Dimethylisoxazol-4-yl)-4-pyridin-2-yl-4,5-dihydroimidazo[1,5,4-de][1,4]benzoxazin-2-yl]ethanol

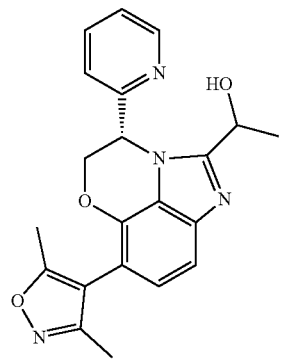 [SMILES: Cc1noc(C)c1-c1ccc2nc(C(C)O)n3c2c1OC[C@@H]3c1ccccn1]

Step 1. (4S)-7-(3,5-Dimethylisoxazol-4-yl)-4-pyridin-2-yl-4,5-dihydroimidazo[1,5,4-de][1,4]benzoxazine-2-carbaldehyde

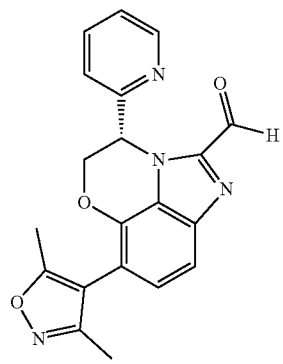 [SMILES: Cc1noc(C)c1-c1ccc2nc(C=O)n3c2c1OC[C@@H]3c1ccccn1]

(4S)-7-(3,5-Dimethylisoxazol-4-yl)-4-pyridin-2-yl-2-vinyl-4,5-dihydroimidazo[1,5,4-de][1,4]benzoxazine (0.05 g, 0.1 mmol) was dissolved in tetrahydrofuran (1.7 mL). The resulting solution was cooled to 0° C., then a solution of 0.16

M osmium tetraoxide in water (0.3 mL, 0.04 mmol) [Aldrich, cat. #251755] and sodium metaperiodate (140 mg, 0.66 mmol) [Aldrich, cat. # S 1878] in water (0.1 mL) were added. The reaction was allowed to warm to room temperature and stirred for 1 h. The reaction was quenched with saturated aqueous sodium sulfite (10 mL) for 10 min at room temperature. The mixture was filtered through a Celite plug and the plug was rinsed with dichloromethane. The organic layer was concentrated under vacuum. The resulting residue was purified by flash chromatography elucting ethyl acetate in hexanes (75-100%, ethyl acetate containing 20% MeOH) to afford the desired product (0.053 g, 100%). LCMS for $C_{20}H_{17}O_3N_4$ (M+H)+: calculated m/z=361.1; found 361.2.

Step 2. 1-[(4S)-7-(3,5-Dimethylisoxazol-4-yl)-4-pyridin-2-yl-4,5-dihydroimidazo[1,5,4-de][1,4]benzoxazin-2-yl]ethanol To the solution of (4S)-7-(3,5-dimethylisoxazol-4-yl)-4-pyridin-2-yl-4,5-dihydroimidazo[1,5,4-de][1,4]benzoxazine-2-carbaldehyde (8 mg, 0.02 mmol) in tetrahydrofuran (1 mL) at 0° C., 3.0 M methylmagnesium chloride in THF (0.01 mL, 0.04 mmol) [Aldrich, cat. #189901] was added dropwise. After continued stirring for 30 min at 0° C., the reaction was quenched by adding saturated aqueous ammonium chloride (0.5 mL) dropwise. The resulting mixture was diluted with ethyl acetate/brine (3:1), and the organic layer was separated. The aqueous layer was extracted with ethyl acetate. The combined organic layers were dried over sodium sulfate, filtered, and concentrated under vacuum. Purification by preparative LCMS (XBridge C18 column, eluting with a gradient of acetonitrile/water containing 0.1% ammonium hydroxide, at flow rate of 60 mL/min) afforded the desired product as a mixture of diastereomers (4 mg, 50%). LCMS for $C_{21}H_{21}O_3N_4$ (M+H)+: calculated m/z=377.2, found 377.1.

Example 91

(4S)-7-(3,5-Dimethylisoxazol-4-yl)-N,N-dimethyl-4-pyridin-2-yl-4,5-dihydroimidazo[1,5,4-de][1,4]benzoxazine-2-carboxamide

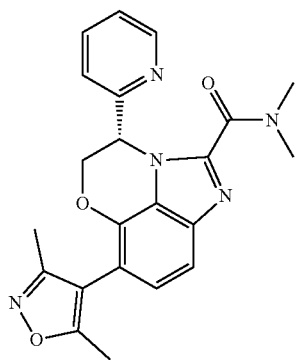 [SMILES: Cc1noc(C)c1-c1ccc2nc(C(=O)N(C)C)n3c2c1OC[C@@H]3c1ccccn1]

Example 92

(4S)-7-(3,5-Dimethylisoxazol-4-yl)-4-pyridin-2-yl-4,5-dihydroimidazo[1,5,4-de][1,4]benzoxazine

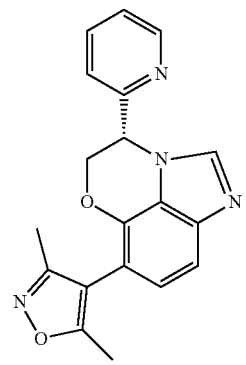 [SMILES: Cc1noc(C)c1-c1ccc2ncn3c2c1OC[C@@H]3c1ccccn1]

Example 93 tert-Butyl (4S)-7-(3,5-dimethylisoxazol-4-yl)-4-pyridin-2-yl-4,5-dihydroimidazo[1,5,4-de][1,4]benzoxazine-2-carboxylate

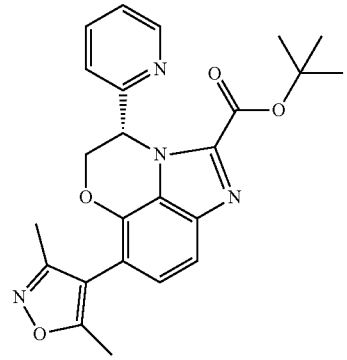 [SMILES: Cc1noc(C)c1-c1ccc2nc(C(=O)OC(C)(C)C)n3c2c1OC[C@@H]3c1ccccn1]

(4S)-7-(3,5-Dimethylisoxazol-4-yl)-4-pyridin-2-yl-4,5-dihydroimidazo[1,5,4-de][1,4]benzoxazine-2-carbaldehyde (15 mg, 0.042 mmol) and dimethylamine hydrochloride (0.0041 g, 0.050 mmol) [Aldrich, cat. #126365] were dissolved in acetonitrile (1.5 mL) at room temperature. To the resulting mixture, copper(II) sulfate pentahydrate (0.0005 g, 0.002 mmol) [Aldrich, cat. #209198], calcium carbonate (0.0046 g, 0.046 mmol) [Aldrich, cat. #C6763] and 6.0 M tert-butyl hydroperoxide in decane (0.0076 mL, 0.046 mmol) [Aldrich, cat. #416665] were added. The reaction vessel was capped, degassed, and allowed to stir at 40° C. for 10 hours. After filtration through Celite, the solution was concentrated and the resulting residue was purified by preparative LCMS (XBridge C18 column, eluting with a gradient of acetonitrile/water containing 0.1% ammonium hydroxide, at flow rate of 60 mL/min) afforded the following three compounds:

Example 91 (7.2 mg, 43%) LCMS for $C_{22}H_{22}O_3N_5$ (M+H)+: calculated m/z=404.2; found 404.2. $^1$H NMR (400 MHz, CD$_3$OD) δ 8.49 (d, J=4.6 Hz, 1H), 7.81-7.71 (m, 1H), 7.46 (d, J=8.4 Hz, 1H), 7.37-7.28 (m, 1H), 7.18 (d, J=8.4 Hz, 1H), 7.03 (d, J=7.9 Hz, 2H), 6.15 (d, J=3.6 Hz, 1H), 5.48 (s, 1H), 4.79 (dd, J=11.8, 3.9 Hz, 2H), 4.70 (dd, J=11.7, 3.2 Hz, 1H), 3.38 (s, 3H), 2.94 (s, 3H), 2.30 (s, 3H), 2.15 (s, 3H).

Example 92 (2.4 mg, 17%) LCMS for $C_{19}H_{17}O_2N_4$ (M+H)+: calculated m/z=333.1; found 333.2 $^1$H NMR (400 MHz, CD$_3$OD) δ 8.61 (d, J=3.9 Hz, 1H), 8.23 (s, 1H), 7.83 (dd, J=7.8 Hz, 1H), 7.48-7.36 (m, 2H), 7.14 (d, J=7.8 Hz, 2H), 7.06 (d, J=7.9 Hz, 2H), 5.94 (s, 1H), 4.82-4.74 (m, 2H), 4.74-4.67 (m, 2H), 2.32 (s, 3H), 2.18 (s, 3H).

Example 93 (3.2 mg, 18%) LCMS for $C_{24}H_{25}O_4N_4$ (M+H)+: calculated m/z=433.2, found 433.2; $^1$H NMR (400 MHz, CD$_3$OD) δ 8.52 (d, J=4.8 Hz, 1H), 7.77-7.67 (m, 1H), 7.53 (d, J=8.5 Hz, 1H), 7.38-7.29 (m, 1H), 7.24 (d, J=8.5 Hz, 1H), 6.71 (d, J=7.9 Hz, 1H), 6.40 (s, 1H), 5.00 (dd, J=11.7, 3.1 Hz, 1H), 4.69 (dd, J=11.8, 3.1 Hz, 1H), 2.28 (s, 3H), 2.14 (s, 3H), 1.47 (s, 9H).

Example 94

(4S)-7-(3,5-Dimethylisoxazol-4-yl)-2-(morpholin-4-ylcarbonyl)-4-pyridin-2-yl-4,5-dihydroimidazo[1,5,4-de][1,4]benzoxazine

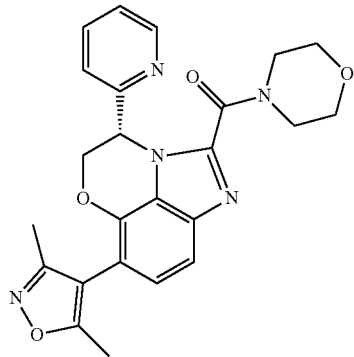 [SMILES: Cc1noc(C)c1-c1ccc2nc(C(=O)N3CCOCC3)n3c2c1OC[C@@H]3c1ccccn1]

The title compound was prepared by methods analogous to Example 91, using morpholine [Aldrich, cat. #252360] as the nucleophile. Purification by preparative LCMS (XBridge C18 column, eluting with a gradient of acetonitrile/water containing 0.1% ammonium hydroxide, at flow rate of 60 mL/min) afforded the title compound. LCMS for $C_{24}H_{24}O_4N_5$ (M+H)+: calculated m/z=446.2, found 446.1; $^1$H NMR (400 MHz, CD$_3$OD) δ 8.51 (d, J=4.2 Hz, 1H), 7.78 (m, 1H), 7.47 (d, J=8.4 Hz, 1H), 7.34 (dd, J=7.1, 5.4 Hz, 1H), 7.20 (d, J=8.4 Hz, 1H), 7.06 (d, J=7.9 Hz, 1H), 6.20 (m, 1H), 4.81 (dd, J=11.8, 3.7 Hz, 1H), 4.72 (dd, J=11.7, 3.3 Hz, 1H), 4.12 (s, 2H), 3.83-3.69 (m, 2H), 3.59 (t, J=8.1 Hz, 4H), 2.16 (s, 3H), 2.04 (s, 3H).

Example 95

(4S)-7-(3,5-Dimethylisoxazol-4-yl)-N-methyl-4-pyridin-2-yl-4,5-dihydroimidazo[1,5,4-de][1,4]benzoxazine-2-carboxamide

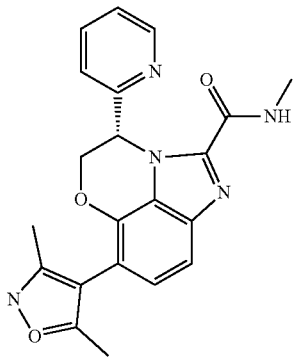

The title compound was prepared by methods analogous to Example 91, using 2.0 M methylamine in tetrahydrofuran [Aldrich, cat. #395056] as the nucleophile. Purification by preparative LCMS (XBridge C18 column, eluting with a gradient of acetonitrile/water containing 0.1% ammonium hydroxide, at flow rate of 60 mL/min) afforded the title compound. LCMS for $C_{21}H_{20}O_3N_5$ (M+H)+: calculated m/z=390.2, found 390.2; $^1$H NMR (400 MHz, CD$_3$OD) δ 8.49 (d, J=4.8 Hz, 1H), 7.69 (m, 1H), 7.49 (d, J=8.5 Hz, 1H), 7.28 (dd, J=6.9, 4.9 Hz, 1H), 7.19 (d, J=8.5 Hz, 1H), 6.64 (d, J=7.9 Hz, 1H), 6.56-6.50 (m, 1H), 4.96 (dd, J=11.7, 3.1 Hz, 1H), 4.65 (dd, J=11.7, 3.0 Hz, 1H), 2.88 (s, 1H), 2.27 (s, 3H), 2.13 (s, 3H).

Example 96

(4S)-7-(3,5-Dimethylisoxazol-4-yl)-4-pyridin-2-yl-4,5-dihydroimidazo[1,5,4-de][1,4]benzoxazine-2-carboxamide

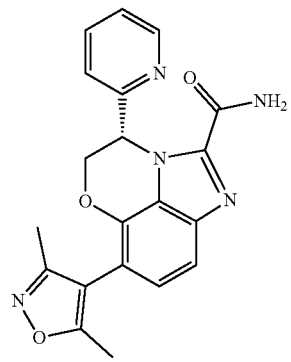 [SMILES: Cc1noc(C)c1-c1ccc2nc(C(N)=O)n3c2c1OC[C@@H]3c1ccccn1]

The title compound was prepared by methods analogous to Example 91, using hydroxylamine hydrochloride [Aldrich, cat. #159417] as the nucleophile. Purification by preparative LCMS (XBridge C18 column, eluting with a gradient of acetonitrile/water containing 0.1% ammonium hydroxide, at flow rate of 60 mL/min) afforded the title compound. LCMS for $C_{20}H_{18}O_3N_5$ (M+H)+: calculated m/z=376.1, found 376.2; $^1$H NMR (400 MHz, CD$_3$OD) δ 8.49 (d, J=4.8 Hz, 1H), 8.20 (s, 1H), 7.69 (m, 1H), 7.43 (d, J=8.5 Hz, 1H), 7.28 (dd, J=6.9, 4.9 Hz, 1H), 7.19 (d, J=8.5 Hz, 1H), 6.54 (d, J=7.9 Hz, 1H), 6.33 (m, 1H), 4.96 (dd, J=11.7, 3.1 Hz, 1H), 4.65 (dd, J=11.7, 3.0 Hz, 1H), 2.27 (s, 3H), 2.13 (s, 3H).

Example 97 tert-Butyl 4-[(4S)-7-(3,5-dimethylisoxazol-4-yl)-4-pyridin-2-yl-4,5-dihydroimidazo[1,5,4-de][1,4]benzoxazin-2-yl]-3,6-dihydropyridine-1 (2H)-carboxylate

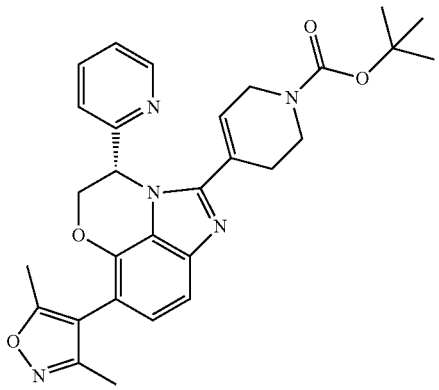 [SMILES: Cc1noc(C)c1-c1ccc2nc(C3=CCN(C(=O)OC(C)(C)C)CC3)n3c2c1OC[C@@H]3c1ccccn1]

(4S)-2-Chloro-7-(3,5-dimethylisoxazol-4-yl)-4-pyridin-2-yl-4,5-dihydroimidazo[1,5,4-de][1,4]benzoxazine (80 mg, 0.2 mmol), tert-butyl 4-(4,4,5,5-tetramethyl-1,3,2-dioxaborolan-2-yl)-3,6-dihydropyridine-1(2H)-carboxylate (100 mg, 0.4 mmol) [Aldrich, cat. # CDS015890], and potassium phosphate (0.09 g, 0.4 mmol) [Aldrich, cat. # P5629] were suspended in 1,4-dioxane (3 mL) and water (0.70 mL). The resulting mixture was degassed with nitrogen for 10 min and dicyclohexyl(2',4',6'-triisopropylbiphenyl-2-yl)phosphine-(2'-aminobiphenyl-2-yl)(chloro)palladium (1:1) (0.008 g, 0.01 mmol) [Aldrich, cat. #741825] was added, followed by an additional 10 min of degassing. The reaction mixture was sealed and heated at 50° C. for 16 h. After cooling to room temperature, the reaction mixture was extracted with dichloromethane. The combined organic layers were washed with brine, dried over sodium sulfate, filtered, and concentrated under reduced pressure. The residue was purified by flash chromatography eluting ethyl acetate in hexanes (75-100%) to afford the desired product (98 mg, 90%). LCMS for $C_{29}H_{32}O_4N_5$ (M+H)+: calculated m/z=514.2, found 514.2; $^1$H NMR (300 MHz, CD$_3$OD) δ 8.54 (d, J=4.7 Hz, 1H), 7.72 (m, 2H), 7.44-7.27 (m, 2H), 7.10 (d, J=8.4 Hz, 1H), 6.75 (d, J=8.1 Hz, 1H), 6.14 (s, 1H), 6.07 (d, J=2.8 Hz, 1H), 4.78 (dd, J=11.6, 2.9 Hz, 1H), 4.59 (dd, J=11.6, 3.1 Hz, 1H), 4.11-3.72 (m, 2H), 3.51 (d, J=16.0 Hz, 2H), 2.60 (s, 2H), 2.25 (s, 3H), 2.10 (s, 3H), 1.42 (s, 9H).

Example 98 tert-Butyl 3-[(4S)-7-(3,5-dimethylisoxazol-4-yl)-4-pyridin-2-yl-4,5-dihydroimidazo[1,5,4-de][1,4]benzoxazin-2-yl]-2,5-dihydro-1H-pyrrole-1-carboxylate

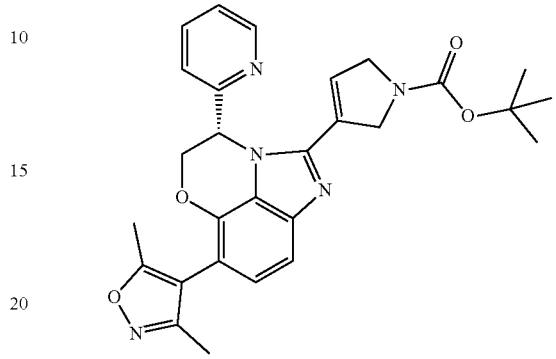

The title compound was prepared by methods analogous to Example 97, using tert-butyl 3-(4,4,5,5-tetramethyl-1,3,2-dioxaborolan-2-yl)-2,5-dihydro-1H-pyrrole-1-carboxylate [Combi-Blocks, cat. # FM2879] as the Suzuki-coupling reagent. The crude product was purified by flash chromatography with ethyl acetate in hexanes (75-100%) to afford the title compound. LCMS for $C_{28}H_{30}O_4N_5$ (M+H)+: calculated m/z=500.2, found 500.4; $^1$H NMR (400 MHz, CD$_3$OD) δ 8.64-8.52 (m, 1H), 7.78-7.67 (m, 1H), 7.43 (d, J=8.4 Hz, 1H), 7.39-7.29 (m, 1H), 7.16 (d, J=8.4 Hz, 1H), 6.70 (m, 1H), 6.30 (d, J=8.5 Hz, 1H), 6.18 (s, 1H), 4.95 (d, J=11.6 Hz, 1H), 4.69 (s, 1H), 4.63 (dd, J=11.6, 3.1 Hz, 1H), 4.57 (s, 1H), 4.32 (d, J=17.3 Hz, 1H), 4.21 (d, J=17.6 Hz, 1H), 2.29 (s, 3H), 2.15 (s, 3H), 1.51 (s, 6H), 1.48 (s, 3H).

Example 99 tert-Butyl 5-[(4S)-7-(3,5-dimethylisoxazol-4-yl)-4-pyridin-2-yl-4,5-dihydroimidazo[1,5,4-de][1,4]benzoxazin-2-yl]-3,6-dihydropyridine-1 (2H)-carboxylate

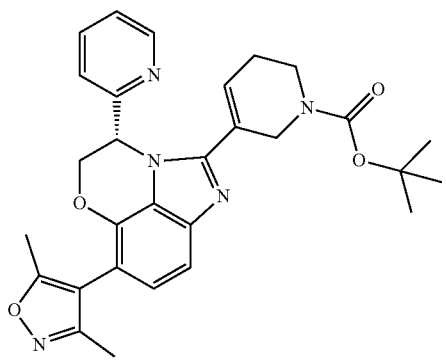 [SMILES: Cc1noc(C)c1-c1ccc2nc(C3=CCCN(C(=O)OC(C)(C)C)C3)n3c2c1OC[C@@H]3c1ccccn1]

The title compound was prepared by methods analogous to Example 97, using tert-butyl 5-(4,4,5,5-tetramethyl-1,3,2-dioxaborolan-2-yl)-3,6-dihydropyridine-1(2H)-carboxy-

Example 100 tert-Butyl 4-[(4S)-7-(3,5-dimethylisoxazol-4-yl)-4-pyridin-2-yl-4,5-dihydroimidazo[1,5,4-de][1,4]benzoxazin-2-yl]piperidine-1-carboxylate

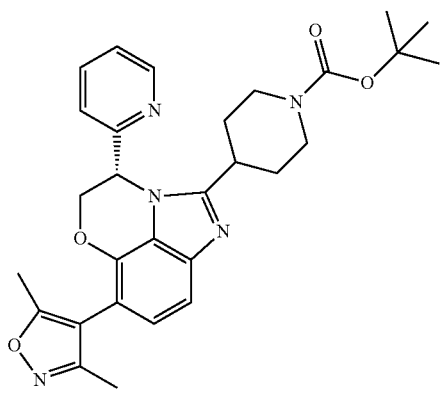 [SMILES: Cc1noc(C)c1-c1ccc2nc(C3CCN(C(=O)OC(C)(C)C)CC3)n3c2c1OC[C@@H]3c1ccccn1]

(tert-Butyl 4-[(4S)-7-(3,5-dimethylisoxazol-4-yl)-4-pyridin-2-yl-4,5-dihydroimidazo[1,5,4-de][1,4]benzoxazin-2-yl]-3,6-dihydropyridine-1(2H)-carboxylate (80 mg, 0.2 mmol) was dissolved in methanol (6 mL), and the mixture was degassed with nitrogen for 15 min, followed by addition of palladium on carbon (30 mg, 0.02 mmol) [Aldrich, cat. #130108]. After three vacuum/nitrogen gas refilling cycles, 1 atm hydrogen gas was charged to the mixture with a balloon. After stirring for 2 h at room temperature, the reaction mixture was filtered through Celite and the filter was subsequently washed with methanol (30 mL). The combined organic layers were concentrated under reduced pressure. The residue was purified by flash chromatography eluting ethyl acetate in hexanes (75-100%) to afford the desired product (48 mg, 60%). LCMS for $C_{29}H_{34}O_4N_5$ (M+H)+: calculated m/z=516.3, found 516.2; $^1$H NMR (400 MHz, CD$_3$OD) δ 8.59-8.49 (m, 1H), 7.73 (m, 1H), 7.36-7.28 (m, 2H), 7.06 (d, J=8.3 Hz, 1H), 6.78 (d, J=7.9 Hz, 1H), 6.00 (m, 1H), 4.89 (dd, J=11.7, 3.1 Hz, 1H), 4.60 (dd, J=11.6, 3.1 Hz, 1H), 4.16 (d, J=13.4 Hz, 1H), 4.04 (d, J=13.5 Hz, 1H), 2.95 (ddd, J=11.8, 8.3, 3.6 Hz, 1H), 2.88-2.51 (m, 2H), 2.25 (s, 3H), 2.11 (s, 3H), 2.06-1.94 (m, 1H), 1.92-1.66 (m, 2H), 1.44 (s, 9H).

Example 101A tert-Butyl 3-[(4S)-7-(3,5-dimethylisoxazol-4-yl)-4-pyridin-2-yl-4,5-dihydroimidazo[1,5,4-de][1,4]benzoxazin-2-yl]pyrrolidine-1-carboxylate (Diastereoisomer 1)

Example 101B tert-Butyl 3-[(4S)-7-(3,5-dimethylisoxazol-4-yl)-4-pyridin-2-yl-4,5-dihydroimidazo[1,5,4-de][1,4]benzoxazin-2-yl]pyrrolidine-1-carboxylate (Diastereoisomer 2)

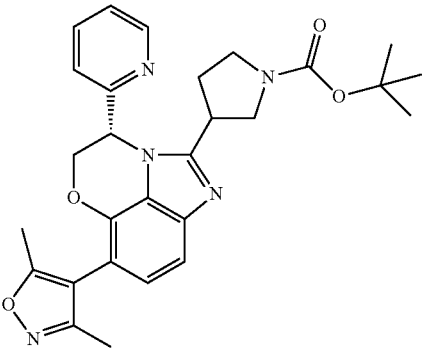 [SMILES: Cc1noc(C)c1-c1ccc2nc(C3CCN(C(=O)OC(C)(C)C)C3)n3c2c1OC[C@@H]3c1ccccn1]

The title compounds were prepared by methods analogous to Example 99, using tert-butyl 3-[(4S)-7-(3,5-dimethylisoxazol-4-yl)-4-pyridin-2-yl-4,5-dihydroimidazo[1,5,4-de][1,4]benzoxazin-2-yl]-2,5-dihydro-1H-pyrrole-1-carboxylate as the starting material. Purification by preparative LCMS (XBridge C18 column, eluting with a gradient of acetonitrile/water containing 0.1% ammonium hydroxide, at flow rate of 60 mL/min) afforded the title compound as two diastereoisomers.

Diastereoisomer 1. Preparative LCMS Peak I. LCMS for $C_{28}H_{32}O_4N_5$ (M+H)+: calculated m/z=502.2; found 502.1; $^1$H NMR (400 MHz, CD$_3$OD) δ 8.57 (s, 1H), 7.78 (s, 1H), 7.37 (d, J=7.9 Hz, 2H), 7.11 (d, J=8.3 Hz, 1H), 6.93-6.77 (m, 1H), 6.04 (s, 1H), 4.96 (d, J=12.8 Hz, 1H), 4.64 (dd, J=11.7, 2.9 Hz, 1H), 3.63 (d, J=5.0 Hz, 2H), 3.38 (m, 1H), 2.40 (m, 1H), 2.29 (s, 3H), 2.15 (s, 3H), 1.45 (s, 3H), 1.39 (s, 6H).

Diastereoisomer 2. Preparative LCMS Peak II. LCMS for $C_{28}H_{32}O_4N_5$ (M+H)+: calculated m/z=502.2; found 502.1; $^1$H NMR (400 MHz, CD$_3$OD) δ 8.57 (d, J=4.5 Hz, 1H), 7.76 (m, 1H), 7.42-7.29 (m, 2H), 7.11 (d, J=8.3 Hz, 1H), 6.91-6.73 (m, 1H), 6.04 (s, 1H), 4.93 (dd, J=11.7, 2.0 Hz, 1H), 4.64 (d, J=10.5 Hz, 1H), 3.96-3.82 (m, 1H), 3.80-3.49 (m, 1H), 2.29 (s, 3H), 2.14 (s, 3H), 2.11-1.82 (m, 2H), 1.47 (s, 9H).

Example 102 tert-Butyl 3-[(4S)-7-(3,5-dimethylisoxazol-4-yl)-4-pyridin-2-yl-4,5-dihydroimidazo[1,5,4-de][1,4]benzoxazin-2-yl]piperidine-1-carboxylate

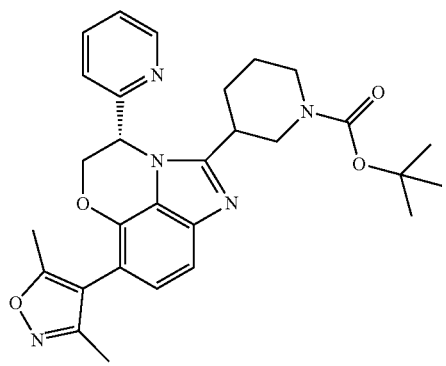 [SMILES: Cc1noc(C)c1-c1ccc2nc(C3CCCN(C(=O)OC(C)(C)C)C3)n3c2c1OC[C@@H]3c1ccccn1]

The title compound was prepared by methods analogous to Example 100, using tert-butyl 5-[(4S)-7-(3,5-dimethylisoxazol-4-yl)-4-pyridin-2-yl-4,5-dihydroimidazo[1,5,4-de][1,4]benzoxazin-2-yl]-3,6-dihydropyridine-1(2H)-carboxylate as starting material. Purification by preparative LCMS (XBridge C18 column, eluting with a gradient of acetonitrile/water containing 0.1% ammonium hydroxide, at flow rate of 60 mL/min) afforded the title compound. LCMS for $C_{29}H_{34}O_4N_5$ (M+H)$^+$: calculated m/z=516.3, found 516.2.

Example 103

(4S)-2-(1-Acetylpiperidin-4-yl)-7-(3,5-dimethylisoxazol-4-yl)-4-pyridin-2-yl-4,5-dihydroimidazo[1,5,4-de][1,4]benzoxazine

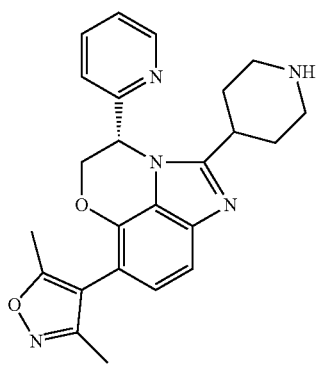 [SMILES: Cc1noc(C)c1-c1ccc2nc(C3CCNCC3)n3c2c1OC[C@@H]3c1ccccn1]

tert-Butyl 4-[(4S)-7-(3,5-dimethylisoxazol-4-yl)-4-pyridin-2-yl-4,5-dihydroimidazo[1,5,4-de][1,4]benzoxazin-2-yl]-3,6-dihydropyridine-1(2H)-carboxylate (3 mg, 0.006 mmol) was dissolved in methanol (0.5 mL) at room temperature, followed by addition of 4.0 M hydrogen chloride in dioxane (0.5 mL, 2 mmol) [Aldrich, cat. #345547]. The resulting mixture was stirred at room temperature for 10 min. The solvents were removed under a flow of nitrogen gas. Purification by preparative LCMS (XBridge C18 column, eluting with a gradient of acetonitrile/water containing 0.1% ammonium hydroxide, at flow rate of 60 mL/min) afforded the title compound (1.8 mg, 70%). LCMS for $C_{24}H_{26}O_2N_5$ (M+H)+: calculated m/z=416.2, found 416.2.

Examples 104-108

The experimental procedures used to prepare the compounds of Examples 104 to 108 in Table 4 were analogous to those used for the synthesis of the Example compound 103.

TABLE 4

| Example No. | Name | R |
|---|---|---|
| 104 | (4S)-7-(3,5-dimethylisoxazol-4-yl)-4-pyridin-2-yl-2-(1,2,3,6-tetrahydropyridin-4-yl)-4,5-dihydroimidazo[1,5,4-de][1,4]benzoxazine | |
| 105 | (4S)-2-(2,5-dihydro-1H-pyrrol-3-yl)-7-(3,5-dimethylisoxazol-4-yl)-4-pyridin-2-yl-4,5-dihydroimidazo[1,5,4-de][1,4]benzoxazine | |
| 106A | (4S)-7-(3,5-dimethylisoxazol-4-yl)-4-pyridin-2-yl-2-pyrrolidin-3-yl-4,5-dihydroimidazo[1,5,4-de][1,4]benzoxazine (diastereomer 1) | |
| 106B | (4S)-7-(3,5-dimethylisoxazol-4-yl)-4-pyridin-2-yl-2-pyrrolidin-3-yl-4,5-dihydroimidazo[1,5,4-de][1,4]benzoxazine (diastereomer 2) | |
| 107 | (4S)-7-(3,5-dimethylisoxazol-4-yl)-4-pyridin-2-yl-2-(1,2,5,6-tetrahydropyridin-3-yl)-4,5-dihydroimidazo[1,5,4-de][1,4]benzoxazine | |
| 108 | (4S)-7-(3,5-dimethylisoxazol-4-yl)-2-piperidin-3-yl-4-pyridin-2-yl-4,5-dihydroimidazo[1,5,4-de][1,4]benzoxazine (mixture of diastereomers) | |

Example 109

(4S)-2-(1-Acetylpiperidin-4-yl)-7-(3,5-dimethylisoxazol-4-yl)-4-pyridin-2-yl-4,5-dihydroimidazo[1,5,4-de][1,4]benzoxazine

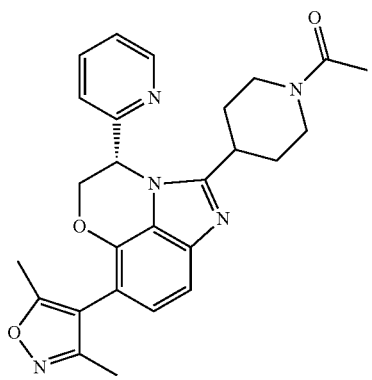 [SMILES: CC(=O)N1CCC(c2nc3ccc(-c4c(C)noc4C)c4c3n2[C@@H](c2ccccn2)CO4)CC1]

To the solution of tert-butyl 4-[(4S)-7-(3,5-dimethylisoxazol-4-yl)-4-pyridin-2-yl-4,5-dihydroimidazo[1,5,4-de][1,4]benzoxazin-2-yl]piperidine-1-carboxylate (8.8 mg, 0.017 mmol) in methanol (1 mL) was added 4.0 M hydrogen chloride in dioxane (1 ml) at room temperature. The resulting mixture was stirred at room temperature for 10 min. The solvents were then evaporated under a steam of nitrogen. Triethylamine (0.23 mL, 1.7 mmol) was added to the resulting residue, followed by acetyl chloride (0.029 mL, 0.41 mmol). The mixture was then stirred under a stream of nitrogen for 5 min at room temperature, followed by removal of solvents and residual reagents. Purification by preparative LCMS (XBridge C18 column, eluting with a gradient of acetonitrile/water containing 0.1% ammonium hydroxide, at flow rate of 60 mL/min) afforded the title compound (6.3 mg, 81%). LCMS for $C_{26}H_{28}O_3N_5$ (M+H)+: calculated m/z=458.2, found 458.2.

Examples 110-121

The experimental procedures used to prepare the compounds of Examples 110 to 121 in Table 5 were analogous to those used for the synthesis of the Example 109.

TABLE 5

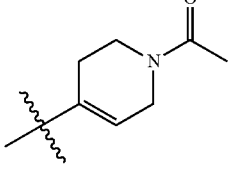

| Example No. | Name | R | Reaction Temperature |
|---|---|---|---|
| 110 | (4S)-2-(1-acetyl-1,2,3,6-tetrahydropyridin-4-yl)-7-(3,5-dimethylisoxazol-4-yl)-4-pyridin-2-yl-4,5-dihydroimidazo[1,5,4-de][1,4]benzoxazine | 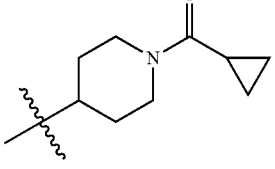 | 23° C. |
| 111 | (4S)-2-[1-(cyclopropylcarbonyl)piperidin-4-yl]-7-(3,5-dimethylisoxazol-4-yl)-4-pyridin-2-yl-4,5-dihydroimidazo[1,5,4-de][1,4]benzoxazine | | 23° C. |
| 112 | (4S)-7-(3,5-dimethylisoxazol-4-yl)-2-[1-(methylsulfonyl)piperidin-4-yl]-4-pyridin-2-yl-4,5-dihydroimidazo[1,5,4-de][1,4]benzoxazine | 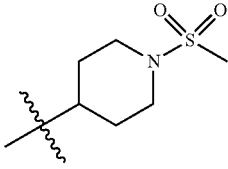 [SMILES: *C1CCN(S(C)(=O)=O)CC1] | 0° C. |

TABLE 5-continued

| Example No. | Name | R | Reaction Temperature |
|---|---|---|---|
| 113A | (4S)-2-(1-acetylpyrrolidin-3-yl)-7-(3,5-dimethylisoxazol-4-yl)-4-pyridin-2-yl-4,5-dihydroimidazo[1,5,4-de][1,4]benzoxazine (diastereomer 1) | | 23° C. |
| 113B | (4S)-2-(1-acetylpyrrolidin-3-yl)-7-(3,5-dimethylisoxazol-4-yl)-4-pyridin-2-yl-4,5-dihydroimidazo[1,5,4-de][1,4]benzoxazine (diastereomer 2) | | 23° C. |
| 114A | (4S)-2-[1-(cyclopropylcarbonyl)pyrrolidin-3-yl]-7-(3,5-dimethylisoxazol-4-yl)-4-pyridin-2-yl-4,5-dihydroimidazo[1,5,4-de][1,4]benzoxazine (diastereomer 1) | | 23° C. |
| 114B | (4S)-2-[1-(cyclopropylcarbonyl)pyrrolidin-3-yl]-7-(3,5-dimethylisoxazol-4-yl)-4-pyridin-2-yl-4,5-dihydroimidazo[1,5,4-de][1,4]benzoxazine (diastereomer 2) | | 23° C. |
| 115 | (4S)-7-(3,5-dimethylisoxazol-4-yl)-2-[1-(methylsulfonyl)pyrrolidin-3-yl]-4-pyridin-2-yl-4,5-dihydroimidazo[1,5,4-de][1,4]benzoxazine (mixture of diastereomers) | | 0° C. |
| 116 | (4S)-2-(1-acetyl-1,2,5,6-tetrahydropyridin-3-yl)-7-(3,5-dimethylisoxazol-4-yl)-4-pyridin-2-yl-4,5-dihydroimidazo[1,5,4-de][1,4]benzoxazine | | 23° C. |
| 117 | (4S)-2-(1-acetylpiperidin-3-yl)-7-(3,5-dimethylisoxazol-4-yl)-4-pyridin-2-yl-4,5-dihydroimidazo[1,5,4-de[1,4]benzoxazine (mixture of diastereomers) | | 23° C. |
| 118 | (4S)-2-[1-(cyclopropylcarbonyl)piperidin-3-yl]-7-(3,5-dimethylisoxazol-4-yl)-4-pyridin-2-yl-4,5-dihydroimidazo[1,5,4-de][1,4]benzoxazine (mixture of diastereomers) | | 23° C. |

TABLE 5-continued

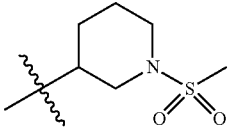 [SMILES: *C1CCCN(S(C)(=O)=O)C1]

| Example No. | Name | R | Reaction Temperature |
|---|---|---|---|
| 119 | (4S)-7-(3,5-dimethylisoxazol-4-yl)-2-[1-(methylsulfonyl)piperidin-3-yl]-4-pyridin-2-yl-4,5-dihydroimidazo[1,5,4-de][1,4]benzoxazine (mixture of diastereomers) | 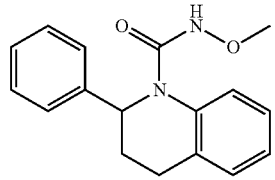 | 0° C. |

Example 120

7-(3,5-Dimethylisoxazol-4-yl)-4-phenyl-5,6-dihydro-4H-imidazo[4,5,1-ij]quinolin-2(1H)-one

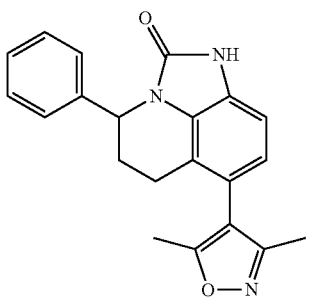 [SMILES: Cc1noc(C)c1-c1ccc2[nH]c(=O)n3c2c1CCC3c1ccccc1]

Step 1. 2-Phenyl-1,2,3,4-tetrahydroquinoline

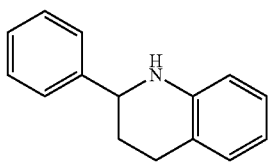 [SMILES: c1ccc(C2CCc3ccccc3N2)cc1]

A solution of 2-phenylquinoline, (0.248 g, 1.21 mmol) [Aldrich, cat. #299650] in acetic acid (6.0 mL) was treated with borane-pyridine complex (0.605 mL, 5.99 mmol) and stirred at room temperature for 18 h. The reaction mixture was diluted with ethyl acetate (50 mL) and washed with 3 M sodium hydroxide solution (70 mL), water (20 mL), and brine (20 mL). The organic layer was dried over sodium sulfate, filtered, and concentrated to give a crude oil. Purification by flash column chromatography (100% hexanes to 25% ethyl acetate/hexanes) gave the desired product (0.247 g, 98%) as a racemic mixture. LCMS calculated for $C_{15}H_{16}N$ (M+H)$^+$: m/z=210.1; found: 210.1.

Step 2.
N-Methoxy-2-phenyl-3,4-dihydroquinoline-1 (2H)-carboxamide

A solution of 2-phenyl-1,2,3,4-tetrahydroquinoline (2.13 g, 10.2 mmol) and triethylamine (4.26 mL, 30.5 mmol) in tetrahydrofuran (30.0 mL) was added to a solution of triphosgene (3.20 g, 10.8 mmol) in tetrahydrofuran (38.0 mL) at 0° C. The reaction mixture was stirred at 0° C. for 1 h, treated with methoxylamine hydrochloride (1.70 g, 20.3 mmol) and triethylamine (4.26 mL, 30.5 mmol), and stirred at room temperature for an additional 19 h. The reaction mixture was diluted with water (200 mL) and extracted with ethyl acetate (2×100 mL). The combined organic extracts were washed with brine, dried over sodium sulfate, filtered, and concentrated to give a crude oil. Purification by flash column chromatography (100% hexanes to 70% ethyl acetate/hexanes, the ethyl acetate containing 5% methanol) gave the desired product (2.25 g, 78%) as a racemic mixture. LCMS calculated for $C_{17}H_{19}N_2O_2$ (M+H)$^+$: m/z=283.1; found: 283.1.

Step 3. 1-Methoxy-4-phenyl-5,6-dihydro-4H-imidazo[4,5,1-ij]quinolin-2(1H)-one

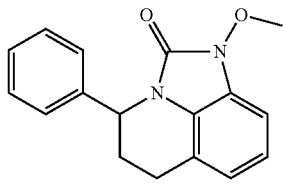 [SMILES: COn1c(=O)n2c3c(cccc31)CCC2c1ccccc1]

A solution of N-methoxy-2-phenyl-3,4-dihydroquinoline-1(2H)-carboxamide (0.869 g, 3.08 mmol) in chloroform (23.2 mL) at 0° C. was with treated with [I,I-bis(trifluoroacetoxy)iodo]benzene (1.59 g, 3.69 mmol) in four portions over 20 min. The resulting mixture was stirred at 0° C. for 30 min and at room temperature for 30 min. The reaction mixture was then diluted with saturated aqueous sodium bicarbonate solution (40 mL) and extracted with dichloromethane (50 mL). The organic layer was washed with brine, dried over sodium sulfate, filtered, and concentrated to give a crude oil. Purification by flash column chromatography (100% hexanes to 70% ethyl acetate/hexanes, the ethyl acetate containing 5% methanol) gave the desired product (0.576 g, 66%) as a racemic mixture. LCMS calculated for $C_{17}H_{17}N_2O_2$ (M+H)$^+$: m/z=281.1; found: 281.1.

Step 4. 4-Phenyl-5,6-dihydro-4H-imidazo[4,5,1-ij]quinolin-2(1H)-one

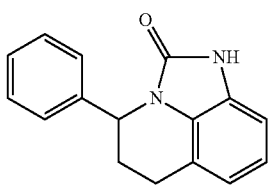 [SMILES: O=c1[nH]c2cccc3c2n1C(c1ccccc1)CC3]

A suspension of 1-methoxy-4-phenyl-5,6-dihydro-4H-imidazo[4,5,1-ij]quinolin-2(1H)-one (0.575 g, 2.05 mmol) in ethanol (35.9 mL, 615 mmol) was heated to dissolve residual solids and the resulting solution was cooled to room temperature. The solution was treated with acetic acid (0.233 mL, 4.10 mmol), degassed with nitrogen, treated with palladium catalyst (0.575 g, 100 wt %) (10% Pd on carbon, Degussa type) and hydrogenated for 17 h. The reaction mixture was filtered and the catalyst was washed with ethanol and methanol. The filtrate was then concentrated to give the desired product (0.436 g, 85%) as a racemic mixture that was used without further purification. LCMS calculated for $C_{16}H_{15}N_2O$ (M+H)$^+$: m/z=251.1; found: 251.1.

Step 5. 7-Bromo-4-phenyl-5,6-dihydro-4H-imidazo[4,5,1-ij]quinolin-2(1H)-one

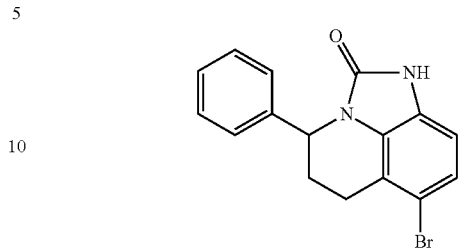

A suspension of 4-phenyl-5,6-dihydro-4H-imidazo[4,5,1-ij]quinolin-2(1H)-one (0.200 g, 0.799 mmol) in acetonitrile (10.0 mL) and acetic acid (2.42 mL) was heated to dissolve residual solids and the resultant solution was cooled to 0° C. The resulting solution was treated with a solution of N-bromosuccinimide (0.144 g, 0.807 mmol) in acetonitrile (3.0 mL), added dropwise, at 0° C. and subsequently stirred at 0° C. for 1 h. The reaction mixture was concentrated to a residue which was dissolved in chloroform (50 mL) and washed with saturated aqueous sodium bicarbonate (40 mL) and brine (20 mL). The organic layer was dried over sodium sulfate, filtered, and concentrated to give a crude solid. Purification by flash column chromatography (100% hexanes to 50% ethyl acetate/hexanes, the ethyl acetate containing 5% methanol) gave the desired product (0.177 g, 67%) as a racemic mixture along with an additional other brominated isomer, 8-bromo-4-phenyl-5,6-dihydro-4H-imidazo[4,5,1-ij]quinolin-2(1H)-one (which was not be separated) in a 4.4:1 ratio. LCMS calculated for $C_{16}H_{14}BrN_2O$ (M+H)$^+$: m/z=329.0, 331.0; found: 329.0, 331.0.

Step 6. 7-(3,5-Dimethylisoxazol-4-yl)-4-phenyl-5,6-dihydro-4H-imidazo[4,5,1-ij]quinolin-2(1H)-one A mixture of 7-bromo-4-phenyl-5,6-dihydro-4H-imidazo[4,5,1-ij]quinolin-2(1H)-one (0.050 g, 0.15 mmol) (4.4:1 mixture of isomers with 8-bromo-4-phenyl-5,6-dihydro-4H-imidazo[4,5,1-ij]quinolin-2(1H)-one as the minor isomer), (3,5-dimethylisoxazol-4-yl)boronic acid (10.7 mg, 0.0759 mmol), and cesium carbonate (99.0 mg, 0.304 mmol) in 1,2-dimethoxyethane (1.21 mL) and water (0.303 mL) was degassed with nitrogen for 5 min. The reaction mixture was treated with PEPPSI-IPr (5.2 mg, 0.0076 mmol) [Aldrich, cat. #669032], degassed with nitrogen for 5 min, and heated at 90° C. for 1 h. The reaction mixture was then diluted with ethyl acetate (25 mL) and water (20 mL). The organic layer was separated, washed with brine, dried over sodium sulfate, filtered, and concentrated to give a crude residue. Purification via preparative LCMS (XBridge C18 column, eluting with a gradient of acetonitrile/water containing 0.1% trifluoroacetic acid, at flow rate of 60 mL/min) gave the desired product (14.7 mg, 28%) as a racemic mixture. $^1$H NMR (500 MHz, CDCl$_3$) δ 10.00 (s, 1H), 7.34-7.20 (m, 3H), 7.08-6.95 (m, 3H), 6.88-6.76 (m, 1H), 5.54 (s, 1H), 2.45-1.96 (m, 10H); LCMS calculated for $C_{21}H_{20}N_3O_2$ (M+H)$^+$: m/z=346.2; found: 346.1.

Example 121

7-(3,5-Dimethylisoxazol-4-yl)-1-methyl-4-phenyl-5,6-dihydro-4H-imidazo[4,5,1-ij]quinolin-2(1H)-one

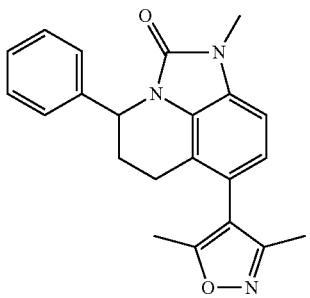 [SMILES: Cc1noc(C)c1-c1ccc2c3c1CCC(c1ccccc1)n3c(=O)n2C]

A solution of 7-(3,5-dimethylisoxazol-4-yl)-4-phenyl-5,6-dihydro-4H-imidazo[4,5,1-ij]quinolin-2(1H)-one (10.7 g, 0.031 mmol) in N,N-dimethylformamide (0.50 mL) was treated with cesium carbonate (20.2 g, 0.062 mmol) followed by methyl iodide (2.9 μL, 46.5 μmol) and stirred at room temperature for 16 h. Purification via preparative LCMS (XBridge C18 column, eluting with a gradient of acetonitrile/water containing 0.1% trifluoroacetic acid, at flow rate of 60 mL/min) gave the desired product (8.2 mg, 74%) as a racemic mixture. $^1$H NMR (400 MHz, CDCl$_3$) δ 7.35-7.20 (m, 3H), 7.03 (d, J=6.9 Hz, 2H), 6.99-6.93 (m, 1H), 6.93-6.84 (m, 1H), 5.53 (s, 1H), 3.49 (s, 3H), 2.48-2.11 (m, 7H), 2.09-1.84 (m, 3H); LCMS calculated for C$_{22}$H$_{22}$N$_3$O$_2$ (M+H)$^+$: m/z=360.2; found: 360.1.

Example 122

7-(3,5-Dimethylisoxazol-4-yl)-1-methoxy-4-pyridin-2-yl-5,6-dihydro-4H-imidazo[4,5,1-ij]quinolin-2(1H)-one trifluoroacetate

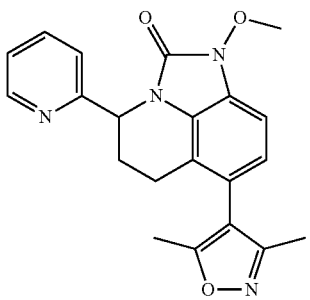 [SMILES: COn1c(=O)n2c3c(c(-c4c(C)noc4C)ccc31)CCC2c1ccccn1]

Step 1. 2-Pyridin-2-ylquinoline

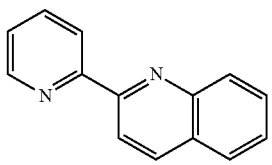 [SMILES: c1ccc(-c2ccc3ccccc3n2)nc1]

A solution of 2-bromoquinoline (1.00 g, 4.81 mmol) [Aldrich, cat. #716278] in N,N-dimethylformamide (10.0 mL) (degassed with nitrogen) was treated with 2-(tributylstannyl)pyridine (1.83 mL, 4.81 mmol) and bis(triphenylphosphine)palladium(II) chloride (0.337 g, 0.481 mmol). The reaction mixture was degassed with nitrogen for 5 min and heated at 110° C. for 17 h. The reaction mixture was then diluted with water (50 mL) and ether (50 mL) and filtered over Celite. The solids were washed with additional ether (150 mL). The filtrate was washed with water (150 mL) and brine, dried over sodium sulfate, filtered, and concentrated to give a crude residue. Purification by flash column chromatography (100% hexanes to 70% ethyl acetate/hexanes, the ethyl acetate containing 5% methanol) gave the desired product (0.771 g, 78%). LCMS calculated for C$_{14}$H$_{11}$N$_2$(M+H)$^+$: m/z=207.1; found: 207.1.

Step 2. 2-Pyridin-2-yl-1,2,3,4-tetrahydroquinoline

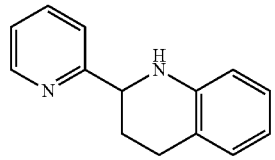 [SMILES: c1ccc(C2CCc3ccccc3N2)nc1]

A suspension of 2-pyridin-2-ylquinoline (0.767 g, 3.72 mmol), 1,4-dihydro-3,5-dicarbethoxy-2,6-dimethylpyridine (2.17 g, 8.55 mmol), and diphenyl hydrogen phosphate (0.0093 g, 0.037 mmol) in benzene (18.6 mL) was heated at 60° C. for 10 h. The reaction mixture was treated with 2-phenylquinoline (0.305 g, 1.49 mmol) and heated at 60° C. for 3 h. The reaction mixture was then concentrated to a crude solid. Purification by flash column chromatography (100% hexanes to 50% ethyl acetate/hexanes [the ethyl acetate contained 5% methanol]) gave the desired product (0.735 g, 94%) as a racemic mixture. LCMS calculated for C$_{14}$H$_{15}$N$_2$(M+H)$^+$: m/z=211.1; found: 211.1.

Step 3. N-Methoxy-2-pyridin-2-yl-3,4-dihydroquinoline-1(2H)-carboxamide

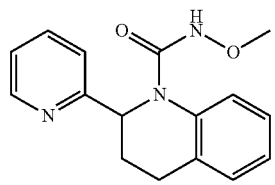 [SMILES: CONC(=O)N1c2ccccc2CCC1c1ccccn1]

A solution of 2-pyridin-2-yl-1,2,3,4-tetrahydroquinoline (0.723 g, 3.44 mmol) in methylene chloride (10.3 mL) was treated with 4-nitrophenyl methoxycarbamate (0.948 g, 4.47 mmol) (Org. Process Res. Dev. 2012, 16, 109-116) followed by the dropwise addition of N,N-diisopropylethylamine (1.20 mL, 6.88 mmol), and the resulting mixture was stirred at room temperature for 1.5 h. The reaction mixture was then poured over water (25 mL) and saturated sodium bicarbonate (25 mL) and extracted with dichloromethane (2×50 mL). The combined organic layers were dried over sodium sulfate, filtered, and concentrated to give a crude oily solid. Purification by flash column chromatography (100% hexanes to 20% ethyl acetate/hexanes [the ethyl acetate contained 5% methanol]) gave the desired product (0.923 g, 95%) as a racemic mixture. LCMS calculated for $C_{16}H_{18}N_3O_2$ (M+H)$^+$: m/z=284.1; found: 284.0.

Step 4. 1-Methoxy-4-pyridin-2-yl-5,6-dihydro-4H-imidazo[4,5,1-ij]quinolin-2(1H)-one

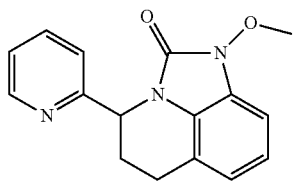 [SMILES: COn1c(=O)n2c3c(cccc31)CCC2c1ccccn1]

This compound was synthesized according to the procedure of Example 120, step 3, using N-methoxy-2-pyridin-2-yl-3,4-dihydroquinoline-1(2H)-carboxamide as the starting material. LCMS calculated for $C_{16}H_{16}N_3O_2$ (M+H)$^+$: m/z=282.1; found: 282.0.

Step 5. 7-Bromo-1-methoxy-4-pyridin-2-yl-5,6-dihydro-4H-imidazo[4,5,1-ij]quinolin-2(1H)-one

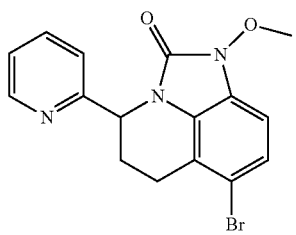 [SMILES: COn1c(=O)n2c3c(c(Br)ccc31)CCC2c1ccccn1]

This compound was synthesized according to the procedure of Example 120, step 5, using 1-methoxy-4-pyridin-2-yl-5,6-dihydro-4H-imidazo[4,5,1-ij]quinolin-2(1H)-one as the starting material. LCMS calculated for $C_{16}H_{15}BrN_3O_2$ (M+H)$^+$: m/z=360.0, 362.0; found: 359.9, 361.9.

Step 6. 7-(3,5-Dimethylisoxazol-4-yl)-1-methoxy-4-pyridin-2-yl-5,6-dihydro-4H-imidazo[4,5,1-ij]quinolin-2(1H)-one trifluoroacetate A suspension of 7-bromo-1-methoxy-4-pyridin-2-yl-5,6-dihydro-4H-imidazo[4,5,1-ij]quinolin-2(1H)-one (0.132 g, 0.367 mmol) (as a mixture of brominated isomers), and cesium fluoride (0.195 g, 1.29 mmol) in tert-butyl alcohol (1.22 mL) and water (0.612 mL) degassed with nitrogen for 10 min. The reaction mixture was treated with (3,5-dimethylisoxazol-4-yl)boronic acid (0.0518 g, 0.367 mmol) followed by addition of 4-(di-tert-butylphosphino)-N,N-dimethylaniline-dichloropalladium (2:1) (5.2 mg, 7.35 µmol). The mixture was degassed with nitrogen for an additional 5 min, and heated at 80° C. for 1.5 h, at which time the reaction mixture was treated with cesium fluoride (0.0558 g, 0.367 mmol), (3,5-dimethylisoxazol-4-yl)boronic acid (0.104 g, 0.735 mmol), and 4-(di-tert-butylphosphino)-N,N-dimethylaniline-dichloropalladium (2:1) (5.20 mg, 0.00735 mmol), degassed with nitrogen, and stirred at 100° C. for 14 h. The reaction mixture was diluted with ethyl acetate (40 mL) and water (20 mL). The organic layer was separated, washed with brine, dried over sodium sulfate, filtered, and concentrated to give a crude residue. Purification by flash column chromatography (100% hexanes to 20% ethyl acetate/hexanes, the ethyl acetate containing 5% methanol) yielded a crude product. Further purification via preparative LCMS (XBridge C18 column, eluting with a gradient of acetonitrile/water containing 0.1% trifluoroacetic acid, at flow rate of 60 mL/min) gave the desired product (95 mg, 53%) as a racemic mixture. $^1$H NMR (500 MHz, DMSO-d$_6$) δ 8.52 (d, J=4.3 Hz, 1H), 7.84 (dd, J=7.5 Hz, 1H), 7.42-7.31 (m, 1H), 7.31-7.23 (m, 1H), 7.18 (d, J=7.9 Hz, 1H), 7.04-6.90 (m, 1H), 5.44 (s, 1H), 4.02 (s, 3H), 2.54-2.46 (m, 3H), 2.45-2.31 (m, 2H), 2.29-2.16 (m, 2H), 2.08 (d, J=25.9 Hz, 3H); LCMS calculated for $C_{21}H_{21}N_4O_3$ (M+H)$^+$: m/z=377.2; found: 377.0.

Example 123

7-(3,5-Dimethylisoxazol-4-yl)-4-pyridin-2-yl-5,6-dihydro-4H-imidazo[4,5,1-ij]quinolin-2(1H)-one trifluoroacetate

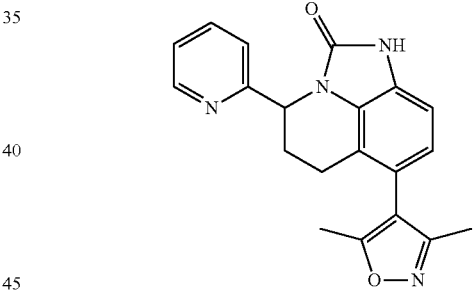

Step 1. 4-Pyridin-2-yl-5,6-dihydro-4H-imidazo[4,5,1-ij]quinolin-2(1H)-one

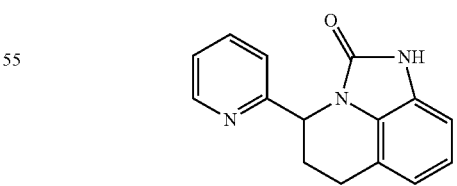

This compound was synthesized according to the procedure of Example 120, step 4, using 1-methoxy-4-pyridin-2-yl-5,6-dihydro-4H-imidazo[4,5,1-ij]quinolin-2(1H)-one as the starting material. LCMS calculated for $C_{15}H_{14}N_3O$ (M+H)$^+$: m/z=252.1; found: 252.1.

Step 2. 7-Bromo-4-pyridin-2-yl-5,6-dihydro-4H-imidazo[4,5,1-ij]quinolin-2(1H)-one

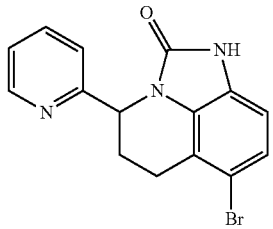 [SMILES: O=c1[nH]c2ccc(Br)c3c2n1C(c1ccccn1)CC3]

This compound was synthesized according to the procedure of example 120, step 5, using 4-pyridin-2-yl-5,6-dihydro-4H-imidazo[4,5,1-ij]quinolin-2(1H)-one as the starting material. LCMS calculated for $C_{15}H_{13}BrN_3O$ (M+H)$^+$: m/z=330.0, 332.0; found: 329.9, 331.9.

Step 3. 7-(3,5-Dimethylisoxazol-4-yl)-4-pyridin-2-yl-5,6-dihydro-4H-imidazo[4,5,1-ij]quinolin-2(1H)-one trifluoroacetate This compound was synthesized according to the procedure of Example 120, step 6, using 7-bromo-4-pyridin-2-yl-5,6-dihydro-4H-imidazo[4,5,1-ij]quinolin-2(1H)-one as the starting material. $^1$H NMR (500 MHz, DMSO-d$_6$) δ 10.89 (s, 1H), 8.55 (d, J=4.3 Hz, 1H), 7.85 (dd, J=7.3 Hz, 1H), 7.49-7.31 (m, 1H), 7.25-7.10 (m, 1H), 6.96 (d, J=7.9 Hz, 1H), 6.90-6.72 (m, 1H), 5.41 (s, 1H), 2.55-2.28 (m, 5H), 2.27-1.89 (m, 5H); LCMS calculated for $C_{20}H_{19}N_4O_2$ (M+H)$^+$: m/z=347.1; found: 347.1.

Example 124

7-[5-(Hydroxymethyl)-3-methylisoxazol-4-yl]-4-pyridin-2-yl-4,5-dihydroimidazo[1,5,4-de][1,4]benzoxazin-2(1H)-one

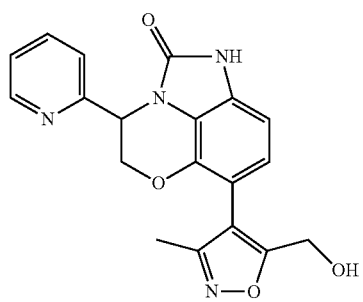 [SMILES: Cc1noc(CO)c1-c1ccc2[nH]c(=O)n3c2c1OCC3c1ccccn1]

Step 1. Prop-2-yn-1-yl benzoate

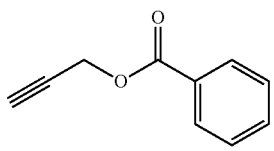

A solution of 2-propyn-1-ol (10.0 mL, 172 mmol) in methylene chloride (496 mL) and triethylamine (47.9 mL, 344 mmol) at 0° C. was treated with benzoyl chloride (20.0 mL, 172 mmol), added over a period of 5 min. The reaction mixture was stirred at 0° C. for 30 min, followed by additional stirring at room temperature for 2 h. The reaction mixture was quenched with water (300 mL). The aqueous layer was separated and extracted with dichloromethane (2×200 mL). The combined organic layers were washed with water (2×200 mL) and brine (100 mL), dried over magnesium sulfate, filtered, and concentrated to give the desired product (27 g, 98%) which was used without further purification. LCMS calculated for $C_{10}H_9O_2$ (M+H)$^+$: m/z=161.1; found: 161.0.

Step 2. (3-Methylisoxazol-5-yl)methyl benzoate

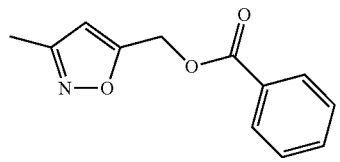 [SMILES: Cc1cc(COC(=O)c2ccccc2)on1]

A solution of prop-2-yn-1-yl benzoate (26.0 g, 162 mmol) in chloroform (598 mL) was treated with triethylamine (11.3 mL, 81.2 mmol) and acetaldoxime (14.4 g, 244 mmol). The reaction mixture was cooled to 0° C., treated with sodium hypochlorite (551 mL, 487 mmol) (commercial grade ~5% aqueous), and stirred overnight at room temperature. The layers were separated and the aqueous layer was extracted with dichloromethane (2×200 mL). The combined organic layers were washed with water and brine, dried over magnesium sulfate, filtered, and concentrated to give the crude product. Purification by flash column chromatography (100% hexanes to 30% ethyl acetate/hexanes) gave the desired product (20.1 g, 57%). LCMS calculated for $C_{12}H_{12}NO_3$ (M+H)$^+$: m/z=218.1; found: 218.1.

Step 3. (4-Bromo-3-methylisoxazol-5-yl)methyl benzoate

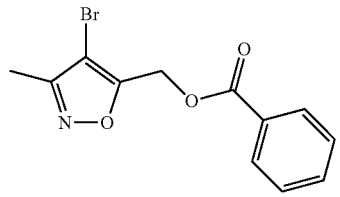 [SMILES: Cc1noc(COC(=O)c2ccccc2)c1Br]

A solution of (3-methylisoxazol-5-yl)methyl benzoate (20.1 g, 92.4 mmol) in acetic acid (77.3 mL) was treated with N-bromosuccinimide (19.7 g, 111 mmol) and heated in a sealed tube at 90° C. for 4 h. The reaction mixture was diluted with brine and extracted with ethyl acetate. The organic layer was separated, washed with brine, dried over magnesium sulfate, filtered, and concentrated to give the crude product. Purification by flash column chromatography (100% hexanes to 20% ethyl acetate/hexanes) gave the desired product (21.6 g, 79%). LCMS calculated for $C_{12}H_{11}BrNO_3$ (M+H)$^+$: m/z=296.0, 298.0; found: 296.0, 298.0.

Step 4. {5-[(Benzoyloxy)methyl]-3-methylisoxazol-4-yl}boronic acid

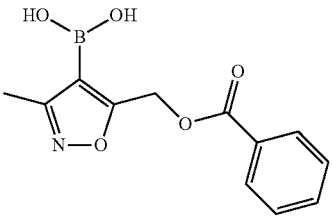 [SMILES: Cc1noc(COC(=O)c2ccccc2)c1B(O)O]

A flask containing bis(acetonitrile)palladium(II) chloride (0.40 g, 1.6 mmol) and 2'-(dicyclohexylphosphino)-N,N-dimethylbiphenyl-2-amine (2.10 g, 5.34 mmol) was evacuated and back-filled with nitrogen (repeated for three cycles). Addition of (4-bromo-3-methylisoxazol-5-yl) methyl benzoate (14.9 g, 50.4 mmol) (as a solution in 1,4-dioxane (32 mL)), was followed by addition of 1.0 M 4,4,5,5-tetramethyl-1,3,2-dioxaborolane in tetrahydrofuran (85.7 mL), and triethylamine (21.1 mL, 151 mmol). The resulting mixture was bubbled with nitrogen for 5 min and then heated at 100° C. for 1 h. The reaction mixture was then diluted with ethyl acetate and water. The organic layer was separated, washed with brine, dried over magnesium sulfate, filtered, and concentrated to give crude boronate ester. Purification by flash column chromatography (100% hexanes to 40% ethyl acetate/hexanes) gave the intermediate boronate ester. The purified boronate ester was dissolved in tetrahydrofuran (110 mL), diluted with water (50 mL), and treated with sodium periodate (20.3 g, 94.7 mmol). The reaction mixture was stirred vigorously for 15 min, treated with 1.0 M hydrogen chloride in water (64.0 mL), and stirred at room temperature for 2 h. The reaction mixture was then extracted with ethyl acetate (3×60 mL), washed with water and brine, dried over magnesium sulfate, filtered, and concentrated to give the crude boronic acid. Recrystallization from ethyl acetate/hexanes gave the desired product (2.2 g). The filtrate was concentrated and the resulting residue was washed with hexanes to yield additional product (4.85 g) (7.05 g total, 54% combined yield). LCMS calculated for $C_{12}H_{13}BNO_5$ $(M+H)^+$: m/z=262.1; found: 262.1.

Step 5. [3-Methyl-4-(2-oxo-4-pyridin-2-yl-1,2,4,5-tetrahydroimidazo[1,5,4-de][1,4]benzoxazin-7-yl)isoxazol-5-yl]methyl benzoate

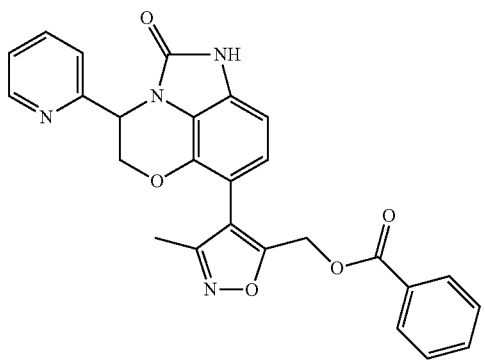 [SMILES: Cc1noc(COC(=O)c2ccccc2)c1-c1ccc2[nH]c(=O)n3c2c1OCC3c1ccccn1]

A solution of 7-bromo-4-pyridin-2-yl-4,5-dihydroimidazo[1,5,4-de][1,4]benzoxazin-2(1H)-one (687 mg, 2.07 mmol) and {5-[(benzoyloxy)methyl]-3-methylisoxazol-4-yl}boronic acid (1.08 g, 4.14 mmol) in 1,4-dioxane (15.7 mL) and water (4 mL) was degassed with nitrogen. The reaction mixture was treated with [1,1'-bis(diphenylphosphino)ferrocene]dichloropalladium(II), complex with dichloromethane (1:1) (253 mg, 0.310 mmol), degassed with nitrogen, and heated in a sealed tube at 80° C. for 30 min, at which time the reaction mixture was treated with {5-[(benzoyloxy)methyl]-3-methylisoxazol-4-yl}boronic acid (1.08 g, 4.14 mmol) and [1,1'-bis(diphenylphosphino)ferrocene]-dichloropalladium(II), complex with dichloromethane (1:1) (10 mg, 12.2 μmol), degassed with nitrogen and heated at 80° C. for a further 30 min. The reaction mixture was then diluted with ethyl acetate and water. The organic layer was separated and washed with brine, dried over magnesium sulfate, filtered, and concentrated to give the crude product. Purification by flash column chromatography (30% ethyl acetate/hexanes to 100% ethyl acetate [the ethyl acetate contained 5% methanol]) gave the desired product (0.589 g, 58%) as a racemic mixture. LCMS calculated for $C_{26}H_{21}N_4O_5$ $(M+H)^+$: m/z=469.1; found: 469.1.

Step 6. 7-[5-(Hydroxymethyl)-3-methylisoxazol-4-yl]-4-pyridin-2-yl-4,5-dihydroimidazo[1,5,4-de][1,4]benzoxazin-2 (1H)-one A solution of [3-methyl-4-(2-oxo-4-pyridin-2-yl-1,2,4,5-tetrahydroimidazo[1,5,4-de][1,4]benzoxazin-7-yl)isoxazol-5-yl]methyl benzoate (15.0 mg, 0.0320 mmol) in tetrahydrofuran (1.0 mL) and methanol (1.0 mL) was treated with 2.0 M lithium hydroxide in water (0.10 mL, 0.20 mmol) and stirred at room temperature for 20 min. The reaction mixture was quenched with 6 N hydrogen chloride in water (to pH ~2) and then concentrated. Purification by preparative LCMS (XBridge C18 column, eluting with a gradient of acetonitrile/water containing 0.1% ammonium hydroxide, at flow rate of 30 mL/min) gave the desired product (8 mg, 69%) as a racemic mixture. $^1$H NMR (300 MHz, DMSO-$d_6$) δ 8.51 (d, J=4.8 Hz, 1H), 7.77 (ddd, J=7.7, 7.7, 1.7 Hz, 1H), 7.31 (dd, J=7.4, 4.9 Hz, 1H), 7.09 (d, J=7.9 Hz, 1H), 6.85 (d, J=8.0 Hz, 1H), 6.75 (d, J=8.0 Hz, 1H), 5.51 (s, 1H), 4.77 (dd, J=11.4, 1.8 Hz, 1H), 4.42 (dd, J=11.4, 3.1 Hz, 1H), 4.36 (s, 2H), 3.15 (s, 1H), 2.06 (s, 3H); LCMS calculated for $C_{19}H_{17}N_4O_4$ $(M+H)^+$: m/z=365.1; found: 365.1.

Example 125

7-[5-(Fluoromethyl)-3-methylisoxazol-4-yl]-4-pyridin-2-yl-4,5-dihydroimidazo[1,5,4-de][1,4]benzoxazin-2(1H)-one trifluoroacetate

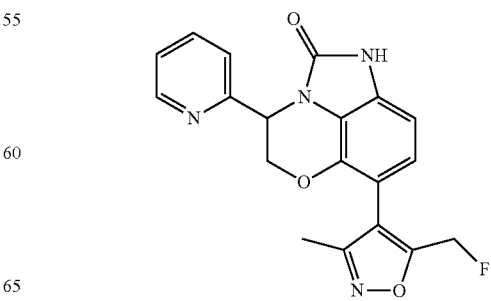

A solution of 7-[5-(hydroxymethyl)-3-methylisoxazol-4-yl]-4-pyridin-2-yl-4,5-dihydroimidazo[1,5,4-de][1,4]benzoxazin-2(1H)-one (15.0 mg, 0.0412 mmol) in methylene chloride (0.30 mL) was cooled to −78° C., treated with dimethylaminosulfur trifluoride (6.03 mg, 0.0453 mmol) and was allowed to warm to room temperature overnight. The reaction mixture was then concentrated to give a crude residue. Purification via preparative LCMS (XBridge C18 column, eluting with a gradient of acetonitrile/water containing 0.1% trifluoroacetic acid, at flow rate of 30 mL/min) gave the desired product (8 mg, 40%) as a racemic mixture. $^1$H NMR (300 MHz, CD$_3$OD) δ 8.59 (d, J=4.2 Hz, 1H), 7.89 (ddd, J=7.8, 7.8, 1.7 Hz, 1H), 7.43 (dd, J=7.5, 5.0 Hz, 1H), 7.20 (d, J=7.9 Hz, 1H), 6.97 (d, J=8.1 Hz, 1H), 6.90 (d, J=8.1 Hz, 1H), 5.60 (dd, J=2.7, 2.7 Hz, 1H), 5.37 (s, 1H), 5.21 (s, 1H), 4.82 (dd, J=11.5, 2.6 Hz, 1H), 4.52 (dd, J=11.5, 3.2 Hz, 1H), 2.19 (s, 3H); LCMS calculated for C$_{19}$H$_{16}$FN$_4$O$_3$(M+H)$^+$: m/z=367.1; found: 367.1.

Example 126

3-[7-(3,5-Dimethylisoxazol-4-yl)-2-oxo-1,2,4,5-tetrahydroimidazo[1,5,4-de][1,4]benzoxazin-4-yl]pyridine-2-carbonitrile

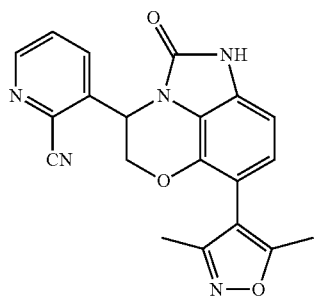 [SMILES: Cc1noc(C)c1-c1ccc2[nH]c(=O)n3c2c1OCC3c1cccnc1C#N]

Step 1. 2-Bromo-1-(2-bromopyridin-3-yl)ethanone

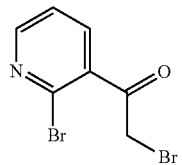 [SMILES: O=C(CBr)c1cccnc1Br]

A solution of 1-(2-bromopyridin-3-yl)ethanone (2.10 g, 10.5 mmol) in acetic acid (28.0 mL) was treated with bromine (595 µL, 11.5 mmol) and heated at 90° C. for 1 h. The reaction mixture was diluted with ethyl acetate and saturated aqueous sodium bicarbonate solution. The aqueous layer was separated and further extracted with ethyl acetate (2×80 mL). The combined organic layers were washed with brine, dried over magnesium sulfate, filtered, and concentrated to give the crude product. Purification by flash column chromatography (10% ethyl acetate/hexanes to 30% ethyl acetate/hexanes) gave the desired product (2.15 g, 73%). LCMS calculated for C$_7$H$_6$Br$_2$NO (M+H)$^+$: m/z=277.9, 279.9, 281.9; found: 277.7, 279.7, 281.8.

Step 2. 3-(2-Bromopyridin-3-yl)-5-nitro-3,4-dihydro-2H-1,4-benzoxazin-3-ol

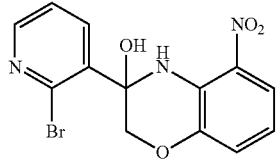 [SMILES: O=[N+]([O-])c1cccc2c1NC(O)(c1cccnc1Br)CO2]

A solution of 2-bromo-1-(2-bromopyridin-3-yl)ethanone (2.15 g, 7.71 mmol) in methylene chloride (77.1 mL) and water (19.3 mL) was treated with potassium carbonate (2.13 g, 15.4 mmol), tetra-N-butylammonium bromide (500 mg, 1.50 mmol), and 2-amino-3-nitrophenol (1.31 g, 8.48 mmol), and heated at 40° C. for 5 h. The reaction mixture was then diluted with brine. The aqueous layer was separated and extracted with dichloromethane (2×100 mL). The combined organic layers were washed with water and brine, dried over magnesium sulfate, filtered, and concentrated to give the crude product. Purification by flash column chromatography (100% hexanes to 35% ethyl acetate/hexanes) gave the desired product (2.45 g, 90%) as a racemic mixture. LCMS calculated for C$_{13}$H$_{11}$BrN$_3$O$_4$(M+H)$^+$: m/z=352.0, 354.0; found: 351.7, 353.8.

Step 3. 3-(2-Bromopyridin-3-yl)-2H-1,4-benzoxazin-5-amine

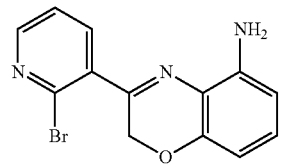 [SMILES: Nc1cccc2c1N=C(c1cccnc1Br)CO2]

A suspension of iron (1.71 g, 30.7 mmol) (<10 micron) in ethanol (33.5 mL) was treated with 1.0 M hydrogen chloride in water (3.1 mL, 3.1 mmol) and was stirred at 60° C. for 2 h. The mixture was then cooled to 55-60° C. and treated with 5.0 M ammonium chloride in water (5.3 mL, 26.4 mmol) followed by addition of 3-(2-bromopyridin-3-yl)-5-nitro-3,4-dihydro-2H-1,4-benzoxazin-3-ol (2.16 g, 6.13 mmol, washed with 5 mL ethanol). The resulting suspension was stirred at 60-65° C. for 2 h. The suspension was diluted with acetonitrile to about 100 mL and filtered over Celite. The solid was washed with additional acetonitrile and the filtrate was concentrated to a solid. This solid was dissolved in ethyl acetate which was then dried over magnesium sulfate, filtered, and concentrated to give the desired product (1.85 g, 99%), used without further purification. LCMS calculated for C$_{13}$H$_{11}$BrN$_3$O (M+H)$^+$: m/z=304.0, 306.0; found: 304.0, 306.0.

Step 4. 3-(2-Bromopyridin-3-yl)-3,4-dihydro-2H-1,4-benzoxazin-5-amine tris-trifluoroacetate

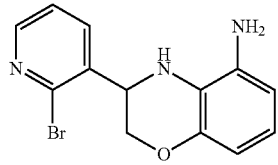 [SMILES: Nc1cccc2c1NC(c1cccnc1Br)CO2]

A suspension of 3-(2-bromopyridin-3-yl)-2H-1,4-benzoxazin-5-amine (1.85 g, 6.08 mmol) in ethanol (20.0 mL) and water (4.0 mL) was treated with sodium tetrahydroborate (460 mg, 12.2 mmol) and stirred at room temperature overnight, at which time the mixture was treated with additional sodium tetrahydroborate (200 mg, 5.3 mmol) and heated at 90° C. for 2 h. The reaction mixture was quenched with acetic acid and diluted with ethyl acetate. The organic layer was separated and washed with saturated aqueous sodium bicarbonate, water and brine, dried over magnesium sulfate, filtered, and concentrated to give the crude product. Purification via preparative LCMS (XBridge C18 column, eluting with a gradient of acetonitrile/water containing 0.1% trifluoroacetic acid, at flow rate of 60 mL/min) gave the desired product (1.69 g, 66%) as a racemic mixture. LCMS calculated for $C_{13}H_{13}BrN_3O$ (M+H)$^+$: m/z=306.0, 308.0; found: 305.9, 307.9.

Step 5. 4-(2-Bromopyridin-3-yl)-4,5-dihydroimidazo[1,5,4-de][1,4]benzoxazin-2(1H)-one

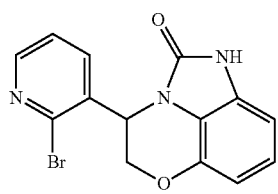 [SMILES: O=c1[nH]c2cccc3c2n1C(c1cccnc1Br)CO3]

A solution of 3-(2-bromopyridin-3-yl)-3,4-dihydro-2H-1,4-benzoxazin-5-amine tris-trifluoroacetate (1.69 g, 4.01 mmol) in ethyl acetate (17.8 mL) at 50° C. was treated with N,N-carbonyldiimidazole (0.78 g, 4.8 mmol) and stirred at 50° C. for 1 h. The reaction mixture was then cooled to 0° C. The resulting precipitate was collected via filtration and washed with ether. The filtrate was concentrated to give a crude solid. Purification by preparative LCMS (XBridge C18 column, eluting with a gradient of acetonitrile/water containing 0.1% ammonium hydroxide, at flow rate of 30 mL/min) gave the desired product that was combined with the precipitated material (0.970 g total, 73% combined yield) as a racemic mixture. LCMS calculated for $C_{14}H_{11}BrN_3O_2$(M+H)$^+$: m/z=332.0, 334.0; found: 331.8, 333.8.

Step 6. 3-(2-Oxo-1,2,4,5-tetrahydroimidazo[1,5,4-de][1,4]benzoxazin-4-yl)pyridine-2-carbonitrile

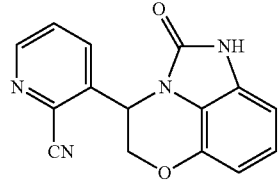 [SMILES: N#Cc1ncccc1C1COc2cccc3[nH]c(=O)n1c23]

A suspension of 4-(2-bromopyridin-3-yl)-4,5-dihydroimidazo[1,5,4-de][1,4]benzoxazin-2(1H)-one (964 mg, 2.90 mmol), zinc cyanide (1.00 g, 8.70 mmol) and tetrakis(triphenylphosphine)palladium(0) (335 mg, 0.290 mmol) in N,N-dimethylformamide (20.4 mL) was degassed and heated in a microwave at 160° C. for 20 min. The reaction mixture was diluted with ethyl acetate and washed with saturated aqueous sodium bicarbonate, water and brine, dried over magnesium sulfate, filtered, and concentrated to give the crude product. The crude product was suspended in hot ethyl acetate and diluted with hexanes to twice the volume, which resulted in the precipitation of a solid. The solid was collected by filtration and washed with ethyl acetate to give the desired product (656 mg). The filtrate was concentrated to a residue which was purified by preparative LCMS (XBridge C18 column, eluting with a gradient of acetonitrile/water containing 0.1% ammonium hydroxide, at flow rate of 60 mL/min) to give the desired product that was combined with the precipitated material (0.709 g total, 88% combined yield) as a racemic mixture. LCMS calculated for $C_{15}H_{11}N_4O_2$ (M+H)$^+$: m/z=279.1; found: 278.9.

Step 7. 3-(7-Bromo-2-oxo-1,2,4,5-tetrahydroimidazo[1,5,4-de][1,4]benzoxazin-4-yl)pyridine-2-carbonitrile

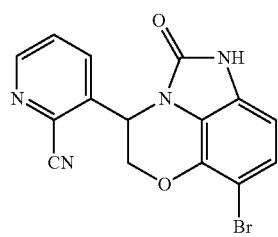 [SMILES: N#Cc1ncccc1C1COc2c(Br)ccc3[nH]c(=O)n1c23]

A solution of 3-(2-oxo-1,2,4,5-tetrahydroimidazo[1,5,4-de][1,4]benzoxazin-4-yl)pyridine-2-carbonitrile (709 mg, 2.548 mmol) in N,N-dimethylformamide (25.0 mL) was treated with N-bromosuccinimide (630 mg, 3.54 mmol) and stirred at room temperature overnight. The reaction mixture was diluted with ethyl acetate and washed with water and brine, dried over magnesium sulfate, filtered, and concentrated to give the crude product. Purification by preparative LCMS (XBridge C18 column, eluting with a gradient of acetonitrile/water containing 0.1% ammonium hydroxide, at flow rate of 60 mL/min) gave the desired product (0.44 g, 48%) as a racemic mixture. LCMS calculated for $C_{15}H_{10}BrN_4O_2$(M+H)$^+$: m/z=357.0, 359.0; found: 356.8, 358.8.

Step 8. 3-[7-(3,5-Dimethylisoxazol-4-yl)-2-oxo-1,2,4,5-tetrahydroimidazo[1,5,4-de][1,4]benzoxazin-4-yl]pyridine-2-carbonitrile A sealed tube containing 4-(di-tert-butylphosphino)-N,N-dimethylaniline-dichloropalladium (2:1) (11.5 mg, 0.0162 mmol), cesium fluoride (574 mg, 3.78 mmol), 3-(7-bromo-2-oxo-1,2,4,5-tetrahydroimidazo[1,5,4-de][1,4]benzoxazin-4-yl)pyridine-2-carbonitrile (386 mg, 1.01 mmol) and (3,5-dimethylisoxazol-4-yl)boronic acid (533 mg, 3.78 mmol) was placed under vacuum and back-filled with nitrogen (repeated 3×). The sealed tube was charged with 1-butanol (4.92 mL) and water (1.2 mL) and the mixture was degassed by bubbling nitrogen for 15 min and heated at 100° C. for 2 h. The reaction mixture was diluted with ethyl acetate, washed with water and brine, dried over magnesium sulfate, filtered, and concentrated to give the crude product. Purification by preparative LCMS (XBridge C18 column, eluting with a gradient of acetonitrile/water containing 0.1% ammonium hydroxide, at flow rate of 60 mL/min) gave the desired product (342 mg, 85%) as a racemic mixture. $^1$H NMR (300 MHz, DMSO-d$_6$) δ 11.00 (br s, 1H), 8.81-8.66 (m, 1H), 7.80-7.62 (m, 2H), 6.90 (d, J=8.0 Hz, 1H), 6.80 (d, J=8.0 Hz, 1H), 5.74-5.51 (m, 1H), 4.58 (d, J=3.4 Hz, 2H), 2.29 (s, 3H), 2.12 (s, 3H); LCMS calculated for $C_{20}H_{16}N_5O_3$ (M+H)$^+$: m/z=374.1; found: 374.1.

Example 127

3-[7-(3,5-Dimethylisoxazol-4-yl)-2-oxo-1,2,4,5-tetrahydroimidazo[1,5,4-de][1,4]benzoxazin-4-yl]pyridine-2-carboxamide trifluoroacetate

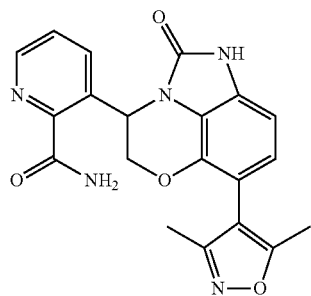 [SMILES: Cc1noc(C)c1-c1ccc2[nH]c(=O)n3c2c1OCC3c1cccnc1C(N)=O]

A solution of 3-[7-(3,5-dimethylisoxazol-4-yl)-2-oxo-1,2,4,5-tetrahydroimidazo[1,5,4-de][1,4]benzoxazin-4-yl]pyridine-2-carbonitrile (12.0 mg, 0.0321 mmol) in dimethyl sulfoxide (120 µL) at 0° C. was treated with hydrogen peroxide (5.36 µL, 0.0524 mmol) (30% solution), followed by potassium carbonate (1 mg, 0.008 mmol) and stirred overnight at room temperature. Purification via preparative LCMS (XBridge C18 column, eluting with a gradient of acetonitrile/water containing 0.1% trifluoroacetic acid, at flow rate of 30 mL/min) gave the desired product (10 mg, 62%) as a racemic mixture. $^1$H NMR (300 MHz, DMSO-d$_6$) δ 11.06 (s, 1H), 8.73-8.49 (m, 1H), 8.34 (s, 1H), 7.84 (s, 1H), 7.49 (dd, J=8.0, 4.6 Hz, 1H), 7.11 (d, J=7.9 Hz, 1H), 6.88 (d, J=8.0 Hz, 1H), 6.81 (d, J=8.0 Hz, 1H), 6.56-6.41 (m, 1H), 4.53 (d, J=2.1 Hz, 2H), 2.24 (s, 3H), 2.07 (s, 3H); LCMS calculated for $C_{20}H_{18}N_5O_4$ (M+H)$^+$: m/z=392.1; found: 392.1.

Example 128

3-[7-(3,5-Dimethylisoxazol-4-yl)-2-oxo-1,2,4,5-tetrahydroimidazo[1,5,4-de][1,4]benzoxazin-4-yl]-N-methylpyridine-2-carboxamide

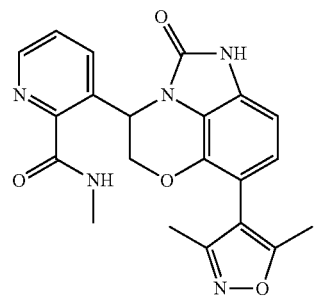 [SMILES: CNC(=O)c1ncccc1C1COc2c(-c3c(C)noc3C)ccc3[nH]c(=O)n1c23]

Step 1. 3-[7-(3,5-Dimethylisoxazol-4-yl)-2-oxo-1,2,4,5-tetrahydroimidazo[1,5,4-de][1,4]benzoxazin-4-yl]pyridine-2-carboxylic acid hydrochloride

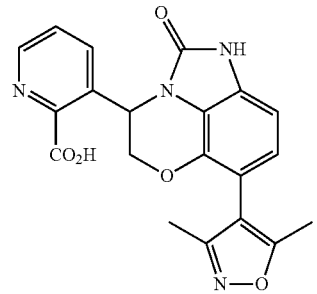 [SMILES: Cc1noc(C)c1-c1ccc2[nH]c(=O)n3c2c1OCC3c1cccnc1C(=O)O]

A solution of 3-[7-(3,5-dimethylisoxazol-4-yl)-2-oxo-1,2,4,5-tetrahydroimidazo[1,5,4-de][1,4]benzoxazin-4-yl]pyridine-2-carbonitrile (342 mg, 0.916 mmol) in 6.0 M hydrogen chloride in water (32.6 mL, 196 mmol) was heated in the microwave at 160° C. for 30 min. The reaction mixture was concentrated to give the desired product (357 mg, 91%) as a racemic mixture which was used without further purification. LCMS calculated for $C_{20}H_{17}N_4O_5$ (M+H)$^+$: m/z=393.1; found: 392.9.

Step 2. 3-[7-(3,5-Dimethylisoxazol-4-yl)-2-oxo-1,2,4,5-tetrahydroimidazo[1,5,4-de][1,4]benzoxazin-4-yl]-N-methylpyridine-2-carboxamide A solution of 3-[7-(3,5-dimethylisoxazol-4-yl)-2-oxo-1,2,4,5-tetrahydroimidazo[1,5,4-de][1,4]benzoxazin-4-yl]pyridine-2-carboxylic acid (10.0 mg, 0.026 mmol) in N,N-dimethylformamide (0.50 mL) was treated with methylammonium chloride (4.30 mg, 0.064 mmol) followed by N,N-diisopropylethylamine (22.2 µL, 0.127 mmol) and stirred at room temperature for 5 min. The reaction mixture was treated with benzotriazol-1-yloxytris(dimethylamino)phosphonium hexafluorophosphate [Aldrich #: 226084] (16.9 mg, 0.038 mmol) and stirred at room temperature for 1 h. Purification by preparative LCMS (XBridge C18 column, eluting with a gradient of acetonitrile/water containing 0.1% ammonium hydroxide, at flow rate of 60 mL/min)

gave the desired product (5 mg, 48%) as a racemic mixture. ¹H NMR (300 MHz, DMSO-d₆) δ 9.06-8.91 (m, 1H), 8.57 (d, J=3.6 Hz, 1H), 7.49 (dd, J=8.1, 4.6 Hz, 1H), 7.10 (d, J=7.4 Hz, 1H), 6.93-6.74 (m, 2H), 6.47 (s, 1H), 4.65-4.37 (m, 2H), 2.62 (d, J=10.1 Hz, 6H), 2.24 (s, 1.5H), 2.07 (s, 1.5H); LCMS calculated for $C_{21}H_{20}N_5O_4$ (M+H)⁺: m/z=406.1; found: 406.1.

Example 129

3-[7-(3,5-Dimethylisoxazol-4-yl)-2-oxo-1,2,4,5-tetrahydroimidazo[1,5,4-de][1,4]benzoxazin-4-yl]-N,N-dimethylpyridine-2-carboxamide

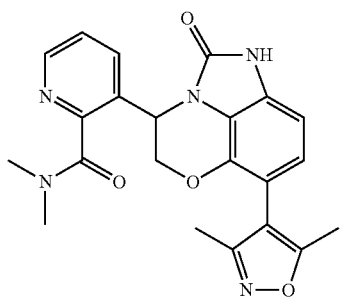

The title compound was synthesized according to the procedure of Example 128, step 2, substituting dimethylamine as the starting material. ¹H NMR (300 MHz, DMSO-d₆) δ 8.53 (dd, J=4.6, 1.5 Hz, 1H), 7.40 (dd, J=8.0, 4.7 Hz, 1H), 7.33 (dd, J=8.0, 1.5 Hz, 1H), 6.86 (d, J=8.0 Hz, 1H), 6.78 (d, J=8.0 Hz, 1H), 5.27 (dd, J=3.3, 3.3 Hz, 1H), 4.47-4.28 (m, 2H), 3.04 (s, 1.5H), 2.86 (s, 1.5H), 2.62 (d, J=10.1 Hz, 6H), 2.27 (s, 1.5H), 2.10 (s, 1.5H); LCMS calculated for $C_{22}H_{22}N_5O_4$ (M+H)⁺: m/z=420.2; found: 420.1.

Example 130

4-[2-(Aminomethyl)pyridin-3-yl]-7-(3,5-dimethyl-isoxazol-4-yl)-4,5-dihydroimidazo[1,5,4-de][1,4]benzoxazin-2(1H)-one bis(trifluoroacetate)

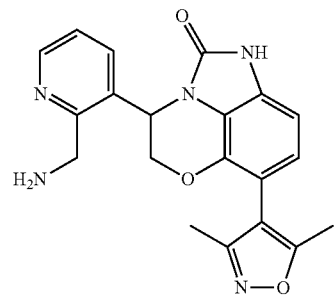 [SMILES: Cc1noc(C)c1-c1ccc2[nH]c(=O)n3c2c1OCC3c1cccnc1CN]

A solution of 3-[7-(3,5-dimethylisoxazol-4-yl)-2-oxo-1,2,4,5-tetrahydroimidazo[1,5,4-de][1,4]benzoxazin-4-yl]pyridine-2-carbonitrile (50.0 mg, 0.134 mmol) in methanol (25.0 mL) and 6.0 M hydrogen chloride in water (0.250 mL, 1.50 mmol) in a Parr bottle was flushed with nitrogen and treated with palladium catalyst (28.5 mg, 0.013 mmol) (10% Pd on carbon, Degussa type). The reaction vessel was charged to 50 PSI hydrogen and shaken for 5 h. The reaction mixture was then filtered over Celite. The solids were washed with additional methanol (150 mL) and the filtrate was concentrated to give the crude product. Purification via preparative LCMS (XBridge C18 column, eluting with a gradient of acetonitrile/water containing 0.1% trifluoroacetic acid, at flow rate of 60 mL/min) gave the desired product (39 mg, 48%) as a racemic mixture. ¹H NMR (300 MHz, DMSO-d₆) δ 11.08 (s, 1H), 8.60 (dd, J=4.5, 1.8 Hz, 1H), 8.48-8.23 (m, 2H), 7.54-7.28 (m, 2H), 6.90 (d, J=8.0 Hz, 1H), 6.80 (d, J=8.0 Hz, 1H), 5.80-5.54 (m, 1H), 4.85-4.30 (m, 4H), 2.29 (s, 3H), 2.12 (s, 3H); LCMS calculated for $C_{20}H_{20}N_5O_3$ (M+H)⁺: m/z=378.2; found: 378.1.

Example 131

N-({3-[7-(3,5-Dimethylisoxazol-4-yl)-2-oxo-1,2,4,5-tetrahydroimidazo[1,5,4-de][1,4]benzoxazin-4-yl]pyridin-2-yl}methyl)acetamide

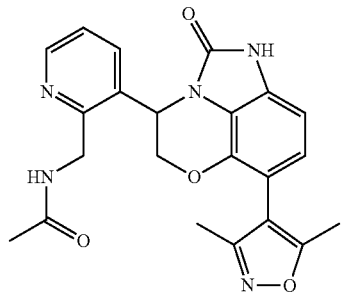 [SMILES: CC(=O)NCc1ncccc1C1COc2c(-c3c(C)noc3C)ccc3[nH]c(=O)n1c23]

A solution of 4-[2-(aminomethyl)pyridin-3-yl]-7-(3,5-dimethylisoxazol-4-yl)-4,5-dihydroimidazo[1,5,4-de][1,4]benzoxazin-2(1H)-one bis(trifluoroacetate) (35.0 mg, 0.058 mmol) in methylene chloride (2.0 mL) was treated with N,N-diisopropylethylamine (50.3 µL, 0.289 mmol) and stirred. Once the starting material was completely dissolved, the reaction mixture was treated with acetyl chloride (49.3 µL, 0.069 mmol) (added as a 10% solution in dichloromethane) and stirred at room temperature for 1 h. The reaction mixture was quenched with methanol and the solvent was concentrated to give the crude product. Purification by preparative LCMS (XBridge C18 column, eluting with a gradient of acetonitrile/water containing 0.1% ammonium hydroxide, at flow rate of 60 mL/min) gave the desired product (18 mg, 74%) as a racemic mixture. ¹H NMR (500 MHz, DMSO-d₆) δ 10.98 (br s, 1H), 8.50-8.47 (m, 1H), 8.44 (dd, J=5.2, 5.2 Hz, 1H), 7.26 (dd, J=7.9, 4.7 Hz, 1H), 7.23-7.16 (m, 1H), 6.88 (d, J=8.0 Hz, 1H), 6.78 (d, J=8.0 Hz, 1H), 5.68 (dd, J=3.1, 3.1 Hz, 1H), 4.71 (dd, J=15.1, 6.1 Hz, 1H), 4.55-4.47 (m, 2H), 4.44 (dd, J=11.6, 3.2 Hz, 1H), 2.28 (s, 3H), 2.12 (s, 3H), 1.88 (s, 3H); LCMS calculated for $C_{22}H_{22}N_5O_4$ (M+H)⁺: m/z=420.2; found: 420.1.

Example 132

Methyl 3-[7-(3,5-dimethylisoxazol-4-yl)-2-oxo-1,2,4,5-tetrahydroimidazo[1,5,4-de][1,4]benzoxazin-4-yl]pyridine-2-carboxylate

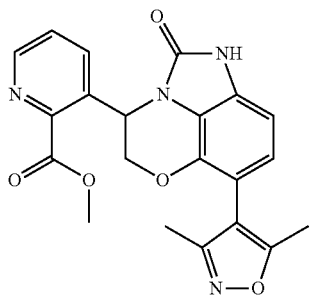 [SMILES: COC(=O)c1ncccc1C1COc2c(-c3c(C)noc3C)ccc3[nH]c(=O)n1c23]

A solution of 3-[7-(3,5-dimethylisoxazol-4-yl)-2-oxo-1,2,4,5-tetrahydroimidazo[1,5,4-de][1,4]benzoxazin-4-yl]pyridine-2-carboxylic acid (294 mg, 0.7493 mmol) in methanol (60.0 mL) was treated with one drop of concentrated sulfuric acid and heated in a sealed tube overnight at 80° C. The reaction mixture was then concentrated to a crude residue. This residue was diluted with ethyl acetate (100 mL) and saturated aqueous sodium bicarbonate solution and stirred at room temperature for 1 hour. After dissolution, the aqueous layer was separated and extracted with ethyl acetate (2×). The combined organic layers were washed with water and brine, dried over magnesium sulfate, filtered, and concentrated to give the crude product. Purification by preparative LCMS (XBridge C18 column, eluting with a gradient of acetonitrile/water containing 0.1% ammonium hydroxide, at flow rate of 60 mL/min) gave the desired product (300 mg, 99%) as a racemic mixture. $^1$H NMR (400 MHz, DMSO-$d_6$) δ 8.63 (dd, J=4.6, 1.5 Hz, 1H), 7.56 (dd, J=8.1, 4.6 Hz, 1H), 7.29 (dd, J=8.1, 1.4 Hz, 1H), 6.89 (d, J=8.0 Hz, 1H), 6.80 (d, J=8.0 Hz, 1H), 6.00 (dd, J=2.9, 2.9 Hz, 1H), 4.53 (d, J=2.9 Hz, 2H), 3.91 (s, 3H), 2.26 (s, 3H), 2.09 (s, 3H); LCMS calculated for $C_{21}H_{19}N_4O_5$ (M+H)$^+$: m/z=407.1; found: 407.0.

Example 133

Single enantiomer of 3-[7-(3,5-dimethylisoxazol-4-yl)-2-oxo-1,2,4,5-tetrahydroimidazo[1,5,4-de][1,4]benzoxazin-4-yl]-N-ethylpyridine-2-carboxamide

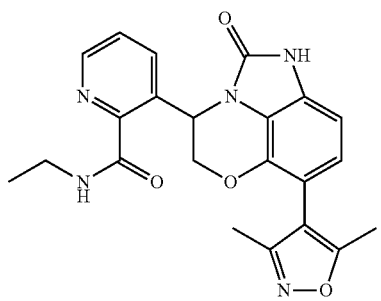 [SMILES: CCNC(=O)c1ncccc1C1COc2c(-c3c(C)noc3C)ccc3[nH]c(=O)n1c23]

Step 1. Separation of isomers of 3-[7-(3,5-dimethylisoxazol-4-yl)-2-oxo-1,2,4,5-tetrahydroimidazo[1,5,4-de][1,4]benzoxazin-4-yl]pyridine-2-carbonitrile

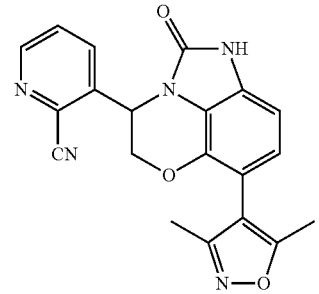 [SMILES: Cc1noc(C)c1-c1ccc2[nH]c(=O)n3c2c1OCC3c1cccnc1C#N]

The racemic mixture of 3-[7-(3,5-dimethylisoxazol-4-yl)-2-oxo-1,2,4,5-tetrahydroimidazo[1,5,4-de][1,4]benzoxazin-4-yl]pyridine-2-carbonitrile was separated by chiral HPLC (Phenomenex Lux Cellulose C2 column, 21.2×250 mm, 5 micron particle size, eluting with 60% ethanol in hexanes at 18 mL/min, 90 mg per injection) to give peak 1 (RT=9.2 min) and peak 2 (RT=15.9 min). Peak 1 was determined to be more active and was used for the synthesis of subsequent analogs.

Step 2. Single enantiomer of 3-[7-(3,5-Dimethylisoxazol-4-yl)-2-oxo-1,2,4,5-tetrahydroimidazo[1,5,4-de][1,4]benzoxazin-4-yl]pyridine-2-carboxylic acid

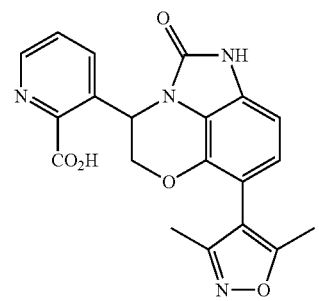 [SMILES: Cc1noc(C)c1-c1ccc2[nH]c(=O)n3c2c1OCC3c1cccnc1C(=O)O]

A solution of 3-[7-(3,5-dimethylisoxazol-4-yl)-2-oxo-1,2,4,5-tetrahydroimidazo[1,5,4-de][1,4]benzoxazin-4-yl]pyridine-2-carbonitrile (2.23 g, 5.97 mmol) (Peak 1 from step 1) in 6.0 M hydrogen chloride in water (50 mL, 300 mmol) was heated in the microwave at 160° C. for 30 min. The reaction mixture was concentrated to give the crude product. Purification by preparative LCMS (XBridge C18 column, eluting with a gradient of acetonitrile/water containing 0.1% ammonium hydroxide, at flow rate of 60 mL/min) gave the desired product (1.41 g, 60%) as a single enantiomer. LCMS calculated for $C_{20}H_{17}N_4O_5$ (M+H)$^+$: m/z=393.1; found: 393.1.

Step 3. 3-[(4S)-7-(3,5-Dimethylisoxazol-4-yl)-2-oxo-1,2,4,5-tetrahydroimidazo[1,5,4-de][1,4]benzoxazin-4-yl]-N-ethylpyridine-2-carboxamide A solution of 3-[7-(3,5-Dimethylisoxazol-4-yl)-2-oxo-1,2,4,5-tetrahydroimidazo[1,5,4-de][1,4]benzoxazin-4-yl]pyridine-2-carboxylic acid (30.0 mg, 0.0764 mmol) (from step 2) in N, N-dimethylformamide (1.0 mL) was treated with ethylamine (10.8 µL, 0.191 mmol) followed by N,N-diisopropylethylamine (66.6 µL, 0.382 mmol) and stirred at room temperature for 5 min. The reaction mixture was subsequently treated with benzotriazol-1-yloxytris(dimethylamino)phosphonium hexafluorophosphate [Aldrich #: 226084] (50.7 mg, 0.115 mmol) and stirred at room temperature for 1 h. Purification by preparative LCMS (XBridge C18 column, eluting with a gradient of acetonitrile/water containing 0.1% ammonium hydroxide, at flow rate of 60 mL/min) gave the desired product (23 mg, 71%) as a single enantiomer. $^1$H NMR (400 MHz, DMSO-$d_6$) δ 9.03 (t, J=5.9 Hz, 1H), 8.58 (dd, J=4.6, 1.4 Hz, 1H), 7.49 (dd, J=8.0, 4.6 Hz, 1H), 7.11 (dd, J=8.0, 1.2 Hz, 1H), 6.87 (d, J=8.0 Hz, 1H), 6.80 (d, J=8.0 Hz, 1H), 6.54-6.41 (m, 1H), 4.64-4.45 (m, 2H), 3.43-3.24 (m, 2H), 2.24 (s, 3H), 2.07 (s, 3H), 1.15 (t, J=7.2 Hz, 3H); LCMS calculated for $C_{22}H_{22}N_5O_4$ (M+H)$^+$: m/z=420.2; found: 420.2.

Examples 134-136

Examples 134-136 listed in Table 6 were synthesized as single enantiomers according to the procedure of Example 133.

TABLE 6

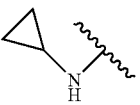

| Ex. No. | Name | R |
|---|---|---|
| 134 | N-Cyclopropyl-3-[7-(3,5-dimethylisoxazol-4-yl)-2-oxo-1,2,4,5-tetrahydroimidazo[1,5,4-de][1,4]benzoxazin-4-yl]pyridine-2-carboxamide |  |
| 135 | 3-[7-(3,5-Dimethylisoxazol-4-yl)-2-oxo-1,2,4,5-tetrahydroimidazo[1,5,4-de][1,4]benzoxazin-4-yl]-N-(2-hydroxyethyl)pyridine-2-carboxamide | 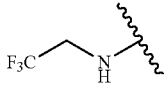 |
| 136 | 3-[7-(3,5-dimethylisoxazol-4-yl)-2-oxo-1,2,4,5-tetrahydroimidazo[1,5,4-de][1,4]benzoxazin-4-yl]-N-(2,2,2-trifluoroethyl)pyridine-2-carboxamide | |

Example 137

(4S)-9-(Aminomethyl)-7-(3,5-dimethylisoxazol-4-yl)-4-pyridin-2-yl-4,5-dihydroimidazo[1,5,4-de][1,4]benzoxazin-2(1H)-one bis(trifluoroacetate)

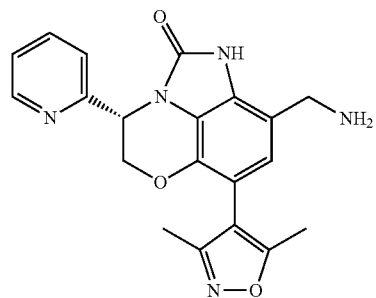 [SMILES: Cc1noc(C)c1-c1cc(CN)c2[nH]c(=O)n3c2c1OC[C@@H]3c1ccccn1]

Step 1. (4S)-9-Bromo-7-(3,5-dimethylisoxazol-4-yl)-4-pyridin-2-yl-4,5-dihydroimidazo[1,5,4-de][1,4]benzoxazin-2 (1H)-one

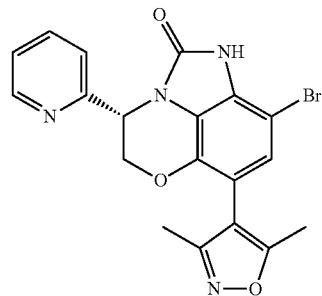 [SMILES: Cc1noc(C)c1-c1cc(Br)c2[nH]c(=O)n3c2c1OC[C@@H]3c1ccccn1]

A solution of (4S)-7-(3,5-dimethylisoxazol-4-yl)-4-pyridin-2-yl-4,5-dihydroimidazo[1,5,4-de][1,4]benzoxazin-2(1H)-one (2.50 g, 7.18 mmol) in tetrahydrofuran (47 mL) was treated with N-bromosuccinimide (1.40 g, 7.89 mmol) and stirred at room temperature for 1 h, at which time the reaction mixture was treated with additional N-bromosuccinimide (0.70 g, 3.93 mmol) and stirred at 45° C. for 3 h. The reaction mixture was diluted with ethyl acetate and washed with water and brine, dried over magnesium sulfate, filtered, and concentrated to give the crude product. Purification by flash column chromatography (50% ethyl acetate/hexanes to 100% ethyl acetate) gave the desired product (3.0 g, 98%) as a single enantiomer. LCMS calculated for $C_{19}H_{16}BrN_4O_3$(M+H)$^+$: m/z=427.1, 429.1; found: 426.8, 428.8.

Step 2. (4S)-7-(3,5-Dimethylisoxazol-4-yl)-4-pyridin-2-yl-9-vinyl-4,5-dihydroimidazo[1,5,4-de][1,4]benzoxazin-2 (1H)-one

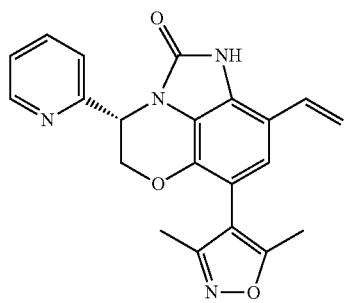 [SMILES: C=Cc1cc(-c2c(C)noc2C)c2c3c1[nH]c(=O)n3[C@@H](c1ccccn1)CO2]

A mixture of (4S)-9-bromo-7-(3,5-dimethylisoxazol-4-yl)-4-pyridin-2-yl-4,5-dihydroimidazo[1,5,4-de][1,4]benzoxazin-2(1H)-one (3.00 g, 7.02 mmol), 4,4,5,5-tetramethyl-2-vinyl-1,3,2-dioxaborolane (2.14 mL, 12.6 mmol), [1,1'-bis(diphenylphosphino)ferrocene]dichloropalladium(II), complex with dichloromethane (1:1) (570 mg, 0.70 mmol) and potassium carbonate (2.90 g, 21 mmol) in 1,4-dioxane (40 mL) and water (20 mL) was heated at 80° C. for 1 h. The mixture was then poured over water and extracted with ethyl acetate. The extracts were washed with brine, dried over sodium sulfate, filtered and concentrated. Purification by flash column chromatography (40% ethyl acetate/hexanes to 90% ethyl acetate/hexanes) gave the desired product (1.69 g, 64%) as a single enantiomer. LCMS calculated for $C_{21}H_{19}N_4O_3$ (M+H)$^+$: m/z=375.1; found: 375.1.

Step 3. (4S)-7-(3,5-Dimethylisoxazol-4-yl)-2-oxo-4-pyridin-2-yl-1,2,4,5-tetrahydroimidazo[1,5,4-de][1,4]benzoxazine-9-carbaldehyde

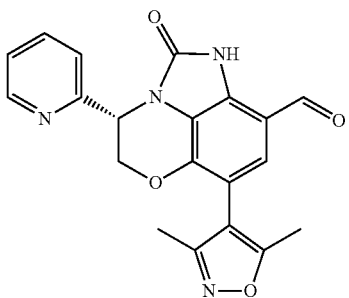 [SMILES: Cc1noc(C)c1-c1cc(C=O)c2[nH]c(=O)n3c2c1OC[C@@H]3c1ccccn1]

A mixture of (4S)-7-(3,5-dimethylisoxazol-4-yl)-4-pyridin-2-yl-9-vinyl-4,5-dihydroimidazo[1,5,4-de][1,4]benzoxazin-2(1H)-one (1690 mg, 4.51 mmol) in water (7.8 mL) and tetrahydrofuran (104 mL) was treated with sodium metaperiodate (2.90 g, 13.5 mmol) and heated at 60° C. for 1 h. The reaction mixture was diluted with ethyl acetate and washed with water and brine, dried over magnesium sulfate, filtered, and concentrated to give the crude product. Purification by flash column chromatography (50% ethyl acetate/hexanes to 100% ethyl acetate/hexanes) gave the desired product (0.797 g, 47%) as a single enantiomer. LCMS calculated for $C_{20}H_{17}N_4O_4$ (M+H)$^+$: m/z=377.1; found: 376.9.

Step 4. (4S)-9-{[(2,4-Dimethoxybenzyl)amino]methyl}-7-(3,5-dimethylisoxazol-4-yl)-4-pyridin-2-yl-4,5-dihydroimidazo[1,5,4-de][1,4]benzoxazin-2 (1H)-one

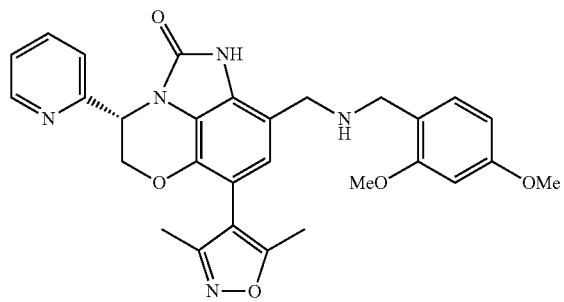 [SMILES: COc1ccc(CNCc2cc(-c3c(C)noc3C)c3c4c2[nH]c(=O)n4[C@@H](c2ccccn2)CO3)c(OC)c1]

A solution (4S)-7-(3,5-dimethylisoxazol-4-yl)-2-oxo-4-pyridin-2-yl-1,2,4,5-tetrahydroimidazo[1,5,4-de][1,4]benzoxazine-9-carbaldehyde (250 mg, 0.664 mmol) in ethanol (12.5 mL) was treated with 1-(2,4-dimethoxyphenyl)methanamine [Aldrich #: 432725] (150 μL, 0.996 mmol) and acetic acid (20.0 μL, 0.352 mmol) and heated at 60° C. for 1 h. The reaction mixture was cooled to room temperature, treated with sodium cyanoborohydride (210 mg, 3.3 mmol) and stirred at room temperature for 3 h. The reaction mixture was then quenched with acetic acid (1 mL) and diluted with ethyl acetate. The organic layer was washed with water and brine, dried over magnesium sulfate, filtered, and concentrated to give the desired product (0.40 g, 97%) as a single enantiomer which was used without further purification. LCMS calculated for $C_{29}H_{30}N_5O_5$ (M+H)$^+$: m/z=528.2; found: 528.0.

Step 5. (4S)-9-(Aminomethyl)-7-(3,5-dimethylisoxazol-4-yl)-4-pyridin-2-yl-4,5-dihydroimidazo[1,5,4-de][1,4]benzoxazin-2(1H)-one bis(trifluoroacetate)

A solution of (4S)-9-{[(2,4-dimethoxybenzyl)amino]methyl}-7-(3,5-dimethylisoxazol-4-yl)-4-pyridin-2-yl-4,5-dihydroimidazo[1,5,4-de][1,4]benzoxazin-2(1H)-one (70.0 mg, 0.133 mmol) in trifluoroacetic acid (5 mL) and water (30 μL) was heated in the microwave at 120° C. for 10 min. The reaction mixture was concentrated to give a crude residue. Purification via preparative LCMS (XBridge C18 column, eluting with a gradient of acetonitrile/water containing 0.1% trifluoroacetic acid, at flow rate of 60 mL/min) gave the desired product (66 mg, 82%) as a single enantiomer. $^1$H NMR (300 MHz, DMSO-d$_6$) δ 11.28 (s, 1H), 8.48 (d, J=4.4 Hz, 1H), 8.18 (br s, 2H), 7.80 (ddd, J=7.7, 7.7, 1.7 Hz, 1H), 7.32 (dd, J=7.1, 5.0 Hz, 1H), 7.19 (d, J=7.9 Hz, 1H), 6.94 (s, 1H), 5.59 (s, 1H), 4.89-4.73 (m, 1H), 4.44 (dd, J=11.5, 3.0 Hz, 1H), 4.13 (d, J=5.5 Hz, 2H), 2.24 (s, 3H), 2.07 (s, 3H); LCMS calculated for C$_{20}$H$_{20}$N$_5$O$_3$ (M+H)$^+$: m/z=378.2; found: 378.0.

Example 138

N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}acetamide trifluoroacetate

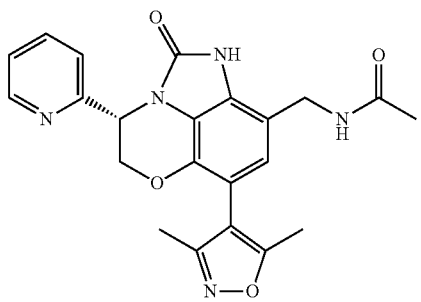 [SMILES: CC(=O)NCc1cc(-c2c(C)noc2C)c2c3c1[nH]c(=O)n3[C@@H](c1ccccn1)CO2]

A solution of (4S)-9-(aminomethyl)-7-(3,5-dimethylisoxazol-4-yl)-4-pyridin-2-yl-4,5-dihydroimidazo[1,5,4-de][1,4]benzoxazin-2(1H)-one bis(trifluoroacetate) (10.0 mg, 0.0265 mmol) in methylene chloride (1.00 mL) was treated with N,N-diisopropylethylamine (13.8 μL, 0.0795 mmol) followed by acetyl chloride (2.26 μL, 0.0318 mmol) and stirred at room temperature for 1 h. The reaction mixture was concentrated to give a crude residue. Purification via preparative LCMS (XBridge C18 column, eluting with a gradient of acetonitrile/water containing 0.1% trifluoroacetic acid, at a flow rate of 60 mL/min) gave the desired product (9 mg, 81%) as a single enantiomer. $^1$H NMR (500 MHz, DMSO-d$_6$) δ 10.89 (s, 1H), 8.52 (d, J=4.1 Hz, 1H), 8.31 (dd, J=5.7, 5.7 Hz, 1H), 7.79 (ddd, J=7.7, 7.7, 1.8 Hz, 1H), 7.41-7.27 (m, 1H), 7.14 (d, J=7.9 Hz, 1H), 6.70 (s, 1H), 5.53 (dd, J=2.4, 2.4 Hz, 1H), 4.76 (dd, J=11.5, 2.0 Hz, 1H), 4.41 (dd, J=11.5, 3.1 Hz, 1H), 4.32 (d, J=5.8 Hz, 2H), 2.22 (s, 3H), 2.05 (s, 3H), 1.87 (s, 3H); LCMS calculated for C$_{22}$H$_{22}$N$_5$O$_4$ (M+H)$^+$: m/z=420.2; found: 420.0.

Examples 139-143

Examples 139 to 142 of Table 7 were synthesized as single enantiomers according to the procedure of Example 138.

Example 143 of Table 7 was synthesized according to the procedure of Example 128, Step 2.

TABLE 7

| Ex. No. | Name | R |
|---|---|---|
| 139 | N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}-2-phenylacetamide | —C(O)CH$_2$Ph |
| 140 | N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}-2-methoxyacetamide | —C(O)CH$_2$OMe |
| 141 | N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}methanesulfonamide | —S(O)$_2$CH$_3$ |
| 142 | N-{[(4S)-7-(3,5-Dimethylisoxazol-4-yl)-2-oxo-4-pyridin-2-yl-1,2,4,5-tetrahydroimidazo[1,5,4-de][1,4]benzoxazin-9-yl]methyl}-N'-isopropylurea | —C(O)NH-iPr |
| 143 | 2-(Dimethylamino)-N-{[(4S)-7-(3,5-dimethylisoxazol-4-yl)-2-oxo-4-pyridin-2-yl-1,2,4,5-tetrahydroimidazo[1,5,4-de][1,4]benzoxazin-9-yl]methyl}acetamide | —C(O)CH$_2$N(CH$_3$)$_2$ |

Example 144A (4S)-7-(3,5-dimethylisoxazol-4-yl)-9-(1-hydroxy-ethyl)-4-pyridin-2-yl-4,5-dihydroimidazo[1,5,4-de][1,4]benzoxazin-2(1H)-one (Diastereoisomer 1)

Example 144B (4S)-7-(3,5-dimethylisoxazol-4-yl)-9-(1-hydroxy-ethyl)-4-pyridin-2-yl-4,5-dihydroimidazo[1,5,4-de][1,4]benzoxazin-2(1H)-one (Diastereoisomer 2)

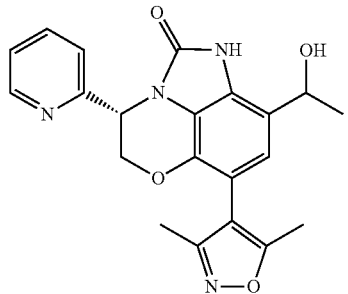 [SMILES: Cc1noc(C)c1-c1cc(C(C)O)c2[nH]c(=O)n3c2c1OC[C@@H]3c1ccccn1]

A solution of (4S)-7-(3,5-dimethylisoxazol-4-yl)-2-oxo-4-pyridin-2-yl-1,2,4,5-tetrahydroimidazo[1,5,4-de][1,4]benzoxazine-9-carbaldehyde (1.30 g, 3.45 mmol) (single enantiomer from Example 137, step 3) in tetrahydrofuran (30.0 mL) was treated with 3.0 M methylmagnesium iodide in diethyl ether (4.03 mL, 12.1 mmol) and stirred at room temperature for 30 min. The reaction mixture was diluted with ethyl acetate, washed with water and brine, dried over magnesium sulfate, filtered, and concentrated to give the crude product. Purification by preparative LCMS (XBridge C18 column, eluting with a gradient of acetonitrile/water containing 0.1% ammonium hydroxide, at flow rate of 60 mL/min) gave the desired product as a mixture of diastereoisomers. The diastereoisomers were separated by chiral HPLC (Chiracel AD-H column, 20×250 mm, 5 micron particle size, eluting with 50% ethanol in hexanes at 12 mL/min, 45 mg per injection) to give Peak 1 (Diastereoisomer 1, RT=10.2 min) and Peak 2 (Diastereoisomer 2, RT=12.6 min).

Diastereoisomer 1, Peak 1: $^1$H NMR (400 MHz, DMSO-$d_6$) δ 11.03 (br s, 1H), 8.51 (d, J=4.7 Hz, 1H), 7.78 (ddd, J=7.7, 7.7, 1.6 Hz, 1H), 7.31 (dd, J=7.3, 5.0 Hz, 1H), 7.09 (d, J=7.9 Hz, 1H), 6.83 (s, 1H), 5.52 (s, 1H), 5.21 (br s, 1H), 4.95 (q, J=6.3 Hz, 1H), 4.76 (dd, J=11.4, 1.5 Hz, 1H), 4.42 (dd, J=11.4, 3.0 Hz, 1H), 2.22 (s, 3H), 2.05 (s, 3H), 1.37 (d, J=6.4 Hz, 3H); LCMS calculated for $C_{21}H_{21}N_4O_4$ $(M+H)^+$: m/z=393.2; found: 393.0.

Diastereoisomer 2, Peak 2: $^1$H NMR (400 MHz, DMSO-$d_6$) δ 10.97 (br s, 1H), 8.52 (d, J=4.7 Hz, 1H), 7.78 (ddd, J=7.7, 7.7, 1.4 Hz, 1H), 7.32 (dd, J=7.4, 4.9 Hz, 1H), 7.11 (d, J=7.8 Hz, 1H), 6.80 (s, 1H), 5.50 (s, 1H), 5.20 (br s, 1H), 4.92 (q, J=6.3 Hz, 1H), 4.75 (dd, J=11.4, 1.7 Hz, 1H), 4.39 (dd, J=11.4, 3.0 Hz, 1H), 2.23 (s, 3H), 2.06 (s, 3H), 1.40 (d, J=6.4 Hz, 3H); LCMS calculated for $C_{21}H_{21}N_4O_4$ $(M+H)^+$: m/z=393.2; found: 393.1.

Example 145

(3R)-1-[(4S)-7-(3,5-Dimethylisoxazol-4-yl)-4-pyridin-2-yl-4,5-dihydroimidazo[1,5,4-de][1,4]benzoxazin-2-yl]-N-isopropylpyrrolidine-3-carboxamide

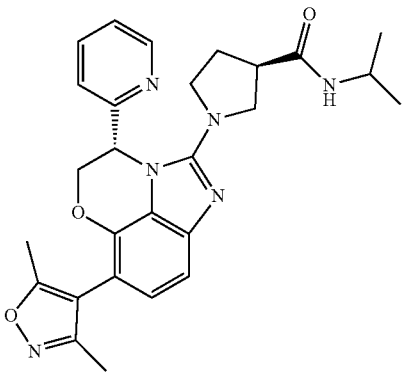 [SMILES: Cc1noc(C)c1-c1ccc2nc(N3CC[C@@H](C(=O)NC(C)C)C3)n3c2c1OC[C@@H]3c1ccccn1]

Step 1.
(3R)—N-Isopropylpyrrolidine-3-carboxamide

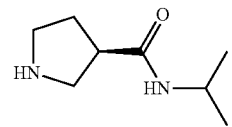

To (3R)-1-(tert-butoxycarbonyl)pyrrolidine-3-carboxylic acid (150 mg, 0.70 mmol) in N,N-dimethylformamide (3.0 mL), N,N-diisopropylethylamine (0.25 mL, 1.4 mmol) and 1-hydroxybenzotriazole (94 mg, 0.70 mmol) were added. The mixture was stirred at room temperature for 5 min, followed by addition of N-(3-dimethylaminopropyl)-N'-ethylcarbodiimide hydrochloride (150 mg, 0.77 mmol). The mixture was then stirred for 20 min. 2-Propanamine (59 µL, 0.69 mmol) was added and the mixture was stirred overnight. The mixture was then diluted with ethyl acetate and washed with saturated aqueous sodium bicarbonate. The aqueous layer was separated and extracted with additional ethyl acetate. The combined organic layers were dried over magnesium sulfate, concentrated, and purified by preparative LCMS using pH 2 buffer to give desired boc-protected intermediate. The product fractions were concentrated and treated with 4.0 M hydrogen chloride in 1,4-dioxane (2.0 mL) for 30 min, at which time the mixture was concentrated and dissolved in DCM/MeOH and treated with Trisamine resin (Silicycle) for 30 min. The resulting mixture was filtered and the solvents were evaporated to give the desired compound (63 mg, 58%) which was used in the next step without further purification. LCMS calc. for $C_8H_{17}N_2O$ $(M+H)^+$: m/z=157.1; found: 157.2.

Step 2. (3R)-1-[(4S)-7-(3,5-dimethylisoxazol-4-yl)-4-pyridin-2-yl-4,5-dihydroimidazo[1,5,4-de][1,4]benzoxazin-2-yl]-N-isopropylpyrrolidine-3-carboxamide Triethylamine (110 µL, 0.79 mmol) and (3R)—N-isopropylpyrrolidine-3-carboxamide (120 mg, 0.74 mmol) were added to a solution of (4S)-2-chloro-7-(3,5-dimethylisoxazol-4-yl)-4-pyridin-2-yl-4,5-dihydroimidazo[1,5,4-de][1,4]benzoxazine (66.0 mg, 0.18 mmol) in N-methylpyrrolidinone (1.5 mL), and the resulting mixture was heated in a microwave at 120° C. for 5 min. The mixture was diluted with methanol and purified twice by preparative LCMS using pH 10 buffer to give the title compound, (8.9 mg, 10%). LCMS calc. for $C_{27}H_{31}N_6O_3$ (M+H)$^+$: m/z=487.2; found: 487.3. $^1$H NMR (500 MHz, DMSO) δ 8.54 (dd, J=4.8, 0.8 Hz, 1H), 7.79 (d, J=7.6 Hz, 1H), 7.72 (td, J=7.7, 1.8 Hz, 1H), 7.29 (dd, J=6.8, 4.9 Hz, 1H), 6.95 (d, J=8.1 Hz, 1H), 6.80 (d, J=8.1 Hz, 1H), 6.60 (d, J=7.9 Hz, 1H), 6.09 (t, 1H), 4.82 (dd, J=11.4, 1.3 Hz, 1H), 4.53 (dd, J=11.5, 2.8 Hz, 1H), 3.85-3.71 (m, 3H), 3.43 (dd, J=9.6, 7.6 Hz, 1H), 3.39-3.32 (m, 1H), 2.90 (p, J=7.8 Hz, 1H), 2.19 (s, 3H), 2.02 (s, 3H), 2.00-1.89 (m, 2H), 1.01 (dd, J=10.1, 6.6 Hz, 6H).

Example 146A

1-[(4S)-7-(3,5-Dimethylisoxazol-4-yl)-4-pyridin-2-yl-4,5-dihydroimidazo[1,5,4-de][1,4]benzoxazin-2-yl]-3-methylpyrrolidin-3-ol (Diastereoisomer 1)

Example 146B

1-[(4S)-7-(3,5-Dimethylisoxazol-4-yl)-4-pyridin-2-yl-4,5-dihydroimidazo[1,5,4-de][1,4]benzoxazin-2-yl]-3-methylpyrrolidin-3-ol (Diastereoisomer 2)

Example 146C

1-[(4S)-7-(3,5-Dimethylisoxazol-4-yl)-4-pyridin-2-yl-4,5-dihydroimidazo[1,5,4-de][1,4]benzoxazin-2-yl]-3-methylpyrrolidin-3-ol (Mixture of diastereoisomers)

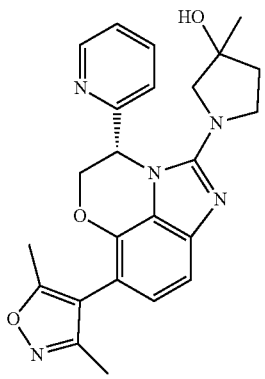 [SMILES: Cc1noc(C)c1-c1ccc2nc(N3CCC(C)(O)C3)n3c2c1OC[C@@H]3c1ccccn1]

Triethylamine (0.76 mL, 5.5 mmol) and 3-methylpyrrolidin-3-ol hydrochloride (563 mg, 4.09 mmol) were added to (4S)-2-chloro-7-(3,5-dimethylisoxazol-4-yl)-4-pyridin-2-yl-4,5-dihydroimidazo[1,5,4-de][1,4]benzoxazine (100 mg, 0.27 mmol) in N-methylpyrrolidinone (3 mL) and the resulting mixture was heated in a microwave at 150° C. for 20 min. The mixture was then diluted with methanol and purified by preparative LCMS at pH 2 buffer followed by preparative LCMC at pH 10 buffer to give the title compound as a mixture of diastereomers (47.1 mg, 40%). LCMS calc. for $C_{24}H_{26}N_5O_3$ (M+H)$^+$: m/z=432.2; found: 432.2. The isomers were separated by prep chiral column chromatography: Column: phenomenex Lux Cellulose C-2 5 μm, 21, 2×250 mm, Mobile phase: 20% EtOH/Hexanes, gradient condition: isocratic at 18 mL/min, run time: 30 min, peak time: 23.0 and 25.7 min.

Example 146A, Peak 1, 12.6 mg, 11%, LCMS calc. for $C_{24}H_{26}N_5O_3$ (M+H)$^+$: m/z=432.2; found: 432.2.

Example 146B, Peak 2, 12.6 mg, 11%, LCMS calc. for $C_{24}H_{26}N_5O_3$ (M+H)$^+$: m/z=432.2; found: 432.2.

Example 147

4-[(4S)-7-(3,5-Dimethylisoxazol-4-yl)-4-pyridin-2-yl-4,5-dihydroimidazo[1,5,4-de][1,4]benzoxazin-2-yl]-1,4-diazepane-1-sulfonamide

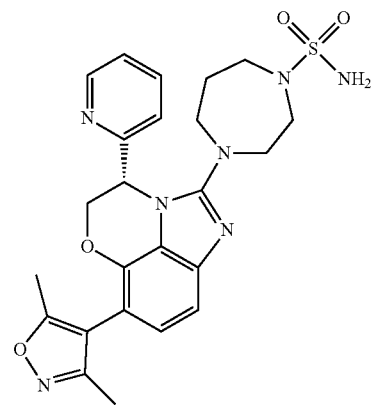 [SMILES: Cc1noc(C)c1-c1ccc2nc(N3CCCN(S(N)(=O)=O)CC3)n3c2c1OC[C@@H]3c1ccccn1]

Step 1. tert-Butyl 4-[(4S)-7-(3,5-dimethylisoxazol-4-yl)-4-pyridin-2-yl-4,5-dihydroimidazo[1,5,4-de][1,4]benzoxazin-2-yl]-1,4-diazepane-1-carboxylate

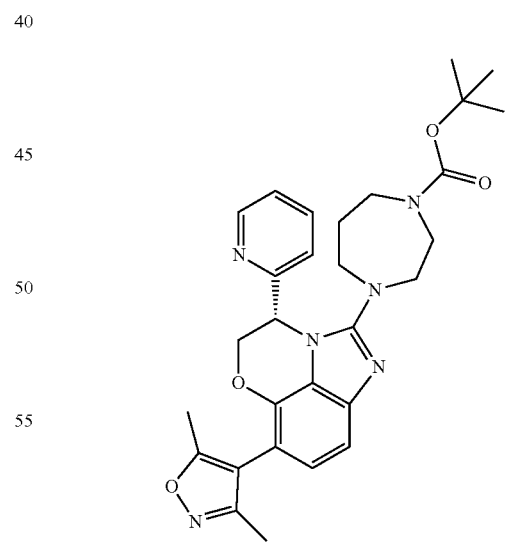

The title compound was prepared by methods analogous to Example 146, substituting with tert-butyl 1,4-diazepane-1-carboxylate. The mixture was concentrated and purified by preparative LCMS using pH 10 buffer to give the title compound (63 mg, 36%). LCMS calc. for $C_{29}H_{35}N_6O_4$ (M+H)$^+$: m/z=531.3; found: 531.3.

Step 2. (4S)-2-(1,4-Diazepan-1-yl)-7-(3,5-dimethyl-isoxazol-4-yl)-4-pyridin-2-yl-4,5-dihydroimidazo[1,5,4-de][1,4]benzoxazine

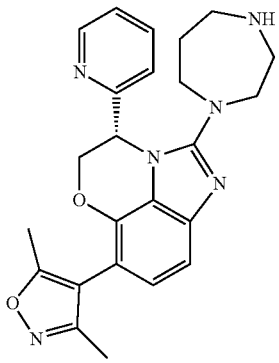 [SMILES: Cc1noc(C)c1-c1ccc2nc(N3CCCNCC3)n3c2c1OC[C@@H]3c1ccccn1]

tert-Butyl 4-[(4S)-7-(3,5-dimethylisoxazol-4-yl)-4-pyridin-2-yl-4,5-dihydroimidazo[1,5,4-de][1,4]benzoxazin-2-yl]-1,4-diazepane-1-carboxylate (53 mg, 0.10 mmol) was treated with a solution of 4.0 M hydrogen chloride in 1,4-dioxane (2.0 mL) for 10 min. The mixture was concentrated and purified by preparative LCMS using pH 10 buffer to give the title compound (28.5 mg, 66%). LCMS calc. for $C_{24}H_{27}N_6O_2$ (M+H)$^+$: m/z=431.2; found: 431.3.

Step 3. 4-[(4S)-7-(3,5-Dimethylisoxazol-4-yl)-4-pyridin-2-yl-4,5-dihydroimidazo[1,5,4-de][1,4]benzoxazin-2-yl]-1,4-diazepane-1-sulfonamide (4S)-2-(1,4-diazepan-1-yl)-7-(3,5-dimethylisoxazol-4-yl)-4-pyridin-2-yl-4,5-dihydroimidazo[1,5,4-de][1,4]benzoxazine (5.8 mg, 0.013 mmol) and sulfamide (7.8 mg, 0.081 mmol) were dissolved in pyridine (0.71 mL) and the solution was heated at 120° C. for 3 min in a microwave. The mixture was diluted with methanol and purified by preparative LCMS using pH 10 buffer to give the title compound (5.1 mg, 74%). LCMS calc. for $C24H_{27}N_7O_4S$ (M+H)$^+$: m/z=510.2; found: 509.7.

Example 148

(4S)-2-(4-Acetyl-1,4-diazepan-1-yl)-7-(3,5-dimethylisoxazol-4-yl)-4-pyridin-2-yl-4,5-dihydroimidazo[1,5,4-de][1,4]benzoxazine

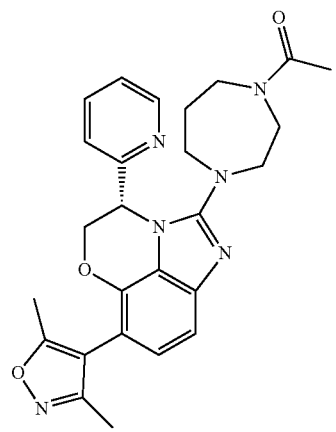 [SMILES: CC(=O)N1CCCN(c2nc3ccc(-c4c(C)noc4C)c4c3n2[C@@H](c2ccccn2)CO4)CC1]

To a solution of (4S)-2-(1,4-diazepan-1-yl)-7-(3,5-dimethylisoxazol-4-yl)-4-pyridin-2-yl-4,5-dihydroimidazo[1,5,4-de][1,4]benzoxazine (5.0 mg, 0.012 mmol) in methylene chloride (0.44 mL), triethylamine (8.1 μL, 0.058 mmol) was added followed by acetyl chloride (1.6 μL, 0.023 mmol) and the mixture was stirred for 5 min. The mixture was then diluted with methanol and purified by preparative LCMS using pH 10 buffer to give the title compound (3.5 mg, 64%). LCMS calc. for $C_{26}H_{29}N_6O_3$ (M+H)$^+$: m/z=473.2; found: 473.3.

Example 149

(4S)-7-(3,5-Dimethylisoxazol-4-yl)-2-[4-(methylsulfonyl)-1,4-diazepan-1-yl]-4-pyridin-2-yl-4,5-dihydroimidazo[1,5,4-de][1,4]benzoxazine

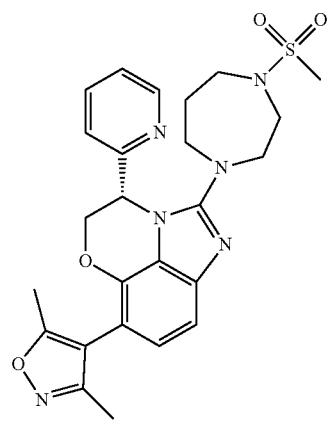 [SMILES: Cc1noc(C)c1-c1ccc2nc(N3CCCN(S(C)(=O)=O)CC3)n3c2c1OC[C@@H]3c1ccccn1]

Triethylamine (8.1 μL, 0.058 mmol) was added to a solution of (4S)-2-(1,4-diazepan-1-yl)-7-(3,5-dimethylisoxazol-4-yl)-4-pyridin-2-yl-4,5-dihydroimidazo[1,5,4-de][1,4]benzoxazine (5.0 mg, 0.012 mmol) in methylene chloride (0.44 mL), and the mixture was cooled to 0° C. Methanesulfonyl chloride (1.8 μL, 0.023 mmol) was then added and the mixture was stirred for 5 min at 0° C. The mixture was diluted with methanol and purified by preparative LCMS using pH 10 buffer to give the title compound (3.8 mg, 64%). LCMS calc. for $C_{25}H_{29}N_6O_4S$ (M+H)$^+$: m/z=509.2; found: 509.2.

Example 150

(4S)-7-(3,5-Dimethylisoxazol-4-yl)-2-piperazin-1-yl-4-pyridin-2-yl-4,5-dihydroimidazo[1,5,4-de][1,4]benzoxazine trihydrochloride

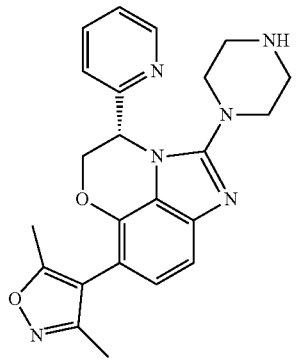 [SMILES: Cc1noc(C)c1-c1ccc2nc(N3CCNCC3)n3c2c1OC[C@@H]3c1ccccn1]

Step 1. tert-Butyl 4-[(4S)-7-(3,5-dimethylisoxazol-4-yl)-4-pyridin-2-yl-4,5-dihydroimidazo[1,5,4-de][1,4]benzoxazin-2-yl]piperazine-1-carboxylate

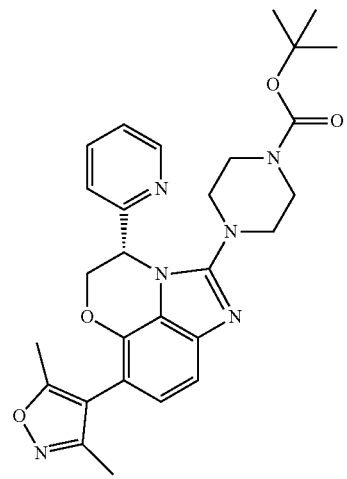 [SMILES: Cc1noc(C)c1-c1ccc2nc(N3CCN(C(=O)OC(C)(C)C)CC3)n3c2c1OC[C@@H]3c1ccccn1]

The title compound was prepared by methods analogous to Example 146, substituting tert-butyl piperazine-1-carboxylate. The mixture was concentrated and purified by preparative LCMS using pH 10 buffer to give the product. LCMS calc. for $C_{28}H_{33}N_6O_4$ (M+H)$^+$: m/z=517.3; found: 517.4.

Step 2. (4S)-7-(3,5-Dimethylisoxazol-4-yl)-2-piperazin-1-yl-4-pyridin-2-yl-4,5-dihydroimidazo[1,5,4-de][1,4]benzoxazine trihydrochloride tert-Butyl 4-[(4S)-7-(3,5-dimethylisoxazol-4-yl)-4-pyridin-2-yl-4,5-dihydroimidazo[1,5,4-de][1,4]benzoxazin-2-yl]piperazine-1-carboxylate (45 mg, 0.087 mmol) was stirred in 4 N HCl in dioxanes (3 mL) and methanol (2 mL) for 30 min, at which time the solvent was evaporated to give the title compound (45 mg, 92%). LCMS calc. for $C_{27}H_{32}N_7O_3$ (M+H)$^+$: m/z=417.2; found: 417.3.

Example 151

2-{4-[(4S)-7-(3,5-Dimethylisoxazol-4-yl)-4-pyridin-2-yl-4,5-dihydroimidazo[1,5,4-de][1,4]benzoxazin-2-yl]piperazin-1-yl}-N,N-dimethylacetamide

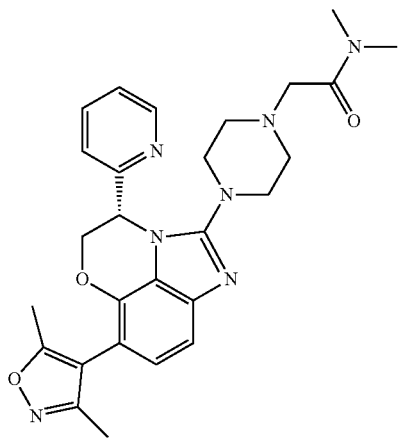 [SMILES: Cc1noc(C)c1-c1ccc2nc(N3CCN(CC(=O)N(C)C)CC3)n3c2c1OC[C@@H]3c1ccccn1]

To a solution of (4S)-7-(3,5-dimethylisoxazol-4-yl)-2-piperazin-1-yl-4-pyridin-2-yl-4,5-dihydroimidazo[1,5,4-de][1,4]benzoxazine trihydrochloride (10 mg, 0.03 mmol) in methylene chloride (1.0 mL), potassium carbonate (18 mg, 0.13 mmol) was added, followed by 2-chloro-N,N-dimethylacetamide (2.7 µL, 0.026 mmol) and the mixture was stirred for 5 min. The mixture was then heated at 60° C. overnight. The mixture was diluted with methanol and purified by preparative LCMS using pH 10 buffer to give the title compound, (3.7 mg, 30%). LCMS calc. for $C_{27}H_{32}N_7O_3$ (M+H)$^+$: m/z=502.2; found: 502.3.

Example 152

2-Cyano-N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N-methylacetamide

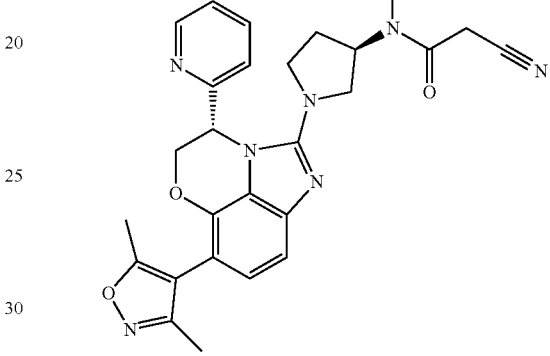

Triethylamine (8.2 µL, 0.059 mmol) and ethanol (1.0 mL) were added to a solution of (3R)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidin-3-amine (8.5 mg, 0.020 mmol) in methylene chloride (0.50 mL), followed by addition of 3-[(2,5-dioxopyrrolidin-1-yl)oxy]-3-oxopropanenitrile (7.2 mg, 0.039 mmol) and the mixture was stirred overnight at room temperature. The mixture was then diluted with methanol and purified by preparative LCMS using pH 10 buffer to give the title compound (1.4 mg, 14%). LCMS calc. for $C_{27}H_{28}N_7O_3$ (M+H)$^+$: m/z=498.2; found: 498.3.

Example 153

N-{(3R)-1-[(4S)-7-(3,5-Dimethylisoxazol-4-yl)-4-pyridin-2-yl-4,5-dihydroimidazo[1,5,4-de][1,4]benzoxazin-2-yl]pyrrolidin-3-yl}morpholine-4-carboxamide

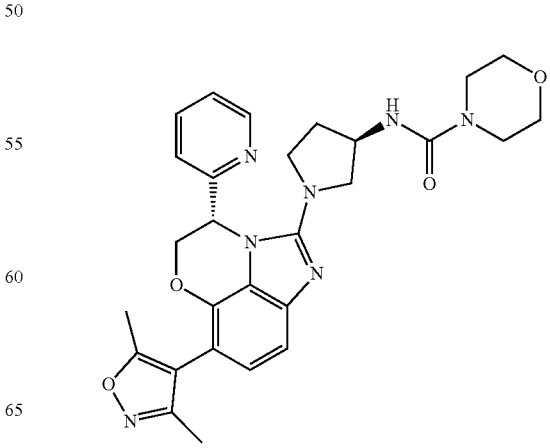

To a solution of (3R)-1-[(4S)-7-(3,5-dimethylisoxazol-4-yl)-4-pyridin-2-yl-4,5 dihydroimidazo[1,5,4-de][1,4]benzoxazin-2-yl]pyrrolidin-3-amine trihydrochloride (35 mg, 0.068 mmol) in methylene chloride (1.0 mL), triethylamine (18 µL, 0.13 mmol) was added followed by morpholine-4-carbamoyl chloride (10 µL, 0.1 mmol) and the mixture was stirred for 5 min. The mixture was diluted with methanol and purified by preparative LCMS using pH 10 buffer to give the title compound, (4.1 mg, 30%). LCMS calc. for $C_{28}H_{32}N_7O_4$ (M+H)$^+$: m/z=530.2; found: 530.3.

Example 154

7-(3,5-Dimethylisoxazol-4-yl)-2-methyl-4-pyridin-2-yl-4,5-dihydroimidazo[1,5,4-de][1,4]benzoxazine

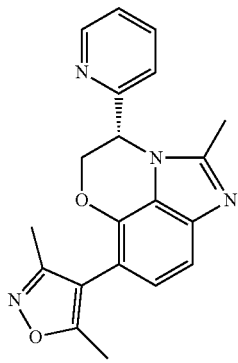 [SMILES: Cc1noc(C)c1-c1ccc2nc(C)n3c2c1OC[C@@H]3c1ccccn1]

A mixture of 2-chloro-7-(3,5-dimethylisoxazol-4-yl)-4-pyridin-2-yl-4,5-dihydroimidazo[1,5,4-de][1,4]benzoxazine (45 mg, 0.12 mmol), 2.0 M methylzinc chloride in THF (310 µL), and tetrakis(triphenylphosphine)palladium(0) (7 mg, 0.006 mmol) in THF (2 mL) under nitrogen was heated in a microwave at 150° C. for 5 min. Purification by preparative LCMS using pH 10 buffer gave the title compound (21 mg, 49%). LCMS calc. for $C_{20}H_{19}N_4O_2$ (M+H)$^+$: m/z=347.1; found: 347.2. $^1$H NMR (300 MHz, CD$_3$OD) δ 8.58 (d, J=4.8 Hz, 1H), 7.69 (td, J=7.8, 1.8 Hz, 1H), 7.32 (dd, J=7.1, 5.3 Hz, 1H), 7.05 (d, J=8.1 Hz, 2H), 6.89 (d, J=8.1 Hz, 2H), 6.59 (d, J=7.9 Hz, 1H), 6.03 (s, 1H), 4.55 (dd, J=11.5, 2.8 Hz, 2H), 4.29-4.09 (m, 1H), 4.00-3.71 (m, 2H), 3.63-3.50 (m, 3H), 3.40 (dd, J=9.8, 4.6 Hz, 1H), 2.23 (s, 3H), 2.23-2.11 (m, 1H), 2.08 (s, 3H), 1.98-1.83 (m, 1H).

Example 155

Methyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate

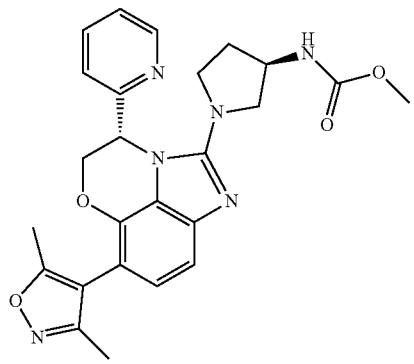 [SMILES: COC(=O)N[C@@H]1CCN(c2nc3ccc(-c4c(C)noc4C)c4c3n2[C@@H](c2ccccn2)CO4)C1]

Step 1. (3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-amine trihydrochloride

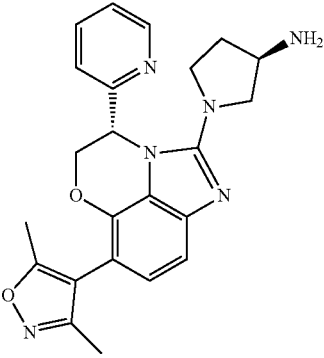 [SMILES: Cc1noc(C)c1-c1ccc2nc(N3CC[C@@H](N)C3)n3c2c1OC[C@@H]3c1ccccn1]

(4S)-2-Chloro-7-(3,5-dimethylisoxazol-4-yl)-4-pyridin-2-yl-4,5-dihydroimidazo[1,5,4-de][1,4]benzoxazine (300 mg, 0.8 mmol) tert-butyl (3R)-pyrrolidin-3-ylcarbamate (4.57 g, 24.5 mmol) and triethylamine (570 µL, 4.1 mmol) were stirred in N-methylpyrrolidinone (10 mL) and heated to 150° C. in a microwave for 5 min. Purification by preparative LCMS (pH 10) gave the desired boc-protected intermediate. Treatment with 4 N HCl in dioxanes/methanol and subsequent evaporation of the solvents afforded the title compound (36 mg, 100%). LCMS calc. for $C_{23}H_{25}N_6O_2$ (M+H)$^+$: m/z=417.2; found: 417.3.

Step 2. Methyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate (3R)-1-[(4S)-7-(3,5-Dimethylisoxazol-4-yl)-4-pyridin-2-yl-4,5-dihydroimidazo[1,5,4-de][1,4]benzoxazin-2-yl]pyrrolidin-3-amine trihydrochloride (35 mg, 0.068 mmol) was stirred in methylene chloride (1.0 mL) with triethylamine (47 µL, 0.34 mmol), followed by addition of methyl chloroformate (10 µL, 0.14 mmol). The mixture was stirred at room temperature for 30 min and concentrated. Purification by preparative LCMS using pH 10 buffer gave the title compound (24 mg, 75%). LCMS calc. for $C_{25}H_{27}N_6O_4$ (M+H)$^+$: m/z=475.2; found: 475.3. $^1$H NMR (300 MHz, CD$_3$OD) δ 8.58 (d, J=4.8 Hz, 1H), 7.69 (td, J=7.8, 1.8 Hz, 1H), 7.32 (dd, J=7.1, 5.3 Hz, 1H), 7.05 (d, J=8.1 Hz, 2H), 6.89 (d, J=8.1 Hz, 2H), 6.59 (d, J=7.9 Hz, 1H), 6.03 (s, 1H), 4.55 (dd, J=11.5, 2.8 Hz, 2H), 4.29-4.09 (m, 1H), 4.00-3.71 (m, 2H), 3.63-3.50 (m, 3H), 3.40 (dd, J=9.8, 4.6 Hz, 1H), 2.23 (s, 3H), 2.23-2.11 (m, 1H), 2.08 (s, 3H), 1.98-1.83 (m, 1H).

Example 156

7-(3,5-Dimethylisoxazol-4-yl)-9-fluoro-N,N-dimethyl-4-pyridin-3-yl-4,5-dihydroimidazo[1,5,4-de][1,4]benzoxazin-2-amine

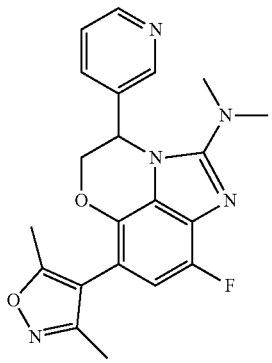 [SMILES: Cc1noc(C)c1-c1cc(F)c2nc(N(C)C)n3c2c1OCC3c1cccnc1]

Step 1. 6-Bromo-4-fluoro-2,3-dinitrophenol

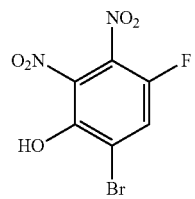 [SMILES: O=[N+]([O-])c1c(F)cc(Br)c(O)c1[N+](=O)[O-]]

To a solution of 2-bromo-4-fluoro-5-nitrophenol (4.0 g, 17 mmol) in methylene chloride (29.5 mL), 2.0 M nitric acid in DCM (25 mL) was added and the mixture was stirred for 15 min at room temperature. The mixture was poured over cold water and extracted with methylene chloride to give the product.

Step 2. 2-Amino-6-bromo-4-fluoro-3-nitrophenol

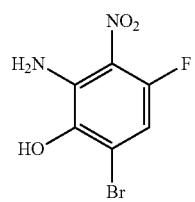

6-Bromo-4-fluoro-2,3-dinitrophenol (4.4 g, 16 mmol) was stirred in methanol (88 mL) and 12.0 M hydrogen chloride in water (40 mL), followed by addition of stannous chloride dihydrate (11 g, 47 mmol) and the mixture was stirred at room temperature for 15 min. The mixture was diluted with water and extracted with ethyl acetate. The organic layer was separated and concentrated. Purification on silica gel eluting ethyl acetate in hexanes gave the amine product.

Step 3. 8-Bromo-6-fluoro-5-nitro-3-pyridin-3-yl-3,4-dihydro-2H-1,4-benzoxazin-3-ol

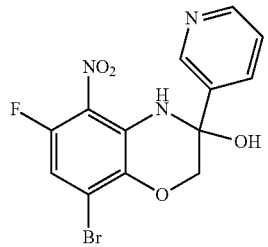 [SMILES: O=[N+]([O-])c1c(F)cc(Br)c2c1NC(O)(c1cccnc1)CO2]

2-Amino-6-bromo-4-fluoro-3-nitrophenol (500 mg, 2.0 mmol) and potassium carbonate (780 mg, 5.7 mmol) were stirred in acetone (8 mL) for 15 min followed by addition of 2-bromo-1-pyridin-3-ylethanone hydrobromide (530 mg, 1.9 mmol) over a period of 5 min. The mixture was stirred at room temperature for 15 min and poured over water. The aqueous mixture was extracted with ethyl acetate. The organic extracts were washed with brine, dried over sodium sulfate, filtered, and concentrated. Purification on silica gel eluting ethyl acetate in hexanes afforded the bicyclic product. LCMS calc. for $C_{13}H_{10}BrFN_3O_4(M+H)^+$: m/z=370.0; found: 370.0.

Step 4. 8-Bromo-6-fluoro-3-pyridin-3-yl-2H-1,4-benzoxazin-5-amine

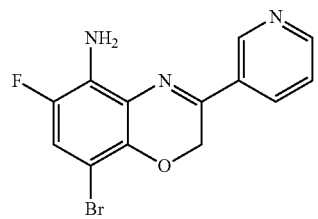 [SMILES: Nc1c(F)cc(Br)c2c1N=C(c1cccnc1)CO2]

Iron (91 mg, 1.6 mmol) was added to a mixture of 8-bromo-6-fluoro-5-nitro-3-pyridin-3-yl-3,4-dihydro-2H-1,4-benzoxazin-3-ol (121.0 mg, 0.3269 mmol) in acetic acid (3 mL), and heated overnight at 60° C. The mixture was extracted with ethyl acetate and the organic layer concentrated. Purification on silica gel eluting ethyl acetate in hexanes afforded product. LCMS calc. for $C_{13}H_{10}BrFN_3O$ $(M+H)^+$: m/z=322.0; found: 322.0.

Step 5. 8-Bromo-6-fluoro-3-pyridin-3-yl-3,4-dihydro-2H-1,4-benzoxazin-5-amine

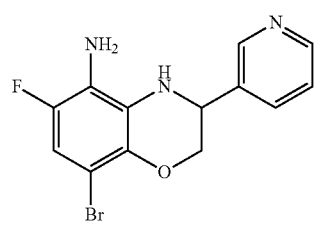 [SMILES: Nc1c(F)cc(Br)c2c1NC(c1cccnc1)CO2]

Sodium tetrahydroborate (44 mg, 1.2 mmol) was added to a solution of 8-bromo-6-fluoro-3-pyridin-3-yl-2H-1,4-benzoxazin-5-amine (190 mg, 0.58 mmol) in ethanol (4 mL) and water (1 mL), and heated at 90° C. for 15 minutes. The mixture was concentrated, diluted with water, and extracted with ethyl acetate. The organic solvents were evaporated to afford the product. LCMS calc. for $C_{13}H_{12}BrFN_3O$ (M+H)$^+$: m/z=324.0; found: 324.0.

Step 6. 7-Bromo-9-fluoro-4-pyridin-3-yl-4,5-dihydroimidazo[1,5,4-de][1,4]benzoxazin-2(1H)-one

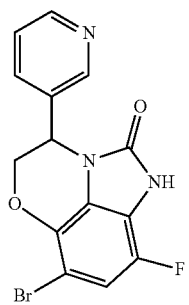 [SMILES: O=c1[nH]c2c(F)cc(Br)c3c2n1C(c1cccnc1)CO3]

Triethylamine (140 µL, 1.0 mmol) was added to a solution of 8-bromo-6-fluoro-3-pyridin-3-yl-3,4-dihydro-2H-1,4-benzoxazin-5-amine (160 mg, 0.50 mmol)) in THF (6.0 mL), followed by addition of triphosgene (60 mg, 0.2 mmol), and the mixture was subsequently stirred at room temperature for 10 min. The mixture was diluted with water and extracted with ethyl acetate. The organic extracts were washed with brine and concentrated. Purification on silica gel eluting ethyl acetate in hexanes afforded the title compound. LCMS calc. for $C_{14}H_{10}BrFN_3O_2$(M+H)$^+$: m/z=350.0; found: 350.0.

Step 7. 7-(3,5-Dimethylisoxazol-4-yl)-9-fluoro-4-pyridin-3-yl-4,5-dihydroimidazo[1,5,4-de][1,4]benzoxazin-2 (1H)-one

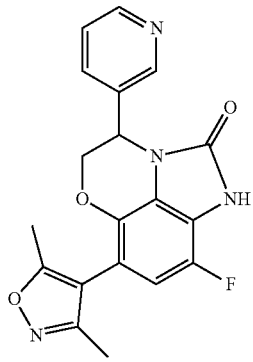 [SMILES: Cc1noc(C)c1-c1cc(F)c2[nH]c(=O)n3c2c1OCC3c1cccnc1]

7-Bromo-9-fluoro-4-pyridin-3-yl-4,5-dihydroimidazo[1,5,4-de][1,4]benzoxazin-2(1H)-one (50 mg, 0.14 mmol), potassium (3,5-dimethylisoxazol-4-yl)(trifluoro)borate(1-) (43 mg, 0.21 mmol), [1,1'-bis(diphenylphosphino)ferrocene]dichloropalladium(II), complex with dichloromethane (1:1) (10 mg, 0.01 mmol) and potassium carbonate (39 mg, 0.28 mmol) were stirred in 1,4-dioxane (1.1 mL) and water (0.28 mL) under a flow of nitrogen gas for 5 min. The mixture was then heated to 90° C. for 6 h. The mixture was diluted with water and extracted with ethyl acetate. The organic extracts were collected and evaporated to give the desired compound. LCMS calc. for $C_{19}H_{16}FN_4O_3$(M+H)$^+$: m/z=367.1; found: 367.1.

Step 8. 2-Chloro-7-(3,5-dimethylisoxazol-4-yl)-9-fluoro-4-pyridin-3-yl-4,5-dihydroimidazo[1,5,4-de][1,4]benzoxazine

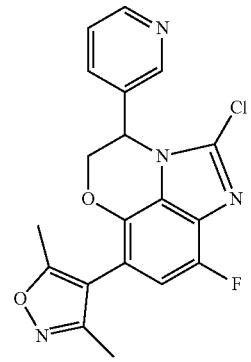 [SMILES: Cc1noc(C)c1-c1cc(F)c2nc(Cl)n3c2c1OCC3c1cccnc1]

Phosphoryl chloride (1.5 mL, 16 mmol) was added to a vial charged with 7-(3,5-dimethylisoxazol-4-yl)-9-fluoro-4-pyridin-3-yl-4,5-dihydroimidazo[1,5,4-de][1,4]benzoxazin-2(1H)-one (32 mg, 0.087 mmol) and the mixture was stirred overnight at 90° C. The mixture was quenched with ice-cold water, diluted with NaHCO$_3$ and extracted with ethyl acetate. The organic extracts were collected and evaporated to afford the title compound. LCMS calc. for $C_{19}H_{15}ClFN_4O_2$ (M+H)$^+$: m/z=385.1; found: 385.1.

Step 9. 7-(3,5-Dimethylisoxazol-4-yl)-9-fluoro-N,N-dimethyl-4-pyridin-3-yl-4,5-dihydroimidazo[1,5,4-de][1,4]benzoxazin-2-amine Triethylamine (16 µL, 0.12 mmol) and dimethylamine (0.2 mL, 4 mmol) were added to 2-chloro-7-(3,5-dimethylisoxazol-4-yl)-9-fluoro-4-pyridin-3-yl-4,5-dihydroimidazo[1,5,4-de][1,4]benzoxazine (15 mg, 0.040 mmol) in N-methylpyrrolidinone (0.41 mL) and the mixture was heated in a microwave at 150° C. for 20 min. The mixture was diluted with methanol and purified by preparative LCMS using pH 10 buffer to afford the title compound (3.0 mg, 19%). LCMS calc. for $C_{21}H_{21}FN_5O_{52}$ (M+H): m/z=394.2; found: 394.1.

Example 157

1-[7-(3,5-Dimethylisoxazol-4-yl)-9-fluoro-4-pyridin-3-yl-4,5-dihydroimidazo[1,5,4-de][1,4]benzoxazin-2-yl]pyrrolidin-3-ol

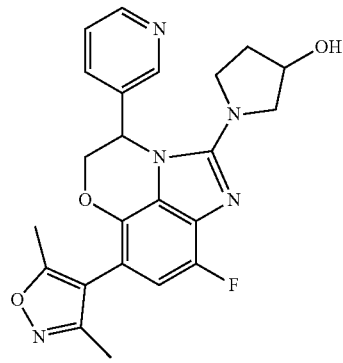 [SMILES: Cc1noc(C)c1-c1cc(F)c2nc(N3CCC(O)C3)n3c2c1OCC3c1cccnc1]

Triethylamine (16 μL, 0.12 mmol) and 3-pyrrolidinol (0.2 mL, 3 mmol) were added to 2-chloro-7-(3,5-dimethylisoxazol-4-yl)-9-fluoro-4-pyridin-3-yl-4,5-dihydroimidazo[1,5,4-de][1,4]benzoxazine (15 mg, 0.040 mmol) in N-methylpyrrolidinone (0.41 mL) and the mixture was heated in a microwave at 150° C. for 20 min. The mixture was diluted with methanol and purified by preparative LCMS using pH 10 buffer to afford the title compound (2.4 mg, 14%). LCMS calc. for $C_{23}H_{23}FN_5O_3(M+H)^+$: m/z=436.2; found: 436.1.

Example 158

7-(3,5-Dimethylisoxazol-4-yl)-N-ethyl-9-fluoro-4-pyridin-3-yl-4,5-dihydroimidazo[1,5,4-de][1,4]benzoxazin-2-amine

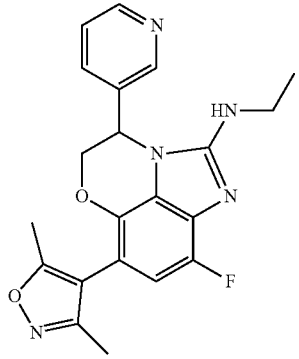 [SMILES: CCNc1nc2c(F)cc(-c3c(C)noc3C)c3c2n1C(c1cccnc1)CO3]

Triethylamine (16 μL, 0.12 mmol) and ethylamine (0.2 mL, 3 mmol) were added to 2-chloro-7-(3,5-dimethylisoxazol-4-yl)-9-fluoro-4-pyridin-3-yl-4,5-dihydroimidazo[1,5,4-de][1,4]benzoxazine (15 mg, 0.040 mmol) in N-methylpyrrolidinone (0.41 mL) and the mixture was heated in a microwave at 150° C. for 20 min. The mixture was diluted with methanol and purified by preparative LCMS using pH 10 buffer to afford the title compound (3.0 mg, 19%). LCMS calc. for $C_{21}H_{21}FN_5O_2$ $(M+H)^+$: m/z=394.2; found: 394.1.

Example 159A (3R)-1-[7-(3,5-Dimethylisoxazol-4-yl)-4-pyridin-3-yl-4,5-dihydroimidazo[1,5,4-de][1,4]benzoxazin-2-yl]pyrrolidin-3-ol (Diastereoisomer 1)

Example 159B (3R)-1-[7-(3,5-Dimethylisoxazol-4-yl)-4-pyridin-3-yl-4,5-dihydroimidazo[1,5,4-de][1,4]benzoxazin-2-yl]pyrrolidin-3-ol (Diastereoisomer 2A)

Example 159C (3R)-1-[7-(3,5-Dimethylisoxazol-4-yl)-4-pyridin-3-yl-4,5-dihydroimidazo[1,5,4-de][1,4]benzoxazin-2-yl]pyrrolidin-3-ol (Diastereoisomer 2B)

Example 159D (3R)-1-[7-(3,5-Dimethylisoxazol-4-yl)-4-pyridin-3-yl-4,5-dihydroimidazo[1,5,4-de][1,4]benzoxazin-2-yl]pyrrolidin-3-ol (Diastereoisomer 3)

Example 159E (3R)-1-[7-(3,5-Dimethylisoxazol-4-yl)-4-pyridin-3-yl-4,5-dihydroimidazo[1,5,4-de][1,4]benzoxazin-2-yl]pyrrolidin-3-ol (Mixture of Diastereoisomers)

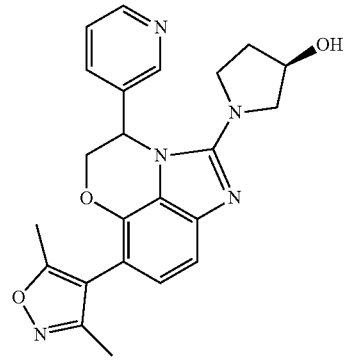 [SMILES: Cc1noc(C)c1-c1ccc2nc(N3CC[C@@H](O)C3)n3c2c1OCC3c1cccnc1]

The title compound was prepared by methods analogous to Example 157, substituting 2-chloro-7-(3,5-dimethylisoxazol-4-yl)-4-pyridin-3-yl-4,5-dihydroimidazo[1,5,4-de][1,4]benzoxazine and 3R-pyrrolidinol. The mixture was diluted with methanol and purified by preparative LCMS using pH 10 buffer to afford the title compound as a mixture of diastereomers (13.3 mg, 75%). LCMS calc. for $C_{23}H_{24}N_5O_3$ $(M+H)^+$: m/z=418.2; found: 418.2. The isomers were separated by prep chiral column chromatography using the following conditions: Column: phenomenex Lux Cellulose C-2 5 μm, 21, 2×250 mm, Mobile phase: 45% EtOH/Hexanes, gradient condition: isocratic at 18 mL/min, Loading: 5.0 mg in 900 μL, run time: 18 min, peak time: 12.0, 14.0 and 16.0 min.

Example 159A, Peak 1, LCMS calc. for $C_{23}H_{24}N_5O_3$ $(M+H)^+$: m/z=418.2; found: 418.2.

Peak 2 was isolated as a mixture of 2 diastereomers and further separated by prep chiral column chromatography: Column: phenomenex Lux Cellulose C-4 5 μm, 21, 2×250 mm, Mobile phase: 30% EtOH/Hexanes, gradient condition: isocratic at 18 mL/min, Loading: 1.5 mg in 900 μL, run time: 23 min, peak time: 18.5 and 20.0 min.

Example 159B, Peak 2A, LCMS calc. for $C_{23}H_{24}N_5O_3$ $(M+H)^+$: m/z=418.2; found: 418.2.

Example 159C, Peak 2B, LCMS calc. for $C_{23}H_{24}N_5O_3$ $(M+H)^+$: m/z=418.2; found: 418.2.

Example 159D, Peak 3, LCMS calc. for $C_{23}H_{24}N_5O_3$ $(M+H)^+$: m/z=418.2; found: 418.2.

Examples 160A

1-[7-(3,5-Dimethylisoxazol-4-yl)-4-pyridin-3-yl-4,5-dihydroimidazo[1,5,4-de][1,4]benzoxazin-2-yl]azetidin-3-ol Examples 160B 1-[7-(3,5-Dimethylisoxazol-4-yl)-4-pyridin-3-yl-4,5-dihydroimidazo[1,5,4-de][1,4]benzoxazin-2-yl]azetidin-3-ol Examples 160C 1-[7-(3,5-Dimethylisoxazol-4-yl)-4-pyridin-3-yl-4,5-dihydroimidazo[1,5,4-de][1,4]benzoxazin-2-yl]azetidin-3-ol Examples 160D 1-[7-(3,5-Dimethylisoxazol-4-yl)-4-pyridin-3-yl-4,5-dihydroimidazo[1,5,4-de][1,4]benzoxazin-2-yl]azetidin-3-ol

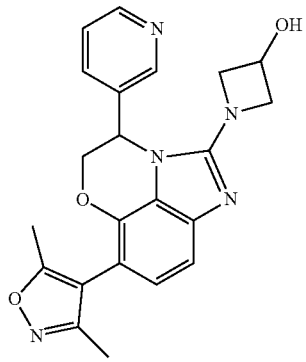 [SMILES: Cc1noc(C)c1-c1ccc2nc(N3CC(O)C3)n3c2c1OCC3c1cccnc1]

The title compound was prepared by methods analogous to Example 157, substituting 2-chloro-7-(3,5-dimethylisoxazol-4-yl)-4-pyridin-3-yl-4,5-dihydroimidazo[1,5,4-de][1,4]benzoxazine, azetidin-3-ol hydrochloride and extending the reaction time to 60 min. The mixture was diluted with methanol and purified by preparative LCMS using pH 10 buffer to give the title compound as a racemic mixture (16 mg, 23%). LCMS calc. for $C_{22}H_{22}N_5O_3$ $(M+H)^+$: m/z=404.2; found: 404.2. The isomers were separated by prep chiral column chromatography using the following conditions: Column: phenomenex Lux Cellulose C-2 5 μm, 21, 2×250 mm, Mobile phase: 45% EtOH/Hexanes, gradient condition: isocratic at 18 mL/min, Loading: 2.0 mg in 900 μL, run time: 24 min, peak time: 12.0, 14.0, 16.0 and 21.0 min.

Example 160A, Peak 1, LCMS calc. for $C_{22}H_{22}N_5O_3$ $(M+H)^+$: m/z=404.2; found: 404.2. $^1$H NMR (500 MHz, DMSO) δ 8.47 (dd, J=4.8, 1.6 Hz, 1H), 8.43 (d, J=2.2 Hz, 1H), 7.58 (dt, J=7.9, 1.9 Hz, 1H), 7.35 (dd, J=7.9, 4.8 Hz, 1H), 6.74 (d, J=7.9 Hz, 1H), 6.70 (d, J=8.0 Hz, 1H), 5.42 (t, 1H), 5.07 (d, J=3.8 Hz, 1H), 4.61 (dd, J=11.6, 1.9 Hz, 1H), 4.36 (dd, J=11.6, 2.9 Hz, 1H), 4.00 (d, J=3.5 Hz, 1H), 3.91 (dd, J=11.5, 2.8 Hz, 1H), 3.67 (dd, J=11.5, 4.2 Hz, 1H), 3.40-3.34 (m, 1H), 3.17 (dd, J=14.3, 4.2 Hz, 1H), 2.24 (s, 3H), 2.07 (s, 3H).

Example 160B, Peak 2, LCMS calc. for $C_{22}H_{22}N_5O_3$ $(M+H)^+$: m/z=404.2; found: 404.2. $^1$H NMR (500 MHz, DMSO) δ 8.47 (dd, J=4.8, 1.6 Hz, 1H), 8.43 (d, J=2.2 Hz, 1H), 7.58 (dt, J=7.9, 1.9 Hz, 1H), 7.35 (dd, J=7.9, 4.8 Hz, 1H), 6.74 (d, J=7.9 Hz, 1H), 6.70 (d, J=8.0 Hz, 1H), 5.42 (t, 1H), 5.07 (d, J=3.8 Hz, 1H), 4.61 (dd, J=11.6, 1.9 Hz, 1H), 4.36 (dd, J=11.6, 2.9 Hz, 1H), 4.00 (d, J=3.5 Hz, 1H), 3.91 (dd, J=11.5, 2.8 Hz, 1H), 3.67 (dd, J=11.5, 4.2 Hz, 1H), 3.40-3.34 (m, 1H), 3.17 (dd, J=14.3, 4.2 Hz, 1H), 2.24 (s, 3H), 2.07 (s, 3H).

Example 160C, Peak 3, LCMS calc. for $C_{22}H_{22}N_5O_3$ $(M+H)^+$: m/z=404.2; found: 404.2. $^1$H NMR (500 MHz, DMSO) δ 8.47 (dd, J=4.8, 1.6 Hz, 1H), 8.43 (d, J=2.2 Hz, 1H), 7.58 (dt, J=7.9, 1.9 Hz, 1H), 7.35 (dd, J=7.9, 4.8 Hz, 1H), 6.74 (d, J=7.9 Hz, 1H), 6.70 (d, J=8.0 Hz, 1H), 5.42 (t, 1H), 5.07 (d, J=3.8 Hz, 1H), 4.61 (dd, J=11.6, 1.9 Hz, 1H), 4.36 (dd, J=11.6, 2.9 Hz, 1H), 4.00 (d, J=3.5 Hz, 1H), 3.91 (dd, J=11.5, 2.8 Hz, 1H), 3.67 (dd, J=11.5, 4.2 Hz, 1H), 3.40-3.34 (m, 1H), 3.17 (dd, J=14.3, 4.2 Hz, 1H), 2.24 (s, 3H), 2.07 (s, 3H).

Example 160D, Peak 4, LCMS calc. for $C_{22}H_{22}N_5O_3$ $(M+H)^+$: m/z=404.2; found: 404.2. $^1$H NMR (500 MHz, DMSO) δ 8.47 (dd, J=4.8, 1.6 Hz, 1H), 8.43 (d, J=2.2 Hz, 1H), 7.58 (dt, J=7.9, 1.9 Hz, 1H), 7.35 (dd, J=7.9, 4.8 Hz, 1H), 6.74 (d, J=7.9 Hz, 1H), 6.70 (d, J=8.0 Hz, 1H), 5.42 (t, 1H), 5.07 (d, J=3.8 Hz, 1H), 4.61 (dd, J=11.6, 1.9 Hz, 1H), 4.36 (dd, J=11.6, 2.9 Hz, 1H), 4.00 (d, J=3.5 Hz, 1H), 3.91 (dd, J=11.5, 2.8 Hz, 1H), 3.67 (dd, J=11.5, 4.2 Hz, 1H), 3.40-3.34 (m, 1H), 3.17 (dd, J=14.3, 4.2 Hz, 1H), 2.24 (s, 3H), 2.07 (s, 3H).

Examples 161-251

The compounds of Examples 161 to 251 are set out in Table 8 below.

TABLE 8

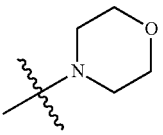

| Ex. No. | Name | R⁵ | Procedure* |
|---|---|---|---|
| 161 | (4S)-7-(3,5-dimethylisoxazol-4-yl)-2-morpholin-4-yl-4-pyridin-2-yl-4,5-dihydroimidazo[1,5,4-de][1,4]benzoxazine | 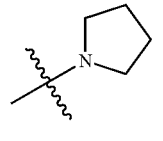 [SMILES: *N1CCCC1] | 25 |
| 162 | (4S)-7-(3,5-dimethylisoxazol-4-yl)-4-pyridin-2-yl-2-pyrrolidin-1-yl-4,5-dihydroimidazo[1,5,4-de][1,4]benzoxazine | 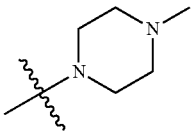 [SMILES: *N1CCN(C)CC1] | 25 |
| 163 | (4S)-7-(3,5-dimethylisoxazol-4-yl)-2-(4-methylpiperazin-1-yl)-4-pyridin-2-yl-4,5-dihydroimidazo[1,5,4-de][1,4]benzoxazine | 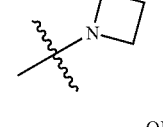 | 25 |
| 164 | (4S)-2-azetidin-1-yl-7-(3,5-dimethylisoxazol-4-yl)-4-pyridin-2-yl-4,5-dihydroimidazo[1,5,4-de][1,4]benzoxazine | 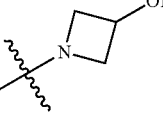 | 25 |
| 165 | 1-[(4S)-7-(3,5-dimethylisoxazol-4-yl)-4-pyridin-2-yl-4,5-dihydroimidazo[1,5,4-de][1,4]benzoxazin-2-yl]azetidin-3-ol | 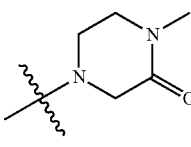 | 25 |
| 166 | 4-[(4S)-7-(3,5-dimethylisoxazol-4-yl)-4-pyridin-2-yl-4,5-dihydroimidazo[1,5,4-de][1,4]benzoxazin-2-yl]-1-methylpiperazin-2-one | 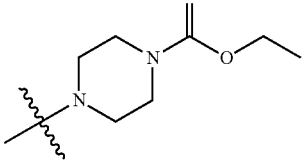 | 25 |
| 167 | ethyl 4-[(4S)-7-(3,5-dimethylisoxazol-4-yl)-4-pyridin-2-yl-4,5-dihydroimidazo[1,5,4-de][1,4]benzoxazin-2-yl]piperazine-1-carboxylate | 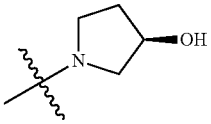 [SMILES: *N1CC[C@@H](O)C1] | 25 |
| 168A | (3R)-1-[(4S)-7-(3,5-Dimethylisoxazol-4-yl)-4-pyridin-3-yl-4,5-dihydroimidazo[1,5,4-de][1,4]benzoxazin-2-yl]pyrrolidin-3-ol | 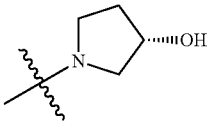 | 25 |
| 168B | (3S)-1-[(4S)-7-(3,5-Dimethylisoxazol-4-yl)-4-pyridin-3-yl-4,5-dihydroimidazo[1,5,4-de][1,4]benzoxazin-2-yl]pyrrolidin-3-ol | | 25 |

TABLE 8-continued

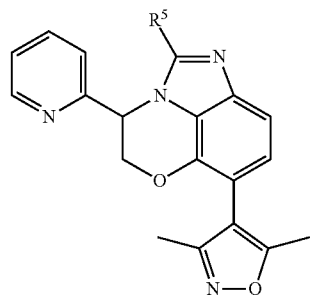

| Ex. No. | Name | R⁵ | Procedure* |
|---|---|---|---|
| 169 | 1-[(4S)-7-(3,5-dimethylisoxazol-4-yl)-4-pyridin-2-yl-4,5-dihydroimidazo[1,5,4-de][1,4]benzoxazin-2-yl]piperidin-4-ol | 4-hydroxypiperidin-1-yl | 25 |
| 170A | (3R)-1-[(4S)-7-(3,5-dimethylisoxazol-4-yl)-4-pyridin-2-yl-4,5-dihydroimidazo[1,5,4-de][1,4]benzoxazin-2-yl]piperidin-3-ol | (3R)-3-hydroxypiperidin-1-yl | 25 |
| 170B | (3S)-1-[(4S)-7-(3,5-dimethylisoxazol-4-yl)-4-pyridin-2-yl-4,5-dihydroimidazo[1,5,4-de][1,4]benzoxazin-2-yl]piperidin-3-ol | (3S)-3-hydroxypiperidin-1-yl | 25 |
| 171 | 1-[(4S)-7-(3,5-dimethylisoxazol-4-yl)-4-pyridin-2-yl-4,5-dihydroimidazo[1,5,4-de][1,4]benzoxazin-2-yl]-N,N-dimethylpiperidin-4-amine | 4-(dimethylamino)piperidin-1-yl | 25 |
| 172 | 4-[(4S)-7-(3,5-dimethylisoxazol-4-yl)-4-pyridin-2-yl-4,5-dihydroimidazo[1,5,4-de][1,4]benzoxazin-2-yl]piperazin-2-one | 3-oxopiperazin-1-yl | 25 |
| 173 | (4S)-7-(3,5-dimethylisoxazol-4-yl)-2-[4-(methylsulfonyl)piperazin-1-yl]-4-pyridin-2-yl-4,5-dihydroimidazo[1,5,4-de][1,4]benzoxazine | 4-(methylsulfonyl)piperazin-1-yl | 25 |
| 174 | (4S)-7-(3,5-dimethylisoxazol-4-yl)-2-(4-isopropylpiperazin-1-yl)-4-pyridin-2-yl-4,5-dihydroimidazo[1,5,4-de][1,4]benzoxazine | 4-isopropylpiperazin-1-yl | 25 |

TABLE 8-continued

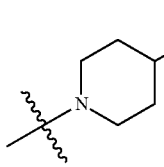

| Ex. No. | Name | R⁵ | Procedure* |
|---|---|---|---|
| 175 | 1-[(4S)-7-(3,5-dimethylisoxazol-4-yl)-4-pyridin-2-yl-4,5-dihydroimidazo[1,5,4-de][1,4]benzoxazin-2-yl]piperidine-4-carbonitrile | 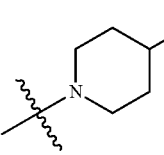 | 25 |
| 176 | {1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}methanol | 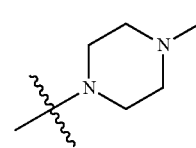 | 25 |
| 177 | 2-{4-[(4S)-7-(3,5-dimethylisoxazol-4-yl)-4-pyridin-2-yl-4,5-dihydroimidazo[1,5,4-de][1,4]benzoxazin-2-yl]piperazin-1-yl}ethanol | 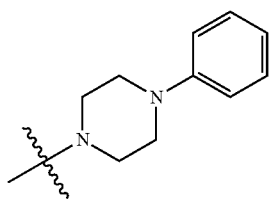 [SMILES: *N1CCN(c2ccccc2)CC1] | 25 |
| 178 | (4S)-7-(3,5-dimethylisoxazol-4-yl)-2-(4-phenylpiperazin-1-yl)-4-pyridin-2-yl-4,5-dihydroimidazo[1,5,4-de][1,4]benzoxazine | 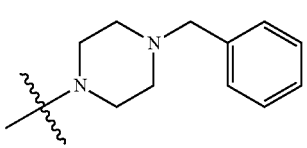 [SMILES: *N1CCN(Cc2ccccc2)CC1] | 25 |
| 179 | (4S)-2-(4-benzylpiperazin-1-yl)-7-(3,5-dimethylisoxazol-4-yl)-4-pyridin-2-yl-4,5-dihydroimidazo[1,5,4-de][1,4]benzoxazine | 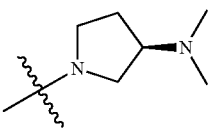 [SMILES: *N1CC[C@@H](N(C)C)C1] | 25 |
| 180A | (3R)-1-[(4S)-7-(3,5-dimethylisoxazol-4-yl)-4-pyridin-2-yl-4,5-dihydroimidazo[1,5,4-de][1,4]benzoxazin-2-yl]-N,N-dimethylpyrrolidin-3-amine | 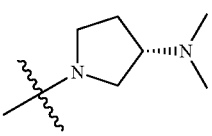 [SMILES: *N1CC[C@H](N(C)C)C1] | 25 |
| 180B | (3S)-1-[(4S)-7-(3,5-dimethylisoxazol-4-yl)-4-pyridin-2-yl-4,5-dihydroimidazo[1,5,4-de][1,4]benzoxazin-2-yl]-N,N-dimethylpyrrolidin-3-amine | 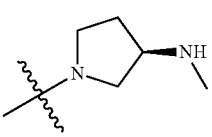 [SMILES: *N1CC[C@@H](NC)C1] | 25 |
| 181A | (3R)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidin-3-amine | | 25 |

TABLE 8-continued

| Ex. No. | Name | R⁵ | Procedure* |
|---|---|---|---|
| 181B | (3S)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidin-3-amine | | 25 |
| 182A | tert-butyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate | | 25 |
| 182B | tert-butyl {(3S)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate | | 25 |
| 183 | (4S)-2-[4-(cyclopropylmethyl)piperazin-1-yl]-7-(3,5-dimethylisoxazol-4-yl)-4-pyridin-2-yl-4,5-dihydroimidazo[1,5,4-de][1,4]benzoxazine | | 25 |
| 184 | (4S)-7-(3,5-dimethylisoxazol-4-yl)-2-[4-(2-methoxyethyl)piperazin-1-yl]-4-pyridin-2-yl-4,5-dihydroimidazo[1,5,4-de][1,4]benzoxazine | | 25 |
| 185 | 2-[[7-(3,5-dimethylisoxazol-4-yl)-4-pyridin-2-yl-4,5-dihydroimidazo[1,5,4-de][1,4]benzoxazin-2-yl](methyl)amino]ethanol | | 25 |
| 186 | 7-(3,5-dimethylisoxazol-4-yl)-N-methyl-4-pyridin-2-yl-4,5-dihydroimidazo[1,5,4-de][1,4]benzoxazin-2-amine | | 25 |
| 187 | 7-(3,5-dimethylisoxazol-4-yl)-N,N-dimethyl-4-pyridin-2-yl-4,5-dihydroimidazo[1,5,4-de][1,4]benzoxazin-2-amine | | 25 |
| 188 | 1-[(4S)-7-(3,5-dimethylisoxazol-4-yl)-4-pyridin-2-yl-4,5-dihydroimidazo[1,5,4-de][1,4]benzoxazin-2-yl]piperidine-4-carboxamide | | 25 |

TABLE 8-continued

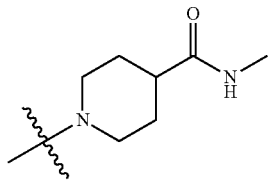 [SMILES: *N1CCC(C(=O)NC)CC1]

| Ex. No. | Name | R⁵ | Procedure* |
|---|---|---|---|
| 189 | 1-[(4S)-7-(3,5-dimethylisoxazol-4-yl)-4-pyridin-2-yl-4,5-dihydroimidazo[1,5,4-de][1,4]benzoxazin-2-yl]-N-methylpiperidine-4-carboxamide | 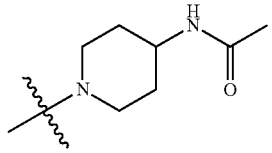 [SMILES: *N1CCC(NC(C)=O)CC1] | 25 |
| 190 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}acetamide | 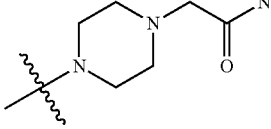 | 25 |
| 191 | 2-{4-[(4S)-7-(3,5-dimethylisoxazol-4-yl)-4-pyridin-2-yl-4,5-dihydroimidazo[1,5,4-de][1,4]benzoxazin-2-yl]piperazin-1-yl}acetamide | 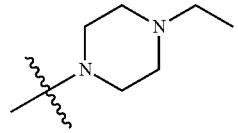 [SMILES: *N1CCN(CC)CC1] | 25 |
| 192 | (4S)-7-(3,5-dimethylisoxazol-4-yl)-2-(4-ethylpiperazin-1-yl)-4-pyridin-2-yl-4,5-dihydroimidazo[1,5,4-de][1,4]benzoxazine | 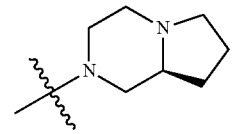 [SMILES: *N1CCN2CCC[C@H]2C1] | 25 |
| 193A | (4S)-7-(3,5-dimethylisoxazol-4-yl)-2-[(8aS)-hexahydropyrrolo[1,2-a]pyrazin-2(1H)-yl]-4-pyridin-2-yl-4,5-dihydroimidazo[1,5,4-de][1,4]benzoxazine | 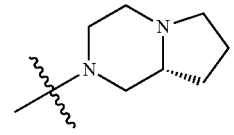 [SMILES: *N1CCN2CCC[C@@H]2C1] | 25 |
| 193B | (4S)-7-(3,5-dimethylisoxazol-4-yl)-2-[(8aR)-hexahydropyrrolo[1,2-a]pyrazin-2(1H)-yl]-4-pyridin-2-yl-4,5-dihydroimidazo[1,5,4-de][1,4]benzoxazine | 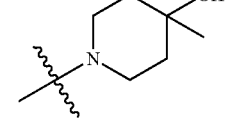 | 25 |
| 194 | 1-[(4S)-7-(3,5-dimethylisoxazol-4-yl)-4-pyridin-2-yl-4,5-dihydroimidazo[1,5,4-de][1,4]benzoxazin-2-yl]-4-methylpiperidin-4-ol | 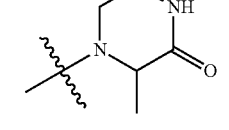 | 25 |
| 195 | 4-[(4S)-7-(3,5-dimethylisoxazol-4-yl)-4-pyridin-2-yl-4,5-dihydroimidazo[1,5,4-de][1,4]benzoxazin-2-yl]-3-methylpiperazin-2-one | | 25 |

TABLE 8-continued

| Ex. No. | Name | R⁵ | Procedure* |
|---|---|---|---|
| 196 | tert-butyl {1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}carbamate | | 25 |
| 197 | tert-butyl 4-[(4S)-7-(3,5-dimethylisoxazol-4-yl)-4-pyridin-2-yl-4,5-dihydroimidazo[1,5,4-de][1,4]benzoxazin-2-yl]-1,4-diazepane-1-carboxylate | | 25 |
| 198 | 2-{[(4S)-7-(3,5-dimethylisoxazol-4-yl)-4-pyridin-2-yl-4,5-dihydroimidazo[1,5,4-de][1,4]benzoxazin-2-yl]amino}ethanol | | 25 |
| 199 | tert-butyl (2-{[(4S)-7-(3,5-dimethylisoxazol-4-yl)-4-pyridin-2-yl-4,5-dihydroimidazo[1,5,4-de][1,4]benzoxazin-2-yl]amino}ethyl)carbamate | | 25 |
| 200 | N-[(4S)-7-(3,5-dimethylisoxazol-4-yl)-4-pyridin-2-yl-4,5-dihydroimidazo[1,5,4-de][1,4]benzoxazin-2-yl]ethane-1,2-diamine | | 150 |
| 201A | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}acetamide | | 25 |
| 201B | N-{(3S)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}acetamide | | 25 |
| 202A | (3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-amine trihydrochloride | | 150 |

TABLE 8-continued

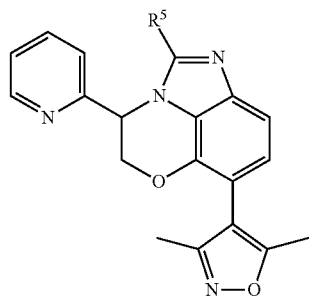

| Ex. No. | Name | R⁵ | Procedure* |
|---|---|---|---|
| 202B | (3S)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-amine trihydrochloride | pyrrolidin-3-yl with NH₂ | 150 |
| 203 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2,2,2-trifluoroacetamide | pyrrolidinyl-NH-C(O)CF₃ | 148 |
| 205 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2-methoxyacetamide | pyrrolidinyl-NH-C(O)CH₂OCH₃ | 148 |
| 206 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}cyclopropanecarboxamide | pyrrolidinyl-NH-C(O)-cyclopropyl | 148 |
| 207 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}methanesulfonamide | pyrrolidinyl-NH-S(O)₂CH₃ | 149 |
| 208 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}propanamide | pyrrolidinyl-NH-C(O)CH₂CH₃ | 148 |
| 209 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2-methylpropanamide | pyrrolidinyl-NH-C(O)CH(CH₃)₂ | 148 |

TABLE 8-continued

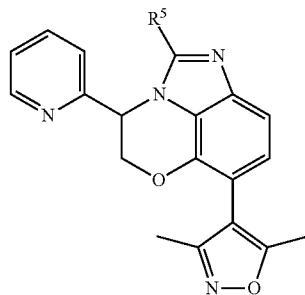

| Ex. No. | Name | R⁵ | Procedure* |
|---|---|---|---|
| 210 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}cyclobutanecarboxamide | | 148 |
| 211 | 2-cyano-N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}acetamide | | 152 |
| 213 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}tetrahydro-2H-pyran-4-carboxamide | | 148 |
| 214 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}ethanesulfonamide | | 149 |
| 215 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}propane-1-sulfonamide | | 149 |
| 216 | N'-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N,N-dimethylurea | | 153 |

TABLE 8-continued

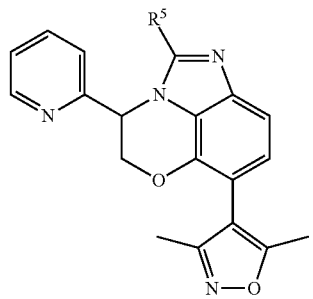

| Ex. No. | Name | R⁵ | Procedure* |
|---|---|---|---|
| 217 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}propane-2-sulfonamide | | 149 |
| 218 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}cyclopropanesulfonamide | | 149 |
| 219 | methyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}methylcarbamate | | 155 |
| 220 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N-methylmethanesulfonamide | | 149 |
| 221 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2-methoxy-N-methylacetamide | | 148 |
| 222 | N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N-methylacetamide | | 148 |
| 224 | (4S)-2-(4-acetylpiperazin-1-yl)-7-(3,5-dimethylisoxazol-4-yl)-4-pyridin-2-yl-4,5-dihydroimidazo[1,5,4-de][1,4]benzoxazine | | 148 |

TABLE 8-continued

| Ex. No. | Name | R⁵ | Procedure* |
|---|---|---|---|
| 225 | (4S)-7-(3,5-dimethylisoxazol-4-yl)-2-(4-propionylpiperazin-1-yl)-4-pyridin-2-yl-4,5-dihydroimidazo[1,5,4-de][1,4]benzoxazine | | 148 |
| 226 | (4S)-7-(3,5-dimethylisoxazol-4-yl)-2-[4-(ethylsulfonyl)piperazin-1-yl]-4-pyridin-2-yl-4,5-dihydroimidazo[1,5,4-de][1,4]benzoxazine | | 149 |
| 228 | (4S)-7-(3,5-dimethylisoxazol-4-yl)-2-[4-(2-oxo-2-pyrrolidin-1-ylethyl)piperazin-1-yl]-4-pyridin-2-yl-4,5-dihydroimidazo[1,5,4-de][1,4]benzoxazine | | 151 |
| 229 | 4-[(4S)-7-(3,5-dimethylisoxazol-4-yl)-4-pyridin-2-yl-4,5-dihydroimidazo[1,5,4-de][1,4]benzoxazin-2-yl]piperazine-1-sulfonamide | | 147 |
| 230 | 1-[(4S)-7-(3,5-dimethylisoxazol-4-yl)-4-pyridin-2-yl-4,5-dihydroimidazo[1,5,4-de][1,4]benzoxazin-2-yl]azetidin-3-amine trihydrochloride | | 150 |
| 231 | N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}acetamide | | 148 |
| 232 | N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}propanamide | | 148 |

TABLE 8-continued

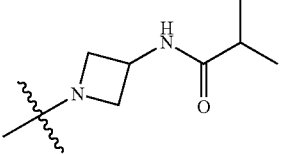 [SMILES: *N1CC(NC(=O)C(C)C)C1]

| Ex. No. | Name | R⁵ | Procedure* |
|---|---|---|---|
| 233 | N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}-2-methylpropanamide | 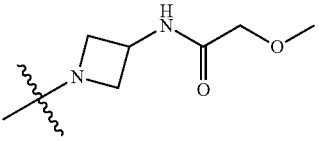 [SMILES: *N1CC(NC(=O)COC)C1] | 148 |
| 234 | N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}-2-methoxyacetamide | 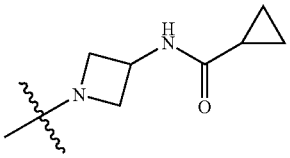 [SMILES: *N1CC(NC(=O)C2CC2)C1] | 148 |
| 235 | N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}cyclopropanecarboxamide | 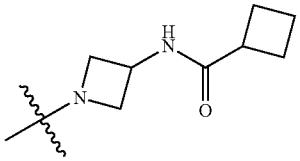 [SMILES: *N1CC(NC(=O)C2CCC2)C1] | 148 |
| 236 | N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}cyclobutanecarboxamide | 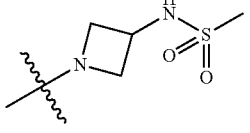 | 148 |
| 237 | N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}methanesulfonamide | 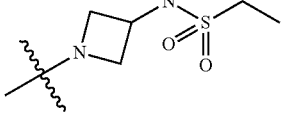 | 149 |
| 238 | N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}ethanesulfonamide | 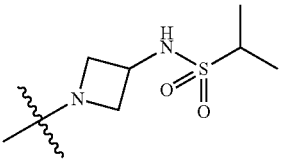 [SMILES: *N1CC(NS(=O)(=O)C(C)C)C1] | 149 |
| 239 | N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}propane-2-sulfonamide | | 149 |

TABLE 8-continued

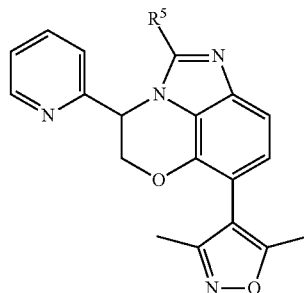

| Ex. No. | Name | R[5] | Procedure* |
|---|---|---|---|
| 240 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}methanesulfonamide | | 149 |
| 241 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-2-methoxyacetamide | | 149 |
| 242 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-2,2,2-trifluoroacetamide | | 148 |
| 243 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}propanamide | | 148 |
| 244 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}propanamide | | 148 |

TABLE 8-continued

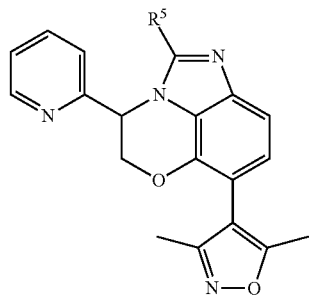

| Ex. No. | Name | R⁵ | Procedure* |
|---|---|---|---|
| 246 | (4S)-7-(3,5-dimethylisoxazol-4-yl)-2-(4-propionyl-1,4-diazepan-1-yl)-4-pyridin-2-yl-4,5-dihydroimidazo[1,5,4-de][1,4]benzoxazine | | 148 |
| 248 | (4S)-7-(3,5-dimethylisoxazol-4-yl)-2-[4-(ethylsulfonyl)-1,4-diazepan-1-yl]-4-pyridin-2-yl-4,5-dihydroimidazo[1,5,4-de][1,4]benzoxazine | | 149 |
| 249 | (3R)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidine-3-carboxamide | | 145 |
| 250 | (3R)-1-[(4S)-7-(3,5-dimethylisoxazol-4-yl)-4-pyridin-2-yl-4,5-dihydroimidazo[1,5,4-de][1,4]benzoxazin-2-yl]-N-ethylpyrrolidine-3-carboxamide | | 145 |
| 251 | (3R)-N-cyclopropyl-1-[(4S)-7-(3,5-dimethylisoxazol-4-yl)-4-pyridin-2-yl-4,5-dihydroimidazo[1,5,4-de][1,4]benzoxazin-2-yl]pyrrolidine-3-carboxamide | | 145 |

*The number in this column indicates the Example number of the procedure used to prepare the compound.

Example 252

(4S)-8,9-dichloro-7-(3,5-dimethylisoxazol-4-yl)-4-pyridin-2-yl-4,5-dihydroimidazo[1,5,4-de][1,4]benzoxazin-2(1H)-one bistrifluoroacetate

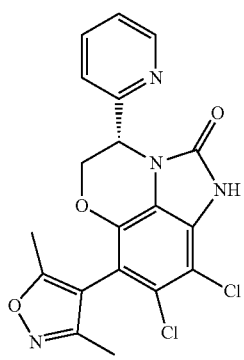 [SMILES: Cc1noc(C)c1-c1c(Cl)c(Cl)c2[nH]c(=O)n3c2c1OC[C@@H]3c1ccccn1]

A mixture of (4S)-7-(3,5-dimethylisoxazol-4-yl)-4-pyridin-2-yl-4,5-dihydroimidazo[1,5,4-de][1,4]benzoxazin-2(1H)-one (35 mg, 0.10 mmol) N-chlorosuccinimide (15 mg, 0.11 mmol) and tetrahydrofuran (1.0 mL) was stirred at 60° C. for 3 hrs. The mixture was extracted with EtOAc, dried, concentrated, purified on silicagel and eluted with 40% EtOAc in hexane. Purification by preparative LCMS using pH 2 buffer gave the title compound as a bistrifluoroacetate salt. LCMS calc. for $C_{19}H_{15}Cl_2N_4O_3$ $(M+H)^+$: m/z=417.0; found: 417.2.

Example 253

7-(3,5-Dimethylisoxazol-4-yl)-9-[(isopropylamino)methyl]-4-pyridin-2-yl-4,5-dihydroimidazo[1,5,4-de][1,4]benzoxazin-2(1H)-one

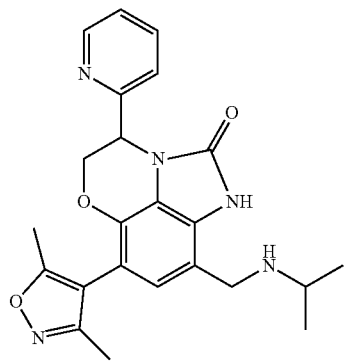 [SMILES: Cc1noc(C)c1-c1cc(CNC(C)C)c2[nH]c(=O)n3c2c1OCC3c1ccccn1]

7-(3,5-Dimethylisoxazol-4-yl)-2-oxo-4-pyridin-2-yl-1,2,4,5-tetrahydroimidazo[1,5,4-de][1,4]benzoxazine-9-carbaldehyde (15 mg, 0.04 mmol) from Example 137, Step 3 was stirred in methanol (1.0 mL) with 2-propanamine (10. L, 0.12 mmol), followed by addition of sodium cyanoborohydride (7.5 mg, 0.12 mmol). The mixture was heated at 60° C. overnight, then diluted with methanol. Purification by preparative LCMS (pH 10) afforded the title compound. LCMS calc. for $C_{23}H_{26}N_5O_3$ $(M+H)^+$: m/z=420.2; found: 420.1.

Example 254

7-(3,5-Dimethylisoxazol-4-yl)-9-(hydroxymethyl)-4-pyridin-2-yl-4,5-dihydroimidazo[1,5,4-de][1,4]benzoxazin-2(1H)-one

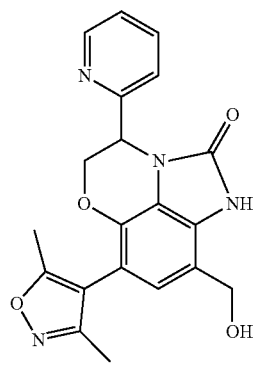 [SMILES: Cc1noc(C)c1-c1cc(CO)c2[nH]c(=O)n3c2c1OCC3c1ccccn1]

7-(3,5-Dimethylisoxazol-4-yl)-2-oxo-4-pyridin-2-yl-1,2,4,5-tetrahydroimidazo[1,5,4-de][1,4]benzoxazine-9-carbaldehyde (15 mg, 0.040 mmol) from Example 137, Step 3 was stirred in ethanol (0.58 mL), followed by addition of sodium tetrahydroborate (2.3 mg, 0.060 mmol). The mixture was stirred at room temperature for 1 h. Purification by preparative LCMS (pH 10) afforded the title compound. LCMS calc. for $C_{20}H_{19}N_4O_4$ $(M+H)^+$: m/z=379.1; found: 379.2.

Example 255

7-(3,5-Dimethylisoxazol-4-yl)-4-pyridin-2-yl-4,5-dihydroimidazo[1,5,4-de][1,4]benzoxazine-2(1H)-thione

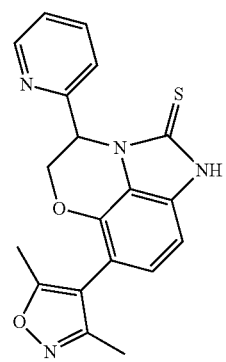 [SMILES: Cc1noc(C)c1-c1ccc2[nH]c(=S)n3c2c1OCC3c1ccccn1]

7-(3,5-Dimethylisoxazol-4-yl)-4-pyridin-2-yl-4,5-dihydroimidazo[1,5,4-de][1,4]benzoxazin-2(1H)-one (50 mg, 0.1 mmol) from Example 13 was stirred in 1,4-dioxane (2 mL) and 2,4-bis(4-methoxyphenyl)-2,4-dithioxo-1,3,2,4-dithiadiphosphetane [Aldrich #: 227439] (58 mg, 0.14 mmol) was added. The mixture was heated to 100° C. for 3 h and concentrated. Purification by preparative LCMS (pH 10) afforded the title compound. LCMS calc. for $C_{19}H_{17}N_4O_2S$ $(M+H)^+$: m/z=365.1; found: 365.1.

Examples 256-269B

The experimental procedures used to prepare the compounds of Examples 256 to 269B are summarized in Table 9 below.

TABLE 9

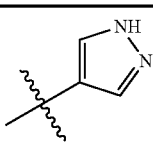

| Ex. No. | Name | R⁷ | Procedure* |
|---|---|---|---|
| 256 | 7-(3,5-dimethylisoxazol-4-yl)-9-(1H-pyrazol-4-yl)-4-pyridin-2-yl-4,5-dihydroimidazo[1,5,4-de][1,4]benzoxazin-2(1H)-one | 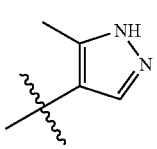 [SMILES: *c1cn[nH]c1C] | 43 |
| 257 | 7-(3,5-dimethylisoxazol-4-yl)-9-(3-methyl-1H-pyrazol-4-yl)-4-pyridin-2-yl-4,5-dihydroimidazo[1,5,4-de][1,4]benzoxazin-2(1H)-one | 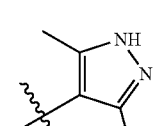 | 43 |
| 258 | 7-(3,5-dimethylisoxazol-4-yl)-9-(3,5-dimethyl-1H-pyrazol-4-yl)-4-pyridin-2-yl-4,5-dihydroimidazo[1,5,4-de][1,4]benzoxazin-2(1H)-one | 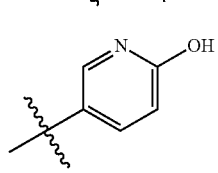 | 43 |
| 259 | (4S)-7-(3,5-dimethylisoxazol-4-yl)-9-(6-hydroxypyridin-3-yl)-4-pyridin-2-yl-4,5-dihydroimidazo[1,5,4-de][1,4]benzoxazin-2(1H)-one | 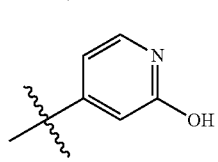 [SMILES: *c1ccnc(O)c1] | 43 |
| 260 | (4S)-7-(3,5-dimethylisoxazol-4-yl)-9-(2-hydroxypyridin-4-yl)-4-pyridin-2-yl-4,5-dihydroimidazo[1,5,4-de][1,4]benzoxazin-2(1H)-one | 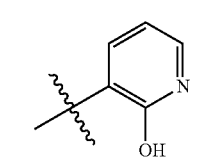 [SMILES: *c1cccnc1O] | 43 |
| 261 | (4S)-7-(3,5-dimethylisoxazol-4-yl)-9-(2-hydroxypyridin-3-yl)-4-pyridin-2-yl-4,5-dihydroimidazo[1,5,4-de][1,4]benzoxazin-2(1H)-one | 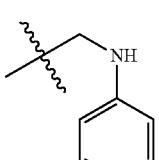 | 43 |
| 262 | 9-(anilinomethyl)-7-(3,5-dimethylisoxazol-4-yl)-4-pyridin-2-yl-4,5-dihydroimidazo[1,5,4-de][1,4]benzoxazin-2(1H)-one | 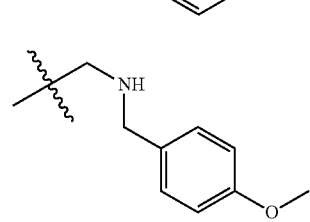 | 253 |
| 263 | 7-(3,5-dimethylisoxazol-4-yl)-9-{[(4-methoxybenzyl)amino]methyl}-4-pyridin-2-yl-4,5-dihydroimidazo[1,5,4-de][1,4]benzoxazin-2(1H)-one | | 253 |

TABLE 9-continued

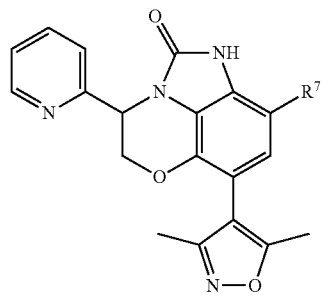

| Ex. No. | Name | R⁷ | Procedure* |
|---|---|---|---|
| 264 | 7-(3,5-dimethylisoxazol-4-yl)-9-(1-hydroxy-2-methylpropyl)-4-pyridin-2-yl-4,5-dihydroimidazo[1,5,4-de][1,4]benzoxazin-2(1H)-one | OH (1-hydroxy-2-methylpropyl group) | 144 |
| 265A | 7-(3,5-dimethylisoxazol-4-yl)-9-fluoro-4-pyridin-2-yl-4,5-dihydroimidazo[1,5,4-de][1,4]benzoxazin-2(1H)-one | F | 155 |
| 265B | 7-(3,5-dimethylisoxazol-4-yl)-9-fluoro-4-pyridin-2-yl-4,5-dihydroimidazo[1,5,4-de][1,4]benzoxazin-2(1H)-one | F | 155 |
| 266A | 9-chloro-7-(3,5-dimethylisoxazol-4-yl)-4-pyridin-2-yl-4,5-dihydroimidazo[1,5,4-de][1,4]benzoxazin-2(1H)-one | Cl | 36 |
| 266B | 9-chloro-7-(3,5-dimethylisoxazol-4-yl)-4-pyridin-2-yl-4,5-dihydroimidazo[1,5,4-de][1,4]benzoxazin-2(1H)-one | Cl | 36 |
| 267A | 9-bromo-7-(3,5-dimethylisoxazol-4-yl)-4-pyridin-2-yl-4,5-dihydroimidazo[1,5,4-de][1,4]benzoxazin-2(1H)-one | Br | 36 |
| 267B | 9-bromo-7-(3,5-dimethylisoxazol-4-yl)-4-pyridin-2-yl-4,5-dihydroimidazo[1,5,4-de][1,4]benzoxazin-2(1H)-one | Br | 36 |
| 268 | 7-(3,5-dimethylisoxazol-4-yl)-9-methyl-4-pyridin-2-yl-4,5-dihydroimidazo[1,5,4-de][1,4]benzoxazin-2(1H)-one | Me | 37 |
| 269A | 7-(3,5-dimethylisoxazol-4-yl)-2-oxo-4-pyridin-2-yl-1,2,4,5-tetrahydroimidazo[1,5,4-de][1,4]benzoxazine-9-carbonitrile | CN | 42 |
| 269B | 7-(3,5-dimethylisoxazol-4-yl)-2-oxo-4-pyridin-2-yl-1,2,4,5-tetrahydroimidazo[1,5,4-de][1,4]benzoxazine-9-carbonitrile | CN | 42 |

*The number in this column indicates the Example number of the procedure used to prepare the compound.

Analytical Data $^1$H NMR data (Varian Inova 500 spectrometer, a Mercury 400 spectrometer, or a Varian (or Mercury) 300 spectrometer) and LCMS mass spectral data (MS) for the compounds of Examples 47A-51, 75-87, 104-108, 110-119, 134-136, and 139-143 are provided below in Table 10.

TABLE 10

| Example No. | MS [M + H]$^+$ | $^1$H NMR Spectrum |
|---|---|---|
| 47A | 419.1 | |
| 47B | 419.1 | |
| 48A | 435.1 | |
| 48B | 435.1 | |
| 49 | 366.1 | $^1$H NMR (300 MHz, DMSO-d6) δ 10.95 (s, 1H), 7.22-7.05 (m, 4H), 6.80 (d, J = 8.0 Hz, 1H), 6.71 (d, J = 8.0 Hz, 1H), 5.43 (s, 1H), 4.50 (dd, J = 11.6, 2.4 Hz, 1H), 4.33 (dd, J = 11.6, 3.0 Hz, 1H), 2.20 (s, 3H), 2.03 (s, 3H). |
| 50 | 465.1 | $^1$H NMR (500 MHz, DMSO) δ 10.91 (s, 1H), 8.51 (d, J = 4.6 Hz, 1H), 7.78 (td, J = 7.7, 1.7 Hz, 1H), 7.32 (dd, J = 7.2, 5.0 Hz, 1H), 7.19 (d, J = 7.8 Hz, 1H), 6.82 (d, J = 8.0 Hz, 1H), 6.73 (d, J = 8.0 Hz, 1H), 5.16 (d, J = 3.9 Hz, 1H), 4.90-4.72 (m, 1H), 2.24 (s, 3H), 2.07 (s, 3H), 1.29 (d, J = 6.5 Hz, 3H). |
| 51 | 449.1 | |
| 75 | 363.1 | $^1$H NMR (400 MHz, dmso) δ 10.98 (s, 1H), 8.47 (s, 1H), 7.79 (s, 1H), 7.55 (s, 1H), 7.41 (s, 1H), 7.33 (s, 1H), 7.22 (s, 1H), 6.78 (s, 1H), 6.72 (s, 1H), 5.73 (m, 1H), 5.40-5.34 (m, 1H), 2.19 (s, 3H), 2.01 (s, 3H). |
| 76 | 406.1 | $^1$H NMR (400 MHz, dmso) δ 11.04 (s, 1H), 8.54 (d, J = 2.7 Hz, 1H), 8.32 (s, 1H), 7.64 (s, 1H), 6.87 (d, J = 8.0 Hz, 1H), 6.77 (d, J = 8.0 Hz, 1H), 5.59 (s, 1H), 4.62 (dd, J = 11.7, 3.4 Hz, 1H), 4.52-4.39 (m, 1H), 2.26 (s, 3H), 2.09 (s, 3H) |
| 77 | 392.1 | $^1$H NMR (400 MHz, dmso) δ 10.78 (s, 1H), 6.76 (d, J = 8.0 Hz, 1H), 6.65 (d, J = 8.0 Hz, 1H), 4.75 (d, 1H), 4.64 (d, 1H), 4.06-4.00 (m, 1H), 3.97-3.90 (m, 1H), 3.67-3.49 (m, 2H), 2.62 (s, 3H), 2.28 (s, 3H), 2.11 (s, 3H), 1.98-1.88 (m, 1H), 1.7-1.58 (m 4H), 1.37 (s, 1H). |
| 78 | 367.0 | $^1$H NMR (500 MHz, DMSO) δ 10.91 (s, 1H), 8.51 (d, J = 4.6 Hz, 1H), 7.78 (td, J = 7.7, 1.7 Hz, 1H), 7.32 (dd, J = 7.2, 5.0 Hz, 1H), 7.19 (d, J = 7.8 Hz, 1H), 6.82 (d, J = 8.0 Hz, 1H), 6.73 (d, J = 8.0 Hz, 1H), 5.16 (d, J = 3.9 Hz, 1H), 4.90-4.72 (m, 1H), 2.24 (s, 3H), 2.07 (s, 3H), 1.29 (d, J = 6.5 Hz, 3H). |
| 79 | 433.1 | $^1$H NMR (400 MHz, dmso) δ 10.61 (s, 1H), 6.74 (d, J = 8.0 Hz, 1H), 6.61 (d, J = 7.9 Hz, 1H), 5.30 (bs, 1H), 4.74-4.59 (m, 2H), 4.43-4.32 (m, 1H), 3.99 (d, J = 9.9 Hz, 1H), 3.80-3.66 (m, 1H), 3.44-3.26 (m, 2H), 2.29 (s, 3H), 2.12 (s, 3H), 1.94-1.86 (m, 1H), 1.69-1.39 (m, 4H), 1.32-1.17 (m, 1H), 0.83 (d, J = 6.5 Hz, 3H), 0.74 (d, J = 6.3 Hz, 3H). |
| 80 | 440.2 | $^1$H NMR (400 MHz, dmso) δ 11.01 (s, 1H), 8.46 (d, J = 4.0 Hz, 1H), 8.19 (s, 1H), 7.90 (s, 1H), 7.73 (td, J = 7.7, 1.7 Hz, 1H), 7.27 (dd, J = 6.7, 4.8 Hz, 1H), 7.10 (d, J = 7.9 Hz, 1H), 6.98 (s, 1H), 5.50 (s, 1H), 4.71 (dd, J = 11.4, 1.9 Hz, 1H), 4.39 (dd, J = 11.4, 3.0 Hz, 1H), 3.81 (s, 3H), 2.19 (s, 3H), 2.02 (s, 3H). |
| 81 | 429.1 | $^1$H NMR (400 MHz, dmso) δ 11.45 (s, 1H), 8.86-8.78 (m, 1H), 8.56-8.48 (m, 1H), 8.12 (dd, J = 8.1, 2.3 Hz, 1H), 7.80 (td, J = 7.7, 1.8 Hz, 1H), 7.63 (dd, J = 8.1, 0.7 Hz, 1H), 7.33 (dd, J = 6.6, 4.8 Hz, 1H), 7.21 (d, J = 8.0 Hz, 1H), 7.06 (s, 1H), 5.59 (s, 1H), 4.82 (dd, J = 11.5, 1.9 Hz, 1H), 4.57-4.44 (m, 1H), 3.02 (s, 6H), 2.26 (s, 3H), 2.09 (s, 3H). |
| 82 | 497.2 | |
| 83 | 530.1 | $^1$H NMR (400 MHz, dmso) δ 11.52 (s, 1H), 9.18 (s, 1H), 9.05 (s, 2H), 8.57-8.45 (m, 1H), 7.80 (td, J = 7.7, 1.8 Hz, 1H), 7.33 (dd, J = 7.0, 5.3 Hz, 1H), 7.22 (d, J = 8.0 Hz, 1H), 7.10 (s, 1H), 5.60 (s, 1H), 4.82 (dd, J = 11.5, 2.0 Hz, 1H), 4.55-4.44 (m, 1H), 2.26 (s, 3H), 2.09 (s, 3H). |
| 84 | 427.1 | $^1$H NMR (400 MHz, dmso) δ 10.61 (s, 1H), 6.74 (d, J = 8.0 Hz, 1H), 6.61 (d, J = 7.9 Hz, 1H), 5.30 (bs, 1H), 4.74-4.59 (m, 2H), 4.43-4.32 (m, 1H), 3.99 (d, J = 9.9 Hz, 1H), 3.80-3.66 (m, 1H), 3.44-3.26 (m, 2H), 2.29 (s, 3H), 2.12 (s, 3H), 1.94-1.86 (m, 1H), 1.69-1.39 (m, 4H), 1.32-1.17 (m, 1H), 0.83 (d, J = 6.5 Hz, 3H), 0.74 (d, J = 6.3 Hz, 3H). |
| 85 | 429.1 | $^1$H NMR (400 MHz, dmso) δ 11.17 (s, 3H), 8.58-8.46 (m, 1H), 7.80 (td, J = 7.7, 1.8 Hz, 1H), 7.51 (d, J = 1.9 Hz, 1H), 7.38-7.28 (m, 1H), 7.22 (d, J = 8.0 Hz, 1H), 6.87 (s, 1H), 6.44 (d, J = 1.9 Hz, 1H), 5.57 (s, 1H), 4.81 (dd, J = 11.5, 2.0 Hz, 1H), 4.50 (dd, J = 11.5, 3.2 Hz, 1H), 3.83 (s, 3H), 2.25 (s, 3H), 2.08 (s, 3H). |
| 86 | 447.1 | $^1$H NMR (400 MHz, dmso) δ 11.62 (s, 1H), 8.48 (d, 1H), 7.86 (d, J = 16.1 Hz, 1H), 7.78 (td, J = 7.7, 1.8 Hz, 1H), 7.36-7.27 (m, 2H), 7.20 (d, J = 7.9 Hz, 1H), 6.66 (d, J = 16.1 Hz, 1H), 5.56 (s, 1H), 4.79 (dd, J = 11.5, 2.0 Hz, 1H), 4.55-4.44 (m, 1H), 2.23 (s, 3H), 2.06 (s, 3H). |
| 87 | 430.1 | $^1$H NMR (400 MHz, dmso) δ 11.19 (s, 1H), 8.85 (bs, 1H), 8.53-8.44 (m, 1H), 7.79 (td, J = 7.7, 1.8 Hz, 1H), 7.32 (dd, J = 7.2, 5.3 Hz, 1H), 7.18 (d, J = 8.0 Hz, 1H), 6.80 (s, 1H), 6.02 (s, 1H), 5.55 (s, 1H), 4.77 |

TABLE 10-continued

| Example No. | MS [M + H]+ | ¹H NMR Spectrum |
|---|---|---|
| | | (dd, J = 11.5, 2.0 Hz, 1H), 4.44 (dd, J = 11.5, 3.1 Hz, 1H), 3.81-3.70 (m, 2H), 3.37-3.25 (m, 2H), 2.78-2.60 (m, 2H), 2.22 (s, 3H), 2.05 (s, 3H). |
| 104 | 414.2 | |
| 105 | 400.2 | 1H NMR (400 MHz, CD₃OD) δ 8.56 (ddd, J = 4.9, 1.7, 0.9 Hz, 1H), 7.69 (ddd, J = 7.8, 1.8 Hz, 1H), 7.40 (d, J = 8.4 Hz, 1H), 7.31 (ddd, J = 7.6, 4.9, 0.9 Hz, 1H), 7.13 (d, J = 8.4 Hz, 1H), 6.62 (d, J = 8.0 Hz, 1H), 6.38 (t, J = 2.1 Hz, 1H), 6.19-6.07 (m, 1H), 4.91 (dd, J = 11.6, 1.4 Hz, 1H), 4.61 (dd, J = 11.6, 3.1 Hz, 1H), 4.32-4.22 (m, 1H), 4.21-4.11 (m, 1H), 3.89 (m, 1H), 3.84-3.73 (m, 1H), 2.26 (s, 3H), 2.12 (s, 3H). |
| 106A | 402.2 | 1H NMR (400 MHz, CD₃OD) δ 8.54 (d, J = 4.1 Hz, 1H), 7.83-7.67 (m, 1H), 7.41-7.28 (m, 2H), 7.07 (d, J = 8.3 Hz, 1H), 6.82 (d, J = 7.9 Hz, 1H), 5.99 (s, 1H), 4.95-4.90 (m, 1H), 4.61 (dd, J = 11.7, 3.1 Hz, 2H), 3.51-3.37 (m, 1H), 3.15 (d, J = 8.6 Hz, 1H), 3.01-2.77 (m, 3H), 2.32 (d, J = 8.6 Hz, 1H), 2.27 (s, 3H), 2.25-2.14 (m, 1H), 2.13 (s, 3H). |
| 106B | 402.2 | 1H NMR (400 MHz, CD₃OD) δ 8.57 (s, 1H), 7.76 (s, 1H), 7.36 (d, J = 8.3 Hz, 2H), 7.10 (d, J = 8.3 Hz, 1H), 6.85-6.75 (m, 1H), 6.00 (s, 1H), 4.94 (s, 2H), 4.71-4.58 (m, 1H), 3.45 (s, 1H), 3.35 (s, 1H), 3.13 (s, 1H), 2.83 (s, 1H), 2.29 (s, 3H), 2.15 (s, 3H), 1.89 (s, 2H). |
| 107 | 414.2 | ¹H NMR (400 MHz, CD₃OD) δ 8.59 (d, J = 4.1 Hz, 1H), 7.78-7.68 (m, 1H), 7.44 (dd, J = 8.4, 1.6 Hz, 1H), 7.35 (dd, J = 6.9, 5.5 Hz, 1H), 7.17 (dd, J = 8.4, 4.6 Hz, 1H), 6.71 (dd, J = 14.3, 8.0 Hz, 1H), 6.36 (s, 1H), 6.19 (d, J = 9.1 Hz, 1H), 4.96 (d, J = 11.7 Hz, 2H), 4.87-4.82 (m, 1H), 4.78 (d, J = 14.4 Hz, 1H), 4.68 (dd, J = 11.7, 2.7 Hz, 3H), 4.60-4.23 (m, 2H), 2.29 (d, J = 2.4 Hz, 3H), 2.19-2.11 (m, 3H). |
| 108 | 416.2 | |
| 110 | 456.2 | |
| 111 | 484.2 | |
| 112 | 494.2 | |
| 113A | 444.2 | |
| 113B | 444.2 | |
| 114A | 470.2 | |
| 114B | 470.2 | |
| 115 | 480.2 | |
| 116 | 456.2 | 1H NMR (400 MHz, CD₃OD) δ 8.58 (d, J = 4.2 Hz, 0H), 7.74 (td, J = 7.8, 1.7 Hz, 1H), 7.46-7.30 (m, 2H), 7.12 (d, J = 8.4 Hz, 1H), 6.71 (d, J = 7.9 Hz, 1H), 6.31 (m, 1H), 6.09 (m, 1H), 4.84 (dd, J = 11.6, 2.5 Hz, 1H), 4.61 (dd, J = 11.6, 3.0 Hz, 1H), 3.85-3.67 (m, 2H), 2.96-2.72 (m, 2H), 2.28 (s, 3H), 2.26-2.18 (m, 1H), 2.13 (s, 3H), 2.10 (s, 1H). |
| 117 | 458.2 | 1H NMR (400 MHz, CD₃OD) δ 8.57 (d, J = 4.0 Hz, 1H), 7.82-7.67 (m, 1H), 7.36 (d, J = 8.3 Hz, 2H), 7.09 (d, J = 8.3 Hz, 1H), 6.77 (d, J = 8.0 Hz, 1H), 6.01 (s, 1H), 4.93 (d, J = 11.8 Hz, 2H), 4.68-4.57 (m, 1H), 3.55-3.42 (m, 1H), 3.26 (d, J = 1.6 Hz, 2H), 2.98 (s, 3H), 2.65 (s, 1H), 2.28 (d, J = 1.7 Hz, 3H), 2.14 (d, J = 1.7 Hz, 6H), 1.66 (d, J = 11.6 Hz, 1H), 1.24 (s, 1H). |
| 118 | 484.2 | |
| 119 | 494.2 | |
| 134 | 432.2 | (400 MHz, DMSO-d₆) δ 8.96 (d, J = 4.9 Hz, 1H), 8.56 (dd, J = 4.6, 1.5 Hz, 1H), 7.49 (dd, J = 8.0, 4.7 Hz, 1H), 7.12 (dd, J = 8.0, 1.4 Hz, 1H), 6.88 (d, J = 8.0 Hz, 1H), 6.80 (d, J = 8.0 Hz, 1H), 6.41 (dd, J = 2.5, 2.5 Hz, 1H), 4.65-4.43 (m, 2H), 3.01-2.82 (m, 1H), 2.24 (s, 3H), 2.08 (s, 3H), 0.70 (dd, J = 9.0, 2.7 Hz, 4H). |
| 135 | 436.2 | (400 MHz, DMSO-d₆) δ 8.93 (t, J = 5.9 Hz, 1H), 8.59 (dd, J = 4.6, 1.5 Hz, 1H), 7.51 (dd, J = 8.0, 4.6 Hz, 1H), 7.11 (dd, J = 8.0, 1.4 Hz, 1H), 6.87 (d, J = 8.0 Hz, 1H), 6.80 (d, J = 8.0 Hz, 1H), 6.59-6.49 (m, 1H), 4.65-4.44 (m, 2H), 3.55 (t, J = 6.0 Hz, 2H), 3.45-3.35 (m, 2H), 2.24 (s, 3H), 2.07 (s, 3H). |
| 136 | 474.1 | (400 MHz, DMSO-d₆) δ 11.10 (s, 1H), 9.58 (t, J = 6.6 Hz, 1H), 8.64 (dd, J = 4.6, 1.4 Hz, 1H), 7.57 (dd, J = 8.1, 4.6 Hz, 1H), 7.18 (dd, J = 8.0, 1.3 Hz, 1H), 6.89 (d, J = 8.0 Hz, 1H), 6.81 (d, J = 8.0 Hz, 1H), 6.54-6.29 (m, 1H), 4.60-4.46 (m, 2H), 4.21-4.03 (m, 2H), 2.24 (s, 3H), 2.07 (s, 3H). |
| 139 | 496.0 | (500 MHz, DMSO-d₆) δ 10.97 (s, 1H), 8.56-8.46 (m, 2H), 7.78 (ddd, J = 7.7, 7.7, 1.8 Hz, 1H), 7.31 (dd, J = 6.7, 4.9 Hz, 1H), 7.29-7.16 (m, 5H), 7.12 (d, J = 7.9 Hz, 1H), 6.60 (s, 1H), 5.52 (t, J = 2.4 Hz, 1H), 4.75 (dd, J = 11.5, 2.0 Hz, 1H), 4.40 (dd, J = 11.5, 3.1 Hz, 1H), 4.34 (d, J = 5.8 Hz, 2H), 3.48 (s, 2H), 2.15 (s, 3H), 1.99 (s, 3H). |
| 140 | 450.0 | (500 MHz, DMSO-d₆) δ 10.94 (s, 1H), 8.52 (d, J = 4.2 Hz, 1H), 8.34 (dd, J = 6.2, 6.2 Hz, 1H), 7.78 (ddd, J = 7.7, 7.7, 1.8 Hz, 1H), 7.32 (dd, J = 6.9, 4.9 Hz, 1H), 7.15 (d, J = 7.9 Hz, 1H), 6.70 (s, 1H), 5.52 (s, 1H), 4.75 (dd, J = 11.4, 2.0 Hz, 1H), 4.41 (dd, J = 11.5, 3.1 Hz, 1H), 4.36 (d, J = 6.2 Hz, 2H), 3.85 (s, 2H), 3.32 (s, 3H), 2.22 (s, 3H), 2.05 (s, 3H). |

TABLE 10-continued

| Example No. | MS [M + H]+ | 1H NMR Spectrum |
|---|---|---|
| 141 | 456.1 | (500 MHz, DMSO-d$_6$) δ 11.04 (s, 1H), 8.51 (d, J = 4.1 Hz, 1H), 7.78 (ddd, J = 7.7, 7.7, 1.8 Hz, 1H), 7.42 (d, J = 6.1, 6.1 Hz, 1H), 7.32 (dd, J = 6.7, 4.9 Hz, 1H), 7.14 (d, J = 7.9 Hz, 1H), 6.84 (s, 1H), 5.54 (t, J = 2.4 Hz, 1H), 4.77 (dd, J = 11.5, 2.0 Hz, 1H), 4.43 (dd, J = 11.5, 3.1 Hz, 1H), 4.27 (d, J = 6.0 Hz, 2H), 2.88 (s, 3H), 2.23 (s, 3H), 2.05 (s, 3H). |
| 142 | 463.2 | (500 MHz, DMSO-d$_6$) δ 10.88 (s, 1H), 8.52 (d, J = 4.1 Hz, 1H), 7.78 (ddd, J = 7.7, 7.7, 1.7 Hz, 1H), 7.31 (dd, J = 6.9, 4.9 Hz, 1H), 7.13 (d, J = 7.9 Hz, 1H), 6.70 (s, 1H), 6.35-6.13 (m, 1H), 6.04-5.78 (m, 1H), 5.52 (s, 1H), 4.75 (dd, J = 11.4, 2.0 Hz, 1H), 4.41 (dd, J = 11.4, 3.1 Hz, 1H), 4.25 (s, 2H), 3.87-3.52 (m, 1H), 2.22 (s, 3H), 2.05 (s, 3H), 1.02 (d, J = 6.5 Hz, 6H). |
| 143 | 463.1 | (500 MHz, DMSO-d$_6$) δ 11.08 (s, 1H), 9.71 (br s, 1H), 8.94 (t, J = 5.5 Hz, 1H), 8.50 (d, J = 4.2 Hz, 1H), 7.79 (ddd, J = 7.7, 7.7, 1.7 Hz, 1H), 7.32 (dd, J = 6.9, 4.9 Hz, 1H), 7.16 (d, J = 7.9 Hz, 1H), 6.73 (s, 1H), 5.55 (s, 1H), 4.78 (dd, J = 11.5, 2.0 Hz, 1H), 4.49-4.36 (m, 3H), 3.97 (s, 2H), 2.81 (s, 6H), 2.22 (s, 3H), 2.05 (s, 3H). |
| 161 | 418.0 | |
| 162 | 402.0 | |
| 163 | 431.0 | |
| 164 | 388.2 | 1H NMR (500 MHz, CD$_3$OD) δ 8.48 (d, J = 4.7 Hz, 1H), 7.95-7.73 (m, 1H), 7.40 (d, J = 7.9 Hz, 1H), 7.37 (dd, J = 7.6, 4.9 Hz, 1H), 7.21 (d, J = 8.3 Hz, 1H), 7.17 (d, J = 8.3 Hz, 1H), 5.85 (t, 1H), 5.02 (dd, J = 12.0, 1.8 Hz, 1H), 4.64 (dd, J = 11.9, 2.9 Hz, 1H), 4.29 (p, J = 6.2 Hz, 2H), 3.61 (q, J = 5.1 Hz, 2H), 2.36-2.28 (m, 2H), 2.23 (s, 3H), 2.08 (s, 3H). |
| 165 | 404.2 | 1H NMR (500 MHz, CD$_3$OD) δ 8.49 (d, J = 4.9 Hz, 1H), 7.88 (td, J = 7.8, 1.7 Hz, 1H), 7.43 (d, J = 7.9 Hz, 1H), 7.38 (dd, J = 6.8, 5.0 Hz, 1H), 7.14 (d, J = 8.2 Hz, 1H), 7.11 (d, J = 8.2 Hz, 1H), 6.01 (t, 1H), 4.98 (dd, J = 12.1, 1.8 Hz, 1H), 4.66 (dd, J = 12.1, 2.9 Hz, 1H), 4.33 (dd, J = 8.9, 3.1 Hz, 2H), 3.46-3.41 (m, 2H), 2.81 (s, 1H), 2.24 (s, 3H), 2.08 (s, 3H). |
| 166 | 445.2 | 1H NMR (500 MHz, DMSO) δ 8.55-8.49 (m, 1H), 7.75 (td, J = 7.7, 1.8 Hz, 1H), 7.32 (dd, J = 6.8, 4.9 Hz, 1H), 7.09 (d, J = 8.1 Hz, 1H), 6.89 (d, J = 8.1 Hz, 1H), 6.84 (d, J = 7.9 Hz, 1H), 6.07 (t, J = 2.5 Hz, 1H), 4.75 (dd, J = 11.6, 2.3 Hz, 1H), 4.56 (dd, J = 11.6, 3.0 Hz, 1H), 4.03-3.90 (m, 2H), 3.62 (t, J = 5.5 Hz, 2H), 3.31 (d, J = 5.3 Hz, 1H), 3.21 (dt, J = 12.0, 5.5 Hz, 1H), 2.80 (s, 3H), 2.21 (s, 3H), 2.04 (s, 3H). |
| 167 | 489.2 | |
| 168A | 418.2 | 1H NMR (300 MHz, CD$_3$OD) δ 8.49-8.44 (m, 1H), 7.87 (td, J = 7.8, 1.8 Hz, 1H), 7.44 (d, J = 8.0 Hz, 1H), 7.37 (dd, J = 7.1, 5.3 Hz, 1H), 7.14 (s, 2H), 6.35 (t, 1H), 5.07 (dd, J = 12.1, 1.5 Hz, 1H), 4.67 (dd, J = 12.1, 2.6 Hz, 1H), 4.55 (d, J = 3.8 Hz, 2H), 3.99 (dd, J = 10.5, 4.5 Hz, 2H), 3.75 (td, J = 9.2, 3.4 Hz, 1H), 3.53 (d, J = 10.4 Hz, 1H), 2.22 (s, 3H), 2.11 (dd, J = 7.5, 3.8 Hz, 2H), 2.06 (s, 3H). |
| 168B | 418.2 | 1H NMR (500 MHz, DMSO) δ 8.56-8.51 (m, 1H), 7.71 (td, J = 7.8, 1.8 Hz, 1H), 7.32-7.26 (m, 1H), 6.95 (d, J = 8.1 Hz, 1H), 6.80 (d, J = 8.1 Hz, 1H), 6.60 (d, J = 7.9 Hz, 1H), 6.10 (t, 1H), 4.94 (s, 1H), 4.81 (dd, J = 11.4, 1.3 Hz, 1H), 4.53 (dd, J = 11.5, 2.8 Hz, 1H), 4.29 (s, 2H), 3.71 (tt, J = 8.7, 4.1 Hz, 1H), 3.52 (d, J = 10.3 Hz, 1H), 3.49-3.43 (m, 2H), 2.19 (s, 3H), 2.02 (s, 3H), 1.90 (dtd, J = 13.1, 8.8, 4.6 Hz, 1H), 1.82-1.75 (m, 1H). |
| 169 | 432.2 | 1H NMR (500 MHz, DMSO) δ 8.55 (d, J = 4.0 Hz, 1H), 7.76 (td, J = 7.7, 1.8 Hz, 1H), 7.35-7.30 (m, 1H), 7.04 (d, J = 8.1 Hz, 1H), 6.85 (d, J = 8.1 Hz, 1H), 6.80 (d, J = 7.9 Hz, 1H), 5.96 (t, J = 2.8 Hz, 1H), 4.65 (dd, J = 11.5, 2.8 Hz, 1H), 4.62 (d, J = 4.1 Hz, 1H), 4.54 (dd, J = 11.5, 3.1 Hz, 1H), 3.62 (td, J = 8.6, 4.5 Hz, 2H), 3.57 (dt, J = 8.6, 4.3 Hz, 1H), 3.03 (ddd, J = 12.9, 9.9, 3.0 Hz, 2H), 2.21 (s, 3H), 2.05 (s, 3H), 1.65-1.55 (m, 2H), 1.31 (ddt, J = 13.0, 9.1, 4.8 Hz, 1H), 1.19-1.09 (m, 1H). |
| 170A | 432.2 | |
| 170B | 432.2 | |
| 171 | 459.2 | |
| 172 | 431.2 | 1H NMR (300 MHz, CD$_3$OD) δ 8.57 (d, J = 4.9 Hz, 1H), 7.75 (td, J = 7.8, 1.8 Hz, 1H), 7.35 (dd, J = 7.6, 4.9 Hz, 1H), 7.18 (d, J = 8.2 Hz, 1H), 6.98 (d, J = 8.2 Hz, 1H), 6.83 (d, J = 7.9 Hz, 1H), 5.95 (t, J = 2.9 Hz, 1H), 4.76 (dd, J = 11.6, 2.8 Hz, 1H), 4.60 (dd, J = 11.6, 3.1 Hz, |

TABLE 10-continued

| Example No. | MS [M + H]+ | 1H NMR Spectrum |
|---|---|---|
| | | 1H), 4.06 (d, J = 1.5 Hz, 2H), 3.69-3.51 (m, 2H), 3.25-3.15 (m, 2H), 2.26 (s, 3H), 2.11 (s, 3H). |
| 173 | 495.2 | 1H NMR (500 MHz, DMSO) δ 8.58-8.51 (m, 1H), 7.76 (td, J = 7.7, 1.8 Hz, 1H), 7.33 (ddd, J = 7.5, 4.8, 0.9 Hz, 1H), 7.09 (d, J = 8.1 Hz, 1H), 6.89 (d, J = 8.2 Hz, 1H), 6.85 (d, J = 7.9 Hz, 1H), 6.02 (t, J = 2.8 Hz, 1H), 4.74 (dd, J = 11.5, 2.8 Hz, 1H), 4.58 (dd, J = 11.5, 3.0 Hz, 1H), 3.44 (pt, J = 6.3, 3.1 Hz, 4H), 3.12-2.99 (m, 4H), 2.84 (s, 3H), 2.21 (s, 3H), 2.04 (s, 3H). |
| 174 | 459.2 | |
| 175 | 441.2 | |
| 176 | 446.2 | |
| 177 | 461.2 | 1H NMR (500 MHz, DMSO) δ 8.54 (d, J = 4.6 Hz, 1H), 7.76 (td, J = 7.7, 1.6 Hz, 1H), 7.33 (dd, J = 7.5, 4.9 Hz, 1H), 7.06 (d, J = 8.1 Hz, 1H), 6.86 (d, J = 8.1 Hz, 1H), 6.81 (d, J = 7.9 Hz, 1H), 5.99 (t, J = 2.6 Hz, 1H), 4.68 (dd, J = 11.5, 2.7 Hz, 1H), 4.55 (dd, J = 11.5, 3.0 Hz, 1H), 4.35 (t, J = 5.0 Hz, 1H), 3.45 (q, J = 5.8 Hz, 2H), 3.31 (dd, J = 6.2, 3.2 Hz, 4H), 2.40-2.33 (m, 4H), 2.33-2.26 (m, 2H), 2.21 (s, 3H), 2.04 (s, 3H). |
| 178 | 493.2 | |
| 179 | 507.2 | |
| 180A | 445.2 | |
| 180B | 445.2 | 1H NMR (500 MHz, DMSO) δ 8.55 (ddd, J = 4.8, 1.6, 0.8 Hz, 1H), 7.77 (td, J = 7.7, 1.8 Hz, 1H), 7.33 (ddd, J = 7.5, 4.8, 0.9 Hz, 1H), 7.08 (d, J = 8.1 Hz, 1H), 6.89 (d, J = 5.1 Hz, 1H), 6.87 (d, J = 4.9 Hz, 1H), 6.02 (t, J = 2.9 Hz, 1H), 4.70 (dd, J = 11.5, 3.0 Hz, 1H), 4.57 (dd, J = 11.5, 3.1 Hz, 1H), 3.44 (d, J = 12.2 Hz, 4H), 3.35 (d, J = 10.6 Hz, 4H), 2.29 (q, J = 7.4 Hz, 3H), 2.22 (s, 3H), 2.05 (s, 3H), 0.95 (t, J = 7.4 Hz, 2H). |
| 181A | 431.2 | 1H NMR (500 MHz, DMSO) δ 8.99 (s, 1H), 8.47 (d, J = 4.3 Hz, 1H), 7.92-7.79 (m, 1H), 7.36 (dd, J = 7.2, 5.2 Hz, 1H), 7.28 (s, 1H), 7.12 (d, J = 8.2 Hz, 1H), 7.06 (d, J = 8.1 Hz, 1H), 6.35 (t, 1H), 5.05 (d, J = 11.9 Hz, 1H), 4.59 (dd, J = 12.0, 2.5 Hz, 1H), 4.17-4.08 (m, 1H), 3.99 (d, J = 7.7 Hz, 1H), 3.91 (s, 1H), 3.69 (dd, J = 11.1, 4.5 Hz, 1H), 3.54 (d, J = 6.3 Hz, 1H), 2.56 (s, 3H), 2.36 (dt, J = 13.5, 6.9 Hz, 1H), 2.20 (s, 3H), 2.16 (d, J = 6.2 Hz, 1H), 2.02 (s, 3H). |
| 181B | 431.2 | 1H NMR (500 MHz, DMSO) δ 8.94 (d, J = 44.9 Hz, 1H), 8.46 (d, J = 4.5 Hz, 1H), 7.85 (td, J = 7.8, 1.6 Hz, 1H), 7.36 (dd, J = 7.1, 5.2 Hz, 1H), 7.29 (s, 1H), 7.13 (d, J = 8.2 Hz, 1H), 7.08 (d, J = 8.2 Hz, 1H), 6.40 (t, 1H), 5.05 (d, J = 11.5 Hz, 1H), 4.61 (dd, J = 12.0, 2.4 Hz, 1H), 4.01 (d, J = 10.0 Hz, 1H), 3.91 (s, 1H), 3.89 (d, J = 5.2 Hz, 1H), 3.79 (dd, J = 11.3, 6.5 Hz, 1H), 3.72-3.66 (m, 1H), 2.62 (s, 3H), 2.35 (dq, J = 14.8, 8.1, 7.3 Hz, 2H), 2.20 (s, 3H), 2.02 (s, 3H). |
| 182A | 517.3 | |
| 182B | 517.3 | |
| 183 | 471.4 | |
| 184 | 475.2 | |
| 185 | 406.2 | 1H NMR (500 MHz, CD3OD) δ 8.61-8.53 (m, 1H), 7.69 (td, J = 7.8, 1.8 Hz, 1H), 7.31 (dd, J = 6.9, 4.9 Hz, 1H), 7.06 (d, J = 8.1 Hz, 1H), 6.89 (d, J = 8.1 Hz, 1H), 6.59 (d, J = 7.9 Hz, 1H), 6.08 (tff, 1H), 4.85 (d, J = 1.8 Hz, 1H), 4.54 (dd, J = 11.5, 2.8 Hz, 1H), 3.75 (ddd, J = 11.7, 7.1, 4.8 Hz, 1H), 3.71-3.65 (m, 1H), 3.60 (ddd, J = 14.7, 7.0, 4.7 Hz, 1H), 3.51-3.42 (m, 1H), 3.15 (s, 3H), 2.81 (s, 3H), 2.22 (s, 3H), 2.07 (s, 3H). |
| 186 | 362.2 | 1H NMR (500 MHz, CD3OD) δ 8.59 (d, J = 4.9 Hz, 1H), 7.70 (td, J = 7.8, 1.7 Hz, 1H), 7.31 (dd, J = 6.9, 5.0 Hz, 1H), 7.05 (d, J = 8.1 Hz, 1H), 6.85 (d, J = 8.1 Hz, 1H), 6.62 (d, J = 7.9 Hz, 1H), 5.66 (t, 1H), 4.91 (dd, J = 11.4, 1.6 Hz, 1H), 4.48 (dd, J = 11.4, 3.0 Hz, 1H), 3.00 (s, 3H), 2.24 (s, 3H), 2.09 (s, 3H). |
| 187 | 376.2 | 1H NMR (500 MHz, CD3OD) δ 8.57 (ddd, J = 4.9, 1.6, 0.9 Hz, 1H), 7.69 (td, J = 7.8, 1.8 Hz, 1H), 7.31 (ddd, J = 7.6, 4.9, 0.8 Hz, 1H), 7.07 (d, J = 8.1 Hz, 1H), 6.90 (d, J = 8.1 Hz, 1H), 6.58 (d, J = 8.0 Hz, 1H), 6.01 (t, J = 2.2 Hz, 1H), 4.82 (dd, J = 1.9 Hz, 1H), 4.56 (dd, J = 11.5, 2.9 Hz, 1H), 3.08 (s, 6H), 2.22 (s, 3H), 2.07 (s, 3H). |
| 188 | 459.2 | 1H NMR (300 MHz, CD3OD) δ 8.54 (d, J = 4.1 Hz, 1H), 7.85-7.76 (m, 1H), 7.37 (dd, J = 7.1, 5.4 Hz, 1H), 7.16 (d, J = 8.2 Hz, 1H), 7.09 (d, J = 7.8 Hz, 1H), 7.05 (d, J = 8.2 Hz, 1H), 6.03 (t, 1H), 4.80 (d, J = 11.5 Hz, 2H), 4.69- |

TABLE 10-continued

| Example No. | MS [M + H]+ | 1H NMR Spectrum |
|---|---|---|
| | | 4.59 (m, 2H), 3.95 (d, J = 13.4 Hz, 2H), 3.88-3.82 (m, 1H), 3.23-3.05 (m, 2H), 2.25 (s, 3H), 2.10 (s, 3H), 1.77 (d, J = 20.7 Hz, 2H), 1.47 (d, J = 12.0 Hz, 2H). |
| 189 | 473.2 | |
| 190 | 473.2 | 1H NMR (500 MHz, DMSO) δ 8.54 (d, J = 4.2 Hz, 1H), 7.80-7.68 (m, 1H), 7.32 (dd, J = 6.9, 4.9 Hz, 1H), 7.05 (d, J = 8.1 Hz, 1H), 6.86 (d, J = 8.1 Hz, 1H), 6.79 (d, J = 7.9 Hz, 1H), 5.97 (t, J = 2.6 Hz, 1H), 4.68 (dd, J = 11.5, 2.6 Hz, 1H), 4.54 (dd, J = 11.5, 3.0 Hz, 1H), 3.79-3.71 (m, 2H), 3.71-3.61 (m, 1H), 2.99 (t, J = 11.4 Hz, 2H), 2.21 (s, 3H), 2.05 (s, 3H), 1.75 (s, 3H), 1.62 (dd, J = 34.6, 10.1 Hz, 2H), 1.39-1.27 (m, 1H), 1.21-1.09 (m, 1H). |
| 191 | 474.2 | |
| 192 | 445.2 | |
| 193A | 457.2 | |
| 193B | 457.2 | |
| 194 | 446.2 | |
| 195 | 445.2 | |
| 196 | 503.2 | |
| 197 | 531.2 | |
| 198 | 392.2 | |
| 199 | 491.3 | |
| 200 | 391.2 | |
| 201A | 459.2 | |
| 201B | 459.2 | |
| 202A | 417.3 | |
| 202B | 417.3 | |
| 203 | 513.3 | |
| 205 | 489.4 | 1H NMR (300 MHz, CD3OD) δ 8.58 (d, J = 4.0 Hz, 1H), 7.69 (t, J = 7.7 Hz, 1H), 7.41-7.23 (m, 1H), 7.05 (d, J = 8.1 Hz, 1H), 6.90 (d, J = 8.2 Hz, 1H), 6.58 (d, J = 8.1 Hz, 1H), 6.04 (s, 1H), 4.84 (s, 1H), 4.57 (dd, J = 11.5, 2.6 Hz, 1H), 4.53-4.42 (m, 1H), 4.01-3.89 (m, 1H), 3.87-3.76 (m, 3H), 3.58 (q, J = 9.7, 8.5 Hz, 1H), 3.43 (dd, J = 9.8, 5.4 Hz, 1H), 3.34-3.24 (m, 3H), 2.23 (s, 4H), 2.08 (s, 3H), 2.04-1.92 (m, 1H). |
| 206 | 485.4 | 1H NMR (500 MHz, DMSO) δ 8.63-8.44 (m, 4H), 8.25 (d, J = 6.9 Hz, 1H), 7.72 (td, J = 7.8, 1.8 Hz, 1H), 7.44-7.21 (m, 1H), 6.96 (d, J = 8.1 Hz, 1H), 6.81 (d, J = 8.1 Hz, 1H), 6.66 (d, J = 7.9 Hz, 1H), 6.09 (s, 1H), 4.84 (dd, J = 11.5, 1.3 Hz, 1H), 4.50 (dd, J = 11.5, 2.8 Hz, 1H), 4.28 (h, J = 6.2 Hz, 1H), 3.95-3.67 (m, 2H), 3.54-3.38 (m, 1H), 3.24 (dd, J = 9.9, 4.8 Hz, 1H), 2.20 (s, 3H), 2.05 (d, J = 19.4 Hz, 4H), 1.79 (dq, J = 13.0, 6.3 Hz, 1H), 1.47 (ddd, J = 12.4, 7.6, 4.9 Hz, 1H), 0.61 (tdd, J = 13.1, 6.5, 3.4 Hz, 4H). |
| 207 | 495.3 | |
| 208 | 473.2 | |
| 209 | 487.2 | 1H NMR (300 MHz, CD3OD) δ 8.74-8.45 (m, 1H), 7.69 (td, J = 7.8, 1.7 Hz, 1H), 7.31 (dd, J = 7.6, 4.9 Hz, 1H), 7.05 (d, J = 8.1 Hz, 1H), 6.89 (d, J = 8.1 Hz, 1H), 6.59 (d, J = 7.9 Hz, 1H), 6.04 (s, 1H), 4.85 (dd, J = 11.5, 1.3 Hz, 1H), 4.55 (dd, J = 11.5, 2.8 Hz, 1H), 4.40 (p, J = 5.8 Hz, 1H), 3.95 (dd, J = 9.8, 6.3 Hz, 1H), 3.89-3.75 (m, 1H), 3.60 (td, J = 9.6, 8.8, 6.0 Hz, 1H), 3.45-3.33 (m, 1H), 2.35 (dq, J = 14.1, 7.1 Hz, 1H), 2.23 (s, 4H), 2.08 (s, 3H), 1.91 (dq, J = 12.8, 5.8 Hz, 1H), 1.02 (dd, J = 19.1, 6.9 Hz, 6H). |
| 210 | 499.2 | |
| 211 | 484.2 | |
| 213 | 529.2 | |
| 214 | 509.2 | 1H NMR (300 MHz, DMSO) δ 8.53 (d, J = 4.0 Hz, 1H), 7.72 (td, J = 7.7, 1.8 Hz, 1H), 7.42 (s, 1H), 7.29 (dd, J = 6.8, 4.9 Hz, 1H), 6.95 (d, J = 8.1 Hz, 1H), 6.80 (d, J = 8.1 Hz, 1H), 6.63 (d, J = 7.9 Hz, 1H), 6.10 (t, 1H), 4.81 (d, J = 10.5 Hz, 1H), 4.49 (d, J = 8.7 Hz, 1H), 3.91 (d, J = 5.6 Hz, 2H), 3.81-3.71 (m, 1H), 3.36 (d, J = 9.8 Hz, 1H), 3.21 (d, J = 3.4 Hz, 1H), 3.03-2.93 (m, 2H), 2.18 (s, 3H), 2.01 (s, 3H), 1.86-1.75 (m, 2H), 1.12 (t, J = 7.3 Hz, 3H). |
| 215 | 523.2 | 1H NMR (300 MHz, DMSO) δ 8.53 (d, J = 4.0 Hz, 1H), 7.72 (td, J = 7.7, 1.7 Hz, 1H), 7.43 (s, 1H), 7.30 (dd, J = 6.7, 4.8 Hz, 1H), 6.95 (d, J = 8.1 Hz, 1H), 6.80 (d, J = 8.1 Hz, 1H), 6.63 (d, J = 7.9 Hz, 1H), 6.10 (t, 1H), 4.81 (d, J = 10.9 Hz, 1H), 4.50 (d, J = 8.8 Hz, 1H), 3.91 (d, J = 5.8 Hz, 2H), 3.81-3.71 (m, 1H), 3.41-3.32 (m, 1H), 3.22 (d, J = 3.2 Hz, 1H), 3.02-2.92 (m, 2H), 2.18 (s, 3H), |

TABLE 10-continued

| Example No. | MS [M + H]+ | 1H NMR Spectrum |
|---|---|---|
| | | 2.01 (s, 3H), 1.88-1.73 (m, 2H), 1.67-1.54 (m, 2H), 0.94 (t, J = 7.5 Hz, 3H). |
| 216 | 488.2 | |
| 217 | 523.2 | |
| 218 | 521.2 | |
| 219 | 489.2 | |
| 220 | 509.2 | 1H NMR (300 MHz, CD3OD) δ 8.58 (d, J = 4.9 Hz, 1H), 7.82-7.58 (m, 1H), 7.33 (dd, J = 7.6, 4.9 Hz, 1H), 7.07 (d, J = 8.2 Hz, 1H), 6.91 (d, J = 8.2 Hz, 1H), 6.62 (d, J = 7.9 Hz, 1H), 6.06 (s, 1H), 4.90 (s, 1H), 4.69-4.49 (m, 2H), 4.00-3.80 (m, 2H), 3.59-3.42 (m, 2H), 2.87 (s, 3H), 2.70 (s, 3H), 2.24 (s, 3H), 2.09 (s, 3H), 2.03 (s, 2H). |
| 221 | 503.2 | 1H NMR (300 MHz, CD3OD) δ 8.58 (d, J = 4.0 Hz, 1H), 7.85-7.57 (m, 1H), 7.44-7.21 (m, 1H), 7.07 (d, J = 8.3 Hz, 1H), 6.91 (d, J = 8.2 Hz, 1H), 6.61 (d, J = 8.1 Hz, 1H), 6.05 (s, 1H), 5.14 (s, 1H), 4.84 (s, 1H), 4.61 (d, J = 11.9 Hz, 1H), 4.22 (s, 1H), 4.12 (s, 2H), 3.98-3.78 (m, 2H), 3.61-3.43 (m, 3H), 3.38 (s, 3H), 2.75 (d, J = 18.9 Hz, 3H), 2.24 (s, 3H), 2.09 (s, 3H). |
| 222 | 473.2 | 1H NMR (300 MHz, CD3OD) δ 8.58 (d, J = 4.9 Hz, 1H), 7.81-7.62 (m, 1H), 7.33 (dd, J = 7.6, 4.9 Hz, 1H), 7.07 (dd, J = 8.2, 3.0 Hz, 1H), 6.91 (dd, J = 8.1, 3.0 Hz, 1H), 6.61 (d, J = 7.9 Hz, 1H), 6.04 (s, 1H), 5.34-5.05 (m, 1H), 4.84 (s, 1H), 4.67-4.51 (m, 1H), 4.02-3.78 (m, 2H), 3.57-3.41 (m, 2H), 2.84 (s, 3H), 2.24 (s, 3H), 2.09 (t, J = 6.4 Hz, 6H). |
| 224 | 459.2 | 1H NMR (500 MHz, DMSO) δ 8.63-8.46 (m, 1H), 7.77 (td, J = 7.7, 1.8 Hz, 1H), 7.40-7.26 (m, 1H), 7.08 (d, J = 8.2 Hz, 1H), 6.88 (dd, J = 8.0, 3.8 Hz, 2H), 6.02 (t, J = 2.9 Hz, 1H), 4.64 (ddd, J = 65.0, 11.5, 3.0 Hz, 2H), 3.54-3.14 (m, 8H), 2.22 (s, 3H), 2.06 (d, J = 5.8 Hz, 3H), 1.97 (s, 3H). |
| 225 | 473.2 | 1H NMR (500 MHz, DMSO) δ 8.55 (ddd, J = 4.8, 1.6, 0.8 Hz, 1H), 7.77 (td, J = 7.7, 1.8 Hz, 1H), 7.33 (ddd, J = 7.5, 4.8, 0.9 Hz, 1H), 7.08 (d, J = 8.1 Hz, 1H), 6.89 (d, J = 5.1 Hz, 1H), 6.87 (d, J = 4.9 Hz, 1H), 6.02 (t, J = 2.9 Hz, 1H), 4.70 (dd, J = 11.5, 3.0 Hz, 1H), 4.57 (dd, J = 11.5, 3.1 Hz, 1H), 3.44 (d, J = 12.2 Hz, 4H), 3.35 (d, J = 10.6 Hz, 4H), 2.29 (q, J = 7.4 Hz, 3H), 2.22 (s, 3H), 2.05 (s, 3H), 0.95 (t, J = 7.4 Hz, 2H). |
| 226 | 509.2 | 1H NMR (300 MHz, dmso) δ 8.53 (d, J = 4.0 Hz, 1H), 7.76 (td, J = 7.7, 1.8 Hz, 1H), 7.33 (dd, J = 6.7, 4.8 Hz, 1H), 7.08 (d, J = 8.1 Hz, 1H), 6.87 (t, J = 8.4 Hz, 1H), 6.02 (s, 1H), 4.64 (ddd, J = 42.9, 11.4, 2.7 Hz, 2H), 3.35 (d, J = 16.6 Hz, 4H), 3.20-2.91 (m, 6H), 2.20 (s, 3H), 2.04 (s, 3H), 1.15 (t, J = 7.3 Hz, 3H). |
| 228 | 528.2 | |
| 229 | 496.2 | |
| 230 | 403.2 | |
| 231 | 445.2 | |
| 232 | 459.2 | |
| 233 | 473.2 | |
| 234 | 475.2 | |
| 235 | 471.2 | 1H NMR (500 MHz, DMSO) δ 8.72 (d, J = 7.0 Hz, 1H), 8.53 (d, J = 4.0 Hz, 1H), 7.76 (td, J = 7.7, 1.7 Hz, 1H), 7.33 (dd, J = 6.8, 4.9 Hz, 1H), 7.02 (d, J = 8.1 Hz, 1H), 6.85 (d, J = 8.1 Hz, 1H), 6.80 (d, J = 7.9 Hz, 1H), 5.80 (tz, 1H), 4.73 (dd, J = 11.5, 1.6 Hz, 1H), 4.55 (q, J = 6.3 Hz, 1H), 4.49 (dd, J = 11.5, 3.0 Hz, 1H), 4.31 (t, J = 7.8 Hz, 1H), 4.16 (t, J = 7.8 Hz, 1H), 3.97 (dd, J = 7.9, 5.9 Hz, 1H), 3.75 (dd, J = 7.8, 6.0 Hz, 1H), 2.22 (s, 3H), 2.05 (s, 3H), 1.48 (p, J = 6.3 Hz, 1H), 0.64 (d, J = 6.4 Hz, 4H). |
| 236 | 485.2 | |
| 237 | 481.2 | |
| 238 | 495.2 | |
| 239 | 509.2 | |
| 240 | 509.3 | |
| 241 | 503.3 | |
| 242 | 527.3 | |
| 243 | 487.2 | 1H NMR (300 MHz, CD3OD) δ 8.59 (d, J = 4.9 Hz, 1H), 7.87-7.67 (m, 1H), 7.36 (dd, J = 7.6, 4.9 Hz, 1H), 7.15 (d, J = 8.2 Hz, 1H), 6.96 (d, J = 8.2 Hz, 1H), 6.79 (d, J = 7.9 Hz, 1H), 5.86 (s, 1H), 4.75-4.47 (m, 2H), 3.75 (d, J = 11.2 Hz, 2H), 3.07 (t, J = 11.3 Hz, 2H), 2.26 (s, 3H), 2.20-2.05 (m, 6H), 1.77 (d, J = 13.4 Hz, 2H), 1.43 (d, J = 12.5 Hz, 1H), 1.22 (d, J = 9.3 Hz, 1H), 1.09 (t, J = 7.6 Hz, 3H). |

TABLE 10-continued

| Example No. | MS [M + H]+ | 1H NMR Spectrum |
|---|---|---|
| 244 | 501.2 | 1H NMR (500 MHz, DMSO) δ 8.54 (d, J = 4.2 Hz, 1H), 7.75 (td, J = 7.7, 1.7 Hz, 1H), 7.57 (d, J = 7.6 Hz, 1H), 7.32 (dd, J = 7.0, 4.9 Hz, 1H), 7.05 (d, J = 8.1 Hz, 1H), 6.86 (d, J = 8.1 Hz, 1H), 6.77 (d, J = 7.9 Hz, 1H), 5.97 (t, 1H), 4.69 (dd, J = 11.5, 2.5 Hz, 1H), 4.54 (dd, J = 11.5, 3.0 Hz, 1H), 3.75 (t, J = 11.1 Hz, 2H), 3.70-3.63 (m, 1H), 2.99 (t, J = 11.8 Hz, 2H), 2.28 (p, J = 6.8 Hz, 1H), 2.21 (s, 3H), 2.04 (s, 3H), 1.65 (d, J = 10.0 Hz, 1H), 1.58 (d, J = 10.0 Hz, 1H), 1.40-1.30 (m, 1H), 1.25-1.16 (m, 1H), 0.95 (dd, J = 6.8, 1.4 Hz, 6H). |
| 246 | 487.3 | |
| 248 | 523.3 | |
| 249 | 459.2 | |
| 250 | 473.2 | |
| 251 | 485.2 | |
| 256 | 415.4 | |
| 257 | 429.2 | |
| 258 | 443.1 | |
| 259 | 442.0 | |
| 260 | 442.2 | |
| 261 | 442.2 | |
| 262 | 454.0 | |
| 263 | 498.3 | |
| 264 | 421.0 | |
| 265A | 367.1 | |
| 265B | 367.1 | |
| 266A | 383.1 | |
| 266B | 383.0 | |
| 267A | 426.9 428.9 | |
| 267B | 426.8 428.9 | |
| 268 | 363.1 | |
| 269A | 374.1 | |
| 269B | 374.2 | |

Biological Assay Protocols:

Example A1

BRD4 AlphaScreen™ Assay

BRD4-BD1 and BRD4-BD2 assays were conducted in white 384-well polystyrene plate in a final volume of 20 µL for BD1 and 40 µL for BD2. Inhibitors were first serially diluted in DMSO and added to the plate wells before the addition of other reaction components. The final concentration of DMSO in the assay was 1.25% (BD1) and 0.83% (BD2). The assays were carried out at room temperature for 75 min. in the assay buffer (50 mM HEPES, pH 7.4, 100 mM NaCl, 0.05% CHAPS, 0.01% BSA), containing 50 nM Biotin-labeled tetra-acetylated histone H4 peptide (H4Ac4), 3.8 nM (BRD4-BD1, BPS Bioscience #31040) or 20 nM (BRD4-BD2, BPS Bioscience #31041). The reaction followed by the addition of 20 µL of assay buffer supplemented with Streptavidin donor beads (PerkinElmer 6760002) and GSH Acceptor beads (PerkinElmer-AL109C) at 4 µg/mL under reduced light. After plate sealing, the plate was incubated in the dark at room temperature for 75 min. before reading on a PHERAstar FS plate reader (BMG Labtech). $IC_{50}$ determination was performed by fitting the curve of percent control activity versus the log of the inhibitor concentration using the GraphPad Prism 5.0 software.

$IC_{50}$ data for the compounds of the Examples as determined by Assay A1 is presented in Table 11.

TABLE 11

| Example No. | BRD4 BD-1 enzyme $IC_{50}$ (nM)* | BRD4 BD-2 enzyme $IC_{50}$ (nM)* |
|---|---|---|
| 1A | + | + |
| 1B | ++ | ++ |
| 2 | + | + |
| 3 | + | + |
| 4 | + | + |
| 5 | + | + |
| 6 | + | + |
| 7 | + | + |
| 8 | + | + |
| 9 | + | + |
| 10 | ++ | + |
| 11 | +++ | ++ |
| 12 | ++ | + |
| 13 | + | + |
| 14 | +++ | +++ |
| 15 | + | + |
| 17 | + | + |
| 18A | ++ | + |
| 18B | ++ | + |
| 21 | + | + |
| 22 | + | + |
| 23 | + | + |
| 24A | ++ | + |
| 24B | ++ | + |
| 25 | + | + |
| 26 | + | + |
| 27 | + | + |
| 28 | + | + |
| 29 | + | + |
| 30 | + | + |
| 31 | + | + |
| 32 | + | + |
| 33 | +++ | ++ |

TABLE 11-continued

| Example No. | BRD4 BD-1 enzyme IC$_{50}$ (nM)* | BRD4 BD-2 enzyme IC$_{50}$ (nM)* |
|---|---|---|
| 34 | + | + |
| 35 | ++ | + |
| 36 | ++ | + |
| 37 | ++ | + |
| 38 | +++ | ++ |
| 39 | + | + |
| 40 | ++ | + |
| 49 | + | + |
| 50 | + | + |
| 51 | + | + |
| 53 | + | + |
| 54 | + | + |
| 55 | + | + |
| 56 | + | + |
| 57 | + | + |
| 58 | + | + |
| 59 | + | + |
| 60 | + | + |

*Symbols used:
+: IC$_{50}$ ≤100 nM
++: 100 nM < IC$_{50}$ ≤ 1000 nM
+++: 1000 nM to 10000 nM
NT = not tested Example A2

BRD4 AlphaScreen™ Assay

BRD4-BD1 and BRD4-BD2 assays were conducted in white 384-well polystyrene plate in a final volume of 40 µL for BD1 and 60 µL for BD2. Inhibitors were first serially diluted in DMSO and added to the plate wells before the addition of other reaction components. The final concentration of DMSO in the assay was 1.25% (BD1) and 0.83% (BD2). The assays were carried out at room temperature in the assay buffer (50 mM Tris-HCl, pH 7.5, 0.01% Tween-20, 0.01% BSA, 5 mM DTT), containing 50 nM Biotin-labeled tetra-acetylated histone H4 peptide (H4Ac4) and BRD4-BD1 or BRD4-BD2 protein at concentration less than 1 nM. The incubation for 75 min. was followed by the addition of 20 µL of assay buffer supplemented with Streptavidin donor beads (PerkinElmer 6760002) and GSH Acceptor beads (PerkinElmer-AL109C) at final concentration 2-4 µg/mL under reduced light. After plate sealing, the plate was incubated in the dark at room temperature for 75 min. before reading on a PHERAstar FS plate reader (BMG Labtech). IC$_{50}$ determination was performed by fitting the curve of percent control activity versus the log of the inhibitor concentration using the GraphPad Prism 5.0 software.

IC$_{50}$ data for the compounds of the Examples as determined by Assay A2 is presented in Table 12.

TABLE 12

| Example No. | BRD4 BD-1 enzyme IC$_{50}$ (nM)* | BRD4 BD-2 enzyme IC$_{50}$ (nM)* |
|---|---|---|
| 16 | + | + |
| 19 | + | + |
| 20 | ++ | + |
| 41 | + | + |
| 42 | + | + |
| 43 | + | + |
| 44 | +++ | ++ |
| 45 | + | + |
| 46 | + | + |
| 47A | ++ | ++ |
| 47B | ++ | + |
| 48A | ++ | + |
| 48B | ++ | + |
| 52 | + | + |
| 61A | + | + |
| 62B | + | + |
| 63A | ++ | ++ |
| 69 | + | + |
| 70 | + | + |
| 71 | ++ | + |
| 72 | ++ | + |
| 73 | ++ | + |
| 74 | ++ | + |
| 75 | + | + |
| 76 | ++ | ++ |
| 77 | ++ | ++ |
| 78 | + | + |
| 79 | +++ | +++ |
| 80 | +++ | +++ |
| 81 | ++ | + |
| 82 | ++ | + |
| 83 | + | + |
| 84 | ++ | + |
| 85 | +++ | ++ |
| 86 | ++ | + |
| 87 | ++ | + |
| 88 | + | + |
| 89 | + | + |
| 90 | + | + |
| 91 | + | + |
| 92 | + | + |
| 93 | + | + |
| 94 | + | + |
| 95 | + | + |
| 96 | + | + |
| 97 | + | + |
| 98 | + | + |
| 99 | + | + |
| 100 | + | + |
| 101A | + | + |
| 101B | + | + |
| 102 | NT | NT |
| 103 | + | + |
| 104 | + | + |
| 105 | + | + |
| 106A | + | + |
| 106B | + | + |
| 107 | + | + |
| 108 | NT | NT |
| 109 | + | + |
| 110 | + | + |
| 111 | + | + |
| 112 | + | + |
| 113A | + | + |
| 113B | + | + |
| 114A | + | + |
| 114B | + | + |
| 115 | + | + |
| 116 | + | + |
| 117 | + | + |
| 118 | + | + |
| 119 | + | + |
| 120 | + | + |
| 121 | ++ | + |
| 122 | ++ | + |
| 123 | ++ | + |
| 124 | +++ | ++ |
| 125 | +++ | + |
| 126 | ++ | + |
| 127 | + | + |
| 128 | + | + |
| 129 | ++ | + |
| 130 | + | + |
| 131 | + | + |
| 132 | + | + |
| 133 | + | + |
| 134 | + | + |
| 135 | + | + |
| 136 | + | + |

TABLE 12-continued

| Example No. | BRD4 BD-1 enzyme IC$_{50}$ (nM)* | BRD4 BD-2 enzyme IC$_{50}$ (nM)* |
|---|---|---|
| 137 | +++ | + |
| 138 | + | + |
| 139 | + | + |
| 140 | + | + |
| 141 | + | + |
| 142 | ++ | + |
| 143 | ++ | + |
| 144A | ++ | + |
| 144B | ++ | + |
| 145 | + | + |
| 146A | + | + |
| 146B | + | + |
| 146C | + | + |
| 147 | + | + |
| 148 | + | + |
| 149 | + | + |
| 150 | + | + |
| 151 | + | + |
| 152 | + | + |
| 153 | + | + |
| 154 | + | + |
| 155 | + | + |
| 156 | ++ | + |
| 157 | + | + |
| 158 | + | + |
| 159A | +++ | ++ |
| 159B | + | + |
| 159C | ++ | + |
| 159D | + | + |
| 159E | + | + |
| 160A | +++ | ++ |
| 160B | +++ | +++ |
| 160C | +++ | +++ |
| 160D | +++ | +++ |
| 161 | + | + |
| 162 | + | + |
| 163 | + | + |
| 164 | + | + |
| 165 | + | + |
| 166 | + | + |
| 167 | + | + |
| 168A | + | + |
| 168B | + | + |
| 169 | + | + |
| 170A | + | + |
| 170B | + | + |
| 171 | + | + |
| 172 | + | + |
| 173 | + | + |
| 174 | + | + |
| 175 | + | + |
| 176 | + | + |
| 177 | + | + |
| 178 | + | + |
| 179 | + | + |
| 180A | + | + |
| 180B | + | + |
| 181A | + | + |
| 181B | + | + |
| 182A | + | + |
| 182B | + | + |
| 183 | + | + |
| 184 | + | + |
| 185 | ++ | + |
| 186 | + | + |
| 187 | + | + |
| 188 | + | + |
| 189 | + | + |
| 190 | + | + |
| 191 | + | + |
| 192 | + | + |
| 193A | + | + |
| 193B | + | + |
| 194 | + | + |
| 195 | + | + |
| 196 | + | + |
| 197 | + | + |
| 198 | +++ | + |
| 199 | ++ | + |
| 200 | ++ | + |
| 201A | + | + |
| 201B | + | + |
| 202A | + | + |
| 202B | + | + |
| 203 | + | + |
| 205 | + | + |
| 206 | + | + |
| 207 | + | + |
| 208 | + | + |
| 209 | + | + |
| 210 | + | + |
| 211 | + | + |
| 213 | + | + |
| 214 | + | + |
| 215 | + | + |
| 216 | + | + |
| 217 | + | + |
| 218 | + | + |
| 219 | + | + |
| 220 | + | + |
| 221 | + | + |
| 222 | + | + |
| 224 | + | + |
| 225 | + | + |
| 226 | + | + |
| 228 | + | + |
| 229 | + | + |
| 230 | + | + |
| 231 | + | + |
| 232 | + | + |
| 233 | + | + |
| 234 | + | + |
| 235 | + | + |
| 236 | + | + |
| 237 | + | + |
| 238 | + | + |
| 239 | + | + |
| 240 | + | + |
| 241 | + | + |
| 242 | + | + |
| 243 | + | + |
| 244 | + | + |
| 246 | + | + |
| 248 | + | + |
| 249 | + | + |
| 250 | + | + |
| 251 | + | + |
| 252 | ++ | ++ |
| 253 | ++ | ++ |
| 254 | + | + |
| 255 | + | + |
| 256 | + | + |
| 257 | ++ | + |
| 258 | +++ | ++ |
| 259 | ++ | + |
| 260 | ++ | + |
| 261 | ++ | + |
| 262 | +++ | + |
| 263 | ++ | + |
| 264 | ++ | + |
| 265A | +++ | +++ |
| 265B | + | + |
| 266A | ++ | + |
| 266B | +++ | ++ |
| 267A | +++ | +++ |
| 267B | + | + |
| 268 | +++ | ++ |

TABLE 12-continued

| Example No. | BRD4 BD-1 enzyme IC$_{50}$ (nM)* | BRD4 BD-2 enzyme IC$_{50}$ (nM)* |
|---|---|---|
| 269A | + | + |
| 269B | +++ | +++ |

*Symbols used:
+: IC$_{50}$ ≤100 nM
++: 100 nM < IC$_{50}$ ≤ 1000 nM
+++: 1000 nM to 10000 nM
NT = not tested Example B1: KMS.12.BM Cell Viability Assay KMS.12.BM cell line (human myeloma) was purchased from JCRB (Osaka, Japan) and maintained in RPMI with 10% FBS culture medium. To measure the cytotoxic activity of the compounds through ATP quantitation, the KMS.12.BM cells are plated in the RPMI culture medium at 5000 cells/well/per 100 µL into a 96-well polystyrene clear black tissue culture plate (Greiner-bio-one through VWR, NJ), in the presence or absence of a concentration range of test compounds. After 3 days, 100 mL Cell Titer-GLO Luminescent (Promega, Madison, Wis.) cell culture agent is added to each well for 10 min. at room temperature to stabilize the luminescent signal. This determines the number of viable cells in culture based on quantitation of the ATP present, which signals the presence of metabolically active cells. Luminescence is measured with the Top Count 384 (Packard Bioscience through Perkin Elmer, Boston, Mass.). Compound inhibition is determined relative to cells cultured with no drug and the IC$_{50}$ reported as the compound concentration required for 50% cell death.

IC$_{50}$ data for the compounds of the Examples as determined by Assay B1 is presented in Table 13.

TABLE 13

| Example No. | KMS cellular IC$_{50}$ (nM)* |
|---|---|
| 1 | + |
| 1A | + |
| 1B | NT |
| 2 | + |
| 3 | + |
| 4 | + |
| 5 | + |
| 6 | + |
| 7 | + |
| 8 | + |
| 9 | + |
| 10 | + |
| 11 | NT |
| 12 | ++ |
| 13 | + |
| 14 | NT |
| 15 | + |
| 16 | + |
| 17 | + |
| 18A | + |
| 18B | + |
| 19 | + |
| 20 | + |
| 21 | + |
| 22 | + |
| 23 | + |
| 24A | ++ |
| 24B | ++ |
| 25 | + |
| 26 | + |
| 27 | + |
| 28 | + |

TABLE 13-continued

| Example No. | KMS cellular IC$_{50}$ (nM)* |
|---|---|
| 29 | + |
| 30 | + |
| 31 | + |
| 32 | + |
| 33 | ++ |
| 34 | + |
| 35 | + |
| 36 | + |
| 37 | + |
| 38 | NT |
| 39 | + |
| 40 | + |
| 41 | + |
| 42 | + |
| 43 | + |
| 44 | NT |
| 45 | + |
| 46 | + |
| 47A | NT |
| 47B | ++ |
| 48A | NT |
| 48B | ++ |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61A | + |
| 62B | + |
| 62C | + |
| 63A | ++ |
| 69-87 | NT |
| 88 | + |
| 89 | + |
| 90 | + |
| 91 | + |
| 92 | + |
| 93 | + |
| 94 | + |
| 95 | + |
| 96 | + |
| 97 | + |
| 98 | NT |
| 99 | NT |
| 100 | + |
| 101A | NT |
| 101B | NT |
| 102 | NT |
| 103 | + |
| 104 | + |
| 105 | NT |
| 106A | NT |
| 106B | NT |
| 107 | NT |
| 108 | NT |
| 109 | + |
| 110 | + |
| 111 | + |
| 112 | + |
| 113A | NT |
| 113B | NT |
| 114A | NT |
| 114B | NT |
| 115 | NT |
| 116 | NT |
| 117 | NT |
| 118 | NT |
| 119 | NT |
| 120 | + |
| 121 | + |

TABLE 13-continued

| Example No. | KMS cellular IC$_{50}$ (nM)* |
|---|---|
| 122 | + |
| 123 | + |
| 124 | NT |
| 125 | NT |
| 126 | + |
| 127 | + |
| 128 | + |
| 129 | + |
| 130 | + |
| 131 | + |
| 132 | + |
| 133 | + |
| 134 | + |
| 135 | + |
| 136 | + |
| 137 | NT |
| 138 | + |
| 139 | + |
| 140 | + |
| 141 | + |
| 142 | + |
| 143 | + |
| 144A | + |
| 144B | + |
| 145 | + |
| 146A | + |
| 146B | + |
| 146C | + |
| 147 | + |
| 148 | + |
| 149 | + |
| 150 | + |
| 151 | + |
| 152 | + |
| 153 | + |
| 154 | + |
| 155 | + |
| 156 | + |
| 157 | + |
| 158 | + |
| 159A | NT |
| 159B | + |
| 159C | ++ |
| 159D | + |
| 159E | + |
| 160A | NT |
| 160B | NT |
| 160C | NT |
| 160D | NT |
| 161 | + |
| 162 | + |
| 163 | + |
| 164 | + |
| 165 | + |
| 166 | + |
| 167 | + |
| 168A | + |
| 168B | + |
| 169 | + |
| 170A | + |
| 170B | + |
| 171 | + |
| 172 | + |
| 173 | + |
| 174 | + |
| 175 | + |
| 176 | + |
| 177 | + |
| 178 | + |
| 179 | + |
| 180A | + |
| 180B | + |
| 181A | + |
| 181B | + |
| 182A | + |
| 182B | + |
| 183 | + |
| 184 | + |
| 185 | + |
| 186 | + |
| 187 | + |
| 188 | + |
| 189 | + |
| 190 | + |
| 191 | + |
| 192 | + |
| 193A | + |
| 193B | + |
| 194 | + |
| 195 | + |
| 196 | + |
| 197 | + |
| 198 | NT |
| 199 | NT |
| 200 | NT |
| 201A | + |
| 201B | + |
| 202A | + |
| 202B | + |
| 203 | + |
| 205 | + |
| 206 | + |
| 207 | + |
| 208 | + |
| 209 | + |
| 210 | + |
| 211 | + |
| 213 | + |
| 214 | + |
| 215 | + |
| 216 | + |
| 217 | + |
| 218 | + |
| 219 | + |
| 220 | + |
| 221 | + |
| 222 | + |
| 224 | + |
| 225 | + |
| 226 | + |
| 228 | + |
| 229 | + |
| 230 | + |
| 231 | + |
| 232 | + |
| 233 | + |
| 234 | + |
| 235 | + |
| 236 | + |
| 237 | + |
| 238 | + |
| 239 | + |
| 240 | + |
| 241 | + |
| 242 | + |
| 243 | + |
| 244 | + |
| 246 | + |
| 248 | + |
| 249 | + |
| 250 | + |
| 251 | + |
| 252 | NT |
| 253 | ++ |
| 254 | + |
| 255 | + |
| 256 | + |
| 257 | + |
| 258 | NT |
| 259 | ++ |
| 260 | ++ |
| 261 | NT |
| 262 | + |
| 263 | + |

TABLE 13-continued

| Example No. | KMS cellular IC$_{50}$ (nM)* |
|---|---|
| 264 | + |
| 265A | NT |
| 265B | + |
| 266A | + |
| 266B | NT |
| 267A | NT |
| 267B | + |
| 268 | NT |
| 269A | + |
| 269B | NT |

*Symbols used:
+: IC$_{50}$ ≤1000 nM
++: 1000 nM < IC$_{50}$ ≤ 10000 nM
NT = not tested

Example C1

KMS.12.BM C-Myc ELISA Assay

KMS.12.BM cell line (human myeloma) was purchased from JCRB (Osaka, Japan) and maintained in RPMI with 10% FBS culture medium. To measure the C-myc inhibitory activity of the compounds, the KMS.12.BM cells are plated in the RPMI culture medium at 75000 cells/well/per 200 µL into a 96-well flat bottom polystyrene tissue culture plate (Corning through VWR, NJ), in the presence or absence of a concentration range of test compounds. After 2 h, cells are pelleted and lysed with Cell Extraction Buffer (BioSource, Carlsbad, Calif.) in the presence of protease inhibitors (Life Technologies, Grand Island, N.Y. and Sigma, St Louis, Mo.). Clarified lyses are tested in a C-myc commercial ELISA (Life Technologies, Grand Island, N.Y.). Compound inhibition is determined relative to cells cultured with no drug and the IC$_{50}$ reported as the compound concentration required for 50% C-myc inhibition.

IC$_{50}$ data for the compounds of the Examples as determined by Assay C1 is presented in Table 14.

TABLE 14

| Example No. | KMS C-myc IC$_{50}$ (nM)* |
|---|---|
| 1A | + |
| 1B | NT |
| 2 | + |
| 3 | + |
| 4 | + |
| 5 | + |
| 6 | NT |
| 7 | + |
| 8 | + |
| 9 | + |
| 10 | + |
| 11 | NT |
| 12 | NT |
| 13 | + |
| 14 | NT |
| 15 | + |
| 16 | NT |
| 17 | NT |
| 18A | NT |
| 18B | NT |
| 19 | NT |
| 20 | NT |
| 21 | + |
| 22 | NT |
| 23 | NT |
| 24A | NT |
| 24B | NT |
| 25 | + |
| 26 | + |
| 27 | + |
| 28 | + |
| 29 | + |
| 30 | + |
| 31 | + |
| 32 | + |
| 33 | NT |
| 34 | + |
| 35-49 | NT |
| 50 | + |
| 61A-63B | NT |
| 69-93 | NT |
| 94 | + |
| 95 | + |
| 96 | + |
| 97 | NT |
| 98 | NT |
| 99 | NT |
| 100 | NT |
| 101A | NT |
| 101B | NT |
| 102 | NT |
| 103 | NT |
| 104 | NT |
| 105 | NT |
| 106A | + |
| 106B | NT |
| 107 | NT |
| 108 | NT |
| 109 | + |
| 110 | + |
| 111 | NT |
| 112 | NT |
| 113A | NT |
| 113B | NT |
| 114A | NT |
| 114B | NT |
| 115 | NT |
| 116 | NT |
| 117 | NT |
| 118 | NT |
| 119 | NT |
| 120 | NT |
| 121 | NT |
| 122 | NT |
| 123 | NT |
| 124 | NT |
| 125 | NT |
| 126 | NT |
| 127 | + |
| 128 | + |
| 129 | NT |
| 130 | + |
| 131 | NT |
| 132 | NT |
| 133 | + |
| 134 | + |
| 135 | + |
| 136 | + |
| 137 | NT |
| 138 | + |
| 139 | ++ |
| 140 | + |
| 141 | + |
| 142 | + |
| 143 | NT |
| 144A | + |
| 144B | + |
| 145-269B | |

*Symbols used:
+: IC$_{50}$ ≤1000 nM
++: 1000 nM < IC$_{50}$ ≤ 10000 nM
NT = not tested Various modifications of the invention, in addition to those described herein, will be apparent to those skilled in the art from the foregoing description. Such modifications are also intended to fall within the scope of the appended claims. Each reference cited in the present disclosure, including all patent, patent applications, and publications, is incorporated herein by reference in its entirety.

What is claimed is:
1. A compound of Formula (I):

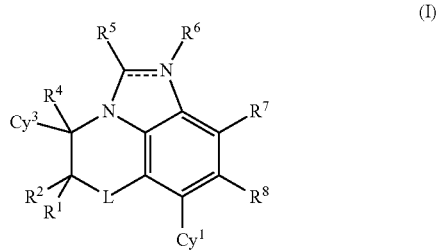

or a pharmaceutically acceptable salt thereof, wherein:
═ represents a double bond;
L is O;
$Cy^1$ is selected from phenyl or a 5-6 membered heteroaryl group comprising carbon and 1, 2, 3 or 4 heteroatoms selected from N, O and S, wherein said phenyl or 5-6 membered heteroaryl of $Cy^1$ is optionally substituted with 1, 2, 3, or 4 groups independently selected from $R^{11}$;
$R^1$ and $R^2$ are independently selected from H, halo, CN, OH, $C_{1-6}$ alkyl, $C_{2-6}$ alkenyl, $C_{2-6}$ alkynyl, $C_{1-6}$ haloalkyl, $OR^{a1}$, $SR^{a1}$, $C(\!=\!O)R^{b1}$, $C(\!=\!O)NR^{c1}R^{d1}$, $C(\!=\!O)OR^{a1}$, $OC(\!=\!O)R^{b1}$, $OC(\!=\!O)NR^{c1}R^{d1}$, $NR^{c1}R^{d1}$, $NR^{c1}C(\!=\!O)R^{b1}$, $NR^{c1}C(\!=\!O)NR^{c1}R^{d1}$, $NR^{c1}C(\!=\!O)OR^{a1}$, $S(\!=\!O)R^{b1}$, $S(\!=\!O)NR^{c1}R^{d1}$, $S(\!=\!O)_2R^{b1}$, $NR^{c1}S(\!=\!O))_2R^{b1}$ and $S(\!=\!O)_2NR^{c1}R^{d1}$, wherein said $C_{1-6}$ alkyl, $C_{2-6}$ alkenyl, and $C_{2-6}$ alkynyl of $R^1$ and $R^2$ are optionally substituted with 1, 2, or 3 groups independently selected from halo, CN, OH, $OR^{a1}$, $SR^{a1}$, $C(\!=\!O)R^{b1}$, $C(\!=\!O)NR^{c1}R^{d1}$, $C(\!=\!O)OR^{a1}$, $OC(\!=\!O)R^{b1}$, $OC(\!=\!O)NR^{c1}R^{d1}$; $NR^{c1}R^{d1}$, $NR^{c1}C(\!=\!O)R^{b1}$, $NR^{c1}C(\!=\!O)NR^{c1}R^{d1}$, $NR^{c1}C(\!=\!O)R^{a1}$, $S(\!=\!O)R^{b1}$, $S(\!=\!O)NR^{c1}R^{d1}$; $S(\!=\!O)_2R^{b1}$, $NR^{c1}S(\!=\!O)_2R^{b1}$ and $S(\!=\!O)_2NR^{c1}R^{d1}$;
provided neither $R^1$ nor $R^2$ are Cl, Br, I, CN, or OH when L is O or S;
alternatively, $R^1$ and $R^2$ together with the carbon atom to which they are attached are combined to form a $C_{3-7}$ cycloalkyl group, wherein said cycloalkyl group is optionally substituted with 1, 2, 3, or 4 groups independently selected from $R^{20}$;
$Cy^3$ is selected from phenyl, $C_{3-7}$ cycloalkyl, a 5-10 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said phenyl, $C_{3-7}$ cycloalkyl, 5-10 membered heteroaryl, and 4-10 membered heterocycloalkyl of $Cy^3$ is optionally substituted with 1, 2, 3, or 4 groups independently selected from $R^{13}$, wherein a ring-forming nitrogen atom of said 5-10 membered heteroaryl group or a ring-forming nitrogen atom of said 4-10 membered heterocycloalkyl group is optionally oxidized;

$R^4$ is H, $C(\!=\!O)NR^{14a}R^{14b}$, $C(\!=\!O)R^{14a}$, $C(\!=\!O)OR^{14a}$, or $C_{1-6}$ alkyl optionally substituted by 1, 2, or 3 substituents independently selected from halo, $NR^{14a}R^{14b}$, $OR^{14a}$, $SR^{14a}$, CN, $C(\!=\!O)R^{14a}$, $C(\!=\!O)NR^{14a}R^{14b}$, $C(\!=\!O)OR^{14a}$, $OC(\!=\!O)R^{14b}$, $OC(\!=\!O)NR^{14a}R^{14b}$, $NR^{14a}C(\!=\!O)R^{14b}$, $NR^{14a}C(\!=\!O)NR^{14a}R^{14b}$, $NR^{14a}C(\!=\!O)OR^{14b}$, $S(\!=\!O)R^{14a}$, $S(\!=\!O)NR^{14a}R^{14b}$, $S(\!=\!O)_2R^{14a}$, $NR^{14a}S(\!=\!O)_2R^{14b}$, and $S(\!=\!O)_2NR^{14a}R^{14b}$;
$R^5$ is selected from H, $C_{1-6}$ alkyl, $C_{2-6}$ alkenyl, $C_{2-6}$ alkynyl, $C_{1-6}$ haloalkyl, $NR^{15a}R^{15b}$, —$C(\!=\!O)NR^{15a}R^{15b}$, —$C(\!=\!O)OR^{15a}$, phenyl, $C_{3-7}$ cycloalkyl, 5-6 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said $C_{1-6}$ alkyl, phenyl, $C_{3-7}$ cycloalkyl, 5-6 membered heteroaryl, and 4-10 membered heterocycloalkyl of $R^5$ is optionally substituted by 1, 2, 3, or 4 groups independently selected from $R^{15}$;
$R^6$ is absent;
$R^7$ is selected from H, halo, CN, $OR^a$, $NR^cR^d$, $SR^b$, $C(\!=\!O)NR^cR^d$, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, $C_{2-6}$ alkenyl, $C_{2-6}$ alkynyl, phenyl, $C_{3-7}$ cycloalkyl, 5-6 membered heteroaryl group, and a 4-7 membered heterocycloalkyl group of $R^7$ are optionally substituted with 1, 2, or 3 groups independently selected from $R^{17}$;
$R^8$ is selected from H, $C_{1-3}$ alkyl, $C_{2-3}$ alkenyl, $C_{2-3}$ alkynyl, $C_{1-3}$ haloalkyl, halo, CN, $OR^a$, $NR^cR^d$, $SR^b$, and $C(\!=\!O)NR^cR^d$, wherein said $C_{1-3}$ alkyl of $R^8$ is optionally substituted with 1, 2, or 3 groups independently selected from $R^{18}$;
$R^9$ and $R^{9a}$ are independently selected from H, $C_{1-3}$ alkyl, $C_{1-3}$ haloalkyl, halo, CN, $OR^a$, $NR^cR^d$, $SR^b$, and $C(\!=\!O)NR^cR^d$;
$R^{11}$ is independently at each occurrence selected from H, $C_{1-3}$ alkyl, $C_{1-3}$ haloalkyl, halo, CN, $OR^a$, $NR^cR^d$, $SR^b$, and $C(\!=\!O)NR^cR^d$, wherein said $C_{1-3}$ alkyl is optionally substituted by OH;
$R^{13}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a3}$, $SR^{a3}$, $C(\!=\!O)R^{b3}$, $C(\!=\!O)NR^{c3}R^{d3}$, $C(\!=\!O)OR^{a3}$, $OC(\!=\!O)R^{b3}$, $OC(\!=\!O)NR^{c3}R^{d3}$, $NR^{c3}R^{d3}$, $NR^{c3}C(\!=\!O)R^{b3}$, $NR^{c3}C(\!=\!O)NR^{c3}R^{d3}$, $NR^{c3}C(\!=\!O)OR^{a3}$, $S(\!=\!O)R^{b3}$, $S(\!=\!O)NR^{c3}R^{d3}$, $S(\!=\!O)_2R^{b3}$, $NR^{c3}S(\!=\!O)_2R^{b3}$ and $S(\!=\!O)_2NR^{c3}R^{d3}$, wherein said $C_{1-6}$ alkyl, $C_{2-6}$ alkenyl, and $C_{2-6}$ alkynyl of $R^{13}$ is optionally substituted with 1, 2, or 3 groups independently selected from halo, CN, OH, $OR^{a3}$, $SR^{a3}$, $C(\!=\!O)R^{b3}$, $C(\!=\!O)NR^{c3}R^{d3}$, $C(\!=\!O)OR^{a3}$, $OC(\!=\!O)R^{b3}$, $OC(\!=\!O)NR^{c3}R^{d3}$, $NR^{c3}R^{d3}$, $NR^{c3}C(\!=\!O)R^{b3}$, $NR^{c3}C(\!=\!O)NR^{c3}R^{d3}$, $NR^{c3}C(\!=\!O)OR^{a3}$, $S(\!=\!O)R^{b3}$, $S(\!=\!O)NR^{c3}R^{d3}$, $S(\!=\!O)_2R^{b3}$, $NR^{c3}S(\!=\!O)_2R^{b3}$ and $S(\!=\!O)_2NR^{c3}R^{d3}$;
$R^{15}$ is independently at each occurrence selected from H, $C_{1-6}$ alkyl, $C_{3-7}$ cycloalkyl, 4-7 membered heterocycloalkyl, phenyl, 5-6 membered heteroaryl, halo, CN, $OR^{a5}$, $SR^{a5}$, $C(\!=\!O)R^{b5}$, $C(\!=\!O)NR^{c5}R^{d5}$, $C(\!=\!O)OR^{a5}$, $OC(\!=\!O)R^{b5}$, $OC(\!=\!O)NR^{c5}R^{d5}$, $NR^{c5}R^{d5}$, $NR^{c5}C(\!=\!O)R^{b5}$, $NR^{c5}C(\!=\!O)NR^{c5}R^{d5}$, $NR^{c5}C(O)OR^{a5}$, $S(\!=\!O)R^{b5}$, $S(\!=\!O)NR^{c5}R^{d5}$, $S(\!=\!O)_2R^{b5}$, NR$^{c5}$S(=O)$_2$R$^{b5}$, and S(=O)$_2$NR$^{c5}$R$^{d5}$, wherein said C$_{1-6}$ alkyl, C$_{3-7}$ cycloalkyl, 4-7 membered heterocycloalkyl, phenyl, and 5-6 membered heteroaryl are each optionally substituted by 1, 2, or 3 substituents independently selected from halo, CN, OR$^{a5}$, SR$^{a5}$, C(=O)R$^{b5}$, C(=O)NR$^{c5}$R$^{d5}$, C(=O)OR$^{a5}$, OC(=O)R$^{b5}$, OC(=O)NR$^{c5}$R$^{d5}$, NR$^{c5}$R$^{d5}$, NR$^{c5}$C(=O)R$^{b5}$, NR$^{c5}$C(=O)NR$^{c5}$R$^{d5}$, NR$^{c5}$C(=O)OR$^{a5}$, S(=O)R$^{b5}$, S(=O)NR$^{c5}$R$^{d5}$, S(=O)$_2$R$^{b5}$, NR$^{c5}$S(=O)$_2$R$^{b5}$, S(=O)$_2$NR$^{c5}$R$^{d5}$, 5-6 membered heteroaryl, 4-7 membered heterocycloalkyl, phenyl, and C$_{3-7}$ cycloalkyl;

R$^{14a}$ and R$^{14b}$ are independently at each occurrence selected from H and C$_{1-6}$ alkyl, wherein said C$_{1-6}$ alkyl of R$^{14a}$ and R$^{14b}$ is optionally substituted with 1, 2, or 3 substituents selected from R$^{20}$;

or R$^{14a}$ and R$^{14b}$ together with the N atom to which they are attached form a 4-7 membered heterocycloalkyl ring optionally substituted with 1, 2, or 3 substituents selected from R$^{20}$;

R$^{15a}$ and R$^{15b}$ are independently at each occurrence selected from H and C$_{1-6}$ alkyl, wherein said C$_{1-6}$ alkyl of R$^{15a}$ and R$^{15b}$ is optionally substituted with 1, 2, or 3 substituents selected from R$^{20}$;

or R$^{15a}$ and R$^{15b}$ together with the N atom to which they are attached form a 4-7 membered heterocycloalkyl ring optionally substituted with 1, 2, or 3 substituents selected from R$^{20}$;

R$^{17}$ and R$^{18}$ are independently at each occurrence selected from halo, C$_{1-4}$ alkyl, CN, OR$^a$, NR$^c$R$^d$, SR$^b$, C(=O)NR$^c$R$^d$, C(=O)OR$^a$, and NR$^c$C(=O)R$^a$;

R$^a$, R$^c$, and R$^d$ are independently at each occurrence selected from H, C$_{1-6}$ alkyl, C(O)R$^e$, S(=O)$_2$R$^f$, C(=O)NR$^g$R$^h$, and phenyl optionally substituted by C$_{1-4}$ alkoxy;

R$^b$ is at each occurrence C$_{1-6}$ alkyl;

R$^e$ is at each occurrence C$_{1-4}$ alkyl optionally substituted by a group selected from phenyl, C$_{1-4}$ alkoxy, amino, C$_{1-4}$ alkylamino, and C$_{2-8}$ dialkylamino;

R$^f$ is C$_{1-4}$ alkyl;

R$^g$ and R$^h$ are independently at each occurrence selected from H and C$_{1-4}$ alkyl;

R$^{a1}$, R$^{b1}$, R$^{c1}$ and R$^{d1}$ are independently at each occurrence selected from H, C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl forming R$^{a1}$, R$^{b1}$, R$^{c1}$ and R$^{d1}$ are each optionally substituted with 1, 2, or 3 substituents independently selected from R$^{20}$;

R$^{a3}$, R$^{b3}$, R$^{c3}$ and R$^{d3}$ are independently at each occurrence selected from H, C$_{1-6}$ alkyl, C$_{2-6}$ alkenyl, C$_{2-6}$ alkynyl, C$_{3-6}$ cycloalkyl, and C$_{1-6}$ haloalkyl, wherein said C$_{1-6}$ alkyl, C$_{2-6}$ alkenyl, and C$_{2-6}$ alkynyl forming R$^{a3}$, R$^{b3}$, R$^{c3}$ and R$^{d3}$ are each optionally substituted with 1, 2, or 3 substituents independently selected from halo, CN, OH, OR$^{a4}$, SR$^{a4}$, C(=O)R$^{b4}$, C(=O)NR$^{c4}$R$^{d4}$, C(=O)OR$^{a4}$, OC(=O)R$^{b4}$, OC(=O)NR$^{c4}$R$^{d4}$, NR$^{c4}$R$^{d4}$, NR$^{c4}$C(=O)R$^{b4}$, NR$^{c4}$C(=O)NR$^{c4}$R$^{d4}$, NR$^{c4}$C(=O)OR$^{a4}$, S(O)R$^{b4}$, S(=O)NR$^{c4}$R$^{d4}$, S(=O)$_2$R$^{b4}$, NR$^{c4}$S(=O)$_2$R$^{b4}$ and S(=O)$_2$NR$^{c4}$R$^{d4}$;

R$^{a4}$, R$^{b4}$, R$^{c4}$ and R$^{d4}$ are independently at each occurrence selected from H, C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl forming R$^{a4}$, R$^{b4}$, R$^{c4}$ and R$^{d4}$ are each optionally substituted with 1, 2, or 3 substituents independently selected from R$^{20}$;

R$^{a5}$, R$^{b5}$, R$^{c5}$ and R$^{d5}$ are independently at each occurrence selected from H, C$_{1-6}$ alkyl, C$_{2-6}$ alkenyl, C$_{2-6}$ alkynyl, C$_{3-6}$ cycloalkyl, 5-6 membered heterocycloalkyl, and C$_{1-6}$ haloalkyl wherein said C$_{1-6}$ alkyl, C$_{2-6}$ alkenyl, and C$_{2-6}$ alkynyl forming R$^{a5}$, R$^{b5}$, R$^{c5}$ and R$^{d5}$ are each optionally substituted with 1, 2, or 3 substituents independently selected from R$^{20}$;

or R$^{c5}$ and R$^{d5}$ together with the N atom to which they are attached form a 4-7 membered heterocycloalkyl ring optionally substituted with 1, 2, or 3 substituents independently selected from R$^{20}$; and R$^{20}$ is at each occurrence independently selected from H, halo, OH, CN, amino, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, C$_{1-4}$ haloalkoxy, C$_{1-4}$ alkyl-C(=O)—, C$_{1-4}$ alkyl-C(=O)O—, C$_{1-4}$ alkyl-OC(=O)—, HOC(=O)—, H$_2$NC(=O)—, C$_{1-4}$ alkyl-NHC(=O)—, di(C$_{1-4}$ alkyl)NC(=O)—, C$_{1-4}$ alkyl-C(=O)NH—, C$_{1-4}$ alkyl-O—C(=O)NH—, C$_{1-4}$ alkyl-S(=O)—, H$_2$NS(=O)—, C$_{1-4}$ alkyl-NHS(=O)—, di(C$_{1-4}$ alkyl)NS(=O)—, C$_{1-4}$ alkyl-S(=O)$_2$—, C$_{1-4}$ alkyl-S(=O)$_2$NH—, H$_2$NS(=O)$_2$—, C$_{1-4}$ alkyl-NHS(=O)$_2$—, and di(C$_{1-4}$ alkyl)NS(=O)$_2$—.

2. The compound of claim 1, or a pharmaceutically acceptable salt thereof, wherein:

= represents a double bond;

L is O;

Cy$^1$ is a five membered heteroaryl group comprising carbon and 1, 2, 3 or 4 heteroatoms selected from N, O and S, wherein said five membered heteroaryl of Cy$^1$ is optionally substituted with 1, 2, or 3 groups independently selected from R$^{11}$;

R$^1$ is selected from H, F, C$_{1-6}$ alkyl, C$_{2-6}$ alkenyl, C$_{2-6}$ alkynyl, C$_{1-6}$ haloalkyl, OR$^{a1}$, C(=O)R$^{b1}$, C(=O)NR$^{c1}$R$^{d1}$, and C(O)OR$^{a1}$;

R$^2$ is selected from H, F, and C$_{1-6}$ alkyl;

Cy$^3$ is selected from phenyl, C$_{3-7}$ cycloalkyl, a 5-10 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said phenyl, C$_{3-7}$ cycloalkyl, 5-10 membered heteroaryl, and 4-10 membered heterocycloalkyl of Cy$^3$ is optionally substituted with 1, 2, 3, or 4 groups independently selected from R$^{13}$; additionally, wherein a ring-forming nitrogen atom of said 5-10 membered heteroaryl group or a ring-forming nitrogen atom of said 4-10 membered heterocycloalkyl group is optionally oxidized;

R$^4$ is H or C$_{1-6}$ alkyl;

R$^5$ is selected from H, C$_{1-6}$ alkyl, C$_{2-6}$ alkenyl, C$_{2-6}$ alkynyl, C$_{1-6}$ haloalkyl, NR$^{15a}$R$^{15b}$, phenyl, C$_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said C$_{1-6}$ alkyl, phenyl, C$_{3-7}$ cycloalkyl, 5-6 membered heteroaryl, and 4-7 membered heterocycloalkyl of R$^5$ is optionally substituted by 1, 2, 3, or 4 groups independently selected from R$^{15}$;

R$^6$ is absent;

R$^7$ is selected from H, halo, CN, C$_{1-6}$ alkyl, C$_{1-6}$ alkoxy, phenyl, and 5-6 membered heteroaryl group comprising carbon and 1, 2, 3 or 4 heteroatoms selected from N, O and S, wherein said C$_{1-6}$ alkyl, phenyl, or 5-6 membered heteroaryl group, of R$^7$ are optionally substituted with 1, 2, or 3 groups independently selected from R$^{17}$;

$R^8$ is selected from H, halo, CN, OH, and $C_{1-6}$ alkyl;

$R^{11}$ is independently at each occurrence selected from H, $C_{1-3}$ alkyl, $C_{1-3}$ haloalkyl, halo, CN, $OR^a$, $NR^cR^d$, $SR^b$, and $C(=O)NR^cR^d$;

$R^{13}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$, wherein said $C_{1-6}$ alkyl, $C_{2-6}$ alkenyl, and $C_{2-6}$ alkynyl of $R^{13}$ is optionally substituted with 1, 2, or 3 groups independently selected from halo, CN, OH, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$;

$R^{15}$ is independently at each occurrence selected from H, halo, CN, OH, $OR^{a5}$, $C(=O)R^{b5}$, $C(=O)NR^{c5}R^{d5}$, $C(=O)OR^{a5}$, $NR^{c5}R^{d5}$, and $NR^{c5}C(=O)R^{b5}$;

$R^{15a}$ and $R^{15b}$ are independently selected from H and $C_{1-6}$ alkyl, wherein said $C_{1-6}$ alkyl of $R^{15a}$ and $R^{15b}$ is optionally substituted with 0, 1, 2, or 3 substituents selected from $R^{20}$;

$R^{17}$ is independently at each occurrence selected from halo, CN, $OR^a$, $NR^cR^d$, $SR^b$, and $C(=O)NR^cR^d$;

$R^a$, $R^c$, and $R^d$ are independently at each occurrence selected from H and $C_{1-6}$ alkyl;

$R^b$ is at each occurrence $C_{1-6}$ alkyl;

$R^{a1}$, $R^{b1}$, $R^{c1}$ and $R^{d1}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a1}$, $R^{b1}$, $R^{c1}$ and $R^{d1}$ are each optionally substituted with 1, 2, or 3 substituents independently selected from $R^{20}$;

$R^{a3}$, $R^{b3}$, $R^{c3}$ and $R^{d3}$ are independently at each occurrence selected from H and $C_{1-6}$ alkyl, wherein said $C_{1-6}$ alkyl forming $R^{a3}$, $R^{b3}$, $R^{c3}$ and $R^{d3}$ is optionally substituted with 1, 2, or 3 substituents independently selected from halo, CN, OH, $OR^{a4}$, $SR^{a4}$, $C(=O)R^{b4}$, $C(=O)NR^{c4}R^{d4}$, $C(=O)R^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)NR^{c4}R^{d4}$, $NR^{c4}C(=O)OR^{a4}$, $S(=O)R^{b4}$, $S(=O)NR^{c4}R^{d4}$, $S(=O)_2R^{b4}$, $NR^{c4}S(=O)_2R^{b4}$ and $S(=O)_2NR^{c4}R^{d4}$;

$R^{a4}$, $R^{b4}$, $R^{c4}$ and $R^{d4}$ are independently at each occurrence selected from H and $C_{1-6}$ alkyl, wherein said $C_{1-6}$ alkyl forming $R^{a4}$, $R^{b4}$, $R^{c4}$ and $R^{d4}$ is optionally substituted with 1, 2, or 3 substituents independently selected from $R^{20}$;

$R^{a5}$, $R^{b5}$, $R^{c5}$ and $R^{d5}$ are independently at each occurrence selected from H and $C_{1-6}$ alkyl, wherein said $C_{1-6}$ alkyl forming $R^{a5}$, $R^{b5}$, $R^{c5}$ and $R^{d5}$ is optionally substituted with 1, 2, or 3 substituents independently selected from $R^{20}$; and $R^{20}$ is at each occurrence independently selected from H, halo, OH, CN, amino, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, $C_{1-4}$ haloalkoxy, $C_{1-4}$ alkyl-C(=O)—, $C_{1-4}$ alkyl-C(=O)O—, $C_{1-4}$ alkyl-OC(=O)—, HOC(=O)—, $H_2NC(=O)$—, $C_{1-4}$ alkyl-NHC(=O)—, di($C_{1-4}$ alkyl)NC(=O)—, $C_{1-4}$ alkyl-C(=O)NH—, $C_{1-4}$ alkyl-S(=O)—, $H_2NS(=O)$—, $C_{1-4}$ alkyl-NHS(=O)—, di($C_{1-4}$ alkyl)NS(=O)—, $C_{1-4}$ alkyl-S(=O)_2—, $C_{1-4}$ alkyl-S(=O)_2NH—, $H_2NS(=O)_2$—, $C_{1-4}$ alkyl-NHS(=O)_2—, and di($C_{1-4}$ alkyl)NS(=O)_2—.

3. The compound of claim 1 having Formula (Ia):

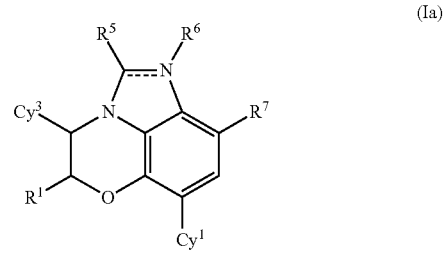

(Ia)

or a pharmaceutically acceptable salt thereof, wherein:

═ represents a double bond;

$Cy^1$ is selected from isoxazolyl and pyrazolyl, wherein said isoxazolyl and pyrazolyl of $Cy^1$ is optionally substituted with 1 or 2 groups independently selected from $R^{11}$;

$R^1$ is selected from H, methyl, —C(=O)OCH$_2$CH$_3$, —C(=O)N(H)CH$_2$CH$_3$, —C(=O)N(H)CH$_2$CH$_2$OH, and —C(=O)N(CH$_3$)$_2$;

$Cy^3$ is selected from phenyl, pyridinyl, oxidopyridinyl, thiazolyl, cyclohexyl, dihydrobenzofuranyl and tetrahydrofuranyl, wherein said phenyl, pyridinyl, oxidopyridinyl, thiazolyl, cyclohexyl, dihydrobenzofuranyl and tetrahydrofuranyl of $Cy^3$ is optionally substituted with 1, 2, 3, or 4 groups independently selected from $R^{13}$;

$R^5$ is H, methyl, —CH═CH$_2$, —N(H)CH$_3$, —N(H)CH$_2$CH$_3$, —N(H)CH(CH$_3$)$_2$, —N(CH$_3$)$_2$, —N(H)CH$_2$CH$_2$OH, —N(H)CH(CH$_3$)CH$_2$OH, —N(H)CH$_2$CH(OH)CH$_3$, —N(H)C(CH$_3$)$_2$CH$_2$OH, —N(CH$_3$)CH$_2$CH$_2$OH, morpholinyl, pyrrolidinyl, hydroxypyrrolidinyl, piperidinyl, hydroxypiperidinyl, azetidinyl, hydroxyazetidinyl, piperazinyl, butoxycarbonylpiperazinyl, and phenyl;

$R^6$ is absent;

$R^7$ is selected from H, F, Cl, Br, methyl, methoxy, ethoxy, CN, phenyl, and pyridinyl;

$R^{11}$ is independently at each occurrence selected from H, methyl, ethyl, chloro, and methoxy; and $R^{13}$ is independently at each occurrence selected from H, F, CN, methoxy, —CF$_3$, —OCH$_2$C(=O)OH, —OCH$_2$C(=O)N(H)CH$_2$CH$_3$, —OCH$_2$C(=O)N(H)CH$_2$CH$_2$OH, and —OCH$_2$C(=O)N(CH$_3$)$_2$.

4. The compound of claim 1, or a pharmaceutically acceptable salt thereof, wherein $Cy^1$ is isoxazolyl substituted with 1 or 2 groups independently selected from $R^{11}$.

5. The compound of claim 1, or a pharmaceutically acceptable salt thereof, wherein $Cy^1$ is pyrazolyl substituted with 1 or 2 groups independently selected from $R^{11}$.

6. The compound of claim 1, or a pharmaceutically acceptable salt thereof, wherein $R^1$ is selected from H, methyl, —CH$_2$OH, —C(=O)OCH$_2$CH$_3$, —C(=O)N(H)CH$_2$CH$_3$, —C(=O)N(H)CH$_3$, —C(=O)NH$_2$, —C(=O)N(H)CH$_2$CH$_2$OH, and —C(=O)N(CH$_3$)$_2$.

7. The compound of claim 1, or a pharmaceutically acceptable salt thereof, wherein $R^1$ is selected from H, methyl, —C(=O)OCH$_2$CH$_3$, —C(=O)N(H)CH$_2$CH$_3$, —C(=O)N(H)CH$_2$CH$_2$OH, and —C(=O)N(CH$_3$)$_2$.

8. The compound of claim 1, or a pharmaceutically acceptable salt thereof, wherein $R^1$ is H.

9. The compound of claim 1, or a pharmaceutically acceptable salt thereof, wherein $R^1$ is methyl.

10. The compound of claim 1, or a pharmaceutically acceptable salt thereof, wherein $R^1$ is —C(=O)OCH$_2$CH$_3$.

11. The compound of claim 1, or a pharmaceutically acceptable salt thereof, wherein $R^1$ is C(=O)N(H)CH$_2$CH$_3$.

12. The compound of any claim 1, or a pharmaceutically acceptable salt thereof, wherein $R^1$ is C(=O)N(H)CH$_2$CH$_2$OH.

13. The compound of claim 1, or a pharmaceutically acceptable salt thereof, wherein $R^1$ is —C(=O)N(CH$_3$)$_2$.

14. The compound of claim 1, or a pharmaceutically acceptable salt thereof, wherein $R^1$ is —C(=O)N(H)CH$_3$.

15. The compound of claim 1, or a pharmaceutically acceptable salt thereof, wherein $R^1$ is —C(=O)NH$_2$.

16. The compound claim 1, or a pharmaceutically acceptable salt thereof, wherein $R^1$ is —CH$_2$OH.

17. The compound of claim 1, or a pharmaceutically acceptable salt thereof, wherein $R^2$ is H.

18. The compound of claim 1, or a pharmaceutically acceptable salt thereof, wherein $R^2$ is methyl.

19. The compound of claim 1, or a pharmaceutically acceptable salt thereof, wherein $Cy^3$ is selected from phenyl, pyridinyl, oxidopyridinyl, thiazolyl, cyclohexyl, dihydrobenzofuranyl, tetrahydrofuranyl, and piperinyl, wherein said phenyl, pyridinyl, oxidopyridinyl, thiazolyl, cyclohexyl, dihydrobenzofuranyl, tetrahydrofuranyl, and piperidinyl of $Cy^3$ is optionally substituted with 1, 2, 3, or 4 groups independently selected from $R^{13}$.

20. The compound of claim 1, or a pharmaceutically acceptable salt thereof, wherein $Cy^3$ is selected from phenyl, pyridinyl, oxidopyridinyl, thiazolyl, cyclohexyl, dihydrobenzofuranyl and tetrahydrofuranyl, wherein said phenyl, pyridinyl, oxidopyridinyl, thiazolyl, cyclohexyl, dihydrobenzofuranyl and tetrahydrofuranyl of $Cy^3$ is optionally substituted with 1, 2, 3, or 4 groups independently selected from $R^{13}$.

21. The compound of claim 1, or a pharmaceutically acceptable salt thereof, wherein $Cy^3$ is phenyl optionally substituted with 1, 2, 3, or 4 groups independently selected from $R^{13}$.

22. The compound of claim 1, or a pharmaceutically acceptable salt thereof, wherein $Cy^3$ is pyridinyl optionally substituted with 1, 2, 3, or 4 groups independently selected from $R^{13}$.

23. The compound of claim 1, or a pharmaceutically acceptable salt thereof, wherein $Cy^3$ is oxidopyridinyl optionally substituted with 1, 2, 3, or 4 groups independently selected from $R^{13}$.

24. The compound of claim 1, or a pharmaceutically acceptable salt thereof, wherein $Cy^3$ is thiazolyl optionally substituted with 1, 2, 3, or 4 groups independently selected from $R^{13}$.

25. The compound of claim 1, or a pharmaceutically acceptable salt thereof, wherein $Cy^3$ is cyclohexyl optionally substituted with 1, 2, 3, or 4 groups independently selected from $R^{13}$.

26. The compound of claim 1, or a pharmaceutically acceptable salt thereof, wherein $Cy^3$ is dihydrobenzofuranyl optionally substituted with 1, 2, 3, or 4 groups independently selected from $R^{13}$.

27. The compound of claim 1, or a pharmaceutically acceptable salt thereof, wherein $Cy^3$ is tetrahydrofuranyl optionally substituted with 1, 2, 3, or 4 groups independently selected from $R^{13}$.

28. The compound of claim 1, or a pharmaceutically acceptable salt thereof, wherein $Cy^3$ is piperidinyl optionally substituted with 1, 2, 3, or 4 groups independently selected from $R^{13}$.

29. The compound of claim 1, or a pharmaceutically acceptable salt thereof, wherein $R^4$ is H, —C(=O)NH$_2$, —CH$_2$NH$_2$, —CH$_2$N(H)C(=O)CH$_3$, —C(=O)N(H)CH$_3$, —CH$_2$CH$_3$, or —CH$_3$.

30. The compound of claim 1, or a pharmaceutically acceptable salt thereof, wherein $R^4$ is H.

31. The compound of claim 1, or a pharmaceutically acceptable salt thereof, wherein $R^5$ is selected from H, $C_{1-4}$ alkyl, —CH=CH$_2$, NR$^{15a}$R$^{15b}$, C(=O)NR$^{15a}$R$^{15b}$, phenyl, and a 4-10 membered heterocycloalkyl group comprising carbon and 1, 2, or 3 heteroatoms selected from N, O and S, wherein said $C_{1-4}$ alkyl, and 4-10 membered heterocycloalkyl of $R^5$ is optionally substituted by 1 or 2 groups independently selected from $R^{15}$.

32. The compound of claim 1, or a pharmaceutically acceptable salt thereof, wherein $R^5$ is selected from H, $C_{1-4}$ alkyl, —CH=CH$_2$, NR$^{15a}$R$^{15b}$, C(=O)NR$^{15a}$R$^{15b}$, phenyl, azetidinyl, pyrrolidinyl, piperidinyl, piperazinyl, 1,2,3,6-tetrahydropyridinyl, 2,5-dihydro-1H-pyrrolyl, 1,4-diazepanyl, morpholinyl, and octahydropyrrolo[1,2-a]pyrazinyl, wherein said $C_{1-4}$ alkyl, phenyl, azetidinyl, pyrrolidinyl, piperidinyl, piperazinyl, 1,2,3,6-tetrahydropyridinyl, 2,5-dihydro-1H-pyrrolyl, 1,4-diazepanyl, morpholinyl, and octahydropyrrolo[1,2-a]pyrazinyl of $R^5$ is optionally substituted by 1 or 2 groups independently selected from $R^{15}$.

33. The compound of claim 1, or a pharmaceutically acceptable salt thereof, wherein $R^5$ is H, methyl, —CH=CH$_2$, —N(H)CH$_3$, —N(H)CH$_2$CH$_3$, —N(H)CH(CH$_3$)$_2$, —N(CH$_3$)$_2$, —N(H)CH$_2$CH$_2$OH, —N(H)CH(CH$_3$)CH$_2$OH, —N(H)CH$_2$CH(OH)CH$_3$, —N(H)C(CH$_3$)$_2$CH$_2$OH, —N(CH$_3$)CH$_2$CH$_2$OH, morpholinyl, pyrrolidinyl, hydroxypyrrolidinyl, piperidinyl, hydroxypiperidinyl, azetidinyl, hydroxyazetidinyl, piperazinyl, butoxycarbonylpiperazinyl or phenyl.

34. The compound of claim 1, or a pharmaceutically acceptable salt thereof, wherein $R^5$ is selected from a 4-6 membered heterocycloalkyl group comprising carbon and 1, 2, or 3 heteroatoms selected from N, O and S, wherein said 4-6 membered heterocycloalkyl of $R^5$ is optionally substituted by 1 or 2 groups independently selected from $R^{15}$.

35. The compound of claim 1, or a pharmaceutically acceptable salt thereof, wherein $R^5$ is pyrrolidinyl, piperidinyl, azetidinyl, or piperazinyl, wherein said pyrrolidinyl, piperidinyl, azetidinyl, or piperazinyl of $R^5$ is optionally substituted by 1 or 2 groups independently selected from $R^{15}$.

36. The compound of claim 1, or a pharmaceutically acceptable salt thereof, wherein $R^5$ is pyrrolidinyl, wherein said pyrrolidinyl of $R^5$ is optionally substituted by 1 or 2 groups independently selected from $R^{15}$.

37. The compound of claim 1, or a pharmaceutically acceptable salt thereof, wherein $R^5$ is piperidinyl, wherein said piperidinyl of $R^5$ is optionally substituted by 1 or 2 groups independently selected from $R^{15}$.

38. The compound of claim 1, or a pharmaceutically acceptable salt thereof, wherein $R^5$ is azetidinyl, wherein said azetidinyl of $R^5$ is optionally substituted by 1 or 2 groups independently selected from $R^{15}$.

39. The compound of claim 1, or a pharmaceutically acceptable salt thereof, wherein $R^5$ is piperazinyl, wherein said piperazinyl of $R^5$ is optionally substituted by 1 or 2 groups independently selected from $R^{15}$.

40. The compound of claim 1, or a pharmaceutically acceptable salt thereof, wherein $R^{15}$ is independently at each occurrence selected from $C_{1-6}$ alkyl, CN, $OR^{a5}$, $C(=O)R^{b5}$, $C(=O)NR^{c5}R^{d5}$, $C(=O)OR^{a5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $S(=O)_2R^{b5}$, $NR^{c5}S(=O)_2R^{b5}$, and $S(=O)_2NR^{c5}R^{d5}$, wherein said $C_{1-6}$ alkyl, is optionally substituted by 1, 2, or 3 substituents independently selected from halo, CN, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $S(=O)R^{b5}$, $S(=O)NR^{c5}R^{d5}$, $S(=O)_2R^{b5}$, $NR^{c5}S(=O)_2R^{b5}$, $S(=O)_2NR^{c5}R^{d5}$, 5-6 membered heteroaryl, 4-7 membered heterocycloalkyl, phenyl, and $C_{3-7}$ cycloalkyl.

41. The compound of claim 1, or a pharmaceutically acceptable salt thereof, wherein IC is selected from H, halo, CN, $NR^cR^d$, $C_{1-6}$ alkyl, $C_{2-6}$ alkenyl, 5-6 membered heteroaryl group comprising carbon and 1, 2, 3 or 4 heteroatoms selected from N, O and S, and a 5-6 membered heterocycloalkyl group comprising carbon and 1, 2, or 3 heteroatoms selected from N, O and S, wherein said $C_{1-6}$ alkyl, $C_{2-6}$ alkenyl, 5-6 membered heteroaryl group, and 5-6 membered heterocycloalkyl group of IC are optionally substituted with 1, 2, or 3 groups independently selected from $R^{17}$.

42. The compound of claim 1, or a pharmaceutically acceptable salt thereof, wherein $R^7$ selected from H, F, Cl, Br, CN, $NR^cR^d$, $C_{1-4}$ alkyl, $C_{2-4}$ alkenyl, pyrazolyl, pyridinyl, pyrimidinyl, and 1,2,3,6-tetrahydropyridinyl, wherein said $C_{1-4}$ alkyl, $C_{2-4}$ alkenyl, pyrazolyl, pyridinyl, pyrimidinyl, and 1,2,3,6-tetrahydropyridinyl of $R^7$ are optionally substituted with 1, 2, or 3 groups independently selected from $R^{17}$.

43. The compound of claim 1, or a pharmaceutically acceptable salt thereof, wherein $R^7$ is selected from H, halo, $C_{1-4}$ alkyl, and CN.

44. The compound of claim 1, or a pharmaceutically acceptable salt thereof, wherein $R^7$ is selected from H, Br, methyl, and CN.

45. The compound of claim 1, or a pharmaceutically acceptable salt thereof, wherein $R^7$ is H.

46. The compound of claim 1, or a pharmaceutically acceptable salt thereof, wherein $R^7$ is Br.

47. The compound of claim 1, or a pharmaceutically acceptable salt thereof, wherein $R^7$ is methyl.

48. The compound of claim 1, or a pharmaceutically acceptable salt thereof, wherein $R^7$ is CN.

49. The compound of claim 1, or a pharmaceutically acceptable salt thereof, wherein $R^8$ is selected from H, halo, $C_{1-4}$ alkyl, and CN.

50. The compound of claim 1, or a pharmaceutically acceptable salt thereof, wherein $R^8$ is H.

51. The compound of claim 1, or a pharmaceutically acceptable salt thereof, having Formula (IIIb):

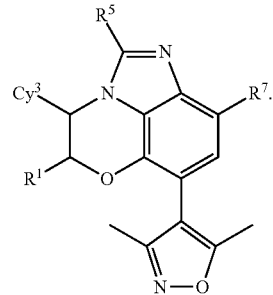

(IIIb)

52. The compound of claim 1, or a pharmaceutically acceptable salt thereof, having Formula (IVb):

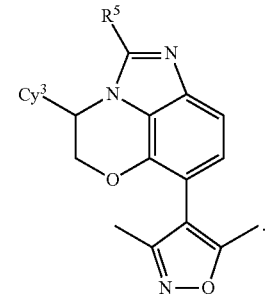

(IVb)

53. The compound of claim 1 selected from:
7-(3,5-dimethylisoxazol-4-yl)-2-methyl-4-phenyl-4,5-dihydroimidazo[1,5,4-de][1,4]benzoxazine;
7-(3,5-Dimethylisoxazol-4-yl)-N-isopropyl-4-phenyl-4,5-dihydroimidazo[1,5,4-de][1,4]benzoxazin-2-amine;
7-(3,5-Dimethylisoxazol-4-yl)-N-methyl-4-phenyl-4,5-dihydroimidazo[1,5,4-de][1,4]benzoxazin-2-amine;
7-(3,5-Dimethylisoxazol-4-yl)-N-ethyl-4-phenyl-4,5-dihydroimidazo[1,5,4-de][1,4]benzoxazin-2-amine;
7-(3,5-Dimethylisoxazol-4-yl)-N,N-dimethyl-4-phenyl-4,5-dihydroimidazo[1,5,4-de][1,4]benzoxazin-2-amine;
2-{[7-(3,5-Dimethylisoxazol-4-yl)-4-phenyl-4,5-dihydroimidazo[1,5,4-de][1,4]benzoxazin-2-yl]amino}ethanol;
2-{[7-(3,5-Dimethylisoxazol-4-yl)-4-phenyl-4,5-dihydroimidazo[1,5,4-de][1,4]benzoxazin-2-yl]amino}propan-1-ol;
1-{[7-(3,5-Dimethylisoxazol-4-yl)-4-phenyl-4,5-dihydroimidazo[1,5,4-de][1,4]benzoxazin-2-yl]amino}propan-2-ol;
2-1 [7-(3,5-Dimethylisoxazol-4-yl)-4-phenyl-4,5-dihydroimidazo[1,5,4-de][1,4]benzoxazin-2-yl]amino-2-methylpropan-1-ol;
2-[[7-(3,5-Dimethylisoxazol-4-yl)-4-phenyl-4,5-dihydroimidazo[1,5,4-de][1,4]benzoxazin-2-yl](methyl)amino]ethanol;
7-(3,5-Dimethylisoxazol-4-yl)-4-phenyl-4,5-dihydroimidazo[1,5,4-de][1,4]benzoxazine;
7-(3,5-dimethylisoxazol-4-yl)-4-phenyl-2-piperazin-1-yl-4,5-dihydroimidazo[1,5,4-de][1,4]benzoxazine;
7-(3,5-Dimethylisoxazol-4-yl)-2,4-diphenyl-4,5-dihydroimidazo[1,5,4-de][1,4]benzoxazine;
7-(3,5-Dimethylisoxazol-4-yl)-2-morpholin-4-yl-4-phenyl-4,5-dihydroimidazo[1,5,4-de][1,4]benzoxazine;

7-(3,5-Dimethylisoxazol-4-yl)-4-phenyl-2-pyrrolidin-1-yl-4,5-dihydroimidazo[1,5,4-de][1,4]benzoxazine;
1-[7-(3,5-Dimethylisoxazol-4-yl)-4-phenyl-4,5-dihydroimidazo[1,5,4-de][1,4]benzoxazin-2-yl]pyrrolidin-3-ol;
7-(3,5-Dimethylisoxazol-4-yl)-4-phenyl-2-piperidin-1-yl-4,5-dihydroimidazo[1,5,4-de][1,4]benzoxazine;
1-[7-(3,5-Dimethylisoxazol-4-yl)-4-phenyl-4,5-dihydroimidazo[1,5,4-de][1,4]benzoxazin-2-yl]piperidin-4-ol;
1-[7-(3,5-Dimethylisoxazol-4-yl)-4-phenyl-4,5-dihydroimidazo[1,5,4-de][1,4]benzoxazin-2-yl]piperidin-3-ol;
1-[7-(3,5-Dimethylisoxazol-4-yl)-4-phenyl-4,5-dihydroimidazo[1,5,4-de][1,4]benzoxazin-2-yl]azetidin-3-ol; and
4-[7-(3,5-Dimethylisoxazol-4-yl)-4-phenyl-4,5-dihydroimidazo[1,5,4-de][1,4]benzoxazin-2-yl]piperazine-1-carboxylate;
or a pharmaceutically acceptable salt thereof.

54. The compound of claim 1, selected from:
(4S)-7-(3,5-Dimethylisoxazol-4-yl)-4-pyridin-2-yl-2-vinyl-4,5-dihydroimidazo[1,5,4-de][1,4]benzoxazine;
(1R)-1-[(4S)-7-(3,5-Dimethylisoxazol-4-yl)-4-pyridin-2-yl-4,5-dihydroimidazo[1,5,4-de][1,4]benzoxazin-2-yl]ethane-1,2-diol;
1-[(4S)-7-(3,5-Dimethylisoxazol-4-yl)-4-pyridin-2-yl-4,5-dihydroimidazo[1,5,4-de][1,4]benzoxazin-2-yl]ethanol;
(4S)-7-(3,5-Dimethylisoxazol-4-yl)-N,N-dimethyl-4-pyridin-2-yl-4,5-dihydroimidazo[1,5,4-de][1,4]benzoxazine-2-carboxamide;
(4S)-7-(3,5-Dimethylisoxazol-4-yl)-4-pyridin-2-yl-4,5-dihydroimidazo[1,5,4-de][1,4]benzoxazine;
tert-Butyl (4S)-7-(3,5-dimethylisoxazol-4-yl)-4-pyridin-2-yl-4,5-dihydroimidazo[1,5,4-de][1,4]benzoxazine-2-carboxylate;
(4S)-7-(3,5-Dimethylisoxazol-4-yl)-2-(morpholin-4-ylcarbonyl)-4-pyridin-2-yl-4,5-dihydroimidazo[1,5,4-de][1,4]benzoxazine;
(4S)-7-(3,5-Dimethylisoxazol-4-yl)-N-methyl-4-pyridin-2-yl-4,5-dihydroimidazo[1,5,4-de][1,4]benzoxazine-2-carboxamide;
(4S)-7-(3,5-Dimethylisoxazol-4-yl)-4-pyridin-2-yl-4,5-dihydroimidazo[1,5,4-de][1,4]benzoxazine-2-carboxamide;
tert-Butyl 4-[(4S)-7-(3,5-dimethylisoxazol-4-yl)-4-pyridin-2-yl-4,5-dihydroimidazo[1,5,4-de][1,4]benzoxazin-2-yl]-3,6-dihydropyridine-1(2H)-carboxylate;
tert-Butyl 3-[(4S)-7-(3,5-dimethylisoxazol-4-yl)-4-pyridin-2-yl-4,5-dihydroimidazo[1,5,4-de][1,4]benzoxazin-2-yl]-2,5-dihydro-1H-pyrrole-1-carboxylate;
tert-Butyl 5-[(4S)-7-(3,5-dimethylisoxazol-4-yl)-4-pyridin-2-yl-4,5-dihydroimidazo[1,5,4-de][1,4]benzoxazin-2-yl]-3,6-dihydropyridine-1(2H)-carboxylate;
tert-Butyl 4-[(4S)-7-(3,5-dimethylisoxazol-4-yl)-4-pyridin-2-yl-4,5-dihydroimidazo[1,5,4-de][1,4]benzoxazin-2-yl]piperidine-1-carboxylate;
tert-Butyl 3-[(4S)-7-(3,5-dimethylisoxazol-4-yl)-4-pyridin-2-yl-4,5-dihydroimidazo[1,5,4-de][1,4]benzoxazin-2-yl]pyrrolidine-1-carboxylate;
tert-Butyl 3-[(4S)-7-(3,5-dimethylisoxazol-4-yl)-4-pyridin-2-yl-4,5-dihydroimidazo[1,5,4-de][1,4]benzoxazin-2-yl]piperidine-1-carboxylate;
(4S)-2-(1-Acetylpiperidin-4-yl)-7-(3,5-dimethylisoxazol-4-yl)-4-pyridin-2-yl-4,5-dihydroimidazo[1,5,4-de][1,4]benzoxazine;
(4S)-7-(3,5-dimethylisoxazol-4-yl)-4-pyridin-2-yl-2-(1,2,3,6-tetrahydropyridin-4-yl)-4,5-dihydroimidazo[1,5,4-de][1,4]benzoxazine;
(4S)-2-(2,5-dihydro-1H-pyrrol-3-yl)-'7-(3,5-dimethylisoxazol-4-yl)-4-pyridin-2-yl-4,5-dihydroimidazo[1,5,4-de][1,4]benzoxazine;
(4S)-7-(3,5-dimethylisoxazol-4-yl)-4-pyridin-2-yl-2-pyrrolidin-3-yl-4,5-dihydroimidazo[1,5,4-de][1,4]benzoxazine;
(4S)-7-(3,5-dimethylisoxazol-4-yl)-4-pyridin-2-yl-2-(1,2,5,6-tetrahydropyridin-3-yl)-4,5-dihydroimidazo[1,5,4-de][1,4]benzoxazine;
(4S)-7-(3,5-dimethylisoxazol-4-yl)-2-piperidin-3-yl-4-pyridin-2-yl-4,5-dihydroimidazo[1,5,4-de][1,4]benzoxazine;
(4S)-2-(1-Acetylpiperidin-4-yl)-7-(3,5-dimethylisoxazol-4-yl)-4-pyridin-2-yl-4,5-dihydroimidazo[1,5,4-de][1,4]benzoxazine;
(4S)-2-(1-acetyl-1,2,3,6-tetrahydropyridin-4-yl)-7-(3,5-dimethylisoxazol-4-yl)-4-pyridin-2-yl-4,5-dihydroimidazo[1,5,4-de][1,4]benzoxazine;
(4S)-2-[1-(cyclopropylcarbonyl)piperidin-4-yl]-7-(3,5-dimethylisoxazol-4-yl)-4-pyridin-2-yl-4,5-dihydroimidazo[1,5,4-de][1,4]benzoxazine;
(4S)-7-(3,5-dimethylisoxazol-4-yl)-2-[1-(methylsulfonyl)piperidin-4-yl]-4-pyridin-2-yl-4,5-dihydroimidazo[1,5,4-de][1,4]benzoxazine;
(4S)-2-(1-acetylpyrrolidin-3-yl)-7-(3,5-dimethylisoxazol-4-yl)-4-pyridin-2-yl-4,5-dihydroimidazo[1,5,4-de][1,4]benzoxazine;
(4S)-2-[1-(cyclopropylcarbonyl)pyrrolidin-3-yl]-7-(3,5-dimethylisoxazol-4-yl)-4-pyridin-2-yl-4,5-dihydroimidazo[1,5,4-de][1,4]benzoxazine;
(4S)-7-(3,5-dimethylisoxazol-4-yl)-2-[1-(methylsulfonyl)pyrrolidin-3-yl]-4-pyridin-2-yl-4,5-dihydroimidazo[1,5,4-de][1,4]benzoxazine;
(4S)-2-(1-acetyl-1,2,5,6-tetrahydropyridin-3-yl)-7-(3,5-dimethylisoxazol-4-yl)-4-pyridin-2-yl-4,5-dihydroimidazo[1,5,4-de][1,4]benzoxazine;
(4S)-2-(1-acetylpiperidin-3-yl)-7-(3,5-dimethylisoxazol-4-yl)-4-pyridin-2-yl-4,5-dihydroimidazo [1,5,4-de][1,4]benzoxazine;
(4S)-2-[1-(cyclopropylcarbonyl)piperidin-3-yl]-7-(3,5-dimethylisoxazol-4-yl)-4-pyridin-2-yl-4,5-dihydroimidazo[1,5,4-de][1,4]benzoxazine;
(4S)-7-(3,5-dimethylisoxazol-4-yl)-2-[1-(methylsulfonyl)piperidin-3-yl]-4-pyridin-2-yl-4,5-dihydroimidazo [1,5,4-de][1,4]benzoxazine;
(3R)-1-[(4S)-7-(3,5-Dimethylisoxazol-4-yl)-4-pyridin-2-yl-4,5-dihydroimidazo[1,5,4-de][1,4]benzoxazin-2-yl]-N-isopropylpyrrolidine-3-carboxamide;
1-[(4S)-7-(3,5-Dimethylisoxazol-4-yl)-4-pyridin-2-yl-4,5-dihydroimidazo[1,5,4-de][1,4]benzoxazin-2-yl]-3-methylpyrrolidin-3-ol;
4-[(4S)-7-(3,5-Dimethylisoxazol-4-yl)-4-pyridin-2-yl-4,5-dihydroimidazo[1,5,4-de][1,4]benzoxazin-2-yl]-1,4-diazepane-1-sulfonamide;
(4S)-2-(4-Acetyl-1,4-diazepan-1-yl)-7-(3,5-dimethylisoxazol-4-yl)-4-pyridin-2-yl-4,5-dihydroimidazo [1,5,4-de][1,4]benzoxazine;
(4S)-7-(3,5-Dimethylisoxazol-4-yl)-2-[4-(methylsulfonyl)-1,4-diazepan-1-yl]-4-pyridin-2-yl-4,5-dihydroimidazo[1,5,4-de][1,4]benzoxazine;
(4S)-7-(3,5-Dimethylisoxazol-4-yl)-2-piperazin-1-yl-4-pyridin-2-yl-4,5-dihydroimidazo[1,5,4-de][1,4]benzoxazine;

2-{4-[(4S)-7-(3,5-Dimethylisoxazol-4-yl)-4-pyridin-2-yl-4,5-dihydroimidazo[1,5,4-de][1,4]benzoxazin-2-yl]piperazin-1-yl}-N,N-dimethylacetamide;

2-Cyano-N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N-methylacetamide;

N-{(3R)-1-[(4S)-7-(3,5-Dimethylisoxazol-4-yl)-4-pyridin-2-yl-4,5-dihydroimidazo[1,5,4-de][1,4]benzoxazin-2-yl]pyrrolidin-3-yl}morpholine-4-carboxamide;

7-(3,5-Dimethylisoxazol-4-yl)-2-methyl-4-pyridin-2-yl-4,5-dihydroimidazo[1,5,4-de][1,4]benzoxazine;

Methyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate;

7-(3,5-Dimethylisoxazol-4-yl)-9-fluoro-N,N-dimethyl-4-pyridin-3-yl-4,5-dihydroimidazo[1,5,4-de][1,4]benzoxazin-2-amine;

1-[7-(3,5-Dimethylisoxazol-4-yl)-9-fluoro-4-pyridin-3-yl-4,5-dihydroimidazo[1,5,4-de][1,4]benzoxazin-2-yl]pyrrolidin-3-ol;

7-(3,5-Dimethylisoxazol-4-yl)-N-ethyl-9-fluoro-4-pyridin-3-yl-4,5-dihydroimidazo[1,5,4-de][1,4]benzoxazin-2-amine;

(3R)-1-[7-(3,5-Dimethylisoxazol-4-yl)-4-pyridin-3-yl-4,5-dihydroimidazo[1,5,4-de][1,4]benzoxazin-2-yl]pyrrolidin-3-ol;

1-[7-(3,5-Dimethylisoxazol-4-yl)-4-pyridin-3-yl-4,5-dihydroimidazo[1,5,4-de][1,4]benzoxazin-2-yl]azetidin-3-ol;

(4S)-7-(3,5-dimethylisoxazol-4-yl)-2-morpholin-4-yl-4-pyridin-2-yl-4,5-dihydroimidazo[1,5,4-de][1,4]benzoxazine;

(4S)-7-(3,5-dimethylisoxazol-4-yl)-4-pyridin-2-yl-2-pyrrolidin-1-yl-4,5-dihydroimidazo[1,5,4-de][1,4]benzoxazine;

(4S)-7-(3,5-dimethylisoxazol-4-yl)-2-(4-methylpiperazin-1-yl)-4-pyridin-2-yl-4,5-dihydroimidazo[1,5,4-de][1,4]benzoxazine;

(4S)-2-azetidin-1-yl-7-(3,5-dimethylisoxazol-4-yl)-4-pyridin-2-yl-4,5-dihydroimidazo[1,5,4-de][1,4]benzoxazine;

1-[(4S)-7-(3,5-dimethylisoxazol-4-yl)-4-pyridin-2-yl-4,5-dihydroimidazo[1,5,4-de][1,4]benzoxazin-2-yl]azetidin-3-ol;

4-[(4S)-7-(3,5-dimethylisoxazol-4-yl)-4-pyridin-2-yl-4,5-dihydroimidazo[1,5,4-de][1,4]benzoxazin-2-yl]-1-methylpiperazin-2-one;

ethyl 4-[(4S)-7-(3,5-dimethylisoxazol-4-yl)-4-pyridin-2-yl-4,5-dihydroimidazo[1,5,4-de][1,4]benzoxazin-2-yl]piperazine-1-carboxylate;

(3R)-1-[(4S)-7-(3,5-Dimethylisoxazol-4-yl)-4-pyridin-3-yl-4,5-dihydroimidazo[1,5,4-de][1,4]benzoxazin-2-yl]pyrrolidin-3-ol;

(3 S)-1-[(4S)-7-(3,5-Dimethylisoxazol-4-yl)-4-pyridin-3-yl-4,5-dihydroimidazo[1,5,4-de][1,4]benzoxazin-2-yl]pyrrolidin-3-ol;

1-[(4S)-7-(3,5-dimethylisoxazol-4-yl)-4-pyridin-2-yl-4,5-dihydroimidazo[1,5,4-de][1,4]benzoxazin-2-yl]piperidin-4-ol;

(3R)-1-[(4S)-7-(3,5-dimethylisoxazol-4-yl)-4-pyridin-2-yl-4,5-dihydroimidazo[1,5,4-de][1,4]benzoxazin-2-yl]piperidin-3-ol;

(3S)-1-[(4S)-7-(3,5-dimethylisoxazol-4-yl)-4-pyridin-2-yl-4,5-dihydroimidazo[1,5,4-de][1,4]benzoxazin-2-yl]piperidin-3-ol;

1-[(4S)-7-(3,5-dimethylisoxazol-4-yl)-4-pyridin-2-yl-4,5-dihydroimidazo[1,5,4-de][1,4]benzoxazin-2-yl]-N,N-dimethylpiperidin-4-amine;

4-[(4S)-7-(3,5-dimethylisoxazol-4-yl)-4-pyridin-2-yl-4,5-dihydroimidazo[1,5,4-de][1,4]benzoxazin-2-yl]piperazin-2-one;

(4S)-7-(3,5-dimethylisoxazol-4-yl)-2-[4-(methylsulfonyl)piperazin-1-yl]-4-pyridin-2-yl-4,5-dihydroimidazo[1,5,4-de][1,4]benzoxazine;

(4S)-7-(3,5-dimethylisoxazol-4-yl)-2-(4-isopropylpiperazin-1-yl)-4-pyridin-2-yl-4,5-dihydroimidazo[1,5,4-de][1,4]benzoxazine;

1-[(4S)-7-(3,5-dimethylisoxazol-4-yl)-4-pyridin-2-yl-4,5-dihydroimidazo[1,5,4-de][1,4]benzoxazin-2-yl]piperidine-4-carbonitrile;

{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}methanol;

2-{4-[(4S)-7-(3,5-dimethylisoxazol-4-yl)-4-pyridin-2-yl-4,5-dihydroimidazo[1,5,4-de][1,4]benzoxazin-2-yl]piperazin-1-yl}ethanol;

(4S)-7-(3,5-dimethylisoxazol-4-yl)-2-(4-phenylpiperazin-1-yl)-4-pyridin-2-yl-4,5-dihydroimidazo[1,5,4-de][1,4]benzoxazine;

(4S)-2-(4-benzylpiperazin-1-yl)-7-(3,5-dimethylisoxazol-4-yl)-4-pyridin-2-yl-4,5-dihydroimidazo[1,5,4-de][1,4]benzoxazine;

(3R)-1-[(4S)-7-(3,5-dimethylisoxazol-4-yl)-4-pyridin-2-yl-4,5-dihydroimidazo[1,5,4-de][1,4]benzoxazin-2-yl]-N,N-dimethylpyrrolidin-3-amine;

(3S)-1-[(4S)-7-(3,5-dimethylisoxazol-4-yl)-4-pyridin-2-yl-4,5-dihydroimidazo[1,5,4-de][1,4]benzoxazin-2-yl]-N,N-dimethylpyrrolidin-3-amine;

(3R)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidin-3-amine;

(3S)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidin-3-amine;

tert-butyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate;

tert-butyl {(3S)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}carbamate;

(4S)-2-[4-(cyclopropylmethyl)piperazin-1-yl]-7-(3,5-dimethylisoxazol-4-yl)-4-pyridin-2-yl-4,5-dihydroimidazo[1,5,4-de][1,4]benzoxazine;

(4S)-7-(3,5-dimethylisoxazol-4-yl)-2-[4-(2-methoxyethyl)piperazin-1-yl]-4-pyridin-2-yl-4,5-dihydroimidazo[1,5,4-de][1,4]benzoxazine;

2-[[7-(3,5-dimethylisoxazol-4-yl)-4-pyridin-2-yl-4,5-dihydroimidazo[1,5,4-de][1,4]benzoxazin-2-yl](methyl)amino]ethanol;

7-(3,5-dimethylisoxazol-4-yl)-N-methyl-4-pyridin-2-yl-4,5-dihydroimidazo[1,5,4-de][1,4]benzoxazin-2-amine;

7-(3,5-dimethylisoxazol-4-yl)-N,N-dimethyl-4-pyridin-2-yl-4,5-dihydroimidazo[1,5,4-de][1,4]benzoxazin-2-amine;

1-[(4S)-7-(3,5-dimethylisoxazol-4-yl)-4-pyridin-2-yl-4,5-dihydroimidazo[1,5,4-de][1,4]benzoxazin-2-yl]piperidine-4-carboxamide;

1-[(4S)-7-(3,5-dimethylisoxazol-4-yl)-4-pyridin-2-yl-4,5-dihydroimidazo[1,5,4-de][1,4]benzoxazin-2-yl]-N-methylpiperidine-4-carboxamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}acetamide;
2-{4-[(4S)-7-(3,5-dimethylisoxazol-4-yl)-4-pyridin-2-yl-4,5-dihydroimidazo[1,5,4-de][1,4]benzoxazin-2-yl]piperazin-1-yl}acetamide;
(4S)-7-(3,5-dimethylisoxazol-4-yl)-2-(4-ethylpiperazin-1-yl)-4-pyridin-2-yl-4,5-dihydroimidazo[1,5,4-de][1,4]benzoxazine;
(4S)-7-(3,5-dimethylisoxazol-4-yl)-2-[(8aS)-hexahydropyrrolo[1,2-a]pyrazin-2(1H)-yl]-4-pyridin-2-yl-4,5-dihydroimidazo[1,5,4-de][1,4]benzoxazine;
(4S)-7-(3,5-dimethylisoxazol-4-yl)-2-[(8aR)-hexahydropyrrolo[1,2-a]pyrazin-2(1H)-yl]-4-pyridin-2-yl-4,5-dihydroimidazo[1,5,4-de][1,4]benzoxazine;
1-[(4S)-7-(3,5-dimethylisoxazol-4-yl)-4-pyridin-2-yl-4,5-dihydroimidazo[1,5,4-de][1,4]benzoxazin-2-yl]-4-methylpiperidin-4-ol;
4-[(4S)-7-(3,5-dimethylisoxazol-4-yl)-4-pyridin-2-yl-4,5-dihydroimidazo[1,5,4-de][1,4]benzoxazin-2-yl]-3-methylpiperazin-2-one;
tert-butyl {1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}carbamate;
tert-butyl 4-[(4S)-7-(3,5-dimethylisoxazol-4-yl)-4-pyridin-2-yl-4,5-dihydroimidazo[1,5,4-de][1,4]benzoxazin-2-yl]-1,4-diazepane-1-carboxylate;
2-{[(4S)-7-(3,5-dimethylisoxazol-4-yl)-4-pyridin-2-yl-4,5-dihydroimidazo[1,5,4-de][1,4]benzoxazin-2-yl]amino}ethanol;
tert-butyl (2-{[(4S)-7-(3,5-dimethylisoxazol-4-yl)-4-pyridin-2-yl-4,5-dihydroimidazo[1,5,4-de][1,4]benzoxazin-2-yl]amino}ethyl)carbamate;
N-[(4S)-7-(3,5-dimethylisoxazol-4-yl)-4-pyridin-2-yl-4,5-dihydroimidazo[1,5,4-de][1,4]benzoxazin-2-yl]ethane-1,2-diamine;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}acetamide;
N-{(3 S)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}acetamide;
(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-amine;
(3S)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-amine;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2,2,2-trifluoroacetamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2-methoxyacetamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}cyclopropanecarboxamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}methanesulfonamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}propanamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2-methylpropanamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}cyclobutanecarboxamide;
2-cyano-N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}acetamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}tetrahydro-2H-pyran-4-carboxamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}ethanesulfonamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}propane-1-sulfonamide;
N'-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N,N-dimethylurea;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}propane-2-sulfonamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}cyclopropanesulfonamide;
methyl {(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}methylcarbamate;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N-methylmethanesulfonamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-2-methoxy-N-methylacetamide;
N-{(3R)-1-[(4S)-7-(3,5-dimethylisoxazol-4-yl)-4-pyridin-2-yl-4,5-dihydroimidazo[1,5,4-de][1,4]benzoxazin-2-yl]pyrrolidin-3-yl}-N-methylacetamide;
(4S)-2-(4-acetylpiperazin-1-yl)-'7-(3,5-dimethylisoxazol-4-yl)-4-pyridin-2-yl-4,5-dihydroimidazo[1,5,4-de][1,4]benzoxazine;
(4S)-7-(3,5-dimethylisoxazol-4-yl)-2-(4-propionylpiperazin-1-yl)-4-pyridin-2-yl-4,5-dihydroimidazo[1,5,4-de][1,4]benzoxazine;
(4S)-7-(3,5-dimethylisoxazol-4-yl)-2-[4-(ethylsulfonyl)piperazin-1-yl]-4-pyridin-2-yl-4,5-dihydroimidazo[1,5,4-de][1,4]benzoxazine;
(4S)-7-(3,5-dimethylisoxazol-4-yl)-2-[4-(2-oxo-2-pyrrolidin-1-ylethyl)piperazin-1-yl]-4-pyridin-2-yl-4,5-dihydroimidazo[1,5,4-de][1,4]benzoxazine;
4-[(4S)-7-(3,5-dimethylisoxazol-4-yl)-4-pyridin-2-yl-4,5-dihydroimidazo[1,5,4-de][1,4]benzoxazin-2-yl]piperazine-1-sulfonamide;
1-[(4S)-7-(3,5-dimethylisoxazol-4-yl)-4-pyridin-2-yl-4,5-dihydroimidazo[1,5,4-de][1,4]benzoxazin-2-yl]azetidin-3-amine;
N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}acetamide;
N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}propanamide;
N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}-2-methylpropanamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}-2-methoxyacetamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}cyclopropanecarboxamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}cyclobutanecarboxamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}methanesulfonamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}ethanesulfonamide;

N-{1-[(4S)-7-(3,5-dimethylisoxazol-4-yl)-4-pyridin-2-yl-4,5-dihydroimidazo[1,5,4-de][1,4]benzoxazin-2-yl]azetidin-3-yl}propane-2-sulfonamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}methanesulfonamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-2-methoxyacetamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-2,2,2-trifluoroacetamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}propanamide;

N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}propanamide;

(4S)-7-(3,5-dimethylisoxazol-4-yl)-2-(4-propionyl-1,4-diazepan-1-yl)-4-pyridin-2-yl-4,5-dihydroimidazo[1,5,4-de][1,4]benzoxazine;

(4S)-7-(3,5-dimethylisoxazol-4-yl)-2-[4-(ethylsulfonyl)-1,4-diazepan-1-yl]-4-pyridin-2-yl-4,5-dihydroimidazo[1,5,4-de][1,4]benzoxazine;

(3R)-1-[(4S)-7-(3,5-dimethylisoxazol-4-yl)-4-pyridin-2-yl-4,5-dihydroimidazo[1,5,4-de][1,4]benzoxazin-2-yl]-N-methylpyrrolidine-3-carboxamide;

(3R)-1-[(4S)-7-(3,5-dimethylisoxazol-4-yl)-4-pyridin-2-yl-4,5-dihydroimidazo[1,5,4-de][1,4]benzoxazin-2-yl]-N-ethylpyrrolidine-3-carboxamide; and (3R)—N-cyclopropyl-1-[(4S)-7-(3,5-dimethylisoxazol-4-yl)-4-pyridin-2-yl-4,5-dihydroimidazo[1,5,4-de][1,4]benzoxazin-2-yl]pyrrolidine-3-carboxamide;

or a pharmaceutically acceptable salt thereof.

55. A pharmaceutical composition comprising a compound of claim 1, or a pharmaceutically acceptable salt thereof, and at least one pharmaceutically acceptable carrier.

56. A method of inhibiting a BET protein in vitro comprising contacting a compound of claim 1, or a pharmaceutically acceptable salt thereof, with said BET protein.

\* \* \* \* \*

UNITED STATES PATENT AND TRADEMARK OFFICE
CERTIFICATE OF CORRECTION

PATENT NO. : 10,464,947 B2  
APPLICATION NO. : 15/906163  
DATED : November 5, 2019  
INVENTOR(S) : Andrew P. Combs et al.

Page 1 of 2

It is certified that error appears in the above-identified patent and that said Letters Patent is hereby corrected as shown below:

Column 247, Line 39, Claim 1, delete "S(=O))$_2$R$^{b1}$" and insert -- S(=O)$_2$R$^{b1}$ --;

Column 247, Line 44, Claim 1, delete "NR$^{c1}$R$^{d1}$;" and insert -- NR$^{c1}$R$^{d1}$, --;

Column 247, Lines 45-46, Claim 1, delete "C(=O)R$^{a1}$," and insert -- C(=O)OR$^{a1}$, --;

Column 247, Line 46, Claim 1, delete "NR$^{c1}$R$^{d1}$;" and insert -- NR$^{c1}$R$^{d1}$, --;

Column 248, Line 66, Claim 1, delete "C(O)" and insert -- C(=O) --;

Column 249, Line 55, Claim 1, delete "C(=)" and insert -- C(=O) --;

Column 249, Line 57, Claim 1, delete "S(O)" and insert -- S(=O) --.

Column 250, Line 34, Claim 2, delete "C(O)" and insert -- C(=O) --;

Column 251, Line 44, Claim 2, delete "C(=O)R$^{a4}$," and insert -- C(=O)OR$^{a4}$, --.

Column 253, Line 7, Claim 12, delete "of any" and insert -- of --.

Column 253, Line 17, Claim 16, after "compound" insert -- of --.

Column 254, Line 14, Claim 31, delete "C(=O)" and insert -- -C(=O) --.

Column 254, Line 22, Claim 32, delete "C(=O)" and insert -- -C(=O) --;

Column 254, Line 26, Claim 32, delete "pyrolidinyl," and insert -- pyrrolidinyl, --.

Column 255, Line 20, Claim 41, delete "IC" and insert -- R$^7$ --;

Signed and Sealed this  
Fourteenth Day of January, 2020

Andrei Iancu  
*Director of the United States Patent and Trademark Office*

CERTIFICATE OF CORRECTION (continued)
U.S. Pat. No. 10,464,947 B2

Column 255, Line 29, Claim 41, delete "IC" and insert -- $R^7$ --.

Column 256, Line 54, Claim 53, delete "2-1 [7-" and insert -- 2-{[7- --.

Column 258, Line 4, Claim 54, delete "-'7-" and insert -- -7- --;

Column 258, Line 42, Claim 54, delete "dihydroimidazo [" and insert -- dihydroimidazo[ --;

Column 258, Line 60, Claim 54, delete "dihydroimidazo [" and insert -- dihydroimidazo[ --;

Column 259, Line 56, Claim 54, delete "(3 S)" and insert -- (3S) --;

Column 261, Line 41, Claim 54, delete "(3 S)" and insert -- (3S) --;

Column 262, Line 41, Claim 54, delete "-'7-" and insert -- -7- --.